US009388430B2

(12) United States Patent
Liu et al.

(10) Patent No.: US 9,388,430 B2
(45) Date of Patent: Jul. 12, 2016

(54) CAS9-RECOMBINASE FUSION PROTEINS AND USES THEREOF

(71) Applicant: President and Fellows of Harvard College, Cambridge, MA (US)

(72) Inventors: David R. Liu, Lexington, MA (US); John Paul Guilinger, Ridgway, CO (US); David B. Thompson, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/320,467

(22) Filed: Jun. 30, 2014

(65) Prior Publication Data

US 2015/0071898 A1 Mar. 12, 2015

Related U.S. Application Data

(60) Provisional application No. 61/980,315, filed on Apr. 16, 2014, provisional application No. 61/915,414, filed on Dec. 12, 2013, provisional application No. 61/874,609, filed on Sep. 6, 2013.

(51) Int. Cl.

| | |
|---|---|
| ***C12N 9/22*** | (2006.01) |
| ***C12N 15/63*** | (2006.01) |
| ***C12N 15/90*** | (2006.01) |
| ***C12N 9/12*** | (2006.01) |
| *A61K 47/00* | (2006.01) |
| *A61K 38/00* | (2006.01) |

(52) U.S. Cl.

CPC ............ *C12N 15/907* (2013.01); *C12N 9/1241* (2013.01); *C12N 9/22* (2013.01); *A61K 38/00* (2013.01); *A61K 47/00* (2013.01); *C07K 2319/80* (2013.01)

(58) Field of Classification Search

CPC .................................. C12N 9/22; C12N 15/63

See application file for complete search history.

(56) References Cited

U.S. PATENT DOCUMENTS

| | | | |
|---|---|---|---|
| 5,780,053 | A | 7/1998 | Ashley et al. |
| 6,057,153 | A | 5/2000 | George et al. |
| 6,453,242 | B1 | 9/2002 | Eisenberg et al. |
| 6,503,717 | B2 | 1/2003 | Case et al. |
| 6,534,261 | B1 | 3/2003 | Cox, III et al. |
| 6,599,692 | B1 | 7/2003 | Case et al. |
| 6,607,882 | B1 | 8/2003 | Cox, III et al. |
| 6,824,978 | B1 | 11/2004 | Cox, III et al. |
| 6,933,113 | B2 | 8/2005 | Case et al. |
| 6,979,539 | B2 | 12/2005 | Cox, III et al. |
| 7,013,219 | B2 | 3/2006 | Case et al. |
| 7,163,824 | B2 | 1/2007 | Cox, III et al. |
| 7,479,573 | B2 | 1/2009 | Chu et al. |
| 7,794,931 | B2 | 9/2010 | Breaker et al. |
| 7,919,277 | B2 | 4/2011 | Russell et al. |
| 8,361,725 | B2 | 1/2013 | Russell et al. |
| 8,492,082 | B2 | 7/2013 | De Franciscis et al. |
| 8,546,553 | B2 | 10/2013 | Terns et al. |
| 8,569,256 | B2 | 10/2013 | Heyes et al. |
| 8,680,069 | B2 | 3/2014 | de Fougerolles et al. |
| 8,691,750 | B2 | 4/2014 | Constien et al. |
| 8,697,359 | B1 | 4/2014 | Zhang |
| 8,709,466 | B2 | 4/2014 | Coady et al. |
| 8,728,526 | B2 | 5/2014 | Heller |
| 8,748,667 | B2 | 6/2014 | Budzik et al. |
| 8,758,810 | B2 | 6/2014 | Okada et al. |
| 8,759,103 | B2 | 6/2014 | Kim et al. |
| 8,759,104 | B2 | 6/2014 | Unciti-Broceta et al. |
| 8,771,728 | B2 | 7/2014 | Huang et al. |
| 8,790,664 | B2 | 7/2014 | Pitard et al. |
| 8,846,578 | B2 | 9/2014 | McCray et al. |
| 8,993,233 | B2 * | 3/2015 | Zhang .................... C12N 15/85 424/94.1 |
| 8,999,641 | B2 * | 4/2015 | Zhang .................... C12N 15/63 424/94.1 |
| 9,068,179 | B1 | 6/2015 | Liu et al. |
| 9,163,284 | B2 | 10/2015 | Liu et al. |
| 2006/0088864 | A1 | 4/2006 | Smolke et al. |
| 2008/0124725 | A1 | 5/2008 | Barrangou et al. |
| 2008/0182254 | A1 | 7/2008 | Hall et al. |
| 2009/0130718 | A1 | 5/2009 | Short |
| 2009/0234109 | A1 | 9/2009 | Han et al. |

(Continued)

FOREIGN PATENT DOCUMENTS

| | | |
|---|---|---|
| AU | 2012244264 | 11/2012 |
| AU | 2015252023 A1 | 11/2015 |

(Continued)

OTHER PUBLICATIONS

International Search Report and Written Opinion for PCT/US2014/052231, mailed Dec. 4, 2014.

International Search Report and Written Opinion for PCT/US2014/050283, mailed Nov. 6, 2014.

NCBI Reference Sequence: NM_002427.3. Wu et al., May 3, 2014. 5 pages.

Barrangou, RNA-mediated programmable DNA cleavage. Nat Biotechnol. Sep. 2012;30(9):836-8. doi: 10.1038/nbt.2357.

Carroll, A CRISPR approach to gene targeting. Mol Ther. Sep. 2012;20(9):1658-60. doi: 10.1038/mt.2012.171.

Fuchs et al., Polyarginine as a multifunctional fusion tag. Protein Sci. Jun. 2005;14(6):1538-44.

(Continued)

*Primary Examiner* — Maryam Monshipouri

(74) *Attorney, Agent, or Firm* — Wolf, Greenfield & Sacks, P.C.

(57) ABSTRACT

Some aspects of this disclosure provide compositions, methods, and kits for improving the specificity of RNA-programmable endonucleases, such as Cas9. Also provided are variants of Cas9, e.g., Cas9 dimers and fusion proteins, engineered to have improved specificity for cleaving nucleic acid targets. Also provided are compositions, methods, and kits for site-specific recombination, using Cas9 fusion proteins (e.g., nuclease-inactivated Cas9 fused to a recombinase catalytic domain). Such Cas9 variants are useful in clinical and research settings involving site-specific modification of DNA, for example, genomic modifications.

7 Claims, 35 Drawing Sheets

(56) References Cited

U.S. PATENT DOCUMENTS

| | | | |
|---|---|---|---|
| 2010/0076057 | A1 | 3/2010 | Sontheimer et al. |
| 2010/0093617 | A1 | 4/2010 | Barrangou et al. |
| 2010/0104690 | A1 | 4/2010 | Barrangou et al. |
| 2010/0316643 | A1 | 12/2010 | Eckert et al. |
| 2011/0059160 | A1 | 3/2011 | Essner et al. |
| 2011/0104787 | A1 | 5/2011 | Church et al. |
| 2011/0189776 | A1 | 8/2011 | Terns et al. |
| 2011/0217739 | A1 | 9/2011 | Terns et al. |
| 2012/0141523 | A1 | 6/2012 | Castado et al. |
| 2012/0270273 | A1 | 10/2012 | Zhang et al. |
| 2013/0117869 | A1 | 5/2013 | Duchateau et al. |
| 2013/0130248 | A1 | 5/2013 | Haurwitz et al. |
| 2013/0158245 | A1 | 6/2013 | Russell et al. |
| 2013/0165389 | A1 | 6/2013 | Schellenberger et al. |
| 2013/0344117 | A1 | 12/2013 | Mirosevich et al. |
| 2014/0005269 | A1 | 1/2014 | Ngwuluka et al. |
| 2014/0017214 | A1 | 1/2014 | Cost |
| 2014/0018404 | A1 | 1/2014 | Chen et al. |
| 2014/0044793 | A1 | 2/2014 | Goll et al. |
| 2014/0065711 | A1 | 3/2014 | Liu et al. |
| 2014/0068797 | A1 | 3/2014 | Doudna et al. |
| 2014/0127752 | A1 | 5/2014 | Zhou et al. |
| 2014/0141094 | A1 | 5/2014 | Smyth et al. |
| 2014/0141487 | A1 | 5/2014 | Feldman et al. |
| 2014/0186843 | A1 | 7/2014 | Zhang et al. |
| 2014/0186958 | A1 | 7/2014 | Zhang et al. |
| 2014/0234289 | A1 | 8/2014 | Liu et al. |
| 2014/0273037 | A1 | 9/2014 | Wu |
| 2014/0273226 | A1 | 9/2014 | Wu |
| 2014/0273230 | A1 | 9/2014 | Chen et al. |
| 2014/0295556 | A1 | 10/2014 | Joung et al. |
| 2014/0295557 | A1 | 10/2014 | Joung et al. |
| 2014/0342456 | A1 | 11/2014 | Mali et al. |
| 2014/0342457 | A1 | 11/2014 | Mali et al. |
| 2014/0342458 | A1 | 11/2014 | Mali et al. |
| 2014/0349400 | A1 | 11/2014 | Jakimo et al. |
| 2014/0356867 | A1 | 12/2014 | Peter et al. |
| 2014/0356956 | A1 | 12/2014 | Church et al. |
| 2014/0356958 | A1 | 12/2014 | Mali et al. |
| 2014/0356959 | A1 | 12/2014 | Church et al. |
| 2014/0357523 | A1 | 12/2014 | Zeiner et al. |
| 2014/0377868 | A1 | 12/2014 | Joung et al. |
| 2015/0010526 | A1 | 1/2015 | Liu et al. |
| 2015/0031089 | A1 | 1/2015 | Lindstrom |
| 2015/0031132 | A1 | 1/2015 | Church et al. |
| 2015/0031133 | A1 | 1/2015 | Church et al. |
| 2015/0044191 | A1 | 2/2015 | Liu et al. |
| 2015/0044192 | A1 | 2/2015 | Liu et al. |
| 2015/0044772 | A1 | 2/2015 | Zhao |
| 2015/0050699 | A1 | 2/2015 | Siksnys et al. |
| 2015/0056177 | A1 | 2/2015 | Liu et al. |
| 2015/0056629 | A1 | 2/2015 | Guthrie-Honea |
| 2015/0064138 | A1 | 3/2015 | Liu et al. |
| 2015/0064789 | A1 | 3/2015 | Paschon et al. |
| 2015/0071899 | A1 | 3/2015 | Liu et al. |
| 2015/0071900 | A1 | 3/2015 | Liu et al. |
| 2015/0071901 | A1 | 3/2015 | Liu et al. |
| 2015/0071902 | A1 | 3/2015 | Liu et al. |
| 2015/0071903 | A1 | 3/2015 | Liu et al. |
| 2015/0071906 | A1 | 3/2015 | Liu et al. |
| 2015/0079680 | A1 | 3/2015 | Bradley et al. |
| 2015/0098954 | A1 | 4/2015 | Hyde et al. |
| 2015/0118216 | A1 | 4/2015 | Liu et al. |
| 2015/0132269 | A1 | 5/2015 | Orkin et al. |
| 2015/0140664 | A1 | 5/2015 | Byrne et al. |
| 2015/0159172 | A1 | 6/2015 | Miller et al. |
| 2015/0165054 | A1 | 6/2015 | Liu et al. |
| 2015/0166980 | A1 | 6/2015 | Liu et al. |
| 2015/0166981 | A1 | 6/2015 | Liu et al. |
| 2015/0166982 | A1 | 6/2015 | Liu et al. |
| 2015/0166984 | A1 | 6/2015 | Liu et al. |
| 2015/0166985 | A1 | 6/2015 | Liu et al. |
| 2015/0191744 | A1 | 7/2015 | Wolfe et al. |
| 2015/0197759 | A1 | 7/2015 | Xu et al. |
| 2015/0211058 | A1 | 7/2015 | Carstens et al. |
| 2015/0218573 | A1 | 8/2015 | Loque et al. |
| 2015/0225773 | A1 | 8/2015 | Farmer et al. |
| 2015/0252358 | A1 | 9/2015 | Maeder et al. |

FOREIGN PATENT DOCUMENTS

| | | | |
|---|---|---|---|
| CA | 2 852 593 | A1 | 11/2015 |
| CN | 103233028 | A | 8/2013 |
| CN | 103388006 | A | 11/2013 |
| CN | 103614415 | A | 3/2014 |
| CN | 103642836 | A | 3/2014 |
| CN | 103668472 | A | 3/2014 |
| CN | 103820441 | A | 5/2014 |
| CN | 103820454 | A | 5/2014 |
| CN | 103911376 | A | 7/2014 |
| CN | 103923911 | A | 7/2014 |
| CN | 104004778 | A | 8/2014 |
| CN | 104109687 | A | 10/2014 |
| CN | 104178461 | A | 12/2014 |
| CN | 104342457 | | 2/2015 |
| CN | 104404036 | A | 3/2015 |
| CN | 104450774 | A | 3/2015 |
| CN | 104480144 | A | 4/2015 |
| CN | 104498493 | A | 4/2015 |
| CN | 104504304 | A | 4/2015 |
| CN | 104531704 | A | 4/2015 |
| CN | 104531705 | A | 4/2015 |
| CN | 104560864 | A | 4/2015 |
| CN | 104593418 | A | 5/2015 |
| CN | 104593422 | A | 5/2015 |
| CN | 104611370 | A | 5/2015 |
| CN | 104651392 | A | 5/2015 |
| CN | 104651398 | A | 5/2015 |
| CN | 104651399 | A | 5/2015 |
| CN | 104651401 | A | 5/2015 |
| CN | 104673816 | A | 6/2015 |
| CN | 104726449 | A | 6/2015 |
| CN | 104726494 | A | 6/2015 |
| CN | 104745626 | A | 7/2015 |
| CN | 104762321 | A | 7/2015 |
| CN | 104805078 | A | 7/2015 |
| CN | 104805099 | A | 7/2015 |
| CN | 104805118 | A | 7/2015 |
| CN | 104846010 | A | 8/2015 |
| CN | 104894068 | A | 9/2015 |
| CN | 104894075 | A | 9/2015 |
| CN | 104928321 | A | 9/2015 |
| CN | 105039339 | A | 11/2015 |
| CN | 105039399 | A | 11/2015 |
| CN | 105063061 | A | 11/2015 |
| CN | 105087620 | A | 11/2015 |
| CN | 105112422 | A | 12/2015 |
| CN | 105112445 | A | 12/2015 |
| CN | 105112519 | A | 12/2015 |
| CN | 105132427 | A | 12/2015 |
| CN | 105132451 | A | 12/2015 |
| WO | WO 2006/002547 | A1 | 1/2006 |
| WO | WO 2006/042112 | A2 | 4/2006 |
| WO | WO 2007/025097 | A2 | 3/2007 |
| WO | WO 2007/136815 | A2 | 11/2007 |
| WO | WO 2010/054108 | A2 | 5/2010 |
| WO | WO 2010/054154 | A2 | 5/2010 |
| WO | WO 2010/068289 | A2 | 6/2010 |
| WO | WO 2010/075424 | A2 | 7/2010 |
| WO | WO 2010/102257 | A2 | 9/2010 |
| WO | WO 2010/129019 | A2 | 11/2010 |
| WO | WO 2010/132092 | A2 | 11/2010 |
| WO | WO 2010/144150 | A2 | 12/2010 |
| WO | WO 2011/017293 | A2 | 2/2011 |
| WO | WO 2011/053868 | A1 | 5/2011 |
| WO | WO 2011/053982 | A2 | 5/2011 |
| WO | WO 2011/109031 | A1 | 9/2011 |
| WO | WO 2012/054726 | A1 | 4/2012 |
| WO | WO 2012/065043 | A2 | 5/2012 |
| WO | WO 2012/138927 | A2 | 10/2012 |
| WO | WO 2012/158985 | A2 | 11/2012 |
| WO | WO 2012/158986 | A2 | 11/2012 |
| WO | WO 2012/164565 | A1 | 12/2012 |
| WO | WO 2013/012674 | A1 | 1/2013 |

(56) References Cited

FOREIGN PATENT DOCUMENTS

| | | | |
|---|---|---|---|
| WO | WO 2013/013105 | A2 | 1/2013 |
| WO | WO 2013/066438 | A2 | 5/2013 |
| WO | WO 2013/098244 | A1 | 7/2013 |
| WO | WO 2013/126794 | A1 | 8/2013 |
| WO | WO 2013/130824 | A1 | 9/2013 |
| WO | WO 2013/141680 | A1 | 9/2013 |
| WO | WO 2013/142378 | A9 | 9/2013 |
| WO | WO 2013/142578 | A2 | 9/2013 |
| WO | WO 2013/160230 | A1 | 10/2013 |
| WO | WO 2013/166315 | A1 | 11/2013 |
| WO | WO 2013/169398 | A2 | 11/2013 |
| WO | WO 2013/169802 | A1 | 11/2013 |
| WO | WO 2013/176772 | A2 | 11/2013 |
| WO | WO 2013/176915 | A1 | 11/2013 |
| WO | WO 2013/176916 | A1 | 11/2013 |
| WO | WO 2013/181440 | A1 | 12/2013 |
| WO | WO 2013/186754 | A2 | 12/2013 |
| WO | WO 2013/188037 | A2 | 12/2013 |
| WO | WO 2013/188522 | A2 | 12/2013 |
| WO | WO 2013/188638 | A2 | 12/2013 |
| WO | WO 2013/192278 | A1 | 12/2013 |
| WO | WO 2014/005042 | A2 | 1/2014 |
| WO | WO 2014/011237 | A1 | 1/2014 |
| WO | WO 2014/011901 | A2 | 1/2014 |
| WO | WO 2014/018423 | A2 | 1/2014 |
| WO | WO 2014/020608 | A1 | 2/2014 |
| WO | WO 2014/022120 | A1 | 2/2014 |
| WO | WO 2014/022702 | A2 | 2/2014 |
| WO | WO 2014/036219 | A2 | 3/2014 |
| WO | WO 2014/039513 | A2 | 3/2014 |
| WO | WO 2014/039523 | A1 | 3/2014 |
| WO | WO 2014/039684 | A1 | 3/2014 |
| WO | WO 2014/039692 | A2 | 3/2014 |
| WO | WO 2014/039702 | A2 | 3/2014 |
| WO | WO 2014/039872 | A1 | 3/2014 |
| WO | WO 2014/039970 | A1 | 3/2014 |
| WO | WO 2014/041327 | A1 | 3/2014 |
| WO | WO 2014/043143 | A1 | 3/2014 |
| WO | WO 2014/047103 | A2 | 3/2014 |
| WO | WO 2014/059173 | A2 | 4/2014 |
| WO | WO 2014/059255 | A1 | 4/2014 |
| WO | WO 2014/065596 | A1 | 5/2014 |
| WO | WO 2014/066505 | A1 | 5/2014 |
| WO | WO 2014/068346 | A2 | 5/2014 |
| WO | WO 2014/070887 | A1 | 5/2014 |
| WO | WO 2014/071006 | A1 | 5/2014 |
| WO | WO 2014/071219 | A1 | 5/2014 |
| WO | WO 2014/071235 | A1 | 5/2014 |
| WO | WO 2014/072941 | A1 | 5/2014 |
| WO | WO 2014/081729 | A1 | 5/2014 |
| WO | WO 2014/081730 | A1 | 5/2014 |
| WO | WO 2014/081855 | A1 | 5/2014 |
| WO | WO 2014/082644 | A1 | 6/2014 |
| WO | WO 2014/085261 | A1 | 6/2014 |
| WO | WO 2014/085593 | A1 | 6/2014 |
| WO | WO 2014/085830 | A2 | 6/2014 |
| WO | WO 2014/089212 | A1 | 6/2014 |
| WO | WO 2014/089290 | A1 | 6/2014 |
| WO | WO 2014/089348 | A1 | 6/2014 |
| WO | WO 2014/089513 | A1 | 6/2014 |
| WO | WO 2014/089533 | A2 | 6/2014 |
| WO | WO 2014/089541 | A2 | 6/2014 |
| WO | WO 2014/093479 | A1 | 6/2014 |
| WO | WO 2014/093595 | A1 | 6/2014 |
| WO | WO 2014/093622 | A2 | 6/2014 |
| WO | WO 2014/093635 | A1 | 6/2014 |
| WO | WO 2014/093655 | A2 | 6/2014 |
| WO | WO 2014/093661 | A2 | 6/2014 |
| WO | WO 2014/093694 | A1 | 6/2014 |
| WO | WO 2014/093701 | A1 | 6/2014 |
| WO | WO 2014/093709 | A1 | 6/2014 |
| WO | WO 2014/093712 | A1 | 6/2014 |
| WO | WO 2014/093718 | A1 | 6/2014 |
| WO | WO 2014/093736 | A1 | 6/2014 |
| WO | WO 2014/093768 | A1 | 6/2014 |
| WO | WO 2014/093852 | A1 | 6/2014 |
| WO | WO 2014/096972 | A2 | 6/2014 |
| WO | WO 2014/099744 | A1 | 6/2014 |
| WO | WO 2014/099750 | A2 | 6/2014 |
| WO | WO 2014/104878 | A1 | 7/2014 |
| WO | WO 2014/113493 | A1 | 7/2014 |
| WO | WO 2014/124226 | A1 | 8/2014 |
| WO | WO 2014/127287 | A1 | 8/2014 |
| WO | WO 2014/128324 | A1 | 8/2014 |
| WO | WO 2014/128659 | A1 | 8/2014 |
| WO | WO 2014/130955 | A1 | 8/2014 |
| WO | WO 2014/131833 | A1 | 9/2014 |
| WO | WO 2014/143381 | A1 | 9/2014 |
| WO | WO 2014/144094 | A1 | 9/2014 |
| WO | WO 2014/144155 | A1 | 9/2014 |
| WO | WO 2014/144288 | A1 | 9/2014 |
| WO | WO 2014/144592 | A2 | 9/2014 |
| WO | WO 2014/144761 | A2 | 9/2014 |
| WO | WO 2014/145599 | A2 | 9/2014 |
| WO | WO 2014/150624 | A1 | 9/2014 |
| WO | WO 2014/152432 | A2 | 9/2014 |
| WO | WO 2014/153470 | A2 | 9/2014 |
| WO | WO 2014/161821 | A1 | 10/2014 |
| WO | WO 2014/164466 | A1 | 10/2014 |
| WO | WO 2014/165177 | A1 | 10/2014 |
| WO | WO 2014/165349 | A1 | 10/2014 |
| WO | WO 2014/165612 | A2 | 10/2014 |
| WO | WO 2014/165825 | A2 | 10/2014 |
| WO | WO 2014/172458 | A1 | 10/2014 |
| WO | WO 2014/172470 | A | 10/2014 |
| WO | WO 2014/172489 | A2 | 10/2014 |
| WO | WO 2014/182700 | A1 | 11/2014 |
| WO | WO 2014/183071 | A2 | 11/2014 |
| WO | WO 2014/184143 | A1 | 11/2014 |
| WO | WO 2014/184741 | A1 | 11/2014 |
| WO | WO 2014/184744 | A1 | 11/2014 |
| WO | WO 2014/186585 | A2 | 11/2014 |
| WO | WO 2014/186686 | A2 | 11/2014 |
| WO | WO 2014/190181 | A1 | 11/2014 |
| WO | WO 2014/191128 | A1 | 12/2014 |
| WO | WO 2014/191518 | A1 | 12/2014 |
| WO | WO 2014/191521 | A2 | 12/2014 |
| WO | WO 2014/191525 | A1 | 12/2014 |
| WO | WO 2014/191527 | A1 | 12/2014 |
| WO | WO 2014/194190 | A1 | 12/2014 |
| WO | WO 2014/197568 | A2 | 12/2014 |
| WO | WO 2014/197748 | A2 | 12/2014 |
| WO | WO 2014/199358 | A1 | 12/2014 |
| WO | WO 2014/200659 | A1 | 12/2014 |
| WO | WO 2014/201015 | A2 | 12/2014 |
| WO | WO 2014/204578 | A1 | 12/2014 |
| WO | WO 2014/204723 | A1 | 12/2014 |
| WO | WO 2014/204724 | A1 | 12/2014 |
| WO | WO 2014/204725 | A1 | 12/2014 |
| WO | WO 2014/204726 | A1 | 12/2014 |
| WO | WO 2014/204727 | A1 | 12/2014 |
| WO | WO 2014/204728 | A1 | 12/2014 |
| WO | WO 2014/204729 | A1 | 12/2014 |
| WO | WO 2015/002780 | A1 | 1/2015 |
| WO | WO 2015/004241 | A2 | 1/2015 |
| WO | WO 2015/006290 | A1 | 1/2015 |
| WO | WO 2015/006294 | A2 | 1/2015 |
| WO | WO 2015/006498 | A2 | 1/2015 |
| WO | WO 2015/006747 | A2 | 1/2015 |
| WO | WO 2015/010114 | A1 | 1/2015 |
| WO | WO 2015/013583 | A2 | 1/2015 |
| WO | WO 2015/017866 | A1 | 2/2015 |
| WO | WO 2015/018503 | A1 | 2/2015 |
| WO | WO 2015/021353 | A1 | 2/2015 |
| WO | WO 2015/021426 | A1 | 2/2015 |
| WO | WO 2015/021990 | A1 | 2/2015 |
| WO | WO 2015/024017 | A2 | 2/2015 |
| WO | WO 2015/026883 | A1 | 2/2015 |
| WO | WO 2015/026885 | A1 | 2/2015 |
| WO | WO 2015/026886 | A1 | 2/2015 |
| WO | WO 2015/026887 | A1 | 2/2015 |
| WO | WO 2015/027134 | A1 | 2/2015 |
| WO | WO 2015/030881 | A1 | 3/2015 |
| WO | WO 2015/031619 | A1 | 3/2015 |

(56) References Cited

FOREIGN PATENT DOCUMENTS

| | | | |
|---|---|---|---|
| WO | WO 2015/031775 | A1 | 3/2015 |
| WO | WO 2015/033293 | A1 | 3/2015 |
| WO | WO 2015/034872 | A2 | 3/2015 |
| WO | WO 2015/035136 | A2 | 3/2015 |
| WO | WO 2015/035139 | A2 | 3/2015 |
| WO | WO 2015/035162 | A2 | 3/2015 |
| WO | WO 2015/040075 | A1 | 3/2015 |
| WO | WO 2015/040402 | A1 | 3/2015 |
| WO | WO 2015/048577 | A2 | 4/2015 |
| WO | WO 2015/048690 | A1 | 4/2015 |
| WO | WO 2015/052133 | A1 | 4/2015 |
| WO | WO 2015/052231 | A2 | 4/2015 |
| WO | WO 2015/053995 | A1 | 4/2015 |
| WO | WO 2015/054253 | A1 | 4/2015 |
| WO | WO 2015/057976 | A1 | 4/2015 |
| WO | WO 2015/057980 | A1 | 4/2015 |
| WO | WO 2015/059265 | A1 | 4/2015 |
| WO | WO 2015/065964 | A1 | 5/2015 |
| WO | WO 2015/066119 | A1 | 5/2015 |
| WO | WO 2015/066637 | A1 | 5/2015 |
| WO | WO 2015/070083 | A1 | 5/2015 |
| WO | WO 2015/070193 | A1 | 5/2015 |
| WO | WO 2015/070212 | A1 | 5/2015 |
| WO | WO 2015/071474 | A2 | 5/2015 |
| WO | WO 2015/073683 | A2 | 5/2015 |
| WO | WO 2015/073867 | A1 | 5/2015 |
| WO | WO 2015/073990 | A1 | 5/2015 |
| WO | WO 2015/075056 | A1 | 5/2015 |
| WO | WO 2015/075154 | A2 | 5/2015 |
| WO | WO 2015/075195 | A1 | 5/2015 |
| WO | WO 2015/077058 | A2 | 5/2015 |
| WO | WO 2015/077290 | A2 | 5/2015 |
| WO | WO 2015/077318 | A1 | 5/2015 |
| WO | WO 2015/079056 | A1 | 6/2015 |
| WO | WO 2015/079057 | A2 | 6/2015 |
| WO | WO 2015/086795 | A2 | 6/2015 |
| WO | WO 2015/086798 | A1 | 6/2015 |
| WO | WO 2015/088643 | A1 | 6/2015 |
| WO | WO 2015/089046 | A1 | 6/2015 |
| WO | WO 2015/089077 | A2 | 6/2015 |
| WO | WO 2015/089277 | A1 | 6/2015 |
| WO | WO 2015/089351 | A1 | 6/2015 |
| WO | WO 2015/089354 | A1 | 6/2015 |
| WO | WO 2015/089364 | A1 | 6/2015 |
| WO | WO 2015/089406 | A1 | 6/2015 |
| WO | WO 2015/089419 | A2 | 6/2015 |
| WO | WO 2015/089427 | A1 | 6/2015 |
| WO | WO 2015/089462 | A1 | 6/2015 |
| WO | WO 2015/089465 | A1 | 6/2015 |
| WO | WO 2015/089473 | A1 | 6/2015 |
| WO | WO 2015/089486 | A1 | 6/2015 |
| WO | WO 2015/095804 | A1 | 6/2015 |
| WO | WO 2015/099850 | A1 | 7/2015 |
| WO | WO 2015/100929 | A1 | 7/2015 |
| WO | WO 2015/103153 | A1 | 7/2015 |
| WO | WO 2015/105928 | A1 | 7/2015 |
| WO | WO 2015/108993 | A1 | 7/2015 |
| WO | WO 2015/112790 | A2 | 7/2015 |
| WO | WO 2015/112896 | A2 | 7/2015 |
| WO | WO 2015/113063 | A1 | 7/2015 |
| WO | WO 2015/115903 | A1 | 8/2015 |
| WO | WO 2015/116686 | A1 | 8/2015 |
| WO | WO 2015/116969 | A2 | 8/2015 |
| WO | WO 2015/117041 | A1 | 8/2015 |
| WO | WO 2015/121454 | A1 | 8/2015 |
| WO | WO 2015/122967 | A1 | 8/2015 |
| WO | WO 2015/123339 | A1 | 8/2015 |
| WO | WO 2015/126927 | A2 | 8/2015 |
| WO | WO 2015/127428 | A1 | 8/2015 |
| WO | WO 2015/127439 | A1 | 8/2015 |
| WO | WO 2015/131101 | A1 | 9/2015 |
| WO | WO 2015/134812 | A1 | 9/2015 |
| WO | WO 2015/136001 | A1 | 9/2015 |
| WO | WO 2015/138510 | A1 | 9/2015 |
| WO | WO 2015/138739 | A2 | 9/2015 |
| WO | WO 2015/138855 | A1 | 9/2015 |
| WO | WO 2015/138870 | A2 | 9/2015 |
| WO | WO 2015/139008 | A1 | 9/2015 |
| WO | WO 2015/139139 | A1 | 9/2015 |
| WO | WO 2015/143046 | A2 | 9/2015 |
| WO | WO 2015/148670 | A1 | 10/2015 |
| WO | WO 2015/148680 | A1 | 10/2015 |
| WO | WO 2015/148761 | A1 | 10/2015 |
| WO | WO 2015/148860 | A1 | 10/2015 |
| WO | WO 2015/148863 | A2 | 10/2015 |
| WO | WO 2015/153760 | A2 | 10/2015 |
| WO | WO 2015/153780 | A1 | 10/2015 |
| WO | WO 2015/153789 | A1 | 10/2015 |
| WO | WO 2015/153791 | A1 | 10/2015 |
| WO | WO 2015/153940 | A1 | 10/2015 |
| WO | WO 2015/155341 | A1 | 10/2015 |
| WO | WO 2015/155686 | A2 | 10/2015 |
| WO | WO 2015/157070 | A2 | 10/2015 |
| WO | WO 2015/157534 | A1 | 10/2015 |
| WO | WO 2015/159068 | A1 | 10/2015 |
| WO | WO 2015/159086 | A1 | 10/2015 |
| WO | WO 2015/159087 | A1 | 10/2015 |
| WO | WO 2015/160683 | A1 | 10/2015 |
| WO | WO 2015/161276 | A2 | 10/2015 |
| WO | WO 2015/163733 | A1 | 10/2015 |
| WO | WO 2015/164748 | A1 | 10/2015 |
| WO | WO 2015/166272 | A2 | 11/2015 |
| WO | WO 2015/168125 | A1 | 11/2015 |
| WO | WO 2015/168158 | A1 | 11/2015 |
| WO | WO 2015/168404 | A1 | 11/2015 |
| WO | WO 2015/168547 | A2 | 11/2015 |
| WO | WO 2015/168800 | A1 | 11/2015 |
| WO | WO 2015/171603 | A1 | 11/2015 |
| WO | WO 2015/171894 | A1 | 11/2015 |
| WO | WO 2015/175642 | A2 | 11/2015 |
| WO | WO 2015/179540 | A1 | 11/2015 |
| WO | WO 2015/184259 | A1 | 12/2015 |
| WO | WO 2015/188056 | A1 | 12/2015 |
| WO | WO 2015/188094 | A1 | 12/2015 |
| WO | WO 2015/188109 | A1 | 12/2015 |
| WO | WO 2015/188191 | A1 | 12/2015 |

OTHER PUBLICATIONS

Liu et al., Fast Colorimetric Sensing of Adenosine and Cocaine Based on a General Sensor Design Involving Aptamers and Nanoparticles. Angew Chem. 2006;118(1):96-100.

Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.

Zhang et al., CRISPR/Cas9 for genome editing: progress, implications and challenges. Hum Mol Genet. Sep. 15, 2014;23(R1):R40-6. doi: 10.1093/hmg/ddu125. Epub Mar. 20, 2014.

Invitation to Pay Additional Fees for PCT/US2014/054291, mailed Dec. 18, 2014.

U.S. Appl. No. 61/716,256, filed Oct. 19, 2012, Jinek et al.

U.S. Appl. No. 61/717,324, filed Oct. 23, 2012, Cho et al.

U.S. Appl. No. 61/734,256, filed Dec. 6, 2012, Chen et al.

U.S. Appl. No. 61/758,624, filed Jan. 30, 2013, Chen et al.

U.S. Appl. No. 61/761,046, filed Feb. 5, 2013, Knight et al.

U.S. Appl. No. 61/794,422 filed Mar. 15, 2013, Knight et al.

U.S. Appl. No. 61/803,599, filed Mar. 20, 2013, Kim et al.

U.S. Appl. No. 61/837,481, filed Jun. 20, 2013, Cho et al.

U.S. Appl. No. 14/258,458, filed Apr. 22, 2014, Cong.

International Search Report and Written Opinion for PCT/US2012/047778, mailed May 30, 2013.

International Preliminary Report on Patentability for PCT/US2012/047778, mailed Feb. 6, 2014.

International Search Report for PCT/US2013/032589, mailed Jul. 26, 2013.

Genbank Submission; NIH/NCBI, Accession No. J04623. Kita et al., Apr. 26, 1993. 2 pages.

Genbank Submission; NIH/NCBI, Accession No. NC_002737.1. Ferretti et al., Jun. 27, 2013. 1 page.

Genbank Submission; NIH/NCBI, Accession No. NC_015683.1. Trost et al., Jul. 6, 2013. 1 page.

(56) References Cited

OTHER PUBLICATIONS

Genbank Submission; NIH/NCBI, Accession No. NC_016782.1. Trost et al., Jun. 11, 2013. 1 page.
Genbank Submission; NIH/NCBI, Accession No. NC_016786.1. Trost et al., Aug. 28, 2013. 1 page.
Genbank Submission; NIH/NCBI, Accession No. NC_017053.1. Fittipaldi et al., Jul. 6, 2013. 1 page.
Genbank Submission; NIH/NCBI, Accession No. NC_017317.1. Trost et al., Jun. 11, 2013. 1 page.
Genbank Submission; NIH/NCBI, Accession No. NC_017861.1. Heidelberg et al., Jun. 11, 2013. 1 page.
Genbank Submission; NIH/NCBI, Accession No. NC_018010.1. Lucas et al., Jun. 11, 2013. 2 pages.
Genbank Submission; NIH/NCBI, Accession No. NC_018721.1. Feng et al., Jun. 11, 2013. 1 page.
Genbank Submission; NIH/NCBI, Accession No. NC_021284.1. Ku et al., Jul. 12, 2013. 1 page.
Genbank Submission; NIH/NCBI, Accession No. NC_021314.1. Zhang et al., Jul. 15, 2013. 1 page.
Genbank Submission; NIH/NCBI, Accession No. NC_021846.1. Lo et al., Jul. 22, 2013. 1 page.
Genbank Submission; NIH/NCBI, Accession No. NP_472073.1. Glaser et al., Jun. 27, 2013. 2 pages.
Genbank Submission; NIH/NCBI, Accession No. P42212. Prasher et al., Mar. 19, 2014. 7 pages.
Genbank Submission; NIH/NCBI, Accession No. YP_002342100.1. Bernardini et al., Jun. 10, 2013. 2 pages.
Genbank Submission; NIH/NCBI, Accession No. YP_002344900.1. Gundogdu et al., Mar. 19, 2014. 2 pages.
Genbank Submission; NIH/NCBI, Accession No. YP_820832.1. Makarova et al., Aug. 27, 2013. 2 pages.
UniProt Submission; UniProt, Accession No. P04275. Last modified Jul. 9, 2014, version 107. 29 pages.
UniProt Submission; UniProt, Accession No. P04264. Last modified Jun. 11, 2014, version 6. 15 pages.
UniProt Submission; UniProt, Accession No. P01011. Last modified Jun. 11, 2014, version 2. 15 pages.
Akopian et al., Chimeric recombinases with designed DNA sequence recognition. Proc Natl Acad Sci U S A. Jul. 22, 2003;100(15):8688-91. Epub Jul. 1, 2003.
Arnold et al., Mutants of Tn3 resolvase which do not require accessory binding sites for recombination activity. EMBO J. Mar. 1, 1999;18(5):1407-14.
Barrangou et al., CRISPR provides acquired resistance against viruses in prokaryotes. Science. Mar. 23, 2007;315(5819):1709-12.
Bhagwat, DNA-cytosine deaminases: from antibody maturation to antiviral defense. DNA Repair (Amst). Jan. 5, 2004;3(1):85-9.
Bibikova et al., Stimulation of homologous recombination through targeted cleavage by chimeric nucleases. Mol Cell Biol. Jan. 2001;21(1):289-97.
Brown et al., Serine recombinases as tools for genome engineering. Methods. Apr. 2011;53(4):372-9. doi: 10.1016/j.ymeth.2010.12.031. Epub Dec. 30, 2010.
Burke et al., Activating mutations of Tn3 resolvase marking interfaces important in recombination catalysis and its regulation. Mol Microbiol. Feb. 2004;51(4):937-48.
Carroll et al., Gene targeting in *Drosophila* and Caenorhabditis elegans with zinc-finger nucleases. Methods Mol Biol. 2008;435:63-77. doi: 10.1007/978-1-59745-232-8_5.
Chang et al., Modification of DNA ends can decrease end joining relative to homologous recombination in mammalian cells. Proc Natl Acad Sci U S A. Jul. 1987;84(14):4959-63.
Charpentier et al., Biotechnology: Rewriting a genome. Nature. Mar. 7, 2013;495(7439):50-1. doi: 10.1038/495050a.
Chavez et al., Therapeutic applications of the ΦC31 integrase system. Curr Gene Ther. Oct. 2011;11(5):375-81. Review.
Chelico et al., Biochemical basis of immunological and retroviral responses to DNA-targeted cytosine deamination by activation-induced cytidine deaminase and APOBEC3G. J Biol Chem. Oct. 9, 2009;284(41):27761-5. doi: 10.1074/jbc.R109.052449. Epub Aug. 13, 2009.
Cho et al., Analysis of off-target effects of CRISPR/Cas-derived RNA-guided endonucleases and nickases. Genome Res. Jan. 2014;24(1):132-41. doi: 10.1101/gr.162339.113. Epub Nov. 19, 2013.
Christian et al., Targeting DNA double-strand breaks with TAL effector nucleases. Genetics. Oct. 2010;186(2):757-61. Doi: 10.1534/genetics.110.120717. Epub Jul. 26, 2010.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Cong et al., Multiplex genome engineering using CRISPR/Cas systems. Science. Feb. 15, 2013;339(6121):819-23. doi: 10.1126/science.1231143. Epub Jan. 3, 2013.
Conticello, The AID/APOBEC family of nucleic acid mutators. Genome Biol. 2008;9(6):229. doi: 10.1186/gb-2008-9-6-229. Epub Jun. 17, 2008.
Cradick et al., CRISPR/Cas9 systems targeting β-globin and CCR5 genes have substantial off-target activity. Nucleic Acids Res. Nov. 1, 2013;41(20):9584-92. doi: 10.1093/nar/gkt714. Epub Aug. 11, 2013.
De Souza, Primer: genome editing with engineered nucleases. Nat Methods. Jan. 2012;9(1):27.
Deltcheva et al., CRISPR RNA maturation by trans-encoded small RNA and host factor RNase III. Nature. Mar. 31, 2011;471(7340):602-7. doi: 10.1038/nature09886.
Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.
Fu et al., Improving CRISPR-Cas nuclease specificity using truncated guide RNAs. Nat Biotechnol. Mar. 2014;32(3):279-84. doi: 10.1038/nbt.2808. Epub Jan. 26, 2014.
Fu et al., High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013.
Gaj et al., ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012. Supplementary materials included.
Gasiunas et al., RNA-dependent DNA endonuclease Cas9 of the CRISPR system: Holy Grail of genome editing? Trends Microbiol. Nov. 2013;21(11):562-7. doi: 10.1016/j.tim.2013.09.001. Epub Oct. 1, 2013.
Gerber et al., RNA editing by base deamination: more enzymes, more targets, new mysteries. Trends Biochem Sci. Jun. 2001;26(6):376-84.
Gilbert et al., CRISPR-mediated modular RNA-guided regulation of transcription in eukaryotes. Cell. 2013 154(2):442-51.
Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.
Guilinger et al., Fusion of catalytically inactive Cas9 to Fold nuclease improves the specificity of genome modification. Nat Biotechnol. Jun. 2014;32(6):577-82. doi: 10.1038/nbt.2909. Epub Apr. 25, 2014.
Guo et al., Directed evolution of an enhanced and highly efficient FokI cleavage domain for zinc finger nucleases. J Mol Biol. Jul. 2, 2010;400(1):96-107. doi: 10.1016/j.jmb.2010.04.060. Epub May 4, 2010.
Hale et al., RNA-guided RNA cleavage by a CRISPR RNA-Cas protein complex. Cell. Nov. 25, 2009;139(5):945-56. doi: 10.1016/j.cell.2009.07.040.
Horvath et al., CRISPR/Cas, the immune system of bacteria and archaea. Science. Jan. 8, 2010;327(5962):167-70. doi: 10.1126/science.1179555.

(56) References Cited

OTHER PUBLICATIONS

Hsu et al., DNA targeting specificity of RNA-guided Cas9 nucleases. Nat Biotechnol. Sep. 2013;31(9):827-32. doi: 10.1038/nbt.2647. Epub Jul. 21, 2013.

Humbert et al., Targeted gene therapies: tools, applications, optimization. Crit Rev Biochem Mol Biol. May-Jun. 2012;47(3):264-81. doi: 10.3109/10409238.2012.658112.

Hurt et al., Highly specific zinc finger proteins obtained by directed domain shuffling and cell-based selection. Proc Natl Acad Sci U S A. Oct. 14, 2003;100(21):12271-6. Epub Oct. 3, 2003.

Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.

Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.

Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.

Jinek et al., RNA-programmed genome editing in human cells. Elife. Jan. 29, 2013;2:e00471. doi: 10.7554/eLife.00471.

Jinek et al., Structures of Cas9 endonucleases reveal RNA-mediated conformational activation. Science. Mar. 14, 2014;343(6176):1247997. doi: 10.1126/science.1247997. Epub Feb. 6, 2014.

Jore et al., Structural basis for CRISPR RNA-guided DNA recognition by Cascade. Nat Struct Mol Biol. May 2011;18(5):529-36. doi: 10.1038/nsmb.2019. Epub Apr. 3, 2011.

Kim et al., Highly efficient RNA-guided genome editing in human cells via delivery of purified Cas9 ribonucleoproteins. Genome Res. Jun. 2014;24(6):1012-9. doi: 10.1101/gr.171322.113. Epub Apr. 2, 2014.

Kim et al., Hybrid restriction enzymes: zinc finger fusions to Fok I cleavage domain. Proc Natl Acad Sci U S A. Feb. 6, 1996;93(3):1156-60.

Kim et al., TALENs and ZFNs are associated with different mutationsignatures. Nat Methods. Mar. 2013;10(3):185. doi: 10.1038/nmeth.2364. Epub Feb. 10, 2013.

Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.

Li et al., TAL nucleases (TALNs): hybrid proteins composed of TAL effectors and FokI DNA-cleavage domain. Nucleic Acids Res. Jan. 2011;39(1):359-72. doi: 10.1093/nar/gkq704. Epub Aug. 10, 2010.

Maeder et al., CRISPR RNA-guided activation of endogenous human genes. Nat Methods. Oct. 2013;10(10):977-9. doi: 10.1038/nmeth.2598. Epub Jul. 25, 2013.

Mali et al., Cas9 as a versatile tool for engineeringbiology. Nat Methods. Oct. 2013;10(10):957-63. doi: 10.1038/nmeth.2649.

Mali et al., CAS9 transcriptional activators for target specificity screening and paired nickases for cooperative genome engineering. Nat Biotechnol. Sep. 2013;31(9):833-8. doi: 10.1038/nbt.2675. Epub Aug. 1, 2013.

Mali et al., RNA-guided human genome engineering via Cas9. Science. Feb. 15, 2013;339(6121):823-6. doi: 10.1126/science.1232033. Epub Jan. 3, 2013.

Miller et al., A TALE nuclease architecture for efficient genome editing. Nat Biotechnol. Feb. 2011;29(2):143-8. doi:10.1038/nbt.1755. Epub Dec. 22, 2010.

Narayanan et al., Clamping down on weak terminal base pairs: oligonucleotides with molecular caps as fidelity-enhancing elements at the 5'- and 3'-terminal residues. Nucleic Acids Res. May 20, 2004;32(9):2901-11. Print 2004.

Navaratnam et al., An overview of cytidine deaminases. Int J Hematol. Apr. 2006;83(3):195-200.

Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.

O'Connell et al., Programmable RNA recognition and cleavage by CRISPR/Cas9. Nature. Sep. 28, 2014. doi: 10.1038/nature13769. [Epub ahead of print].

Pan et al., Biological and biomedical applications of engineered nucleases. Mol Biotechnol. Sep. 2013;55(1):54-62. doi: 10.1007/s12033-012-9613-9.

Pattanayak et al., High-throughput profiling of off-target DNA cleavage reveals RNA-programmed Cas9 nuclease specificity. Nat Biotechnol. Sep. 2013;31(9):839-43. doi: 10.1038/nbt.2673. Epub Aug. 11, 2013.

Pattanayak et al., Revealing off-target cleavage specificities of zinc-finger nucleases by in vitro selection. Nat Methods. Aug. 7, 2011;8(9):765-70. doi: 10.1038/nmeth.1670.

Pennisi et al., The CRISPR craze. Science. Aug. 23, 2013;341(6148):833-6. doi: 10.1126/science.341.6148.833.

Perez-Pinera et al., Advances in targeted genome editing. Curr Opin Chem Biol. Aug. 2012;16(3-4):268-77. doi: 10.1016/j.cbpa.2012.06.007. Epub Jul. 20, 2012.

Perez-Pinera et al., RNA-guided gene activation by CRISPR-Cas9-based transcription factors. Nat Methods. Oct. 2013;10(10):973-6. doi: 10.1038/nmeth.2600. Epub Jul. 25, 2013.

Pham et al., Reward versus risk: DNA cytidine deaminases triggering immunity and disease. Biochemistry. Mar. 1, 2005;44(8):2703-15.

Porteus, Design and testing of zinc finger nucleases for use in mammalian cells. Methods Mol Biol. 2008;435:47-61. doi: 10.1007/978-1-59745-232-8_4.

Qi et al., Repurposing CRISPR as an RNA-guided platform for sequence-specific control of gene expression. Cell. Feb. 28, 2013;152(5):1173-83. doi: 10.1016/j.ce11.2013.02.022.

Ran et al., Double nicking by RNA-guided CRISPR Cas9 for enhanced genome editing specificity. Cell. Sep. 12, 2013;154(6):1380-9. doi: 10.1016/j.cell.2013.08.021. Epub Aug. 29, 2013.

Reynaud et al., What role for AID: mutator, or assembler of the immunoglobulin mutasome? Nat Immunol. Jul. 2003;4(7):631-8.

Reyon et al., FLASH assembly of TALENs for high-throughput genome editing. Nat Biotechnol. May 2012;30(5):460-5. doi: 10.1038/nbt.2170.

Sander et al., CRISPR-Cas systems for editing, regulating and targeting genomes. Nat Biotechnol. Apr. 2014;32(4):347-55. doi: 10.1038/nbt.2842. Epub Mar. 2, 2014.

Sapranauskas et al., The *Streptococcus thermophilus* CRISPR/Cas system provides immunity in *Escherichia coli.* Nucleic Acids Res. Nov. 2011;39(21):9275-82. doi: 10.1093/nar/gkr606. Epub Aug. 3, 2011.

Sashital et al., Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.

Schriefer et al., Low pressure DNA shearing: a method for random DNA sequence analysis. Nucleic Acids Res. Dec. 25, 1990;18(24):7455-6.

Schwank et al., Functional repair of CFTR by CRISPR/Cas9 in intestinal stem cell organoids of cystic fibrosis patients. Cell Stem Cell. Dec. 5, 2013;13(6):653-8. doi:10.1016/j.stem.2013.11.002.

Semenova et al., Interference by clustered regularly interspaced short palindromic repeat (CRISPR) RNA is governed by a seed sequence. Proc Natl Acad Sci U S A. Jun. 21, 2011;108(25):10098-103. doi: 10.1073/pnas.1104144108. Epub Jun. 6, 2011.

Shalem et al., Genome-scale CRISPR-Cas9 knockout screening in human cells. Science. Jan. 3, 2014;343(6166):84-7. doi: 10.1126/science.1247005. Epub Dec. 12, 2013.

Sheridan, First CRISPR-Cas patent opens race to stake out intellectual property. Nat Biotechnol. 2014;32(7):599-601.

Siebert et al., An improved PCR method for walking in uncloned genomic DNA. Nucleic Acids Res. Mar. 25, 1995;23(6):1087-8.

Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.

Vanamee et al., FokI requires two specific DNA sites for cleavage. J Mol Biol. May 25, 2001;309(1):69-78.

Wah et al., Structure of FokI has implications for DNA cleavage. Proc Natl Acad Sci U S A. Sep. 1, 1998;95(18):10564-9.

(56) References Cited

OTHER PUBLICATIONS

Wang et al., Genetic screens in human cells using the CRISPR-Cas9 system. Science. Jan. 3, 2014;343(6166):80-4. doi: 10.1126/science.1246981. Epub Dec. 12, 2013.
Wang et al., One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.
Wiedenheft et al., RNA-guided genetic silencing systems in bacteria and archaea. Nature. Feb. 15, 2012;482(7385):331-8. doi: 10.1038/nature10886. Review.
Wood et al., Targeted genome editing across species using ZFNs and TALENs. Science. Jul. 15, 2011;333(6040):307. doi: 10.1126/science.1207773. Epub Jun. 23, 2011.
Wu et al., Correction of a genetic disease in mouse via use of CRISPR-Cas9. Cell Stem Cell. Dec. 5, 2013;13(6):659-62. doi: 10.1016/j.stem.2013.10.016.
Yin et al., Genome editing with Cas9 in adult mice corrects a disease mutation and phenotype. Nat Biotechnol. Jun. 2014;32(6):551-3. doi: 10.1038/nbt.2884. Epub Mar. 30, 2014.
Partial Supplementary European Search Report for Application No. EP 12845790.0, mailed Mar. 18, 2015.
International Search Report and Written Opinion for PCT/US2014/052231, mailed Jan. 30, 2015 (Corrected Version).
International Search Report and Written Opinion for PCT/US2014/054247, mailed Mar. 27, 2015.
International Search Report and Written Opinion for PCT/US2014/054291, mailed Mar. 27, 2015.
International Search Report and Written Opinion for PCT/US2014/054252, mailed Mar. 5, 2015.
International Search Report and Written Opinion for PCT/US2014/070038, mailed Apr. 14, 2015.
Boeckle et al., Melittin analogs with high lytic activity at endosomal pH enhance transfection with purified targeted PEI polyplexes. J Control Release. May 15, 2006;112(2):240-8. Epub Mar. 20, 2006.
Branden and Tooze, Introduction to Protein Structure. 1999; 2nd edition. Garland Science Publisher: 3-12.
Cameron, Recent advances in transgenic technology. Mol Biotechnol. Jun. 1997;7(3):253-65.
Caron et al., Intracellular delivery of a Tat-eGFP fusion protein into muscle cells. Mol Ther. Mar. 2001;3(3):310-8.
Chung-Il et al., Artificial control of gene expression in mammalian cells by modulating RNA interference through aptamer-small molecule interaction. RNA. May 2006;12(5):710-6. Epub Apr. 10, 2006.
Cradick et al., ZFN-site searches genomes for zinc finger nuclease target sites and off-target sites. BMC Bioinformatics. May 13, 2011;12:152. doi: 10.1186/1471-2105-12-152.
Gilleron et al., Image-based analysis of lipid nanoparticle-mediated siRNA delivery, intracellular trafficking and endosomal escape. Nat Biotechnol. Jul. 2013;31(7):638-46. doi: 10.1038/nbt.2612. Epub Jun. 23, 2013.
Guo et al., Protein tolerance to random amino acid change. J Gene Med. Mar.-Apr. 2002;4(2):195-204.
Hasadsri et al., Functional protein delivery into neurons using polymeric nanoparticles. J Biol Chem. Mar. 13, 2009;284(11):6972-81. doi: 10.1074/jbc.M805956200. Epub Jan. 7, 2009.
Hill et al., Functional analysis of conserved histidines in ADP-glucose pyrophosphorylase from *Escherichia coli*.Biochem Biophys Res Commun. Mar. 17, 1998;244(2):573-7.
Houdebine, The methods to generate transgenic animals and to control transgene expression. J Biotechnol. Sep. 25, 2002;98(2-3):145-60.
Kappel et al., Regulating gene expression in transgenic animals.Curr Opin Biotechnol. Oct. 1992;3(5):548-53.
Klauser et al., An engineered small RNA-mediated genetic switch based on a ribozyme expression platform. Nucleic Acids Res. May 1, 2013;41(10):5542-52. doi: 10.1093/nar/gkt253. Epub Apr. 12, 2013.
Lazar et al., Transforming growth factor alpha: mutation of aspartic acid 47 and leucine 48 results in different biological activities. Mol Cell Biol. Mar. 1988;8(3):1247-52.
Lewis et al., A serum-resistant cytofectin for cellular delivery of antisense oligodeoxynucleotides and plasmid DNA. Proc Natl Acad Sci U S A. Apr. 16, 1996;93(8):3176-81.
Lundberg et al., Delivery of short interfering RNA using endosomolytic cell-penetrating peptides. FASEB J. Sep. 2007;21(11):2664-71. Epub Apr. 26, 2007.
Mullins et al., Transgenesis in nonmurine species. Hypertension. Oct. 1993;22(4):630-3.
Nomura et al., Synthetic mammalian riboswitches based on guanine aptazyme. Chem Commun (Camb). Jul. 21, 2012;48(57):7215-7. doi: 10.1039/c2cc33140c. Epub Jun. 13, 2012.
Pattanayak et al., Determining the specificities of TALENs, Cas9, and other genome-editing enzymes. Methods Enzymol. 2014;546:47-78. doi: 10.1016/B978-0-12-801185-0.00003-9.
Phillips, The challenge of gene therapy and DNA delivery. J Pharm Pharmacol. Sep. 2001;53(9):1169-74.
Qi et al., Engineering naturally occurring trans-acting non-coding RNAs to sense molecular signals. Nucleic Acids Res. Jul. 2012;40(12):5775-86. doi: 10.1093/nar/gks168. Epub Mar. 1, 2012.
Ramakrishna et al., Gene disruption by cell-penetrating peptide-mediated delivery of Cas9 protein and guide RNA. Genome Res. Jun. 2014;24(6):1020-7. doi: 10.1101/gr.171264.113. Epub Apr. 2, 2014.
Samal et al., Cationic polymers and their therapeutic potential. Chem Soc Rev. Nov. 7, 2012;41(21):7147-94. doi: 10.1039/c2cs35094g. Epub Aug. 10, 2012.
Sang, Prospects for transgenesis in the chick. Mech Dev. Sep. 2004;121(9):1179-86.
Schwarze et al., In vivo protein transduction: delivery of a biologically active protein into the mouse. Science. Sep. 3, 1999;285(5433):1569-72.
Sells et al., Delivery of protein into cells using polycationic liposomes. Biotechniques. Jul. 1995;19(1):72-6, 78.
Thorpe et al., Functional correction of episomal mutations with short DNA fragments and RNA-DNA oligonucleotides. J Gene Med. Mar.-Apr. 2002;4(2):195-204.
Wacey et al., Disentangling the perturbational effects of amino acid substitutions in the DNA-binding domain of p53. Hum Genet. Jan. 1999;104(1):15-22.
Wadia et al., Modulation of cellular function by TAT mediated transduction of full length proteins. Curr Protein Pept Sci. Apr. 2003;4(2):97-104.
Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.
Supplementary European Search Report for Application No. EP 12845790.0, mailed Oct. 12, 2015.
No Author Listed, EMBL Accession No. Q99ZW2. Nov. 2012. 2 pages.
No Author Listed, Invitrogen Lipofectamine™ 2000 product sheets, 2002. 2 pages.
No Author Listed, Invitrogen Lipofectamine™ 2000 product sheets, 2005. 3 pages.
No Author Listed, Invitrogen Lipofectamine™ LTX product sheets, 2011. 4 pages.
No Author Listed, Thermo Fisher Scientific—How Cationic Lipid Mediated Transfection Works, retrieved from the internet Aug. 27, 2015. 2 pages.
UniProt Submission; UniProt, Accession No. P01011. Last modified Sep. 18, 2013, version 2. 15 pages.
Alexandrov et al., Signatures of mutational processes in human cancer. Nature. Aug. 22, 2013;500(7463):415-21. doi: 10.1038/nature12477. Epub Aug. 14, 2013 .
Li et al., Current approaches for engineering proteins with diverse biological properties. Adv Exp Med Biol. 2007;620:18-33.

* cited by examiner orientation A:

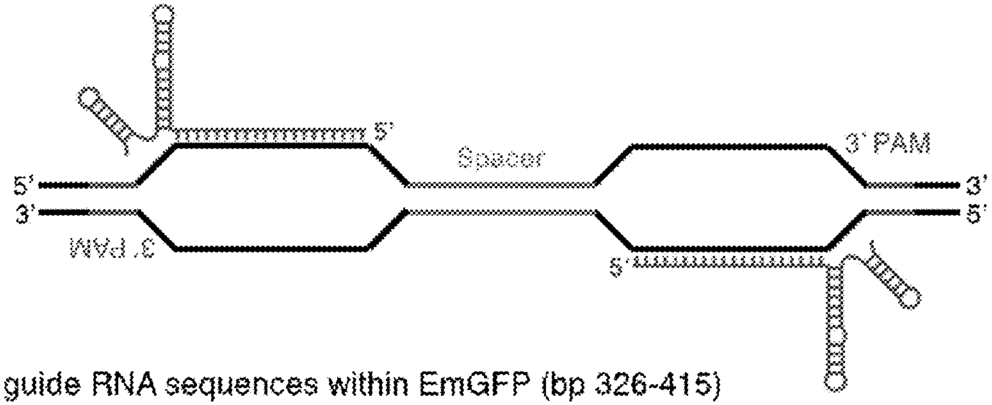

guide RNA spacer length (bp)

| | G4 | G5 | G6 | G7 |
|---|---|---|---|---|
| G1 | 10 | 25 | 32 | 43 |
| G2 | 5 | 20 | | |
| G3 | | | | 14 |

guide RNA sequences within EmGFP (bp 326-415)

5'-CCGCGCCGAGGTGAAGTTCGAGGGCGACACCCTGGTGAACCGCATCGAGCTGAAGGGCATCGACTTCAAGGAGGACGGCAACATCCTGG-3'

G1 CCGCGCCGAGGTGAAGTTCGAGG

G2 CCGAGGTGAAGTTCGAGGGCGAC

G3 CCCTGGTGAACCGCATCGAGCTG

G4 GGTGAACCGCATCGAGCTGAAGG

G5 GCTGAAGGGCATCGACTTCAAGG

G6 GGCATCGACTTCAAGGAGGACGG

G7 CAAGGAGGACGGCAACATCCTGG

FIG. 6C orientation B:

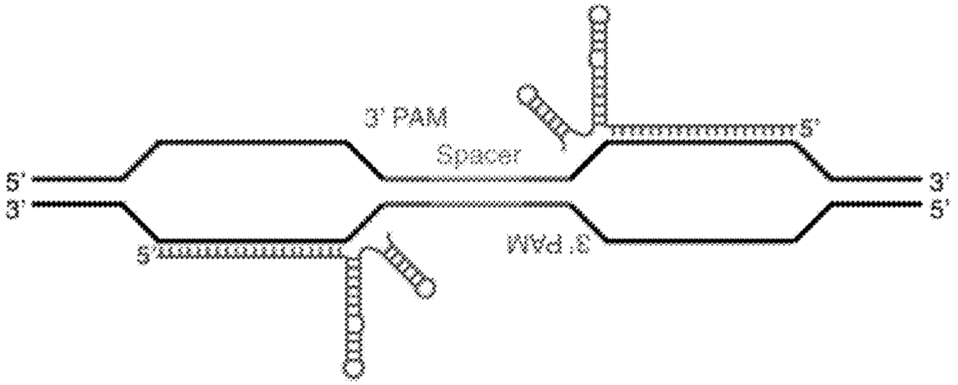

guide RNA spacer length (bp)

| | G12 | G13 | G14 |
|---|---|---|---|
| G8 | 11 | 42 | |
| G9 | | 19 | 28 |
| G10 | | | 16 |
| G11 | | | 4 |

guide RNA sequences within EmGFP (bp 297-388)

5'-GGAGCGCACCATCTTCTTCAAGGACGACGGCAACTACAAGACCCGCGCCGAGGTGAAGTTCGAGGGCGACACCCTGGTGAACCGCATCGAGCTGAAGGGCATCG-3'

G8 ACCATCTTCTTCAAGGACGACGG
G9 CAACTACAAGACCCGCGCCGAGG
G10 CCGCGCCGAGGTGAAGTTCGAGG
G11 GAAGTTCGAGGGCGACACCCTGG
G12 CCCGCGCCGAGGTGAAGTTCGAG
G13 CCTGGTGAACCGCATCGAGCTGA
G14 CCGCATCGAGCTGAAGGGCATCG

FIG. 9

| name | NLS-**linker**-Fok1 | Fok1-**linker**-dCas9 |
|---|---|---|
| *Fok*I-(GGS)x3 | GGS | GGSGGSGGS |
| *Fok*I-(GGS)x6 | GGS | GGSGGSGGSGGSGGSGGS |
| *Fok*I-L0 | GGS | - |
| *Fok*I-L1 | GGS | MKIIEQLPSA |
| *Fok*I-L2 | GGS | VRHKLKRVGS |
| *Fok*I-L3 | GGS | VPFLLEPDNINGKTC |
| *Fok*I-L4 | GGS | GHGTGSTGSGSS |
| *Fok*I-L5 | GGS | MSRPDPA |
| *Fok*I-L6 | GGS | GSAGSAAGSGEF |
| *Fok*I-L7 | GGS | SGSETPGTSESA |
| *Fok*I-L8 | GGS | SGSETPGTSESATPES |
| *Fok*I-L9 | GGS | SGSETPGTSESATPEGGSGGS |
| NLS-(GGS) | GGS | GGSM |
| NLS-(GGS)x3 | GGSGGSGGS | GGSM |
| NLS-L1 | VPFLLEPDNINGKTC | GGSM |
| NLS-L2 | GSAGSAAGSGEF | GGSM |
| NLS-L3 | SIVAQLSRPDPA | GGSM |
| wild-type Cas9 | N/A | N/A |
| Cas9 nickase | N/A | N/A |

FIG. 12A

| | |
|---|---|
| | Spacer (bp) |
| CLTA-1 | |
| CCCCAAGTCTAGCAAGCAGGCCAAAGATGTCTCCCGCATGCGCTCAGTCCTCATCTCCCTCAAGCAGG | |
| CCCCAAGTCTAGCAAGCAGGCCA (C1) AGTCCTCATCTCCCTCAAGCAGG (C2) | 22 |
| CLTA-2 | |
| CCCTGTGGAAACACTACATCTGCAATATCTTAATCCTACTCAGTGAAGCTCTTCACAGTCATTGG | |
| CCCTGTGGAAACACTACATCTGC (C3) GTGAAGCTCTTCACAGTCATTGG (C4) | 19 |

```
HBC
CCGTTACTGCCCTGTGGGGCAAGGTGAACGTGGATGAAGTTGGTGGTGAGGCCCTGGGCAGGTTGGTATCAAGGTTACAAGACAGGTTTAAGG
CCGTTACTGCCCTGTGGGGCAAG(H1) CGTGGATGAAGTTGGTGGTGGG (H2)                                      5
                                 TGAAGTTGGTGGTGAGGCCCTGG (H3)                                11
                                      TTGGTGGTGAGGCCCTGGGCAGG (H4)                           16
                                          TGGTGAGGCCCTGGGCAGGTTGG (H5)                       20
                                                  CCCTGGGCAGGTTGGTATCAAGG (H6)               28
                                                                   AAGGTTACAAGACAGGTTTAAGG (H7) 47

EMX
CCCTTCTTCTTCTGCTCGGACTCAGGCCCTTCCTCCTCCAGCTTCTGCCGTTTGTACTTTGTCCTCCGGTTCTGG
CCCTTCTTCTTCTGCTCGGACTC (E1)                  GCCGTTTGTACTTTGTCCTCCGG (E2)                    23
                                                    TGTACTTTGTCCTCCGGTTCTGG (E3)              29

VEGF
CCAGGAGCAAACTCCCCCCACCCCCTTTCCAAAGCCCATTCCCTCTTTAGCCAGAGCCGGGGTGTGCAGACGG
CCAGGAGCAAACTCCCCCCACCC (V1)        ATTCCCTCTTTAGCCAGAGCCGG (V2)                              14
                                      TCCCTCTTTAGCCAGAGCCGGGG (V3)                            16
                                                 CCAGAGCCGGGGTGTGCAGACGG (V4)                 27
```

FIG. 13 (continued)

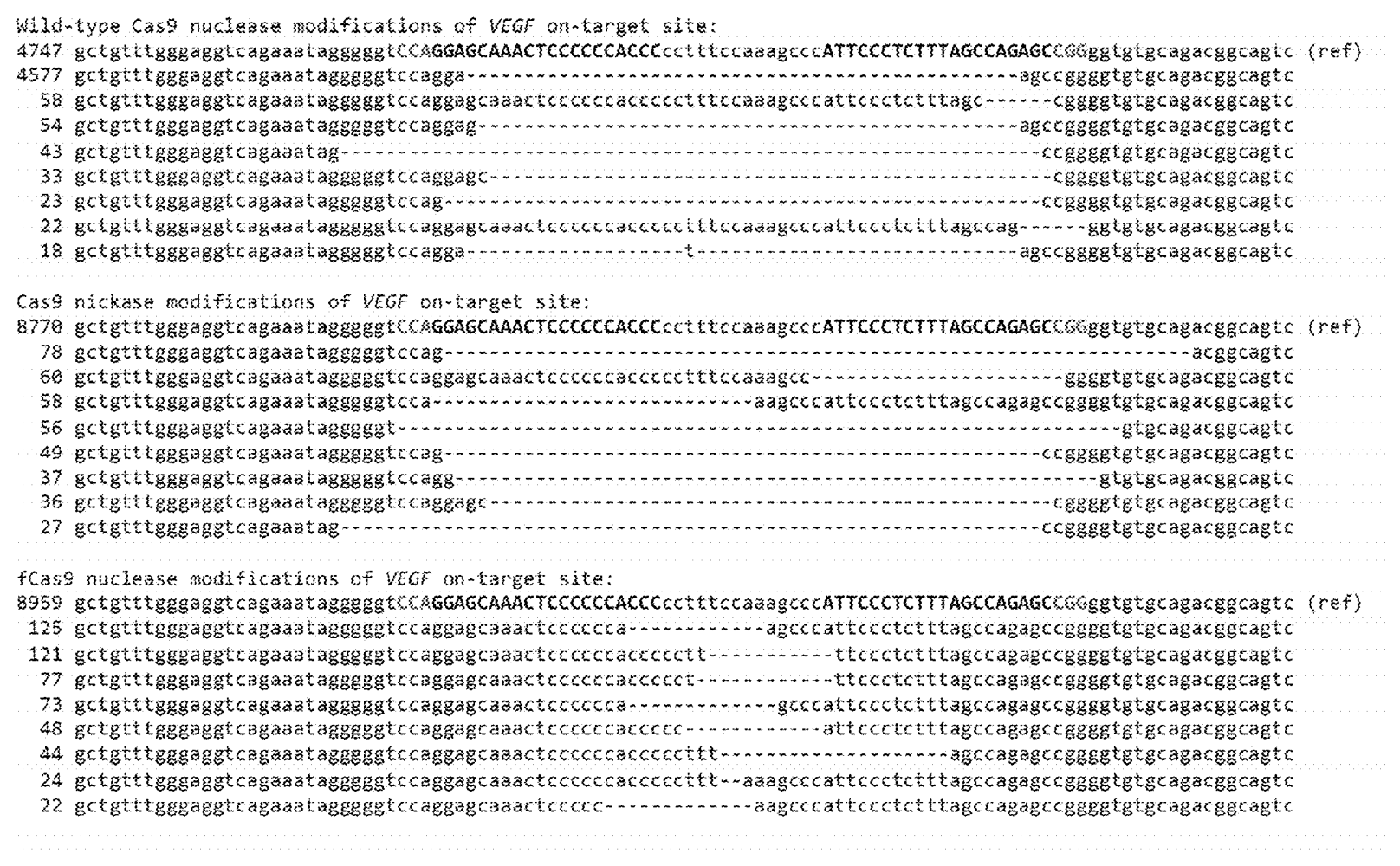

Wild-type Cas9 nuclease modifications of *VEGF* on-target site:

4747 gctgtttgggaggtcagaaatagggggtCCAGGAGCAAACTCCCCCCACCCcctttccaaagcccATTCCCTCTTTAGCCAGAGCCGGggtgtgcagacggcagtc (ref)
4577 gctgtttgggaggtcagaaatagggggtccagga------------------------------------------------agccggggtgtgcagacggcagtc
58 gctgtttgggaggtcagaaatagggggtccaggagcaaactccccccacccccctttccaaagcccattccctctttagc------cggggtgtgcagacggcagtc
54 gctgtttgggaggtcagaaatagggggtccaggag----------------------------------------------agccggggtgtgcagacggcagtc
43 gctgtttgggaggtcagaaatag-------------------------------------------------------------ccggggtgtgcagacggcagtc
33 gctgtttgggaggtcagaaatagggggtccaggagc------------------------------------------------cggggtgtgcagacggcagtc
23 gctgtttgggaggtcagaaatagggggtccag----------------------------------------------------ccggggtgtgcagacggcagtc
22 gctgtttgggaggtcagaaatagggggtccaggagcaaactccccccacccccctttccaaagcccattccctctttagccag------ggtgtgcagacggcagtc
18 gctgtttgggaggtcagaaatagggggtccagga-------------------t----------------------------agccggggtgtgcagacggcagtc Cas9 nickase modifications of *VEGF* on-target site:

8770 gctgtttgggaggtcagaaatagggggtCCAGGAGCAAACTCCCCCCACCCcctttccaaagcccATTCCCTCTTTAGCCAGAGCCGGggtgtgcagacggcagtc (ref)
78 gctgtttgggaggtcagaaatagggggtccag-----------------------------------------------------------------acggcagtc
60 gctgtttgggaggtcagaaatagggggtccaggagcaaactccccccacccccctttccaaagcc-----------------------ggggtgtgcagacggcagtc
58 gctgtttgggaggtcagaaatagggggtcca----------------------------aagcccattccctctttagccagagccggggtgtgcagacggcagtc
56 gctgtttgggaggtcagaaatagggggt---------------------------------------------------------------gtgcagacggcagtc
49 gctgtttgggaggtcagaaatagggggtccag----------------------------------------------------ccggggtgtgcagacggcagtc
37 gctgtttgggaggtcagaaatagggggtccagg--------------------------------------------------------gtgtgcagacggcagtc
36 gctgtttgggaggtcagaaatagggggtccaggagc------------------------------------------------cggggtgtgcagacggcagtc
27 gctgtttgggaggtcagaaatag-------------------------------------------------------------ccggggtgtgcagacggcagtc fCas9 nuclease modifications of *VEGF* on-target site:

8959 gctgtttgggaggtcagaaatagggggtCCAGGAGCAAACTCCCCCCACCCcctttccaaagcccATTCCCTCTTTAGCCAGAGCCGGggtgtgcagacggcagtc (ref)
125 gctgtttgggaggtcagaaatagggggtccaggagcaaactcccccca------------agcccattccctctttagccagagccggggtgtgcagacggcagtc
121 gctgtttgggaggtcagaaatagggggtccaggagcaaactccccccacccccctt-----------ttccctctttagccagagccggggtgtgcagacggcagtc
77 gctgtttgggaggtcagaaatagggggtccaggagcaaactccccccacccccct------------ttccctctttagccagagccggggtgtgcagacggcagtc
73 gctgtttgggaggtcagaaatagggggtccaggagcaaactcccccca--------------gcccattccctctttagccagagccggggtgtgcagacggcagtc
48 gctgtttgggaggtcagaaatagggggtccaggagcaaactccccccacccccc------------attccctctttagccagagccggggtgtgcagacggcagtc
44 gctgtttgggaggtcagaaatagggggtccaggagcaaactccccccacccccctttt--------------------agccagagccggggtgtgcagacggcagtc
24 gctgtttgggaggtcagaaatagggggtccaggagcaaactccccccacccccctttt--aaagcccattccctctttagccagagccggggtgtgcagacggcagtc
22 gctgtttgggaggtcagaaatagggggtccaggagcaaactccccc-------------aagcccattccctctttagccagagccggggtgtgcagacggcagtc

FIG. 18A

Wild-type Cas9 nuclease modifications of VEG_Off1:
79248 cattcaacagatacttactgaatgctaatgtctcagacaggacattctgacaccCCAGGAGCAAACTCCCtCCAtCCCacaaatccgtccttagatgtgcacacccaacctcctaagaaatagaaggatgat (ref)
800 cattcaacagatacttactgaatgctaatgtctcagacaggacattctgacaccccagg--caaactccctccatcccacaaatccgtccttagatgtgcacacccaacctcctaagaaatagaaggatgat
239 cattcaacagatacttactgaatgctaatgtctcagacaggacattctgacacccca-----------------tcccacaaatccgtccttagatgtgcacacccaacctcctaagaaatagaaggatgat
155 cattcaacagatacttactgaatgctaatgtctcagacaggacattctgacaccccag---caaactccctccatcccacaaatccgtccttagatgtgcacacccaacctcctaagaaatagaaggatgat
90 cattcaacagatacttactgaatgctaatgtctcagacaggacattctgacacccca----------------------caaatccgtccttagatgtgcacacccaacctcctaagaaatagaaggatgat
71 cattcaacagatacttactgaatgctaatgtctcagacaggacattctgacac-------------tccctccatcccacaaatccgtccttagatgtgcacacccaacctcctaagaaatagaaggatgat
54 cattcaacagatacttactgaatgctaatgtctcagacaggacattctgacacccc--------------tccatcccacaaatccgtccttagatgtgcacacccaacctcctaagaaatagaaggatgat
53 cattcaacagatacttactgaatgctaatgtctcagacaggacattctgacaccccagga--------------------------------------------------------------------tgat
47 cattcaacagatacttactgaatgctaatgtctcagacaggacattctgac---------------tccctccatcccacaaatccgtccttagatgtgcacacccaacctcctaagaaatagaaggatgat Cas9 nickase modifications of VEG_Off1:
302573 cattcaacagatacttactgaatgctaatgtctcagacaggacattctgacaccCCAGGAGCAAACTCCCtCCAtCCCacaaatccgtccttagatgtgcacacccaacctcctaagaaatagaaggatgat (ref)
28 cattcaacagatacttactgaatgctaatgtctcagacaggacattctgacaccccagga-----c----------------atccgtccttagatgtgcacacccaacctcctaagaaatagaaggatgat
13 cattcaacagatacttactgaatgctaatgtctcagacaggacattctgac---------------tccctccatcccacaaatccgtccttagatgtgcacacccaacctcctaagaaatagaaggatgat
11 cattcaacagatacttactgaatgctaatgtctcagacaggacattctga---------------------------------tccgtccttagatgtgcacacccaacctcctaagaaatagaaggatgat
4 cattcaacagatacttactgaatgctaatgtctcagacaggacattctgacaccccagg--ca---tc--tg-atg--acaaatccgtccttagatgtgcacacccaacctcctaagaaatagaaggatgat
2 cattcaacagatacttactgaatgctaatgtctcagacaggacattctgacaccccaggagcaaactccctccatcccacaaatccgtccttagatgtgca-cccaacctcctaagaaatagaaggatgat
1 cattcaacagatacttactgaatgctaatgtctcagacaggacattctgacaccccaggagcaaactccctccatcccacaaatccgtcctt--atgtgcacacccaacctcctaagaaatagaaggatgat
1 cattcaacagatacttactgaatgctaatgtctcagacaggacattctgacaccccagga-----------------------------------tgtgcacacccaacctcctaagaaatagaaggatgat
1 cattcaacagatacttactgaatgctaatgtctcagacaggacattctga-------------------------------aatccgtccttagatgtgcacacccaacctcctaagaaatagaaggatgat fCas9 nuclease modifications of VEG_Off1:
233567 cattcaacagatacttactgaatgctaatgtctcagacaggacattctgacaccCCAGGAGCAAACTCCCtCCAtCCCacaaatccgtccttagatgtgcacacccaacctcctaagaaatagaaggatgat (ref)
6 cattcaacagatacttactgaatgctaatgtctcagacaggacattctgacaccccaggagcaaactccctcc-------------gtccttagatgtgcacacccaacctcctaagaaatagaaggatgat
5 cattcaacagatacttactgaatgctaatgtctcagacaggacattctgacaccccaggagcaaactccctc-----------tccgtccttagatgtgcacacccaacctcctaagaaatagaaggatgat
4 cattcaacagatacttactgaatgctaatgtctcagacaggacattctgacaccccaggagcaaactccctccat--------tccgtccttagatgtgcacacccaacctcctaagaaatagaaggatgat
3 cattcaacagatacttactgaatgctaatgtctcagacaggacattctgacaccccaggagcaaactccctccatcccacaaatccgtccttagatgtgca--cccaacctcctaagaaatagaaggatgat
3 cattcaacagatacttactgaatgctaatgtctcagacaggacattctgacaccccaggagcaaactccctcc----------tccgtccttagatgtgcacacccaacctcctaagaaatagaaggatgat
2 cattcaacagatacttactgaatgctaatgtctcagacaggacattctgacaccccaggagcaaactccctcc---------atccgtccttagatgtgcacacccaacctcctaagaaatagaaggatgat
1 cattcaacagatacttactgaatgctaatgtctcagacaggacattctgacaccccaggagcaaactccctccatcccacaaatccgtccttagatgtgcacaccc----tcctaagaaatagaaggatgat
1 cattcaacagatacttactgaatgctaatgtctcagacaggacattctgacaccccaggagcaaactccctccatcccacaaatccgtcc--agatgtgcacacccaacctcctaagaaatagaaggatgat

FIG. 18B

CRA
CCAGCAAGAGGCTCCCGAGCGAGCAAGCTCAGTTTACACCCGATCCACTGGGGAGCAGGAAATATCTGTGGGCTTGTGACACGGACTCAAGTGGGCTGG
CCAGCAAGAGGCTCCCGAGCGAG (CRA-1)
CCCGAGCGAGCAAGCTCAGTTTA (CRA-2)
CCCGATCCACTGGGGAGCAGGAA (CRA-3)
AGTTTACACCCGATCCACTGGGG (CRA-4)
TGGGGAGCAGGAAATATCTGTGG (CRA-5)
ATATCTGTGGGCTTGTGACACGG (CRA-6)
GCTTGTGACACGGACTCAAGTGG (CRA-8)
TGACACGGACTCAAGTGGGCTGG (CRA-7)

guide RNA spacer length (bp)

| | CRA-4 | CRA-5 | CRA-6 | CRA-8 |
|---|---|---|---|---|
| CRA-1 | 7 | 25 | 38 | 48 |
| CRA-2 | | 12 | 25 | 35 |
| CRA-3 | | | 0 | 10 |

FIG. 19A

CRB
CCTGGCCATCTCTGACCTGTTTTTCCTTCTTACTGTCCCCTTCTGGGCTCACTATGCTGCCGCCCAGTGGGACTTTGGAAATACAATGTGTCAACTCTTGACAGGGC
TCTATTTTATAGG
CCTGGCCATCTCTGACCTGTTTT (CB-1)
CCCCTTCTGGGCTCACTATGCTG (CB-2)
CCGCCCAGTGGGACTTTGGAAAT (CB-3)
TCACTATGCTGCCGCCCAGTGGG (CB-4)

CAATGTGTCAACTCTTGACAGGG (CB-5)

TTGACAGGGCTCTATTTTATAGG (CB-6)

guide RNA spacer length (bp)

| | CB-4 | CB-5 | CB-6 |
|---|---|---|---|
| CB-1 | **25** | **60** | 74 |
| CB-2 | | **24** | **38** |
| CB-3 | | | **16** |

FIG. 19B

CAS9-RECOMBINASE FUSION PROTEINS AND USES THEREOF

RELATED APPLICATION

This application claims the benefit of the filing date of U.S. provisional applications 61/874,609, filed Sep. 6, 2013; 61/915,414, filed Dec. 12, 2013; and and 61/980,315, filed Apr. 16, 2014; all entitled Cas9 Variants and Uses Thereof, the entire contents of each of which are incorporated herein by reference.

BACKGROUND OF THE INVENTION

Site-specific endonucleases theoretically allow for the targeted manipulation of a single site within a genome and are useful in the context of gene targeting for therapeutic and research applications. In a variety of organisms, including mammals, site-specific endonucleases have been used for genome engineering by stimulating either non-homologous end joining or homologous recombination. In addition to providing powerful research tools, site-specific nucleases also have potential as gene therapy agents, and two site-specific endonucleases have recently entered clinical trials: (1) CCR5-2246, targeting a human CCR-5 allele as part of an anti-HIV therapeutic approach (NCT00842634, NCT01044654, NCT01252641); and (2) VF24684, targeting the human VEGF-A promoter as part of an anti-cancer therapeutic approach (NCT01082926).

Specific cleavage of the intended nuclease target site without or with only minimal off-target activity is a prerequisite for clinical applications of site-specific endonuclease, and also for high-efficiency genomic manipulations in basic research applications. For example, imperfect specificity of engineered site-specific binding domains has been linked to cellular toxicity and undesired alterations of genomic loci other than the intended target. Most nucleases available today, however, exhibit significant off-target activity, and thus may not be suitable for clinical applications. An emerging nuclease platform for use in clinical and research settings are the RNA-guided nucleases, such as Cas9. While these nucleases are able to bind guide RNAs (gRNAs) that direct cleavage of specific target sites, off-target activity is still observed for certain Cas9:gRNA complexes (Pattanayak et al., "High-throughput profiling of off-target DNA cleavage reveals RNA-programmed Cas9 nuclease specificity." *Nat. Biotechnol.* 2013; doi: 10.1038/nbt.2673). Technology for engineering nucleases with improved specificity is therefore needed.

Another class of enzymes useful for targeted genetic manipulations are site-specific recombinases (SSRs). These enzymes perform rearrangements of DNA segments by recognizing and binding to short DNA sequences, at which they cleave the DNA backbone, exchange the two DNA helices involved and rejoin the DNA strands. Such rearrangements allow for the targeted insertion, inversion, excision, or translocation of DNA segments. However, like site-specific endonucleases, naturally-occurring SSRs typically recognize and bind specific consensus sequences, and are thus limited in this respect. Technology for engineering recombinases with altered and/or improved specificity is also needed.

SUMMARY OF THE INVENTION

Some aspects of this disclosure are based on the recognition that the reported toxicity of some engineered site-specific endonucleases is based on off-target DNA cleavage. Thus certain aspects described herein relate to the discovery that increasing the number of sequences (e.g., having a nuclease bind at more than one site at a desired target), and/or splitting the activities (e.g., target binding and target cleaving) of a nuclease between two or more proteins, will increase the specificity of a nuclease and thereby decrease the likelihood of off-target effects. Accordingly, some aspects of this disclosure provide strategies, compositions, systems, and methods to improve the specificity of site-specific nucleases, in particular, RNA-programmable endonucleases, such as Cas9 endonuclease. Certain aspects of this disclosure provide variants of Cas9 endonuclease engineered to have improved specificity.

Other aspects of this disclosure are based on the recognition that site-specific recombinases (SSRs) available today are typically limited to recognizing and binding distinct consensus sequences. Thus certain aspects described herein relate to the discovery that fusions between RNA-programmable (nuclease-inactivated) nucleases (or RNA-binding domains thereof), and a recombinase domain, provide novel recombinases theoretically capable of binding and recombining DNA at any site chosen, e.g., by a practitioner (e.g., sites specified by guide RNAs (gRNAs) that are engineered or selected according the sequence of the area to be recombined). Such novel recombinases are therefore useful, inter alia, for the targeted insertion, deletion, inversion, translocation or other genomic modifications. Thus, also provided are methods of using these inventive recombinase fusion proteins, e.g., for such targeted genomic manipulations.

Accordingly, one embodiment of the disclosure provides fusion proteins and dimers thereof, for example, fusion proteins comprising two domains: (i) a nuclease-inactivated Cas9 domain; and (ii) a nuclease domain (e.g., a monomer of the FokI DNA cleavage domain). See e.g., FIGS. 1A, 6D. The fusion protein may further comprise a nuclear localization signal (NLS) domain, which signals for the fusion proteins to be transported into the nucleus of a cell. In some embodiments, one or more domains of the fusion proteins are separated by a linker. In certain embodiments, the linker is a non-peptidic linker. In certain embodiments, the linker is a peptide linker. In the case of peptide linkers, the peptide linker may comprise an XTEN linker, an amino acid sequence comprising one or more repeats of the tri-peptide GGS, or any sequence as provided in FIG. 12A. In some embodiments, the fusion protein is encoded by a nucleotide sequence set forth as SEQ ID NO:9, SEQ ID NO:10, SEQ ID NO:11, or SEQ ID NO:12, or a variant or fragment of any one of SEQ ID NO:9, SEQ ID NO:10, SEQ ID NO:11, or SEQ ID NO:12. The nuclease-inactivated Cas9 domain is capable of binding a guide RNA (gRNA). In certain embodiments, having dimers of such fusion protein each comprising a gRNA binding two distinct regions of a target nucleic acid provides for improved specificity, for example as compared to monomeric RNA-guided nucleases comprising a single gRNA to direct binding to the target nucleic acid.

According to another aspect of the invention, methods for site-specific DNA cleavage using the inventive Cas9 variants are provided. The methods typically comprise (a) contacting DNA with a fusion protein of the invention (e.g., a fusion protein comprising a nuclease-inactivated Cas9 domain and a FokI DNA cleavage domain), wherein the inactive Cas9 domain binds a gRNA that hybridizes to a region of the DNA; (b) contacting the DNA with a second fusion protein (e.g., a fusion protein comprising a nuclease-inactivated Cas9 and FokI DNA cleavage domain), wherein the inactive Cas9 domain of the second fusion protein binds a second gRNA that hybridizes to a second region of DNA; wherein the binding of the fusion proteins in steps (a) and (b) results in the dimerization of the nuclease domains of the fusion proteins, such that the DNA is cleaved in a region between the bound fusion proteins. In some embodiments, the gRNAs of steps (a) and (b) hybridize to the same strand of the DNA, or the gRNAs of steps (a) and (b) hybridize to opposite strands of the DNA. In some embodiments, the gRNAs of steps (a) and (b) hybridize to regions of the DNA that are no more than 10, no more than 15, no more than 20, no more than 25, no more than 30, no more than 40, no more than 50, no more than 60, no more than 70, no more than 80, no more than 90, or no more than 100 base pairs apart. In some embodiments, the DNA is in a cell, for example, a eukaryotic cell or a prokaryotic cell, which may be in an individual, such as a human.

According to another embodiments, a complex comprising a dimer of fusion proteins of the invention (e.g., a dimer of a fusion protein comprising a nuclease-inactivated Cas9 and a FokI DNA cleavage domain) are provided. In some embodiments, the nuclease-inactivated Cas9 domain of each fusion protein of the dimer binds a single extended gRNA, such that one fusion protein of the dimer binds a portion of the gRNA, and the other fusion protein of the dimer binds another portion of the gRNA. See e.g., FIG. 1B. In some embodiments, the gRNA is at least 50, at least 75, at least 100, at least 150, at least 200, at least 250, or at least 300 nucleotides in length. In some embodiments, the regions of the extended gRNA that hybridize to a target nucleic acid comprise 15-25, 19-21, or 20 nucleotides.

In another embodiment, methods for site-specific DNA cleavage are provided comprising contacting a DNA with a complex of two inventive fusion proteins bound to a single extended gRNA. In some embodiments, the gRNA contains two portions that hybridize to two separate regions of the DNA to be cleaved; the complex binds the DNA as a result of the portions of the gRNA hybridizing to the two regions; and binding of the complex results in dimerization of the nuclease domains of the fusion proteins, such that the domains cleave the DNA in a region between the bound fusion proteins. In some embodiments, the two portions of the gRNA hybridize to the same strand of the DNA. In other embodiments, the two portions of the gRNA hybridize to opposing strands of the DNA. In some embodiments, the two portions of the gRNA hybridize to regions of the DNA that are no more 10, no more than 15, no more than 20, no more than 25, no more than 30, no more than 40, no more than 50, no more than 60, no more than 70, no more than 80, no more than 90, or no more than 100 base pairs apart. In some embodiments, the DNA is in a cell, for example, a eukaryotic cell or a prokaryotic cell, which may be in an individual, such as a human.

According to another embodiment of the invention, split Cas9 proteins (including fusion proteins comprising a split Cas9 protein) comprising fragments of a Cas9 protein are provided. In some embodiments, a protein is provided that includes a gRNA binding domain of Cas9 but does not include a DNA cleavage domain. In other embodiments, proteins comprising a DNA cleavage domain of Cas9, but not a gRNA binding domain, are provided. In some embodiments, a fusion protein comprising two domains: (i) a nuclease-inactivated Cas9 domain, and (ii) a gRNA binding domain of Cas9 are provided, for example, wherein domain (ii) does not include a DNA cleavage domain. See e.g., FIG. 2B. In some embodiments, fusion proteins comprising two domains: (i) a nuclease-inactivated Cas9 domain, and (ii) a DNA cleavage domain are provided, for example, wherein domain (ii) does not include a gRNA binding domain. See e.g., FIG. 2C (fusion protein on right side, comprising a "B" domain). In some embodiments, protein dimers of any of the proteins described herein are provided. For example, in some embodiments, a dimer comprises two halves of a split Cas9 protein, for example, (i) a protein comprising a gRNA binding domain of Cas9, but not a DNA cleavage domain, and (ii) a protein comprising a DNA cleavage domain of Cas9, but not a gRNA binding domain. See e.g., FIG. 2A. In some embodiments, a dimer comprises one half of a split Cas9 protein, and a fusion protein comprising the other half of the split Cas9 protein. See e.g., FIG. 2B. For example, in certain embodiments such a dimer comprises (i) a protein comprising a gRNA binding domain of Cas9, but not a DNA cleavage domain, and (ii) a fusion protein comprising a nuclease-inactivated Cas9 and a DNA cleavage domain. In other embodiments, the dimer comprises (i) a protein comprising a DNA cleavage domain of Cas9, but not a gRNA binding domain, and (ii) a fusion protein comprising a nuclease-inactivated Cas9 and a gRNA binding domain of Cas9. In some embodiments, a dimer is provided that comprises two fusion proteins, each fusion protein comprising a nuclease-inactivated Cas9 and one half of a split Cas9. See e.g., FIG. 2C. For example, in certain embodiments, such a dimer comprises: (i) a fusion protein comprising a nuclease-inactivated Cas9 and a gRNA binding domain of Cas9, and (ii) a fusion protein comprising a nuclease-inactivated Cas9 and a DNA cleavage domain. In some embodiments, any of the provided protein dimers is associated with one or more gRNA(s).

In some embodiments, methods for site-specific DNA cleavage utilizing the inventive protein dimers are provided. For example, in some embodiments, such a method comprises contacting DNA with a protein dimer that comprises (i) a protein comprising a gRNA binding domain of Cas9, but not a DNA cleavage domain, and (ii) a protein comprising a DNA cleavage domain of Cas9, but not a gRNA binding domain, wherein the dimer binds a gRNA that hybridizes to a region of the DNA, and cleavage of the DNA occurs. See e.g., FIG. 2A. In some embodiments, the protein dimer used for site-specific DNA cleavage comprises (i) a protein comprising a gRNA binding domain of Cas9, but not a DNA cleavage domain, and (ii) a fusion protein comprising a nuclease-inactivated Cas9 and a DNA cleavage. See e.g., FIG. 2B. In some embodiments, the dimer used for site-specific DNA cleavage comprises (i) a protein comprising a DNA cleavage domain of Cas9, but not a gRNA binding domain, and (ii) a fusion protein comprising a nuclease-inactivated Cas9 and a gRNA binding domain of Cas9. In some embodiments, the protein dimer binds two gRNAs that hybridize to two regions of the DNA, and cleavage of the DNA occurs. See e.g., FIG. 2B. In some embodiments, the two gRNAs hybridize to regions of the DNA that are no more than 10, no more than 15, no more than 20, no more than 25, no more than 30, no more than 40, no more than 50, no more than 60, no more than 70, no more than 80, no more than 90, or no more than 100 base pairs apart. In some embodiments, the dimer used for site-specific DNA cleavage comprises two fusion proteins: (i) a fusion protein comprising a nuclease-inactivated Cas9 and a gRNA binding domain of Cas9, and (ii) a fusion protein comprising a nuclease-inactivated Cas9 and a DNA cleavage domain. In some embodiments, the protein dimer binds three gRNAs that hybridize to three regions of the DNA, and cleavage of the DNA occurs. Having such an arrangement, e.g., targeting more than one region of a target nucleic acid, for example using dimers associated with more than one gRNA (or a gRNA comprising more than one region that hybridizes to the target) increases the specificity of cleavage as compared to a nuclease binding a single region of a target nucleic acid. In some embodiments, the three gRNAs hybridize to regions of the DNA that are no more than 10, no more than 15, no more than 20, no more than 25, no more than 30, no more than 40, no more than 50, no more than 60, no more than 70, no more than 80, no more than 90, or no more than 100 base pairs apart between the first and second, and the second and third regions. In some embodiments, the DNA is in a cell, for example, a eukaryotic cell or a prokaryotic cell, which may be in an individual, such as a human.

According to another embodiment, minimal Cas9 proteins are provided, for example, wherein the protein comprises N- and/or C-terminal truncations and retains RNA binding and DNA cleavage activity. In some embodiments, the N-terminal truncation removes at least 5, at least 10, at least 15, at least 20, at least 25, at least 40, at least 40, at least 50, at least 75, at least 100, or at least 150 amino acids. In some embodiments, the C-terminal truncation removes at least 5, at least 10, at least 15, at least 20, at least 25, at least 40, at least 40, at least 50, at least 75, at least 100, or at least 150 amino acids. In some embodiments, the minimized Cas9 protein further comprises a bound gRNA.

In some embodiments, methods for site-specific DNA cleavage are provided comprising contacting a DNA with minimized Cas9 protein:gRNA complex.

According to another embodiment, dimers of Cas9 (or fragments thereof) wherein the dimer is coordinated through a single gRNA are provided. In some embodiments, the single gRNA comprises at least two portions that (i) are each able to bind a Cas9 protein and (ii) each hybridize to a target nucleic acid sequence (e.g., DNA sequence). In some embodiments, the portions of the gRNA that hybridize to the target nucleic acid each comprise no more than 5, no more than 10, or no more than 15 nucleotides complementary to the target nucleic acid sequence. In some embodiments, the portions of the gRNA that hybridize to the target nucleic acid are separated by a linker sequence. In some embodiments, the linker sequence hybridizes to the target nucleic acid. See e.g., FIG. 4. In some embodiments, methods for site-specific DNA cleavage are provided comprising contacting DNA with a dimer of Cas9 proteins coordinated through a single gRNA.

According to another embodiment, the disclosure provides fusion proteins and dimers and tetramers thereof, for example, fusion proteins comprising two domains: (i) a nuclease-inactivated Cas9 domain; and (ii) a recombinase catalytic domain. See, e.g., FIG. 5. The recombinase catalytic domain, in some embodiments, is derived from the recombinase catalytic domain of Hin recombinase, Gin recombinase, or Tn3 resolvase. The nuclease-inactivated Cas9 domain is capable of binding a gRNA, e.g., to target the fusion protein to a target nucleic acid sequence. The fusion proteins may further comprise a nuclear localization signal (NLS) domain, which signals for the fusion proteins to be transported into the nucleus of a cell. In some embodiments, one or more domains of the fusion proteins are separated by a linker. In certain embodiments, the linker is a non-peptidic linker. In certain embodiments, the linker is a peptide linker. In the case of peptide linkers, the peptide linker may comprise an XTEN linker, an amino acid sequence comprising one or more repeats of the tri-peptide GGS, or any sequence as provided in FIG. 12A.

In another embodiment, methods for site-specific recombination are provided, which utilize the inventive RNA-guided recombinase fusion proteins described herein. In some embodiments, the method is useful for recombining two separate DNA molecules, and comprises (a) contacting a first DNA with a first RNA-guided recombinase fusion protein, wherein the nuclease-inactivated Cas9 domain binds a first gRNA that hybridizes to a region of the first DNA; (b) contacting the first DNA with a second RNA-guided recombinase fusion protein, wherein the nuclease-inactivated Cas9 domain of the second fusion protein binds a second gRNA that hybridizes to a second region of the first DNA; (c) contacting a second DNA with a third RNA-guided recombinase fusion protein, wherein the nuclease-inactivated Cas9 domain of the third fusion protein binds a third gRNA that hybridizes to a region of the second DNA; and (d) contacting the second DNA with a fourth RNA-guided recombinase fusion protein, wherein the nuclease-inactivated Cas9 domain of the fourth fusion protein binds a fourth gRNA that hybridizes to a second region of the second DNA, wherein the binding of the fusion proteins in steps (a)-(d) results in the tetramerization of the recombinase catalytic domains of the fusion proteins, under conditions such that the DNAs are recombined. In some embodiments, methods for site-specific recombination between two regions of a single DNA molecule are provided. In some embodiments, the method comprises (a) contacting a DNA with a first RNA-guided recombinase fusion protein, wherein the nuclease-inactivated Cas9 domain binds a first gRNA that hybridizes to a region of the DNA; (b) contacting the DNA with a second RNA-guided recombinase fusion protein, wherein the nuclease-inactivated Cas9 domain of the second fusion protein binds a second gRNA that hybridizes to a second region of the DNA; (c) contacting the DNA with a third RNA-guided recombinase fusion protein, wherein the nuclease-inactivated Cas9 domain of the third fusion protein binds a third gRNA that hybridizes to a third region of the DNA; (d) contacting the DNA with a fourth RNA-guided recombinase fusion protein, wherein the nuclease-inactivated Cas9 domain of the fourth fusion protein binds a fourth gRNA that hybridizes to a fourth region of the DNA; wherein the binding of the fusion proteins in steps (a)-(d) results in the tetramerization of the recombinase catalytic domains of the fusion proteins, under conditions such that the DNA is recombined. In some embodiments involving methods for site-specific recombination, gRNAs hybridizing to the same DNA molecule hybridize to opposing strands of the DNA molecule. In some embodiments, e.g., involving site-specific recombination of a single DNA molecule, two gRNAs hybridize to one strand of the DNA, and the other two gRNAs hybridize to the opposing strand. In some embodiments, the gRNAs hybridize to regions of their respective DNAs (e.g., on the same strand) that are no more than 10, no more than 15, no more than 20, no more than 25, no more than 30, no more than 40, no more than 50, no more than 60, no more than 70, no more than 80, no more than 90, or no more than 100 base pairs apart. In some embodiments, the DNA is in a cell, for example, a eukaryotic cell or a prokaryotic cell, which may be in or obtained from an individual, such as a human.

According to another embodiment, polynucleotides are provided, for example, that encode any of the Cas9 proteins described herein (e.g., Cas9 variants, Cas9 dimers, Cas9 fusion proteins, Cas9 fragments, minimized Cas9 proteins, Cas9 variants without a cleavage domain, Cas9 variants without a gRNA domain, Cas9-recombinase fusions, etc.). In some embodiments, polynucleotides encoding any of the gRNAs described herein are provided. In some embodiments, polynucleotides encoding any inventive Cas9 protein described herein and any combination of gRNA(s) as described herein are provided. In some embodiments, vectors that comprise a polynucleotide described herein are provided. In some embodiments, vectors for recombinant protein expression comprising a polynucleotide encoding any of the Cas9 proteins and/or gRNAs described herein are provided. In some embodiments, cells comprising genetic constructs for expressing any of the Cas9 proteins and/or gRNAs described herein are provided.

In some embodiments, kits are provided. For example, kits comprising any of the Cas9 proteins and/or gRNAs described herein are provided. In some embodiments, kits comprising any of the polynucleotides described herein, e.g., those encoding a Cas9 protein and/or gRNA, are provided. In some embodiments, kits comprising a vector for recombinant protein expression, wherein the vectors comprise a polynucleotide encoding any of the Cas9 proteins and/or gRNAs described herein, are provided. In some embodiments, kits comprising a cell comprising genetic constructs for expressing any of the Cas9 proteins and/or gRNAs described herein are provided.

Other advantages, features, and uses of the invention will be apparent from the Detailed Description of Certain Non-Limiting Embodiments of the Invention; the Drawings, which are schematic and not intended to be drawn to scale; and the Claims.

BRIEF DESCRIPTION OF THE DRAWINGS

FIG. 9 shows the target DNA sequences in a genomic GFP gene. Seven gRNA target sites were chosen to test FokI-dCas9 candidate activity in an orientation in which the PAM is adjacent to the cleaved spacer sequence (orientation B). Together, these seven gRNAs enabled testing of FokI-dCas9 fusion variants across six spacer lengths ranging from 4 to 42 bp. The sequences shown are identified as follows: "EmGFP (bp 297-388)" corresponds to SEQ ID NO:212; "G8" corresponds to SEQ ID NO:213; "G9" corresponds to SEQ ID NO:214; "G10" corresponds to SEQ ID NO:215; "G11" corresponds to SEQ ID NO:216; "G12" corresponds to SEQ ID NO:217; "G13" corresponds to SEQ ID NO:218; and "G14" corresponds to SEQ ID NO:219.

FIG. 19 shows the target DNA sequences in a genomic CCR5 gene. (A) Eight gRNA target sites were identified for testing Cas9 variant (e.g., FokI-dCas9) activity in an orientation in which the PAM is adjacent to the cleaved spacer sequence (orientation A). (B) Six gRNA target sites were identified for testing Cas9 variant (e.g., FokI-dCas9) activity in an orientation in which the PAM is adjacent to the cleaved spacer sequence (orientation B). Together, these fourteen gRNAs enable testing of Cas9 fusion variants across spacer lengths ranging from 0 to 74 bp. The sequences shown in (A) are identified as follows: "CRA" corresponds to SEQ ID NO:302; "CRA-1" corresponds to SEQ ID NO:303; "CRA-2" corresponds to SEQ ID NO:304; "CRA-3" corresponds to SEQ ID NO:305; "CRA-4" corresponds to SEQ ID NO:306; "CRA-5" corresponds to SEQ ID NO:307; "CRA-6" corresponds to SEQ ID NO:308; "CRA-7" corresponds to SEQ ID NO:309; and "CRA-8" corresponds to SEQ ID NO:310. The sequences shown in (B) are identified as follows: "CRB" corresponds to SEQ ID NO:311; "CB-1" corresponds to SEQ ID NO:312; "CB-2" corresponds to SEQ ID NO:313; "CB-3" corresponds to SEQ ID NO:314; "CB-4" corresponds to SEQ ID NO:315; "CB-5" corresponds to SEQ ID NO:316; and "CB-6" corresponds to SEQ ID NO:317.

DEFINITIONS

Figure 1A:
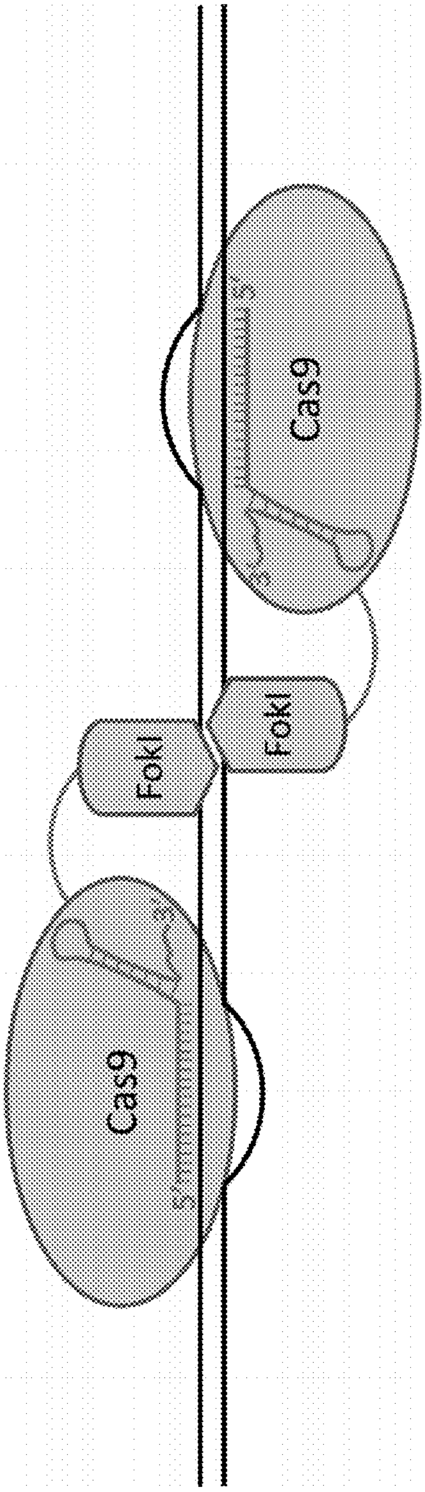
FIG. 1 is a schematic detailing certain embodiments of the invention. (A) In this embodiment, nuclease-inactivated Cas9 protein is fused to a monomer of the FokI nuclease domain. Double-strand DNA-cleavage is achieved through dimerization of FokI monomers at the target site and is dependent on the simultaneous binding of two distinct Cas9:gRNA complexes. (B) In this embodiment, an alternate configuration is provided, wherein two Cas9-FokI fusions are coordinated through the action of a single extended gRNA containing two distinct gRNA motifs. The gRNA motifs comprise regions that hybridize the target in distinct regions, as well as regions that bind each fusion protein. The extended gRNA may enhance cooperative binding and alter the specificity profile of the fusions.

As used herein and in the claims, the singular forms "a," "an," and "the" include the singular and the plural reference unless the context clearly indicates otherwise. Thus, for example, a reference to "an agent" includes a single agent and a plurality of such agents.

The term "Cas9" or "Cas9 nuclease" refers to an RNA-guided nuclease comprising a Cas9 protein, or a fragment thereof (e.g., a protein comprising an active or inactive DNA cleavage domain of Cas9, and/or the gRNA binding domain of Cas9). A Cas9 nuclease is also referred to sometimes as a casn1 nuclease or a CRISPR (clustered regularly interspaced short palindromic repeat)-associated nuclease. CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNA. However, single guide RNAs ("sgRNA", or simply "gNRA") can be engineered so as to incorporate aspects of both the crRNA and tracrRNA into a single RNA species. See e.g., Jinek M., Chylinski K., Fonfara I., Hauer M., Doudna J. A., Charpentier E. *Science* 337:816-821 (2012), the entire contents of which is hereby incorporated by reference. Cas9 recognizes a short motif in the CRISPR repeat sequences (the PAM or protospacer adjacent motif) to help distinguish self versus non-self. Cas9 nuclease sequences and structures are well known to those of skill in the art (see, e.g., "Complete genome sequence of an M1 strain of *Streptococcus pyogenes*." Ferretti et al., J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663 (2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607 (2011); and "A programmable dual-RNA-guided DNA endonuclease in adaptive bacterial immunity." Jinek M., Chylinski K., Fonfara I., Hauer M., Doudna J. A., Charpentier E. *Science* 337:816-821 (2012), the entire contents of each of which are incorporated herein by reference). Cas9 orthologs have been described in various species, including, but not limited to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737; the entire contents of which are incorporated herein by reference. In some embodiments, a Cas9 nuclease has an inactive (e.g., an inactivated) DNA cleavage domain. A nuclease-inactivated Cas9 protein may interchangeably be referred to as a "dCas9" protein (for nuclease "dead" Cas9). In some embodiments, dCas9 corresponds to, or comprises in part or in whole, the amino acid set forth as SEQ ID NO:5, below. In some embodiments, variants of dCas9 (e.g., variants of SEQ ID NO:5) are provided. For example, in some embodiments, variants having mutations other than D10A and H840A are provided, which e.g., result in nuclease inactivated Cas9 (dCas9). Such mutations, by way of example, include other amino acid substitutions at D10 and H840, or other substitutions within the nuclease domains of Cas9 (e.g., substitutions in the HNH nuclease subdomain and/or the RuvC1 subdomain). In some embodiments, variants or homologues of dCas9 (e.g., variants of SEQ ID NO:5) are provided which are at least about 70% identical, at least about 80% identical, at least about 90% identical, at least about 95% identical, at least about 98% identical, at least about 99% identical, at least about 99.5% identical, or at least about 99.9% to SEQ ID NO:5. In some embodiments, variants of dCas9 (e.g., variants of SEQ ID NO:5) are provided having amino acid sequences which are shorter, or longer than SEQ ID NO:5, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids or more.

dCas9 (D10A and H840A):

```
                                          (SEQ ID NO: 5)
MDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR
```

-continued

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDAIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD

Methods for generating a Cas9 protein (or a fragment thereof) having an inactive DNA cleavage domain are known (See, e.g., the Examples; and Jinek et al., *Science.* 337:816-821 (2012); Qi et al., "Repurposing CRISPR as an RNA-Guided Platform for Sequence-Specific Control of Gene Expression" (2013) *Cell.* 28; 152(5):1173-83, the entire contents of each of which are incorporated herein by reference). For example, the DNA cleavage domain of Cas9 is known to include two subdomains, the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H840A completely inactivate the nuclease activity of *S. pyogenes* Cas9 (See e.g., the Examples; and Jinek et al., *Science.* 337:816-821 (2012); Qi et al., *Cell.* 28; 152(5):1173-83 (2013)). In some embodiments, proteins comprising fragments of Cas9 are provided. For example, in some embodiments, a protein comprises one of two Cas9 domains: (1) the gRNA binding domain of Cas9; or (2) the DNA cleavage domain of Cas9. In some embodiments, proteins comprising Cas9 or fragments thereof are referred to as "Cas9 variants." A Cas9 variant shares homology to Cas9, or a fragment thereof. For example a Cas9 variant is at least about 70% identical, at least about 80% identical, at least about 90% identical, at least about 95% identical, at least about 98% identical, at least about 99% identical, at least about 99.5% identical, or at least about 99.9% to wild type Cas9. In some embodiments, the Cas9 variant comprises a fragment of Cas9 (e.g., a gRNA binding domain or a DNA-cleavage domain), such that the fragment is at least about 70% identical, at least about 80% identical, at least about 90% identical, at least about 95% identical, at least about 98% identical, at least about 99% identical, at least about 99.5% identical, or at least about 99.9% to the corresponding fragment of wild type Cas9. In some embodiments, wild type Cas9 corresponds to Cas9 from *Streptococcus pyogenes* (NCBI Reference Sequence: NC_017053.1, SEQ ID NO:1 (nucleotide); SEQ ID NO:2 (amino acid)).

(SEQ ID NO: 1)

```
ATGGATAAGAAATACTCAATAGGCTTAGATATCGGCACAAATAGCGTCGG
ATGGGCGGTGATCACTGATGATTATAAGGTTCCGTCTAAAAAGTTCAAGG
TTCTGGGAAATACAGACCGCCACAGTATCAAAAAAAATCTTATAGGGGCT
CTTTTATTTGGCAGTGGAGAGACAGCGGAAGCGACTCGTCTCAAACGGAC
AGCTCGTAGAAGGTATACACGTCGGAAGAATCGTATTTGTTATCTACAGG
AGATTTTTTCAAATGAGATGGCGAAAGTAGATGATAGTTTCTTTCATCGA
CTTGAAGAGTCTTTTTTGGTGGAAGAAGACAAGAAGCATGAACGTCATCC
TATTTTTGGAAATATAGTAGATGAAGTTGCTTATCATGAGAAATATCCAA
CTATCTATCATCTGCGAAAAAAATTGGCAGATTCTACTGATAAAGCGGAT
TTGCGCTTAATCTATTTGGCCTTAGCGCATATGATTAAGTTTCGTGGTCA
TTTTTTGATTGAGGGAGATTTAAATCCTGATAATAGTGATGTGGACAAAC
TATTTATCCAGTTGGTACAAATCTACAATCAATTATTTGAAGAAAACCCT
ATTAACGCAAGTAGAGTAGATGCTAAAGCGATTCTTTCTGCACGATTGAG
TAAATCAAGACGATTAGAAAATCTCATTGCTCAGCTCCCCGGTGAGAAGA
GAAATGGCTTGTTTGGGAATCTCATTGCTTTGTCATTGGGATTGACCCCT
AATTTTAAATCAAATTTTGATTTGGCAGAAGATGCTAAATTACAGCTTTC
AAAAGATACTTACGATGATGATTTAGATAATTTATTGGCGCAAATTGGAG
ATCAATATGCTGATTTGTTTTTGGCAGCTAAGAATTTATCAGATGCTATT
TTACTTTCAGATATCCTAAGAGTAAATAGTGAAATAACTAAGGCTCCCCT
ATCAGCTTCAATGATTAAGCGCTACGATGAACATCATCAAGACTTGACTC
TTTTAAAAGCTTTAGTTCGACAACAACTTCCAGAAAAGTATAAAGAAATC
TTTTTTGATCAATCAAAAAACGGATATGCAGGTTATATTGATGGGGGAGC
TAGCCAAGAAGAATTTTATAAATTTATCAAACCAATTTTAGAAAAAATGG
ATGGTACTGAGGAATTATTGGTGAAACTAAATCGTGAAGATTTGCTGCGC
AAGCAACGGACCTTTGACAACGGCTCTATTCCCCATCAAATTCACTTGGG
TGAGCTGCATGCTATTTTGAGAAGACAAGAAGACTTTTATCCATTTTTAA
AAGACAATCGTGAGAAGATTGAAAAAATCTTGACTTTTCGAATTCCTTAT
TATGTTGGTCCATTGGCGCGTGGCAATAGTCGTTTTGCATGGATGACTCG
GAAGTCTGAAGAAACAATTACCCCATGGAATTTTGAAGAAGTTGTCGATA
AAGGTGCTTCAGCTCAATCATTTATTGAACGCATGACAAACTTTGATAAA
AATCTTCCAAATGAAAAAGTACTACCAAAACATAGTTTGCTTTATGAGTA
TTTTACGGTTTATAACGAATTGACAAAGGTCAAATATGTTACTGAGGGAA
TGCGAAAACCAGCATTTCTTTCAGGTGAACAGAAGAAAGCCATTGTTGAT
TTACTCTTCAAAACAAATCGAAAAGTAACCGTTAAGCAATTAAAAGAAGA
TTATTTCAAAAAAATAGAATGTTTTGATAGTGTTGAAATTTCAGGAGTTG
AAGATAGATTTAATGCTTCATTAGGCGCCTACCATGATTTGCTAAAAATT
ATTAAAGATAAAGATTTTTTGGATAATGAAGAAAATGAAGATATCTTAGA
GGATATTGTTTTAACATTGACCTTATTTGAAGATAGGGGGATGATTGAGG
AAAGACTTAAAACATATGCTCACCTCTTTGATGATAAGGTGATGAAACAG
CTTAAACGTCGCCGTTATACTGGTTGGGGACGTTTGTCTCGAAAATTGAT
TAATGGTATTAGGGATAAGCAATCTGGCAAAACAATATTAGATTTTTTGA
AATCAGATGGTTTTGCCAATCGCAATTTTATGCAGCTGATCCATGATGAT
AGTTTGACATTTAAAGAAGATATTCAAAAAGCACAGGTGTCTGGACAAGG
CCATAGTTTACATGAACAGATTGCTAACTTAGCTGGCAGTCCTGCTATTA
AAAAAGGTATTTTACAGACTGTAAAAATTGTTGATGAACTGGTCAAAGTA
ATGGGGCATAAGCCAGAAAATATCGTTATTGAAATGGCACGTGAAAATCA
GACAACTCAAAAGGGCCAGAAAAATTCGCGAGAGCGTATGAAACGAATCG
AAGAAGGTATCAAAGAATTAGGAAGTCAGATTCTTAAAGAGCATCCTGTT
GAAAATACTCAATTGCAAAATGAAAAGCTCTATCTCTATTATCTACAAAA
TGGAAGAGACATGTATGTGGACCAAGAATTAGATATTAATCGTTTAAGTG
ATTATGATGTCGATCACATTGTTCCACAAAGTTTCATTAAAGACGATTCA
ATAGACAATAAGGTACTAACGCGTTCTGATAAAAATCGTGGTAAATCGGA
TAACGTTCCAAGTGAAGAAGTAGTCAAAAAGATGAAAAACTATTGGAGAC
AACTTCTAAACGCCAAGTTAATCACTCAACGTAAGTTTGATAATTTAACG
AAAGCTGAACGTGGAGGTTTGAGTGAACTTGATAAAGCTGGTTTTATCAA
ACGCCAATTGGTTGAAACTCGCCAAATCACTAAGCATGTGGCACAAATTT
TGGATAGTCGCATGAATACTAAATACGATGAAAATGATAAACTTATTCGA
GAGGTTAAAGTGATTACCTTAAAATCTAAATTAGTTTCTGACTTCCGAAA
AGATTTCCAATTCTATAAAGTACGTGAGATTAACAATTACCATCATGCCC
ATGATGCGTATCTAAATGCCGTCGTTGGAACTGCTTTGATTAAGAAATAT
CCAAAACTTGAATCGGAGTTTGTCTATGGTGATTATAAAGTTTATGATGT
TCGTAAAATGATTGCTAAGTCTGAGCAAGAAATAGGCAAAGCAACCGCAA
AATATTTCTTTTACTCTAATATCATGAACTTCTTCAAAACAGAAATTACA
CTTGCAAATGGAGAGATTCGCAAACGCCCTCTAATCGAAACTAATGGGGA
AACTGGAGAAATTGTCTGGGATAAAGGGCGAGATTTTGCCACAGTGCGCA
AAGTATTGTCCATGCCCCAAGTCAATATTGTCAAGAAAACAGAAGTACAG
ACAGGCGGATTCTCCAAGGAGTCAATTTTACCAAAAAGAAATTCGGACAA
GCTTATTGCTCGTAAAAAAGACTGGGATCCAAAAAAATATGGTGGTTTTG
ATAGTCCAACGGTAGCTTATTCAGTCCTAGTGGTTGCTAAGGTGGAAAAA
GGGAAATCGAAGAAGTTAAAATCCGTTAAAGAGTTACTAGGGATCACAAT
TATGGAAAGAAGTTCCTTTGAAAAAAATCCGATTGACTTTTTAGAAGCTA
```

-continued

AAGGATATAAGGAAGTTAAAAAAGACTTAATCATTAAACTACCTAAATAT
AGTCTTTTTGAGTTAGAAAACGGTCGTAAACGGATGCTGGCTAGTGCCGG
AGAATTACAAAAAGGAAATGAGCTGGCTCTGCCAAGCAAATATGTGAATT
TTTTATATTTAGCTAGTCATTATGAAAAGTTGAAGGGTAGTCCAGAAGAT
AACGAACAAAAACAATTGTTTGTGGAGCAGCATAAGCATTATTTAGATGA
GATTATTGAGCAAATCAGTGAATTTTCTAAGCGTGTTATTTTAGCAGATG
CCAATTTAGATAAAGTTCTTAGTGCATATAACAAACATAGAGACAAACCA
ATACGTGAACAAGCAGAAAATATTATTCATTTATTTACGTTGACGAATCT
TGGAGCTCCCGCTGCTTTTAAATATTTTGATACAACAATTGATCGTAAAC
GATATACGTCTACAAAAGAAGTTTTAGATGCCACTCTTATCCATCAATCC
ATCACTGGTCTTTATGAAACACGCATTGATTTGAGTCAGCTAGGAGGTGA
CTGA (SEQ ID NO: 2)

MDKKYSIGLDIGTNSVGWAVITDDYKVPSKKFKVLGNTDRHSIKKNLIGA
LLFGSGETAEATRLKRTARRRYTRRKNRICYLQEIFSNEMAKVDDSFFHR
LEESFLVEEDKKHERHPIFGNIVDEVAYHEKYPTIYHLRKKLADSTDKAD
LRLIYLALAHMIKFRGHFLIEGDLNPDNSDVDKLFIQLVQIYNQLFEENP
INASRVDAKAILSARLSKSRRLENLIAQLPGEKRNGLFGNLIALSLGLTP
NFKSNFDLAEDAKLQLSKDTYDDDLDNLLAQIGDQYADLFLAAKNLSDAI
LLSDILRVNSEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGAYHDLLKI
IKDKDFLDNEENEDILEDIVLTLTLFEDRGMIEERLKTYAHLFDDKVMKQ
LKRRRYTGWGRLSRKLINGIRDKQSGKTILDFLKSDGFANRNFMQLIHDD
SLTFKEDIQKAQVSGQGHSLHEQIANLAGSPAIKKGILQTVKIVDELVKV
MGHKPENIVIEMARENQTTQKGQKNSRERMKRIEEGIKELGSQILKEHPV
ENTQLQNEKLYLYYLQNGRDMYVDQELDINRLSDYDVDHIVPQSFIKDDS
IDNKVLTRSDKNRGKSDNVPSEEVVKKMKNYWRQLLNAKLITQRKFDNLT
KAERGGLSELDKAGFIKRQLVETRQITKHVAQILDSRMNTKYDENDKLIR
EVKVITLKSKLVSDFRKDFQFYKVREINNYHHAHDAYLNAVVGTALIKKY
PKLESEFVYGDYKVYDVRKMIAKSEQEIGKATAKYFFYSNIMNFFKTEIT
LANGEIRKRPLIETNGETGEIVWDKGRDFATVRKVLSMPQVNIVKKTEVQ
TGGFSKESILPKRNSDKLIARKKDWDPKKYGGFDSPTVAYSVLVVAKVEK
GKSKKLKSVKELLGITIMERSSFEKNPIDFLEAKGYKEVKKDLIIKLPKY
SLFELENGRKRMLASAGELQKGNELALPSKYVNFLYLASHYEKLKGSPED
NEQKQLFVEQHKHYLDEIIEQISEFSKRVILADANLDKVLSAYNKHRDKP
IREQAENIIHLFTLTNLGAPAAFKYFDTTIDRKRYTSTKEVLDATLIHQS
ITGLYETRIDLSQLGGD

In some embodiments, wild type Cas9 corresponds to, or comprises, SEQ ID NO:3 (nucleotide) and/or SEQ ID NO:4 (amino acid).

(SEQ ID NO: 3)

ATGGATAAAAAGTATTCTATTGGTTTAGACATCGGCACTAATTCCGTTGG
ATGGGCTGTCATAACCGATGAATACAAAGTACCTTCAAAGAAATTTAAGG
TGTTGGGGAACACAGACCGTCATTCGATTAAAAAGAATCTTATCGGTGCC
CTCCTATTCGATAGTGGCGAAACGGCAGAGGCGACTCGCCTGAAACGAAC
CGCTCGGAGAAGGTATACACGTCGCAAGAACCGAATATGTTACTTACAAG
AAATTTTTAGCAATGAGATGGCCAAAGTTGACGATTCTTTCTTTCACCGT
TTGGAAGAGTCCTTCCTTGTCGAAGAGGACAAGAAACATGAACGGCACCC
CATCTTTGGAAACATAGTAGATGAGGTGGCATATCATGAAAAGTACCCAA
CGATTTATCACCTCAGAAAAAAGCTAGTTGACTCAACTGATAAAGCGGAC
CTGAGGTTAATCTACTTGGCTCTTGCCCATATGATAAAGTTCCGTGGGCA
CTTTCTCATTGAGGGTGATCTAAATCCGGACAACTCGGATGTCGACAAAC
TGTTCATCCAGTTAGTACAAACCTATAATCAGTTGTTTGAAGAGAACCCT
ATAAATGCAAGTGGCGTGGATGCGAAGGCTATTCTTAGCGCCCGCCTCTC
TAAATCCCGACGGCTAGAAAACCTGATCGCACAATTACCCGGAGAGAAGA
AAAATGGGTTGTTCGGTAACCTTATAGCGCTCTCACTAGGCCTGACACCA
AATTTTAAGTCGAACTTCGACTTAGCTGAAGATGCCAAATTGCAGCTTAG
TAAGGACACGTACGATGACGATCTCGACAATCTACTGGCACAAATTGGAG
ATCAGTATGCGGACTTATTTTTGGCTGCCAAAAACCTTAGCGATGCAATC
CTCCTATCTGACATACTGAGAGTTAATACTGAGATTACCAAGGCGCCGTT
ATCCGCTTCAATGATCAAAAGGTACGATGAACATCACCAAGACTTGACAC
TTCTCAAGGCCCTAGTCCGTCAGCAACTGCCTGAGAAATATAAGGAAATA
TTCTTTGATCAGTCGAAAAACGGGTACGCAGGTTATATTGACGGCGGAGC
GAGTCAAGAGGAATTCTACAAGTTTATCAAACCCATATTAGAGAAGATGG
ATGGGACGGAAGAGTTGCTTGTAAAACTCAATCGCGAAGATCTACTGCGA
AAGCAGCGGACTTTCGACAACGGTAGCATTCCACATCAAATCCACTTAGG
CGAATTGCATGCTATACTTAGAAGGCAGGAGGATTTTTATCCGTTCCTCA
AAGACAATCGTGAAAAGATTGAGAAAATCCTAACCTTTCGCATACCTTAC
TATGTGGGACCCCTGGCCCGAGGGAACTCTCGGTTCGCATGGATGACAAG
AAAGTCCGAAGAAACGATTACTCCATGGAATTTTGAGGAAGTTGTCGATA
AAGGTGCGTCAGCTCAATCGTTCATCGAGAGGATGACCAACTTTGACAAG
AATTTACCGAACGAAAAAGTATTGCCTAAGCACAGTTTACTTTACGAGTA
TTTCACAGTGTACAATGAACTCACGAAAGTTAAGTATGTCACTGAGGGCA
TGCGTAAACCCGCCTTTCTAAGCGGAGAACAGAAGAAAGCAATAGTAGAT
CTGTTATTCAAGACCAACCGCAAAGTGACAGTTAAGCAATTGAAAGAGGA
CTACTTTAAGAAAATTGAATGCTTCGATTCTGTCGAGATCTCCGGGGTAG
AAGATCGATTTAATGCGTCACTTGGTACGTATCATGACCTCCTAAAGATA
ATTAAAGATAAGGACTTCCTGGATAACGAAGAGAATGAAGATATCTTAGA
AGATATAGTGTTGACTCTTACCCTCTTTGAAGATCGGGAAATGATTGAGG
AAAGACTAAAAACATACGCTCACCTGTTCGACGATAAGGTTATGAAACAG
TTAAAGAGGCGTCGCTATACGGGCTGGGGACGATTGTCGCGGAAACTTAT
CAACGGGATAAGAGACAAGCAAAGTGGTAAAACTATTCTCGATTTTCTAA
AGAGCGACGGCTTCGCCAATAGGAACTTTATGCAGCTGATCCATGATGAC
TCTTTAACCTTCAAAGAGGATATACAAAAGGCACAGGTTTCCGGACAAGG
GGACTCATTGCACGAACATATTGCGAATCTTGCTGGTTCGCCAGCCATCA
AAAAGGGCATACTCCAGACAGTCAAAGTAGTGGATGAGCTAGTTAAGGTC
ATGGGACGTCACAAACCGGAAAACATTGTAATCGAGATGGCACGCGAAAA
TCAAACGACTCAGAAGGGGCAAAAAAACAGTCGAGAGCGGATGAAGAGAA
TAGAAGAGGGTATTAAAGAACTGGGCAGCCAGATCTTAAAGGAGCATCCT
GTGGAAAATACCCAATTGCAGAACGAGAAACTTTACCTCTATTACCTACA
AAATGGAAGGGACATGTATGTTGATCAGGAACTGGACATAAACCGTTTAT
CTGATTACGACGTCGATCACATTGTACCCCAATCCTTTTTGAAGGACGAT
TCAATCGACAATAAAGTGCTTACACGCTCGGATAAGAACCGAGGGAAAAG
TGACAATGTTCCAAGCGAGGAAGTCGTAAAGAAAATGAAGAACTATTGGC
GGCAGCTCCTAAATGCGAAACTGATAACGCAAAGAAAGTTCGATAACTTA
ACTAAAGCTGAGAGGGGTGGCTTGTCTGAACTTGACAAGGCCGGATTTAT
TAAACGTCAGCTCGTGGAAACCCGCCAAATCACAAAGCATGTTGCACAGA
TACTAGATTCCCGAATGAATACGAAATACGACGAGAACGATAAGCTGATT
CGGGAAGTCAAAGTAATCACTTTAAAGTCAAAATTGGTGTCGGACTTCAG
AAAGGATTTTCAATTCTATAAAGTTAGGGAGATAAATAACTACCACCATG
CGCACGACGCTTATCTTAATGCCGTCGTAGGGACCGCACTCATTAAGAAA
TACCCGAAGCTAGAAAGTGAGTTTGTGTATGGTGATTACAAAGTTTATGA
CGTCCGTAAGATGATCGCGAAAAGCGAACAGGAGATAGGCAAGGCTACAG
CCAAATACTTCTTTTATTCTAACATTATGAATTTCTTTAAGACGGAAATC
ACTCTGGCAAACGGAGAGATACGCAAACGACCTTTAATTGAAACCAATGG
GGAGACAGGTGAAATCGTATGGGATAAGGGCCGGGACTTCGCGACGGTGA
GAAAAGTTTTGTCCATGCCCCAAGTCAACATAGTAAAGAAAACTGAGGTG
CAGACCGGAGGGTTTTCAAAGGAATCGATTCTTCCAAAAAGGAATAGTGA
TAAGCTCATCGCTCGTAAAAAGGACTGGGACCCGAAAAAGTACGGTGGCT
TCGATAGCCCTACAGTTGCCTATTCTGTCCTAGTAGTGGCAAAAGTTGAG
AAGGGAAAATCCAAGAAACTGAAGTCAGTCAAAGAATTATTGGGGATAAC
GATTATGGAGCGCTCGTCTTTTGAAAAGAACCCCATCGACTTCCTTGAGG
CGAAAGGTTACAAGGAAGTAAAAAAGGATCTCATAATTAAACTACCAAAG
TATAGTCTGTTTGAGTTAGAAAATGGCCGAAAACGGATGTTGGCTAGCGC
CGGAGAGCTTCAAAAGGGGAACGAACTCGCACTACCGTCTAAATACGTGA
ATTTCCTGTATTTAGCGTCCCATTACGAGAAGTTGAAAGGTTCACCTGAA
GATAACGAACAGAAGCAACTTTTTGTTGAGCAGCACAAACATTATCTCGA
CGAAATCATAGAGCAAATTTCGGAATTCAGTAAGAGAGTCATCCTAGCTG
ATGCCAATCTGGACAAAGTATTAAGCGCATACAACAAGCACAGGGATAAA
CCCATACGTGAGCAGGCGGAAAATATTATCCATTTGTTTACTCTTACCAA
CCTCGGCGCTCCAGCCGCATTCAAGTATTTTGACACAACGATAGATCGCA
AACGATACACTTCTACCAAGGAGGTGCTAGACGCGACACTGATTCACCAA
TCCATCACGGGATTATATGAAACTCGGATAGATTTGTCACAGCTTGGGGG
TGACGGATCCCCCAAGAAGAAGAGGAAAGTCTCGAGCGACTACAAAGACC
ATGACGGTGATTATAAAGATCATGACATCGATTACAAGGATGACGATGAC
AAGGCTGCAGGA (SEQ ID NO: 4)

MDKKYSIGLAIGTNSVGWAVITDEYKVPSKKFKVLGNTDRHSIKKNLIGA
LLFDSGETAEATRLKRTARRRYTRRKNRICYLQEIFSNEMAKVDDSFFHR
LEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENP
INASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQ
LKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVKV
MGRHKPENIVIEMARENQTTQKGQKNSRERMKRIEEGIKELGSQILKEHP
VENTQLQNEKLYLYYLQNGRDMYVDQELDINRLSDYDVDHIVPQSFLKDD
SIDNKVLTRSDKNRGKSDNVPSEEVVKKMKNYWRQLLNAKLITQRKFDNL
TKAERGGLSELDKAGFIKRQLVETRQITKHVAQILDSRMNTKYDENDKLI
REVKVITLKSKLVSDFRKDFQFYKVREINNYHHAHDAYLNAVVGTALIKK
YPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEV
QTGGFSKESILPKRNSDKLIARKKDWDPKKYGGFDSPTVAYSVLVVAKVE
KGKSKKLKSVKELLGITIMERSSFEKNPIDFLEAKGYKEVKKDLIIKLPK
YSLFELENGRKRMLASAGELQKGNELALPSKYVNFLYLASHYEKLKGSPE

-continued

```
DNEQKQLFVEQHKHYLDEIIEQISEFSKRVILADANLDKVLSAYNKHRDK
PIREQAENIIHLFTLTNLGAPAAFKYFDTTIDRKRYTSTKEVLDATLIHQ
SITGLYETRIDLSQLGGD
```

In some embodiments, Cas9 refers to Cas9 from: *Corynebacterium ulcerans* (NCBI Refs: NC_015683.1, NC_017317.1); *Corynebacterium diphtheria* (NCBI Refs: NC_016782.1, NC_016786.1); *Spiroplasma syrphidicola* (NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychroflexus torquisI* (NCBI Ref: NC_018721.1); *Streptococcus thermophilus* (NCBI Ref: YP_820832.1), *Listeria innocua* (NCBI Ref: NP_472073.1), *Campylobacter jejuni* (NCBI Ref: YP_002344900.1) or *Neisseria meningitidis* (NCBI Ref: YP_002342100.1).

The terms "conjugating," "conjugated," and "conjugation" refer to an association of two entities, for example, of two molecules such as two proteins, two domains (e.g., a binding domain and a cleavage domain), or a protein and an agent, e.g., a protein binding domain and a small molecule. In some aspects, the association is between a protein (e.g., RNA-programmable nuclease) and a nucleic acid (e.g., a guide RNA). The association can be, for example, via a direct or indirect (e.g., via a linker) covalent linkage. In some embodiments, the association is covalent. In some embodiments, two molecules are conjugated via a linker connecting both molecules. For example, in some embodiments where two proteins are conjugated to each other, e.g., a binding domain and a cleavage domain of an engineered nuclease, to form a protein fusion, the two proteins may be conjugated via a polypeptide linker, e.g., an amino acid sequence connecting the C-terminus of one protein to the N-terminus of the other protein.

The term "consensus sequence," as used herein in the context of nucleic acid sequences, refers to a calculated sequence representing the most frequent nucleotide residues found at each position in a plurality of similar sequences. Typically, a consensus sequence is determined by sequence alignment in which similar sequences are compared to each other and similar sequence motifs are calculated. In the context of nuclease target site sequences, a consensus sequence of a nuclease target site may, in some embodiments, be the sequence most frequently bound, or bound with the highest affinity, by a given nuclease. In the context of recombinase target site sequences, a consensus sequence of a recombinase target site may, in some embodiments, be the sequence most frequently bound, or bound with the highest affinity, by a given recombinase.

The term "engineered," as used herein refers to a protein molecule, a nucleic acid, complex, substance, or entity that has been designed, produced, prepared, synthesized, and/or manufactured by a human. Accordingly, an engineered product is a product that does not occur in nature.

The term "effective amount," as used herein, refers to an amount of a biologically active agent that is sufficient to elicit a desired biological response. For example, in some embodiments, an effective amount of a nuclease may refer to the amount of the nuclease that is sufficient to induce cleavage of a target site specifically bound and cleaved by the nuclease. In some embodiments, an effective amount of a recombinase may refer to the amount of the recombinase that is sufficient to induce recombination at a target site specifically bound and recombined by the recombinase. As will be appreciated by the skilled artisan, the effective amount of an agent, e.g., a nuclease, a recombinase, a hybrid protein, a fusion protein, a protein dimer, a complex of a protein (or protein dimer) and a polynucleotide, or a polynucleotide, may vary depending on various factors as, for example, on the desired biological response, the specific allele, genome, target site, cell, or tissue being targeted, and the agent being used.

The term "homologous," as used herein is an art-understood term that refers to nucleic acids or polypeptides that are highly related at the level of nucleotide and/or amino acid sequence. Nucleic acids or polypeptides that are homologous to each other are termed "homologues." Homology between two sequences can be determined by sequence alignment methods known to those of skill in the art. In accordance with the invention, two sequences are considered to be homologous if they are at least about 50-60% identical, e.g., share identical residues (e.g., amino acid residues) in at least about 50-60% of all residues comprised in one or the other sequence, at least about 70% identical, at least about 80% identical, at least about 90% identical, at least about 95% identical, at least about 98% identical, at least about 99% identical, at least about 99.5% identical, or at least about 99.9% identical, for at least one stretch of at least 20, at least 30, at least 40, at least 50, at least 60, at least 70, at least 80, at least 90, at least 100, at least 120, at least 150, or at least 200 amino acids.

The term "linker," as used herein, refers to a chemical group or a molecule linking two adjacent molecules or moieties, e.g., a binding domain (e.g., dCas9) and a cleavage domain of a nuclease (e.g., FokI). In some embodiments, a linker joins a nuclear localization signal (NLS) domain to another protein (e.g., a Cas9 protein or a nuclease or recombinase or a fusion thereof). In some embodiments, a linker joins a gRNA binding domain of an RNA-programmable nuclease and the catalytic domain of a recombinase. In some embodiments, a linker joins a dCas9 and a recombinase. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is a peptide linker. In some embodiments, the peptide linker is any stretch of amino acids having at least 1, at least 2, at least 3, at least 4, at least 5, at least 6, at least 7, at least 8, at least 9, at least 10, at least 15, at least 20, at least 25, at least 30, at least 40, at least 50, or more amino acids. In some embodiments, the peptide linker comprises repeats of the tri-peptide Gly-Gly-Ser, e.g., comprising the sequence $(GGS)_n$, wherein n represents at least 1, 2, 3, 4, 5, 6, 7, 8, 9, 10, or more repeats. In some embodiments, the linker comprises the sequence $(GGS)_6$ (SEQ ID NO:15). In some embodiments, the peptide linker is the 16 residue "XTEN" linker, or a variant thereof (See, e.g., the Examples; and Schellenberger et al. A recombinant polypeptide extends the in vivo half-life of peptides and proteins in a tunable manner. *Nat. Biotechnol.* 27, 1186-1190 (2009)). In some embodiments, the XTEN linker comprises the sequence SGSETPGTSESATPES (SEQ ID NO:16), SGSETPGTSESA (SEQ ID NO:17), or SGSETPGTSESATPEGGSGGS (SEQ ID NO:18). In some embodiments, the peptide linker is any linker as provided in FIG. 12A, for example, one or more selected from VPFLLEPDNINGKTC (SEQ ID NO:19), GSAGSAAGSGEF (SEQ ID NO:20), SIVAQLSRPDPA (SEQ ID NO:21), MKIIEQLPSA (SEQ ID NO:22), VRHKLKRVGS (SEQ ID NO:23), GHGTGSTGSGSS (SEQ ID NO:24), MSRPDPA (SEQ ID NO:25); or GGSM (SEQ ID NO:301).

The term "mutation," as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Various methods for making the amino acid substitutions (mutations) provided herein are well known in the art, and are provided by, for example, Green and Sambrook, *Molecular Cloning: A Laboratory Manual* ($4^{th}$ ed., Cold Spring Harbor Laboratory Press, Cold Spring Harbor, N.Y. (2012)).

The term "nuclease," as used herein, refers to an agent, for example, a protein, capable of cleaving a phosphodiester bond connecting two nucleotide residues in a nucleic acid molecule. In some embodiments, "nuclease" refers to a protein having an inactive DNA cleavage domain, such that the nuclease is incapable of cleaving a phosphodiester bond. In some embodiments, a nuclease is a protein, e.g., an enzyme that can bind a nucleic acid molecule and cleave a phosphodiester bond connecting nucleotide residues within the nucleic acid molecule. A nuclease may be an endonuclease, cleaving a phosphodiester bonds within a polynucleotide chain, or an exonuclease, cleaving a phosphodiester bond at the end of the polynucleotide chain. In some embodiments, a nuclease is a site-specific nuclease, binding and/or cleaving a specific phosphodiester bond within a specific nucleotide sequence, which is also referred to herein as the "recognition sequence," the "nuclease target site," or the "target site." In some embodiments, a nuclease is a RNA-guided (i.e., RNA-programmable) nuclease, which is associated with (e.g., binds to) an RNA (e.g., a guide RNA, "gRNA") having a sequence that complements a target site, thereby providing the sequence specificity of the nuclease. In some embodiments, a nuclease recognizes a single stranded target site, while in other embodiments, a nuclease recognizes a double-stranded target site, for example, a double-stranded DNA target site. The target sites of many naturally occurring nucleases, for example, many naturally occurring DNA restriction nucleases, are well known to those of skill in the art. In many cases, a DNA nuclease, such as EcoRI, HindIII, or BamHI, recognize a palindromic, double-stranded DNA target site of 4 to 10 base pairs in length, and cut each of the two DNA strands at a specific position within the target site. Some endonucleases cut a double-stranded nucleic acid target site symmetrically, i.e., cutting both strands at the same position so that the ends comprise base-paired nucleotides, also referred to herein as blunt ends. Other endonucleases cut a double-stranded nucleic acid target sites asymmetrically, i.e., cutting each strand at a different position so that the ends comprise unpaired nucleotides. Unpaired nucleotides at the end of a double-stranded DNA molecule are also referred to as "overhangs," e.g., as "5'-overhang" or as "3'-overhang," depending on whether the unpaired nucleotide(s) form(s) the 5' or the 5' end of the respective DNA strand. Double-stranded DNA molecule ends ending with unpaired nucleotide(s) are also referred to as sticky ends, as they can "stick to" other double-stranded DNA molecule ends comprising complementary unpaired nucleotide(s). A nuclease protein typically comprises a "binding domain" that mediates the interaction of the protein with the nucleic acid substrate, and also, in some cases, specifically binds to a target site, and a "cleavage domain" that catalyzes the cleavage of the phosphodiester bond within the nucleic acid backbone. In some embodiments a nuclease protein can bind and cleave a nucleic acid molecule in a monomeric form, while, in other embodiments, a nuclease protein has to dimerize or multimerize in order to cleave a target nucleic acid molecule. Binding domains and cleavage domains of naturally occurring nucleases, as well as modular binding domains and cleavage domains that can be fused to create nucleases binding specific target sites, are well known to those of skill in the art. For example, the binding domain of RNA-programmable nucleases (e.g., Cas9), or a Cas9 protein having an inactive DNA cleavage domain, can be used as a binding domain (e.g., that binds a gRNA to direct binding to a target site) to specifically bind a desired target site, and fused or conjugated to a cleavage domain, for example, the cleavage domain of FokI, to create an engineered nuclease cleaving the target site. In some embodiments, Cas9 fusion proteins provided herein comprise the cleavage domain of FokI, and are therefore referred to as "fCas9" proteins. In some embodiments, the cleavage domain of FokI, e.g., in a fCas9 protein corresponds to, or comprises in part or whole, the amino acid sequence (or variants thereof) set forth as SEQ ID NO:6, below. In some embodiments, variants or homologues of the FokI cleavage domain include any variant or homologue capable of dimerizing (e.g., as part of fCas9 fusion protein) with another FokI cleavage domain at a target site in a target nucleic acid, thereby resulting in cleavage of the target nucleic acid. In some embodiments, variants of the FokI cleavage domain (e.g., variants of SEQ ID NO:6) are provided which are at least about 70% identical, at least about 80% identical, at least about 90% identical, at least about 95% identical, at least about 98% identical, at least about 99% identical, at least about 99.5% identical, or at least about 99.9% to SEQ ID NO:6. In some embodiments, variants of the FokI cleavage domain (e.g., variants of SEQ ID NO:6) are provided having an amino acid sequence which is shorter, or longer than SEQ ID NO:6, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids or more.

Cleavage Domain of FokI:

```
                                           (SEQ ID NO: 6)
GSQLVKSELEEKKSELRHKLKYVPHEYIELIEIARNSTQDRILEMKVMEF

FMKVYGYRGKHLGGSRKPDGAIYTVGSPIDYGVIVDTKAYSGGYNLPIGQ

ADEMQRYVEENQTRNKHINPNEWWKVYPSSVTEFKFLFVSGHFKGNYKAQ

LTRLNHITNCNGAVLSVEELLIGGEMIKAGTLTLEEVRRKFNNGEINF
```

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, gRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadeno sine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term "pharmaceutical composition," as used herein, refers to a composition that can be administrated to a subject in the context of treatment and/or prevention of a disease or disorder. In some embodiments, a pharmaceutical composition comprises an active ingredient, e.g., a nuclease or recombinase fused to a Cas9 protein, or fragment thereof (or a nucleic acid encoding a such a fusion), and optionally a pharmaceutically acceptable excipient. In some embodiments, a pharmaceutical composition comprises inventive Cas9 variant/fusion (e.g., fCas9) protein(s) and gRNA(s) suitable for targeting the Cas9 variant/fusion protein(s) to a target nucleic acid. In some embodiments, the target nucleic acid is a gene. In some embodiments, the target nucleic acid is an allele associated with a disease, whereby the allele is cleaved by the action of the Cas9 variant/fusion protein(s). In some embodiments, the allele is an allele of the CLTA gene, the EMX gene, the HBB gene, the VEGF gene, or the CCR5 gene. See e.g., the Examples; FIGS. 7, 8, 13, 14, 15, 17 and 19.

The term "proliferative disease," as used herein, refers to any disease in which cell or tissue homeostasis is disturbed in that a cell or cell population exhibits an abnormally elevated proliferation rate. Proliferative diseases include hyperproliferative diseases, such as pre-neoplastic hyperplastic conditions and neoplastic diseases. Neoplastic diseases are characterized by an abnormal proliferation of cells and include both benign and malignant neoplasias. Malignant neoplasia is also referred to as cancer. In some embodiments, the compositions and methods provided herein are useful for treating a proliferative disease. For example, in some embodiments, pharmaceutical compositions comprising Cas9 (e.g., fCas9) protein(s) and gRNA(s) suitable for targeting the Cas9 protein(s) to an VEGF allele, whereby the allele is inactivated by the action of the Cas9 protein(s). See, e.g., the Examples.

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. The term "fusion protein" as used herein refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* ($4^{th}$ ed., Cold Spring Harbor Laboratory Press, Cold Spring Harbor, N.Y. (2012)), the entire contents of which are incorporated herein by reference.

The term "RNA-programmable nuclease," and "RNA-guided nuclease" are used interchangeably herein and refer to a nuclease that forms a complex with (e.g., binds or associates with) one or more RNA that is not a target for cleavage. In some embodiments, an RNA-programmable nuclease, when in a complex with an RNA, may be referred to as a nuclease: RNA complex. Typically, the bound RNA(s) is referred to as a guide RNA (gRNA). gRNAs can exist as a complex of two or more RNAs, or as a single RNA molecule. gRNAs that exist as a single RNA molecule may be referred to as single-guide RNAs (sgRNAs), though "gRNA" is used interchangeabley to refer to guide RNAs that exist as either single molecules or as a complex of two or more molecules. Typically, gRNAs that exist as single RNA species comprise two domains: (1) a domain that shares homology to a target nucleic acid (e.g., and directs binding of a Cas9 complex to the target); and (2) a domain that binds a Cas9 protein. In some embodiments, domain (2) corresponds to a sequence known as a tracrRNA, and comprises a stem-loop structure. For example, in some embodiments, domain (2) is homologous to a tracrRNA as depicted in FIG. 1E of Jinek et al., *Science* 337:816-821 (2012), the entire contents of which is incorporated herein by reference. Other examples of gRNAs (e.g., those including domain 2) can be found in U.S. Provisional Patent Application, U.S. Ser. No. 61/874,682, filed Sep. 6, 2013, entitled "Switchable Cas9 Nucleases And Uses Thereof;" U.S. Provisional Patent Application, U.S. Ser. No. 61/874,746, filed Sep. 6, 2013, entitled "Delivery System For Functional Nucleases;" PCT Application WO 2013/176722, filed Mar. 15, 2013, entitled "Methods and Compositions for RNA-Directed Target DNA Modification and for RNA-Directed Modulation of Transcription;" and PCT Application WO 2013/142578, filed Mar. 20, 2013, entitled "RNA-Directed DNA Cleavage by the Cas9-crRNA Complex;" the entire contents of each are hereby incorporated by reference in their entirety. Still other examples of gRNAs and gRNA structure are provided herein. See e.g., the Examples. In some embodiments, a gRNA comprises two or more of domains (1) and (2), and may be referred to as an "extended gRNA." For example, an extended gRNA will e.g., bind two or more Cas9 proteins and bind a target nucleic acid at two or more distinct regions, as described herein. The gRNA comprises a nucleotide sequence that complements a target site, which mediates binding of the nuclease/RNA complex to said target site, providing the sequence specificity of the nuclease:RNA complex. In some embodiments, the RNA-programmable nuclease is the (CRISPR-associated system) Cas9 endonuclease, for example Cas9 (Csn1) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663 (2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607 (2011); and "A programmable dual-RNA-guided DNA endonuclease in adaptive bacterial immunity." Jinek M., Chylinski K., Fonfara I., Hauer M., Doudna J. A., Charpentier E. Science 337:816-821 (2012), the entire contents of each of which are incorporated herein by reference.

Because RNA-programmable nucleases (e.g., Cas9) use RNA:DNA hybridization to determine target DNA cleavage sites, these proteins are able to cleave, in principle, any sequence specified by the guide RNA. Methods of using RNA-programmable nucleases, such as Cas9, for site-specific cleavage (e.g., to modify a genome) are known in the art (see e.g., Cong, L. et al. Multiplex genome engineering using CRISPR/Cas systems. *Science* 339, 819-823 (2013); Mali, P. et al. RNA-guided human genome engineering via Cas9. *Science* 339, 823-826 (2013); Hwang, W. Y. et al. Efficient genome editing in zebrafish using a CRISPR-Cas system. *Nature biotechnology* 31, 227-229 (2013); Jinek, M. et al. RNA-programmed genome editing in human cells. *eLife* 2, e00471 (2013); Dicarlo, J. E. et al. Genome engineering in *Saccharomyces cerevisiae* using CRISPR-Cas systems. Nucleic acids research (2013); Jiang, W. et al. RNA-guided editing of bacterial genomes using CRISPR-Cas systems. *Nature biotechnology* 31, 233-239 (2013); the entire contents of each of which are incorporated herein by reference).

The term "recombinase," as used herein, refers to a site-specific enzyme that mediates the recombination of DNA between recombinase recognition sequences, which results in the excision, integration, inversion, or exchange (e.g., translocation) of DNA fragments between the recombinase recognition sequences. Recombinases can be classified into two distinct families: serine recombinases (e.g., resolvases and invertases) and tyrosine recombinases (e.g., integrases). Examples of serine recombinases include, without limitation, Hin, Gin, Tn3, β-six, CinH, ParA, γδ, Bxb1, ϕC31, TP901, TG1, ϕBT1, R4, ϕRV1, ϕFC1, MR11, A118, U153, and gp29. Examples of tyrosine recombinases include, without limitation, Cre, FLP, R, Lambda, HK101, HK022, and pSAM2. The serine and tyrosine recombinase names stem from the conserved nucleophilic amino acid residue that the recombinase uses to attack the DNA and which becomes covalently linked to the DNA during strand exchange. Recombinases have numerous applications, including the creation of gene knockouts/knock-ins and gene therapy applications. See, e.g., Brown et al., "Serine recombinases as tools for genome engineering." *Methods.* 2011; 53(4):372-9; Hirano et al., "Site-specific recombinases as tools for heterologous gene integration." *Appl. Microbiol. Biotechnol.* 2011; 92(2):227-39; Chavez and Calos, "Therapeutic applications of the ΦC31 integrase system." *Curr. Gene Ther.* 2011; 11(5):375-81; Turan and Bode, "Site-specific recombinases: from tag-and-target- to tag-and-exchange-based genomic modifications." *FASEB J.* 2011; 25(12):4088-107; Venken and Bellen, "Genome-wide manipulations of *Drosophila melanogaster* with transposons, Flp recombinase, and ΦC31 integrase." *Methods Mol. Biol.* 2012; 859:203-28; Murphy, "Phage recombinases and their applications." *Adv. Virus Res.* 2012; 83:367-414; Zhang et al., "Conditional gene manipulation: Creating a new biological era." *J. Zhejiang Univ. Sci. B.* 2012; 13(7):511-24; Karpenshif and Bernstein, "From yeast to mammals: recent advances in genetic control of homologous recombination." *DNA Repair* (*Amst*). 2012; 1; 11(10):781-8; the entire contents of each are hereby incorporated by reference in their entirety. The recombinases provided herein are not meant to be exclusive examples of recombinases that can be used in embodiments of the invention. The methods and compositions of the invention can be expanded by mining databases for new orthogonal recombinases or designing synthetic recombinases with defined DNA specificities (See, e.g., Groth et al., "Phage integrases: biology and applications." *J. Mol. Biol.* 2004; 335, 667-678; Gordley et al., "Synthesis of programmable integrases." *Proc. Natl. Acad. Sci. USA.* 2009; 106, 5053-5058; the entire contents of each are hereby incorporated by reference in their entirety). Other examples of recombinases that are useful in the methods and compositions described herein are known to those of skill in the art, and any new recombinase that is discovered or generated is expected to be able to be used in the different embodiments of the invention. In some embodiments, the catalytic domains of a recombinase are fused to a nuclease-inactivated RNA-programmable nuclease (e.g., dCas9, or a fragment thereof), such that the recombinase domain does not comprise a nucleic acid binding domain or is unable to bind to a target nucleic acid (e.g., the recombinase domain is engineered such that it does not have specific DNA binding activity). Recombinases lacking DNA binding activity and methods for engineering such are known, and include those described by Klippel et al., "Isolation and characterisation of unusual gin mutants." *EMBO J.* 1988; 7: 3983-3989: Burke et al., "Activating mutations of Tn3 resolvase marking interfaces important in recombination catalysis and its regulation. *Mol Microbiol.* 2004; 51: 937-948; Olorunniji et al., "Synapsis and catalysis by activated Tn3 resolvase mutants." *Nucleic Acids Res.* 2008; 36: 7181-7191; Rowland et al., "Regulatory mutations in Sin recombinase support a structure-based model of the synaptosome." *Mol Microbiol.* 2009; 74: 282-298; Akopian et al., "Chimeric recombinases with designed DNA sequence recognition." *Proc Natl Acad Sci USA.* 2003; 100: 8688-8691; Gordley et al., "Evolution of programmable zinc finger-recombinases with activity in human cells. *J Mol Biol.* 2007; 367: 802-813; Gordley et al., "Synthesis of programmable integrases." *Proc Natl Acad Sci USA.* 2009; 106: 5053-5058; Arnold et al., "Mutants of Tn3 resolvase which do not require accessory binding sites for recombination activity." *EMBO J.* 1999; 18: 1407-1414; Gaj et al., "Structure-guided reprogramming of serine recombinase DNA sequence specificity." *Proc Natl Acad Sci USA.* 2011; 108(2):498-503; and Proudfoot et al., "Zinc finger recombinases with adaptable DNA sequence specificity." *PLoS One.* 2011; 6(4): e19537; the entire contents of each are hereby incorporated by reference. For example, serine recombinases of the resolvase-invertase group, e.g., Tn3 and γδ resolvases and the Hin and Gin invertases, have modular structures with autonomous catalytic and DNA-binding domains (See, e.g., Grindley et al., "Mechanism of site-specific recombination." *Ann Rev Biochem.* 2006; 75: 567-605, the entire contents of which are incorporated by reference). The catalytic domains of these recombinases are thus amenable to being recombined with nuclease-inactivated RNA-programmable nucleases (e.g., dCas9, or a fragment thereof) as described herein, e.g., following the isolation of 'activated' recombinase mutants which do not require any accessory factors (e.g., DNA binding activities) (See, e.g., Klippel et al., "Isolation and characterisation of unusual gin mutants." *EMBO J.* 1988; 7: 3983-3989: Burke et al., "Activating mutations of Tn3 resolvase marking interfaces important in recombination catalysis and its regulation. *Mol Microbiol.* 2004; 51: 937-948; Olorunniji et al., "Synapsis and catalysis by activated Tn3 resolvase mutants." *Nucleic Acids Res.* 2008; 36: 7181-7191; Rowland et al., "Regulatory mutations in Sin recombinase support a structure-based model of the synaptosome." *Mol Microbiol.* 2009; 74: 282-298; Akopian et al., "Chimeric recombinases with designed DNA sequence recognition." *Proc Natl Acad Sci USA.* 2003; 100: 8688-8691). Additionally, many other natural serine recombinases having an N-terminal catalytic domain and a C-terminal DNA binding domain are known (e.g., phiC31 integrase, TnpX transposase, IS607 transposase), and their catalytic domains can be co-opted to engineer programmable site-specific recombinases as described herein (See, e.g., Smith et al., "Diversity in the serine recombinases." *Mol Microbiol.* 2002; 44: 299-307, the entire contents of which are incorporated by reference). Similarly, the core catalytic domains of tyrosine recombinases (e.g., Cre, λ integrase) are known, and can be similarly co-opted to engineer programmable site-specific recombinases as described herein (See, e.g., Guo et al., "Structure of Cre recombinase complexed with DNA in a site-specific recombination synapse." *Nature.* 1997; 389:40-46; Hartung et al., "Cre mutants with altered DNA binding properties." *J Biol Chem* 1998; 273:22884-22891; Shaikh et al., "Chimeras of the Flp and Cre recombinases: Tests of the mode of cleavage by Flp and Cre. *J Mol Biol.* 2000; 302:27-48; Rongrong et al., "Effect of deletion mutation on the recombination activity of Cre recombinase." *Acta Biochim Pol.* 2005; 52:541-544; Kilbride et al., "Determinants of product topology in a hybrid Cre-Tn3 resolvase site-specific recombination system." *J Mol Biol.* 2006; 355:185-195; Warren et al., "A chimeric cre recombinase with regulated directionality." *Proc Natl Acad Sci USA.* 2008 105:18278-18283; Van Duyne, "Teaching Cre to follow directions." *Proc Natl Acad Sci USA.* 2009 Jan. 6; 106(1):4-5; Numrych et al., "A comparison of the effects of single-base and triple-base changes in the integrase arm-type binding sites on the site-specific recombination of bacteriophage λ." *Nucleic Acids Res.* 1990; 18:3953-3959; Tirumalai et al., "The recognition of core-type DNA sites by λ integrase." *J Mol Biol.* 1998; 279:513-527; Aihara et al., "A conformational switch controls the DNA cleavage activity of λ integrase." *Mol Cell.* 2003; 12:187-198; Biswas et al., "A structural basis for allosteric control of DNA recombination by λ integrase." *Nature.* 2005; 435:1059-1066; and Warren et al., "Mutations in the amino-terminal domain of λ-integrase have differential effects on integrative and excisive recombination." *Mol Microbiol.* 2005; 55:1104-1112; the entire contents of each are incorporated by reference).

The term "recombine," or "recombination," in the context of a nucleic acid modification (e.g., a genomic modification), is used to refer to the process by which two or more nucleic acid molecules, or two or more regions of a single nucleic acid molecule, are modified by the action of a recombinase protein (e.g., an inventive recombinase fusion protein provided herein). Recombination can result in, inter alia, the insertion, inversion, excision or translocation of nucleic acids, e.g., in or between one or more nucleic acid molecules.

The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development.

The terms "target nucleic acid," and "target genome," as used herein in the context of nucleases, refer to a nucleic acid molecule or a genome, respectively, that comprises at least one target site of a given nuclease. In the context of fusions comprising a (nuclease-inactivated) RNA-programmable nuclease and a recombinase domain, a "target nucleic acid" and a "target genome" refers to one or more nucleic acid molecule(s), or a genome, respectively, that comprises at least one target site. In some embodiments, the target nucleic acid(s) comprises at least two, at least three, or at least four target sites. In some embodiments, the target nucleic acid(s) comprise four target sites.

The term "target site" refers to a sequence within a nucleic acid molecule that is either (1) bound and cleaved by a nuclease (e.g., Cas9 fusion proteins provided herein), or (2) bound and recombined (e.g., at or nearby the target site) by a recombinase (e.g., a dCas9-recombinase fusion protein provided herein). A target site may be single-stranded or double-stranded. In the context of RNA-guided (e.g., RNA-programmable) nucleases (e.g., a protein dimer comprising a Cas9 gRNA binding domain and an active Cas9 DNA cleavage domain or other nuclease domain such as FokI), a target site typically comprises a nucleotide sequence that is complementary to the gRNA(s) of the RNA-programmable nuclease, and a protospacer adjacent motif (PAM) at the 3' end adjacent to the gRNA-complementary sequence(s). In some embodiments, such as those involving fCas9, a target site can encompass the particular sequences to which fCas9 monomers bind, and/or the intervening sequence between the bound monomers that are cleaved by the dimerized FokI domains (See e.g., the Examples; and FIGS. 1A, 6D). In the context of fusions between RNA-guided (e.g., RNA-programmable, nuclease-inactivated) nucleases and a recombinase (e.g., a catalytic domain of a recombinase), a target site typically comprises a nucleotide sequence that is complementary to the gRNA of the RNA-programmable nuclease domain, and a protospacer adjacent motif (PAM) at the 3' end adjacent to the gRNA-complementary sequence. For example, in some embodiments, four recombinase monomers are coordinated to recombine a target nucleic acid(s), each monomer being fused to a (nuclease-inactivated) Cas9 protein guided by a gRNA. In such an example, each Cas9 domain is guided by a distinct gRNA to bind a target nucleic acid(s), thus the target nucleic acid comprises four target sites, each site targeted by a separate dCas9-recombinase fusion (thereby coordinating four recombinase monomers which recombine the target nucleic acid(s)). For the RNA-guided nuclease Cas9 (or gRNA-binding domain thereof) and inventive fusions of Cas9, the target site may be, in some embodiments, 17-20 base pairs plus a 3 base pair PAM (e.g., NNN, wherein N independently represents any nucleotide). Typically, the first nucleotide of a PAM can be any nucleotide, while the two downstream nucleotides are specified depending on the specific RNA-guided nuclease. Exemplary target sites (e.g., comprising a PAM) for RNA-guided nucleases, such as Cas9, are known to those of skill in the art and include, without limitation, NNG, NGN, NAG, and NGG, wherein N independently represents any nucleotide. In addition, Cas9 nucleases from different species (e.g., *S. thermophilus* instead of *S. pyogenes*) recognizes a PAM that comprises the sequence NGGNG. Additional PAM sequences are known, including, but not limited to, NNAGAAW and NAAR (see, e.g., Esvelt and Wang, Molecular Systems Biology, 9:641 (2013), the entire contents of which are incorporated herein by reference). In some aspects, the target site of an RNA-guided nuclease, such as, e.g., Cas9, may comprise the structure [$N_z$]-[PAM], where each N is, independently, any nucleotide, and z is an integer between 1 and 50, inclusive. In some embodiments, z is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50. In some embodiments, z is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, z is 20. In some embodiments, "target site" may also refer to a sequence within a nucleic acid molecule that is bound but not cleaved by a nuclease. For example, certain embodiments described herein provide proteins comprising an inactive (or inactivated) Cas9 DNA cleavage domain. Such proteins (e.g., when also including a Cas9 RNA binding domain) are able to bind the target site specified by the gRNA; however, because the DNA cleavage site is inactivated, the target site is not cleaved by the particular protein. However, such proteins as described herein are typically conjugated, fused, or bound to another protein (e.g., a nuclease) or molecule that mediates cleavage of the nucleic acid molecule. In other embodiments, such proteins are conjugated, fused, or bound to a recombinase (or a catalytic domain of a recombinase), which mediates recombination of the target nucleic acid. In some embodiments, the sequence actually cleaved or recombined will depend on the protein (e.g., nuclease or recombinase) or molecule that mediates cleavage or recombination of the nucleic acid molecule, and in some cases, for example, will relate to the proximity or distance from which the inactivated Cas9 protein(s) is/are bound.

In the context of inventive proteins that dimerize (or multimerize), for example, dimers of a protein comprising a nuclease-inactivated Cas9 (or a Cas9 RNA binding domain) and a DNA cleavage domain (e.g., FokI cleavage domain or an active Cas9 cleavage domain), or fusions between a nuclease-inactivated Cas9 (or a Cas9 gRNA binding domain) and a recombinase (or catalytic domain of a recombinase), a target site typically comprises a left-half site (bound by one protein), a right-half site (bound by the second protein), and a spacer sequence between the half sites in which the cut or recombination is made. In some embodiments, either the left-half site or the right half-site (and not the spacer sequence) is cut or recombined. In other embodiments, the spacer sequence is cut or recombined. This structure ([left-half site]-[spacer sequence]-[right-half site]) is referred to herein as an LSR structure. In some embodiments, the left-half site and/or the right-half site correspond to an RNA-guided target site (e.g., a Cas9 target site). In some embodiments, either or both half-sites are shorter or longer than e.g., a typical region targeted by Cas9, for example shorter or longer than 20 nucleotides. In some embodiments, the left and right half sites comprise different nucleic acid sequences. In some embodiments involving inventive nucleases, the target site is a sequence comprising three (3) RNA-guided nuclease target site sequences, for example, three sequences corresponding to Cas9 target site sequences (See, e.g., FIG. 2C), in which the first and second, and second and third Cas9 target site sequences are separated by a spacer sequence. In some embodiments, the spacer sequence is at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 60, at least 70, at least 80, at least 90, at least 100, at least 125, at least 150, at least 175, at least 200, or at least 250 bp long. In some embodiments, the spacer sequence is between approximately 15 bp and approximately 25 bp long. In some embodiments, the spacer sequence is approximately 15 bp long. In some embodiments, the spacer sequence is approximately 25 bp long.

The term "Transcriptional Activator-Like Effector," (TALE) as used herein, refers to bacterial proteins comprising a DNA binding domain, which contains a highly conserved 33-34 amino acid sequence comprising a highly variable two-amino acid motif (Repeat Variable Diresidue, RVD). The RVD motif determines binding specificity to a nucleic acid sequence and can be engineered according to methods known to those of skill in the art to specifically bind a desired DNA sequence (see, e.g., Miller, Jeffrey; et. al. (February 2011). "A TALE nuclease architecture for efficient genome editing". *Nature Biotechnology* 29 (2): 143-8; Zhang, Feng; et. al. (February 2011). "Efficient construction of sequence-specific TAL effectors for modulating mammalian transcription" *Nature Biotechnology* 29 (2): 149-53; Geiβler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". *PLoS ONE* 6 (5): e19509; Boch, Jens (February 2011). "TALEs of genome targeting". *Nature Biotechnology* 29 (2): 135-6; Boch, Jens; et. al. (December 2009). "Breaking the Code of DNA Binding Specificity of TAL-Type III Effectors". *Science* 326 (5959): 1509-12; and Moscou, Matthew J.; Adam J. Bogdanove (December 2009). "A Simple Cipher Governs DNA Recognition by TAL Effectors" *Science* 326 (5959): 1501; the entire contents of each of which are incorporated herein by reference). The simple relationship between amino acid sequence and DNA recognition has allowed for the engineering of specific DNA binding domains by selecting a combination of repeat segments containing the appropriate RVDs.

The term "Transcriptional Activator-Like Element Nuclease," (TALEN) as used herein, refers to an artificial nuclease comprising a transcriptional activator-like effector DNA binding domain to a DNA cleavage domain, for example, a FokI domain. A number of modular assembly schemes for generating engineered TALE constructs have been reported (see e.g., Zhang, Feng; et. al. (February 2011). "Efficient construction of sequence-specific TAL effectors for modulating mammalian transcription". *Nature Biotechnology* 29 (2): 149-53; Geiβler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". *PLoS ONE* 6 (5): e19509; Cermak, T.; Doyle, E. L.; Christian, M.; Wang, L.; Zhang, Y.; Schmidt, C.; Baller, J. A.; Somia, N. V. et al.

(2011). “Efficient design and assembly of custom TALEN and other TAL effector-based constructs for DNA targeting”. *Nucleic Acids Research*; Morbitzer, R.; Elsaesser, J.; Hausner, J.; Lahaye, T. (2011). “Assembly of custom TALE-type DNA binding domains by modular cloning”. *Nucleic Acids Research*; Li, T.; Huang, S.; Zhao, X.; Wright, D. A.; Carpenter, S.; Spalding, M. H.; Weeks, D. P.; Yang, B. (2011). “Modularly assembled designer TAL effector nucleases for targeted gene knockout and gene replacement in eukaryotes”. *Nucleic Acids Research*.; Weber, E.; Gruetzner, R.; Werner, S.; Engler, C.; Marillonnet, S. (2011). Bendahmane, Mohammed. ed. “Assembly of Designer TAL Effectors by Golden Gate Cloning”. *PLoS ONE* 6 (5): e19722; the entire contents of each of which are incorporated herein by reference).

The terms “treatment,” “treat,” and “treating,” refer to a clinical intervention aimed to reverse, alleviate, delay the onset of, or inhibit the progress of a disease or disorder, or one or more symptoms thereof, as described herein. As used herein, the terms “treatment,” “treat,” and “treating” refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

The term “vector” refers to a polynucleotide comprising one or more recombinant polynucleotides of the present invention, e.g., those encoding a Cas9 protein (or fusion thereof) and/or gRNA provided herein. Vectors include, but are not limited to, plasmids, viral vectors, cosmids, artificial chromosomes, and phagemids. The vector is able to replicate in a host cell and is further characterized by one or more endonuclease restriction sites at which the vector may be cut and into which a desired nucleic acid sequence may be inserted. Vectors may contain one or more marker sequences suitable for use in the identification and/or selection of cells which have or have not been transformed or genomically modified with the vector. Markers include, for example, genes encoding proteins which increase or decrease either resistance or sensitivity to antibiotics (e.g., kanamycin, ampicillin) or other compounds, genes which encode enzymes whose activities are detectable by standard assays known in the art (e.g., β-galactosidase, alkaline phosphatase, or luciferase), and genes which visibly affect the phenotype of transformed or transfected cells, hosts, colonies, or plaques. Any vector suitable for the transformation of a host cell (e.g., *E. coli*, mammalian cells such as CHO cell, insect cells, etc.) as embraced by the present invention, for example, vectors belonging to the pUC series, pGEM series, pET series, pBAD series, pTET series, or pGEX series. In some embodiments, the vector is suitable for transforming a host cell for recombinant protein production. Methods for selecting and engineering vectors and host cells for expressing proteins (e.g., those provided herein), transforming cells, and expressing/purifying recombinant proteins are well known in the art, and are provided by, for example, Green and Sambrook, *Molecular Cloning: A Laboratory Manual* ($4^{th}$ ed., Cold Spring Harbor Laboratory Press, Cold Spring Harbor, N.Y. (2012)).

The term “zinc finger,” as used herein, refers to a small nucleic acid-binding protein structural motif characterized by a fold and the coordination of one or more zinc ions that stabilize the fold. Zinc fingers encompass a wide variety of differing protein structures (see, e.g., Klug A, Rhodes D (1987). “Zinc fingers: a novel protein fold for nucleic acid recognition”. *Cold Spring Harb. Symp. Quant. Biol.* 52: 473-82, the entire contents of which are incorporated herein by reference). Zinc fingers can be designed to bind a specific sequence of nucleotides, and zinc finger arrays comprising fusions of a series of zinc fingers, can be designed to bind virtually any desired target sequence. Such zinc finger arrays can form a binding domain of a protein, for example, of a nuclease, e.g., if conjugated to a nucleic acid cleavage domain. Different types of zinc finger motifs are known to those of skill in the art, including, but not limited to, $Cys_2His_2$, Gag knuckle, Treble clef, Zinc ribbon, $Zn_2/Cys_6$, and TAZ2 domain-like motifs (see, e.g., Krishna S S, Majumdar I, Grishin N V (January 2003). “Structural classification of zinc fingers: survey and summary”. *Nucleic Acids Res.* 31 (2): 532-50). Typically, a single zinc finger motif binds 3 or 4 nucleotides of a nucleic acid molecule. Accordingly, a zinc finger domain comprising 2 zinc finger motifs may bind 6-8 nucleotides, a zinc finger domain comprising 3 zinc finger motifs may bind 9-12 nucleotides, a zinc finger domain comprising 4 zinc finger motifs may bind 12-16 nucleotides, and so forth. Any suitable protein engineering technique can be employed to alter the DNA-binding specificity of zinc fingers and/or design novel zinc finger fusions to bind virtually any desired target sequence from 3-30 nucleotides in length (see, e.g., Pabo C O, Peisach E, Grant R A (2001). “Design and selection of novel cys2His2 Zinc finger proteins”. *Annual Review of Biochemistry* 70: 313-340; Jamieson A C, Miller J C, Pabo C O (2003). “Drug discovery with engineered zinc-finger proteins”. *Nature Reviews Drug Discovery* 2 (5): 361-368; and Liu Q, Segal D J, Ghiara J B, Barbas C F (May 1997). “Design of polydactyl zinc-finger proteins for unique addressing within complex genomes”. *Proc. Natl. Acad. Sci. U.S.A.* 94 (11); the entire contents of each of which are incorporated herein by reference). Fusions between engineered zinc finger arrays and protein domains that cleave a nucleic acid can be used to generate a “zinc finger nuclease.” A zinc finger nuclease typically comprises a zinc finger domain that binds a specific target site within a nucleic acid molecule, and a nucleic acid cleavage domain that cuts the nucleic acid molecule within or in proximity to the target site bound by the binding domain. Typical engineered zinc finger nucleases comprise a binding domain having between 3 and 6 individual zinc finger motifs and binding target sites ranging from 9 base pairs to 18 base pairs in length. Longer target sites are particularly attractive in situations where it is desired to bind and cleave a target site that is unique in a given genome.

The term “zinc finger nuclease,” as used herein, refers to a nuclease comprising a nucleic acid cleavage domain conjugated to a binding domain that comprises a zinc finger array. In some embodiments, the cleavage domain is the cleavage domain of the type II restriction endonuclease FokI. Zinc finger nucleases can be designed to target virtually any desired sequence in a given nucleic acid molecule for cleavage, and the possibility to design zinc finger binding domains to bind unique sites in the context of complex genomes allows for targeted cleavage of a single genomic site in living cells, for example, to achieve a targeted genomic alteration of therapeutic value. Targeting a double-strand break to a desired genomic locus can be used to introduce frame-shift mutations into the coding sequence of a gene due to the error-prone nature of the non-homologous DNA repair pathway. Zinc finger nucleases can be generated to target a site of interest by methods well known to those of skill in the art. For example, zinc finger binding domains with a desired specificity can be designed by combining individual zinc finger motifs of known specificity. The structure of the zinc finger protein Zif268 bound to DNA has informed much of the work in this field and the concept of obtaining zinc fingers for each of the 64 possible base pair triplets and then mixing and matching these modular zinc fingers to design proteins with any desired sequence specificity has been described (Pavletich N P, Pabo C O (May 1991). "Zinc finger-DNA recognition: crystal structure of a Zif268-DNA complex at 2.1 A". *Science* 252 (5007): 809-17, the entire contents of which are incorporated herein). In some embodiments, separate zinc fingers that each recognizes a 3 base pair DNA sequence are combined to generate 3-, 4-, 5-, or 6-finger arrays that recognize target sites ranging from 9 base pairs to 18 base pairs in length. In some embodiments, longer arrays are contemplated. In other embodiments, 2-finger modules recognizing 6-8 nucleotides are combined to generate 4-, 6-, or 8-zinc finger arrays. In some embodiments, bacterial or phage display is employed to develop a zinc finger domain that recognizes a desired nucleic acid sequence, for example, a desired nuclease target site of 3-30 bp in length. Zinc finger nucleases, in some embodiments, comprise a zinc finger binding domain and a cleavage domain fused or otherwise conjugated to each other via a linker, for example, a polypeptide linker. The length of the linker determines the distance of the cut from the nucleic acid sequence bound by the zinc finger domain. If a shorter linker is used, the cleavage domain will cut the nucleic acid closer to the bound nucleic acid sequence, while a longer linker will result in a greater distance between the cut and the bound nucleic acid sequence. In some embodiments, the cleavage domain of a zinc finger nuclease has to dimerize in order to cut a bound nucleic acid. In some such embodiments, the dimer is a heterodimer of two monomers, each of which comprise a different zinc finger binding domain. For example, in some embodiments, the dimer may comprise one monomer comprising zinc finger domain A conjugated to a FokI cleavage domain, and one monomer comprising zinc finger domain B conjugated to a FokI cleavage domain. In this non-limiting example, zinc finger domain A binds a nucleic acid sequence on one side of the target site, zinc finger domain B binds a nucleic acid sequence on the other side of the target site, and the dimerize FokI domain cuts the nucleic acid in between the zinc finger domain binding sites.

DETAILED DESCRIPTION OF CERTAIN EMBODIMENTS OF THE INVENTION

Site-specific nucleases and site-specific recombinases are powerful tools for targeted genome modification in vitro and in vivo. It has been reported that nuclease cleavage in living cells triggers a DNA repair mechanism that frequently results in a modification of the cleaved and repaired genomic sequence, for example, via homologous recombination. Accordingly, the targeted cleavage of a specific unique sequence within a genome opens up new avenues for gene targeting and gene modification in living cells, including cells that are hard to manipulate with conventional gene targeting methods, such as many human somatic or embryonic stem cells. Another approach utilizes site-specific recombinases, which possess all the functionality required to bring about efficient, precise integration, deletion, inversion, or translocation of specified DNA segments.

Nuclease-mediated modification of disease-related sequences, e.g., the CCR-5 allele in HIV/AIDS patients, or of genes necessary for tumor neovascularization, can be used in the clinical context, and two site specific nucleases are currently in clinical trials (Perez, E. E. et al., "Establishment of HIV-1 resistance in CD4+ T cells by genome editing using zinc-finger nucleases." *Nature biotechnology.* 26, 808-816 (2008); ClinicalTrials.gov identifiers: NCT00842634, NCT01044654, NCT01252641, NCT01082926). Accordingly, nearly any genetic disease can be treated using site-specific nucleases and/or recombinases and include, for example, diseases associated with triplet expansion (e.g., Huntington's disease, myotonic dystrophy, spinocerebellar ataxias, etc.), cystic fibrosis (by targeting the CFTR gene), hematological disease (e.g., hemoglobinopathies), cancer, autoimmune diseases, and viral infections. Other diseases that can be treated using the inventive compositions and/or methods provided herein include, but are not limited to, achondroplasia, achromatopsia, acid maltase deficiency, adenosine deaminase deficiency, adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the 6th codon of beta-globin (HbC), hemophilia, Hurler Syndrome, hypophosphatasia, Klinefleter syndrome, Krabbes Disease, Langer-Giedion Syndrome, leukocyte adhesion deficiency (LAD), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, *Proteus* syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, and X-linked lymphoproliferative syndrome (XLP).

One aspect of site-specific genomic modification is the possibility of off-target nuclease or recombinase effects, e.g., the cleavage or recombination of genomic sequences that differ from the intended target sequence by one or more nucleotides. Undesired side effects of off-target cleavage/recombination range from insertion into unwanted loci during a gene targeting event to severe complications in a clinical scenario. Off-target cleavage or recombination of sequences encoding essential gene functions or tumor suppressor genes by an endonuclease or recombinase administered to a subject may result in disease or even death of the subject. Accordingly, it is desirable to employ new strategies in designing nucleases and recombinases having the greatest chance of minimizing off-target effects.

The methods and compositions of the present disclosure represent, in some aspects, an improvement over previous methods and compositions providing nucleases (and methods of their use) and recombinases (and methods of their use) engineered to have improved specificity for their intended targets. For example, nucleases and recombinases known in the art, both naturally occurring and those engineered, typically have a target (e.g., DNA) binding domain that recognizes a particular sequence. Additionally, known nucleases and recombinases may comprise a DNA binding domain and a catalytic domain in a single protein capable of inducing cleavage or recombination, and as such the chance for off-target effects are increased as cleavage or recombination likely occurs upon off-target binding of the nuclease or recombinase, respectively. Aspects of the present invention relate to the recognition that increasing the number of sequences (e.g., having a nuclease bind at more than one site at a desired target), and/or splitting the activities (e.g., target binding and target cleaving) of a nuclease between two or more proteins, will increase the specificity of a nuclease and thereby decrease the likelihood of off-target effects. Other aspects of the present invention relate to the recognition that fusions between the catalytic domain of recombinases (or recombinases having inactive DNA binding domains) and nuclease-inactivated RNA-programmable nucleases allow for the targeted recombination of DNA at any location.

In the context of site-specific nucleases, the strategies, methods, compositions, and systems provided herein can be utilized to improve the specificity of any site-specific nuclease, for example, variants of the Cas9 endonuclease, Zinc Finger Nucleases (ZFNs) and Transcription Activator-Like Effector Nucleases (TALENs). Suitable nucleases for modification as described herein will be apparent to those of skill in the art based on this disclosure.

In certain embodiments, the strategies, methods, compositions, and systems provided herein are utilized to improve the specificity of the RNA-guided (e.g., RNA-programmable) endonuclease Cas9. Whereas typical endonucleases recognize and cleave a single target sequence, Cas9 endonuclease uses RNA:DNA hybridization to determine target DNA cleavage sites, enabling a single monomeric protein to cleave, in principle, any sequence specified by the guide RNA (gRNA). While Cas9:guide RNA complexes have been successfully used to modify both cells (Cong, L. et al. Multiplex genome engineering using CRISPR/Cas systems. *Science.* 339, 819-823 (2013); Mali, P. et al. RNA-guided human genome engineering via Cas9. *Science.* 339, 823-826 (2013); Jinek, M. et al. RNA-programmed genome editing in human cells. *eLife* 2, e00471 (2013)) and organisms (Hwang, W.Y. et al. Efficient genome editing in zebrafish using a CRISPR-Cas system. *Nature Biotechnology.* 31, 227-229 (2013)), a study using Cas9:guide RNA complexes to modify zebrafish embryos observed toxicity (e.g., off-target effects) at a rate similar to that of ZFNs and TALENs (Hwang, W. Y. et al. *Nature Biotechnology.* 31, 227-229 (2013)). Further, while recently engineered variants of Cas9 that cleave only one DNA strand ("nickases") enable double-stranded breaks to be specified by two distinct gRNA sequences (Cho, S. W. et al. Analysis of off-target effects of CRISPR/Cas-derived RNA-guided endonucleases and nickases. *Genome Res.* 24, 132-141 (2013); Ran, F. A. et al. Double Nicking by RNA-Guided CRISPR Cas9 for Enhanced Genome Editing Specificity. *Cell* 154, 1380-1389 (2013); Mali, P. et al. CAS9 transcriptional activators for target specificity screening and paired nickases for cooperative genome engineering. *Nat. Biotechnol.* 31, 833-838 (2013)), these variants still suffer from off-target cleavage activity (Ran, F. A. et al. Double Nicking by RNA-Guided CRISPR Cas9 for Enhanced Genome Editing Specificity. *Cell* 154, 1380-1389 (2013); Fu, Y., et al., Improving CRISPR-Cas nuclease specificity using truncated guide RNAs. *Nat. Biotechnol.* (2014)) arising from the ability of each monomeric nickase to remain active when individually bound to DNA (Cong, L. et al. Multiplex Genome Engineering Using CRISPR/Cas Systems. *Science* 339, 819-823 (2013); Jinek, M. et al. *Science* 337, 816-821 (2012); Gasiunas, G., et al., Cas9-crRNA ribonucleoprotein complex mediates specific DNA cleavage for adaptive immunity in bacteria. *Proc. Natl. Acad. Sci.* 109, E2579-E2586 (2012). Accordingly, aspects of the present disclosure aim at reducing the chances for Cas9 off-target effects using novel engineered Cas9 variants. In one example, a Cas9 variant (e.g., fCas9) is provided which has improved specificity as compared to the Cas9 nickases or wild type Cas9, exhibiting, e.g., >10-fold, >50-fold, >100-fold, >140-fold, >200-fold, or more, higher specificity than wild type Cas9 (see e.g., the Examples).

Other aspects of the present disclosure provide strategies, methods, compositions, and systems utilizing inventive RNA-guided (e.g., RNA-programmable) Cas9-recombinase fusion proteins. Whereas typical recombinases recognize and recombine distinct target sequences, the Cas9-recombinase fusions provided herein use RNA:DNA hybridization to determine target DNA recombination sites, enabling the fusion proteins to recombine, in principle, any region specified by the gRNA(s).

While of particular relevance to DNA and DNA-cleaving nucleases and/or recombinases, the inventive concepts, methods, strategies and systems provided herein are not limited in this respect, but can be applied to any nucleic acid:nuclease or nucleic acid:recombinase system.

Nucleases

Figure 20:
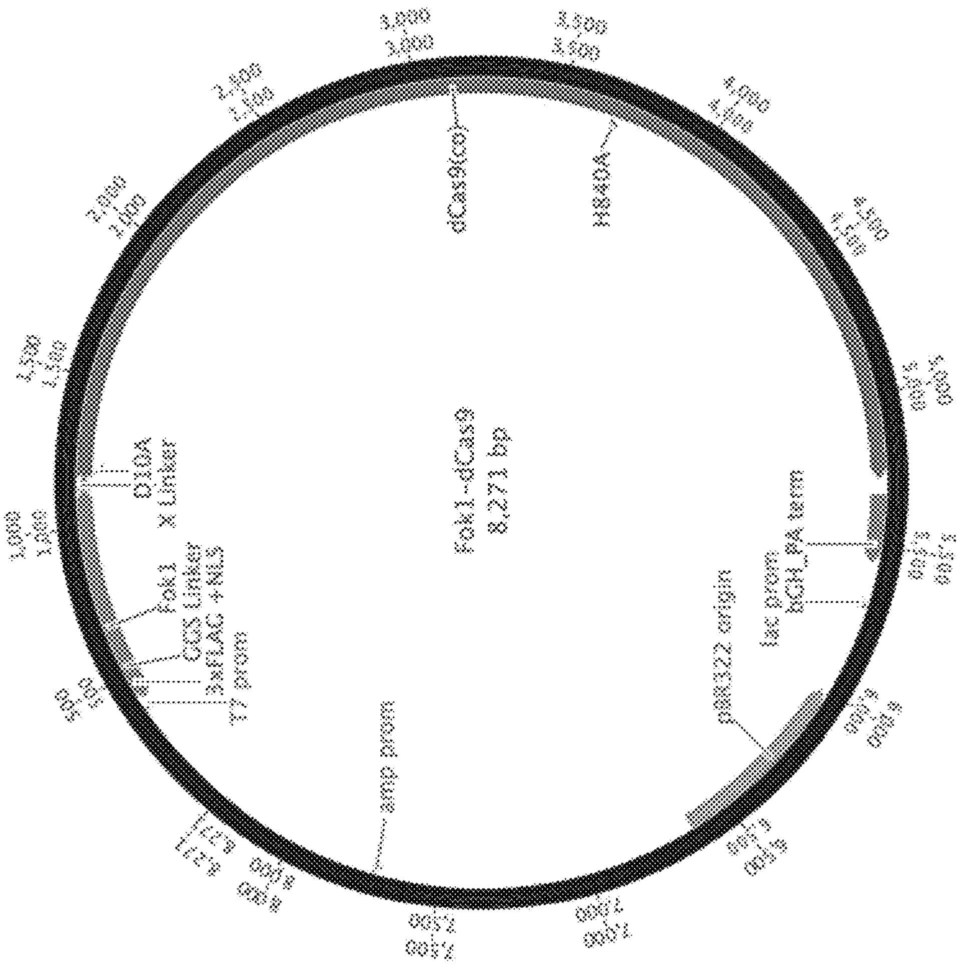
FIG. 20 depicts a vector map detailing an exemplary plasmid containing a Fok1-dCas9 (fCas9) construct.

Some aspects of this disclosure provide site-specific nucleases with enhanced specificity that are designed using the methods and strategies described herein. Some embodiments of this disclosure provide nucleic acids encoding such nucleases. Some embodiments of this disclosure provide expression constructs comprising such encoding nucleic acids (See, e.g., FIG. 20). For example, in some embodiments an isolated nuclease is provided that has been engineered to cleave a desired target site within a genome. In some embodiments, the isolated nuclease is a variant of an RNA-programmable nuclease, such as a Cas9 nuclease.

In one embodiment, fusion proteins are provided comprising two domains: (i) an RNA-programmable nuclease (e.g., Cas9 protein, or fragment thereof) domain fused or linked to (ii) a nuclease domain. For example, in some aspects, the Cas9 protein (e.g., the Cas9 domain of the fusion protein) comprises a nuclease-inactivated Cas9 (e.g., a Cas9 lacking DNA cleavage activity; "dCas9") that retains RNA (gRNA) binding activity and is thus able to bind a target site complementary to a gRNA. In some aspects, the nuclease fused to the nuclease-inactivated Cas9 domain is any nuclease requiring dimerization (e.g., the coming together of two monomers of the nuclease) in order to cleave a target nucleic acid (e.g., DNA). In some embodiments, the nuclease fused to the nuclease-inactivated Cas9 is a monomer of the FokI DNA cleavage domain, e.g., thereby producing the Cas9 variant referred to as fCas9. The FokI DNA cleavage domain is known, and in some aspects corresponds to amino acids 388-583 of FokI (NCBI accession number J04623). In some embodiments, the FokI DNA cleavage domain corresponds to amino acids 300-583,320-583, 340-583, or 360-583 of FokI. See also Wah et al., "Structure of FokI has implications for DNA cleavage" *Proc. Natl. Acad. Sci. USA.* 1998; 1; 95(18): 10564-9; Li et al., "TAL nucleases (TALNs): hybrid proteins composed of TAL effectors and FokI DNA-cleavage domain" *Nucleic Acids Res.* 2011; 39(1):359-72; Kim et al., "Hybrid restriction enzymes: zinc finger fusions to Fok I cleavage domain" *Proc. Natl. Acad. Sci. USA.* 1996; 93:1156-1160; the entire contents of each are herein incorporated by reference). In some embodiments, the FokI DNA cleavage domain corresponds to, or comprises in part or whole, the amino acid sequence set forth as SEQ ID NO:6. In some embodiments, the FokI DNA cleavage domain is a variant of FokI (e.g., a variant of SEQ ID NO:6), as described herein.

In some embodiments, a dimer of the fusion protein is provided, e.g., dimers of fCas9. For example, in some embodiments, the fusion protein forms a dimer with itself to mediate cleavage of the target nucleic acid. In some embodiments, the fusion proteins, or dimers thereof, are associated with one or more gRNAs. In some aspects, because the dimer contains two fusion proteins, each having a Cas9 domain having gRNA binding activity, a target nucleic acid is targeted using two distinct gRNA sequences that complement two distinct regions of the nucleic acid target. See, e.g., FIGS. 1A, 6D. Thus, in this example, cleavage of the target nucleic acid does not occur until both fusion proteins bind the target nucleic acid (e.g., as specified by the gRNA:target nucleic acid base pairing), and the nuclease domains dimerize (e.g., the FokI DNA cleavage domains; as a result of their proximity based on the binding of the Cas9:gRNA domains of the fusion proteins) and cleave the target nucleic acid, e.g., in the region between the bound Cas9 fusion proteins (the "spacer sequence"). This is exemplified by the schematics shown in FIGS. 1A and 6D. This approach represents a notable improvement over wild type Cas9 and other Cas9 variants, such as the nickases (Ran et al. Double Nicking by RNA-Guided CRISPR Cas9 for Enhanced Genome Editing Specificity. *Cell* 154, 1380-1389 (2013); Mali et al. CAS9 transcriptional activators for target specificity screening and paired nickases for cooperative genome engineering. *Nat. Biotechnol.* 31, 833-838 (2013)), which do not require the dimerization of nuclease domains to cleave a nucleic acid. These nickase variants, as described in the Examples, can induce cleaving, or nicking upon binding of a single nickase to a nucleic acid, which can occur at on- and off-target sites, and nicking is known to induce mutagenesis. An exemplary nucleotide encoding a Cas9 nickase (SEQ ID NO:7) and an exemplary amino acid sequence of Cas9 nickase (SEQ ID NO:8) are provided below. As the variants provided herein require the binding of two Cas9 variants in proximity to one another to induce target nucleic acid cleavage, the chances of inducing off-target cleavage is reduced. See, e.g., the Examples. For example, in some embodiments, a Cas9 variant fused to a nuclease domain (e.g., fCas9) has an on-target:off-target modification ratio that is at least 2-fold, at least 5-fold, at least 10-fold, at least 20-fold, at least 30-fold, at least 40-fold, at least 50-fold, at least 60-fold, at least 70-fold, at least 80-fold, at least 90-fold, at least 100-fold, at least 110-fold, at least 120-fold, at least 130-fold, at least 140-fold, at least 150-fold, at least 175-fold, at least 200-fold, at least 250-fold, or more higher than the on-target:off-target modification ratio of a wild type Cas9 or other Cas9 variant (e.g., nickase). In some embodiments, a Cas9 variant fused to a nuclease domain (e.g., fCas9) has an on-target:off-target modification ratio that is between about 60- to 180-fold, between about 80- to 160-fold, between about 100- to 150-fold, or between about 120- to 140-fold higher than the on-target:off-target modification ratio of a wild type Cas9 or other Cas9 variant. Methods for determining on-target:off-target modification ratios are known, and include those described in the Examples. In certain embodiments, the on-target:off-target modification ratios are determined by measuring the number or amount of modifications of known Cas9 off-target sites in certain genes. For example, the Cas9 off-target sites of the CLTA, EMX, and VEGF genes are known, and modifications at these sites can be measured and compared between test proteins and controls. The target site and its corresponding known off-target sites (see, e.g., Table 5 for CLTA, EMX, and VEGF off-target sites) are amplified from genomic DNA isolated from cells (e.g., HEK293) treated with a particular Cas9 protein or variant. The modifications are then analyzed by high-throughput sequencing. Sequences containing insertions or deletions of two or more base pairs in potential genomic off-target sites and present in significantly greater numbers (P value<0.005, Fisher's exact test) in the target gRNA-treated samples versus the control gRNA-treated samples are considered Cas9 nuclease-induced genome modifications.

Cas9 Nickase (Nucleotide Sequence):

(SEQ ID NO: 7)
ATGGACTATAAGGACCACGACGGAGACTACAAGGATCATGATATTGATTA

CAAAGACGATGACGATAAGATGGCCCCAAAGAAGAAGCGGAAGGTCGGTA

TCCACGGAGTCCCAGCAGCCGATAAAAAGTATTCTATTGGTTTAGCTATC

GGCACTAATTCCGTTGGATGGGCTGTCATAACCGATGAATACAAAGTACC

TTCAAAGAAATTTAAGGTGTTGGGGAACACAGACCGTCATTCGATTAAAA

AGAATCTTATCGGTGCCCTCCTATTCGATAGTGGCGAAACGGCAGAGGCG

ACTCGCCTGAAACGAACCGCTCGGAGAAGGTATACACGTCGCAAGAACCG

AATATGTTACTTACAAGAAATTTTTAGCAATGAGATGGCCAAAGTTGACG

ATTCTTTCTTTCACCGTTTGGAAGAGTCCTTCCTTGTCGAAGAGGACAAG

AAACATGAACGGCACCCCATCTTTGGAAACATAGTAGATGAGGTGGCATA

TCATGAAAAGTACCCAACGATTTATCACCTCAGAAAAAAGCTAGTTGACT

CAACTGATAAAGCGGACCTGAGGTTAATCTACTTGGCTCTTGCCCATATG

ATAAAGTTCCGTGGGCACTTTCTCATTGAGGGTGATCTAAATCCGGACAA

CTCGGATGTCGACAAACTGTTCATCCAGTTAGTACAAACCTATAATCAGT

TGTTTGAAGAGAACCCTATAAATGCAAGTGGCGTGGATGCGAAGGCTATT

CTTAGCGCCCGCCTCTCTAAATCCCGACGGCTAGAAAACCTGATCGCACA

ATTACCCGGAGAGAAGAAAAATGGGTTGTTCGGTAACCTTATAGCGCTCT

CACTAGGCCTGACACCAAATTTTAAGTCGAACTTCGACTTAGCTGAAGAT

GCCAAATTGCAGCTTAGTAAGGACACGTACGATGACGATCTCGACAATCT

ACTGGCACAAATTGGAGATCAGTATGCGGACTTATTTTTGGCTGCCAAAA

ACCTTAGCGATGCAATCCTCCTATCTGACATACTGAGAGTTAATACTGAG

ATTACCAAGGCGCCGTTATCCGCTTCAATGATCAAAAGGTACGATGAACA

TCACCAAGACTTGACACTTCTCAAGGCCCTAGTCCGTCAGCAACTGCCTG

AGAAATATAAGGAAATATTCTTTGATCAGTCGAAAAACGGGTACGCAGGT

TATATTGACGGCGGAGCGAGTCAAGAGGAATTCTACAAGTTTATCAAACC

CATATTAGAGAAGATGGATGGGACGGAAGAGTTGCTTGTAAAACTCAATC

GCGAAGATCTACTGCGAAAGCAGCGGACTTTCGACAACGGTAGCATTCCA

CATCAAATCCACTTAGGCGAATTGCATGCTATACTTAGAAGGCAGGAGGA

TTTTTATCCGTTCCTCAAAGACAATCGTGAAAAGATTGAGAAAATCCTAA

CCTTTCGCATACCTTACTATGTGGGACCCCTGGCCCGAGGGAACTCTCGG

TTCGCATGGATGACAAGAAAGTCCGAAGAAACGATTACTCCATGGAATTT

TGAGGAAGTTGTCGATAAAGGTGCGTCAGCTCAATCGTTCATCGAGAGGA

TGACCAACTTTGACAAGAATTTACCGAACGAAAAAGTATTGCCTAAGCAC

-continued

AGTTTACTTTACGAGTATTTCACAGTGTACAATGAACTCACGAAAGTTAA

GTATGTCACTGAGGGCATGCGTAAACCCGCCTTTCTAAGCGGAGAACAGA

AGAAAGCAATAGTAGATCTGTTATTCAAGACCAACCGCAAAGTGACAGTT

AAGCAATTGAAAGAGGACTACTTTAAGAAAATTGAATGCTTCGATTCTGT

CGAGATCTCCGGGGTAGAAGATCGATTTAATGCGTCACTTGGTACGTATC

ATGACCTCCTAAAGATAATTAAAGATAAGGACTTCCTGGATAACGAAGAG

AATGAAGATATCTTAGAAGATATAGTGTTGACTCTTACCCTCTTTGAAGA

TCGGGAAATGATTGAGGAAAGACTAAAAACATACGCTCACCTGTTCGACG

ATAAGGTTATGAAACAGTTAAAGAGGCGTCGCTATACGGGCTGGGGACGA

TTGTCGCGGAAACTTATCAACGGGATAAGAGACAAGCAAAGTGGTAAAAC

TATTCTCGATTTTCTAAAGAGCGACGGCTTCGCCAATAGGAACTTTATGC

AGCTGATCCATGATGACTCTTTAACCTTCAAAGAGGATATACAAAAGGCA

CAGGTTTCCGGACAAGGGGACTCATTGCACGAACATATTGCGAATCTTGC

TGGTTCGCCAGCCATCAAAAAGGGCATACTCCAGACAGTCAAAGTAGTGG

ATGAGCTAGTTAAGGTCATGGGACGTCACAAACCGGAAAACATTGTAATC

GAGATGGCACGCGAAAATCAAACGACTCAGAAGGGGCAAAAAAACAGTCG

AGAGCGGATGAAGAGAATAGAAGAGGGTATTAAAGAACTGGGCAGCCAGA

TCTTAAAGGAGCATCCTGTGGAAAATACCCAATTGCAGAACGAGAAACTT

TACCTCTATTACCTACAAAATGGAAGGGACATGTATGTTGATCAGGAACT

GGACATAAACCGTTTATCTGATTACGACGTCGATCACATTGTACCCCAAT

CCTTTTTGAAGGACGATTCAATCGACAATAAAGTGCTTACACGCTCGGAT

AAGAACCGAGGGAAAAGTGACAATGTTCCAAGCGAGGAAGTCGTAAAGAA

AATGAAGAACTATTGGCGGCAGCTCCTAAATGCGAAACTGATAACGCAAA

GAAAGTTCGATAACTTAACTAAAGCTGAGAGGGGTGGCTTGTCTGAACTT

GACAAGGCCGGATTTATTAAACGTCAGCTCGTGGAAACCCGCCAAATCAC

AAAGCATGTTGCACAGATACTAGATTCCCGAATGAATACGAAATACGACG

AGAACGATAAGCTGATTCGGGAAGTCAAAGTAATCACTTTAAAGTCAAAA

TTGGTGTCGGACTTCAGAAAGGATTTTCAATTCTATAAAGTTAGGGAGAT

AAATAACTACCACCATGCGCACGACGCTTATCTTAATGCCGTCGTAGGGA

CCGCACTCATTAAGAAATACCCGAAGCTAGAAAGTGAGTTTGTGTATGGT

GATTACAAAGTTTATGACGTCCGTAAGATGATCGCGAAAAGCGAACAGGA

GATAGGCAAGGCTACAGCCAAATACTTCTTTTATTCTAACATTATGAATT

TCTTTAAGACGGAAATCACTCTGGCAAACGGAGAGATACGCAAACGACCT

TTAATTGAAACCAATGGGGAGACAGGTGAAATCGTATGGGATAAGGGCCG

GGACTTCGCGACGGTGAGAAAAGTTTTGTCCATGCCCCAAGTCAACATAG

TAAAGAAAACTGAGGTGCAGACCGGAGGGTTTTCAAAGGAATCGATTCTT

CCAAAAAGGAATAGTGATAAGCTCATCGCTCGTAAAAAGGACTGGGACCC

GAAAAAGTACGGTGGCTTCGATAGCCCTACAGTTGCCTATTCTGTCCTAG

TAGTGGCAAAAGTTGAGAAGGGAAAATCCAAGAAACTGAAGTCAGTCAAA

GAATTATTGGGGATAACGATTATGGAGCGCTCGTCTTTTGAAAAGAACCC

-continued

CATCGACTTCCTTGAGGCGAAAGGTTACAAGGAAGTAAAAAAGGATCTCA

TAATTAAACTACCAAAGTATAGTCTGTTTGAGTTAGAAAATGGCCGAAAA

CGGATGTTGGCTAGCGCCGGAGAGCTTCAAAAGGGGAACGAACTCGCACT

ACCGTCTAAATACGTGAATTTCCTGTATTTAGCGTCCCATTACGAGAAGT

TGAAAGGTTCACCTGAAGATAACGAACAGAAGCAACTTTTTGTTGAGCAG

CACAAACATTATCTCGACGAAATCATAGAGCAAATTTCGGAATTCAGTAA

GAGAGTCATCCTAGCTGATGCCAATCTGGACAAAGTATTAAGCGCATACA

ACAAGCACAGGGATAAACCCATACGTGAGCAGGCGGAAAATATTATCCAT

TTGTTTACTCTTACCAACCTCGGCGCTCCAGCCGCATTCAAGTATTTTGA

CACAACGATAGATCGCAAACGATACACTTCTACCAAGGAGGTGCTAGACG

CGACACTGATTCACCAATCCATCACGGGATTATATGAAACTCGGATAGAT

TTGTCACAGCTTGGGGGTGAC

Cas9 Nickase (D10A)(Amino Acid Sequence):

(SEQ ID NO: 8)

MDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

-continued

PIREQAENIIHLFTLTNLGAPAAFKYFDTTIDRKRYTSTKEVLDATLIHQ

SITGLYETRIDLSQLGGD

In some embodiments, the gRNAs which bind the Cas9 variants (e.g., fCas9) can be oriented in one of two ways, with respect to the spacer sequence, deemed the "A" and "B" orientations. In orientation A, the region of the gRNAs that bind the PAM motifs is distal to the spacer sequence with the 5' ends of the gRNAs adjacent to the spacer sequence (FIG. 6C); whereas in orientation B, the region of the gRNAs that bind the PAM motifs is adjacent to the spacer sequence (FIG. 9). In some embodiments, the gRNAs are engineered or selected to bind (e.g., as part of a complex with a Cas9 variant, such as fCas9) to a target nucleic acid in the A or B orientation. In some embodiments, the gRNAs are engineered or selected to bind (e.g., as part of a complex with a Cas9 variant such as fCas9) to a target nucleic acid in the A orientation. In some embodiments, the gRNAs are engineered or selected to bind (e.g., as part of a complex with a Cas9 variant, such as fCas9) to a target nucleic acid in the B orientation.

In some embodiments, the domains of the fusion protein are linked via a linker e.g., as described herein. In certain embodiments, the linker is a peptide linker. In other embodiments, the linker is a non-peptidic linker. In some embodiments, a functional domain is linked via a peptide linker (e.g., fused) or a non-peptidic linker to an inventive fusion protein. In some embodiments, the functional domain is a nuclear localization signal (NLS) domain. An NLS domain comprises an amino acid sequence that "tags" or signals a protein for import into the cell nucleus by nuclear transport. Typically, this signal consists of one or more short sequences of positively charged lysines or arginines exposed on the protein surface. NLS sequences are well known in the art (See e.g., Lange et al., "Classical nuclear localization signals: definition, function, and interaction with importin alpha." *J Biol. Chem.* 2007 Feb. 23; 282(8):5101-5; the entire contents of which is hereby incorporated by reference), and include, for example those described in the Examples section. In some embodiments, the NLS sequence comprises, in part or in whole, the amino acid sequence MAPKKKRKVGIHRGVP (SEQ ID NO:318). The domains (e.g., two or more of a gRNA binding domain (dCas9 domain), a catalytic nuclease domain, and a NLS domain) associated via a linker can be linked in any orientation or order. For example, in some embodiments, any domain can be at the N-terminus, the C-terminus, or in between the domains at the N- and C-termini of the fusion protein. In some embodiments, the orientation or order of the domains in an inventive fusion protein are as provided in FIG. 6B. In some embodiments, wherein the fusion protein comprises three domains (e.g., a gRNA binding domain (e.g., dCas9 domain), a nuclease domain (e.g., FokI), and an NLS domain), each domain is connected via a linker, as provided herein. In some embodiments, the domains are not connected via a linker. In some embodiments, one or more of the domains is/are connected via a linker.

In some embodiments, an inventive fusion protein (e.g., fCas9) comprising three domains (e.g., a gRNA binding domain (e.g., dCas9 domain), a nuclease domain (e.g., FokI), and an NLS domain) is encoded by a nucleotide sequence (or fragment or variant thereof) set forth as SEQ ID NO:9, SEQ ID NO:10, SEQ ID NO:11, SEQ ID NO:12, or SEQ ID NO:319, as shown below.

fCas9 (e.g., dCas9-NLS-GGS3linker-FokI):

(SEQ ID NO: 9)

ATGGATAAAAAGTATTCTATTGGTTTAGCTATCGGCACTAATTCCGTTGG

ATGGGCTGTCATAACCGATGAATACAAAGTACCTTCAAAGAAATTTAAGG

TGTTGGGGAACACAGACCGTCATTCGATTAAAAAGAATCTTATCGGTGCC

CTCCTATTCGATAGTGGCGAAACGGCAGAGGCGACTCGCCTGAAACGAAC

CGCTCGGAGAAGGTATACACGTCGCAAGAACCGAATATGTTACTTACAAG

AAATTTTTAGCAATGAGATGGCCAAAGTTGACGATTCTTTCTTTCACCGT

TTGGAAGAGTCCTTCCTTGTCGAAGAGGACAAGAAACATGAACGGCACCC

CATCTTTGGAAACATAGTAGATGAGGTGGCATATCATGAAAAGTACCCAA

CGATTTATCACCTCAGAAAAAAGCTAGTTGACTCAACTGATAAAGCGGAC

CTGAGGTTAATCTACTTGGCTCTTGCCCATATGATAAAGTTCCGTGGGCA

CTTTCTCATTGAGGGTGATCTAAATCCGGACAACTCGGATGTCGACAAAC

TGTTCATCCAGTTAGTACAAACCTATAATCAGTTGTTTGAAGAGAACCCT

ATAAATGCAAGTGGCGTGGATGCGAAGGCTATTCTTAGCGCCCGCCTCTC

TAAATCCCGACGGCTAGAAAACCTGATCGCACAATTACCCGGAGAGAAGA

AAAATGGGTTGTTCGGTAACCTTATAGCGCTCTCACTAGGCCTGACACCA

AATTTTAAGTCGAACTTCGACTTAGCTGAAGATGCCAAATTGCAGCTTAG

TAAGGACACGTACGATGACGATCTCGACAATCTACTGGCACAAATTGGAG

ATCAGTATGCGGACTTATTTTTGGCTGCCAAAAACCTTAGCGATGCAATC

CTCCTATCTGACATACTGAGAGTTAATACTGAGATTACCAAGGCGCCGTT

ATCCGCTTCAATGATCAAAAGGTACGATGAACATCACCAAGACTTGACAC

TTCTCAAGGCCCTAGTCCGTCAGCAACTGCCTGAGAAATATAAGGAAATA

TTCTTTGATCAGTCGAAAAACGGGTACGCAGGTTATATTGACGGCGGAGC

GAGTCAAGAGGAATTCTACAAGTTTATCAAACCCATATTAGAGAAGATGG

ATGGGACGGAAGAGTTGCTTGTAAAACTCAATCGCGAAGATCTACTGCGA

AAGCAGCGGACTTTCGACAACGGTAGCATTCCACATCAAATCCACTTAGG

CGAATTGCATGCTATACTTAGAAGGCAGGAGGATTTTTATCCGTTCCTCA

AAGACAATCGTGAAAAGATTGAGAAAATCCTAACCTTTCGCATACCTTAC

TATGTGGGACCCCTGGCCCGAGGGAACTCTCGGTTCGCATGGATGACAAG

AAAGTCCGAAGAAACGATTACTCCATGGAATTTTGAGGAAGTTGTCGATA

AAGGTGCGTCAGCTCAATCGTTCATCGAGAGGATGACCAACTTTGACAAG

AATTTACCGAACGAAAAAGTATTGCCTAAGCACAGTTTACTTTACGAGTA

TTTCACAGTGTACAATGAACTCACGAAAGTTAAGTATGTCACTGAGGGCA

TGCGTAAACCCGCCTTTCTAAGCGGAGAACAGAAGAAAGCAATAGTAGAT

CTGTTATTCAAGACCAACCGCAAAGTGACAGTTAAGCAATTGAAAGAGGA

CTACTTTAAGAAAATTGAATGCTTCGATTCTGTCGAGATCTCCGGGGTAG

AAGATCGATTTAATGCGTCACTTGGTACGTATCATGACCTCCTAAAGATA

ATTAAAGATAAGGACTTCCTGGATAACGAAGAGAATGAAGATATCTTAGA

AGATATAGTGTTGACTCTTACCCTCTTTGAAGATCGGGAAATGATTGAGG

AAAGACTAAAAACATACGCTCACCTGTTCGACGATAAGGTTATGAAACAG

-continued

TTAAAGAGGCGTCGCTATACGGGCTGGGGACGATTGTCGCGGAAACTTAT

CAACGGGATAAGAGACAAGCAAAGTGGTAAAACTATTCTCGATTTTCTAA

AGAGCGACGGCTTCGCCAATAGGAACTTTATGCAGCTGATCCATGATGAC

TCTTTAACCTTCAAAGAGGATATACAAAAGGCACAGGTTTCCGGACAAGG

GGACTCATTGCACGAACATATTGCGAATCTTGCTGGTTCGCCAGCCATCA

AAAAGGGCATACTCCAGACAGTCAAAGTAGTGGATGAGCTAGTTAAGGTC

ATGGGACGTCACAAACCGGAAAACATTGTAATCGAGATGGCACGCGAAAA

TCAAACGACTCAGAAGGGGCAAAAAAACAGTCGAGAGCGGATGAAGAGAA

TAGAAGAGGGTATTAAAGAACTGGGCAGCCAGATCTTAAAGGAGCATCCT

GTGGAAAATACCCAATTGCAGAACGAGAAACTTTACCTCTATTACCTACA

AAATGGAAGGGACATGTATGTTGATCAGGAACTGGACATAAACCGTTTAT

CTGATTACGACGTCGATGCCATTGTACCCCAATCCTTTTTGAAGGACGAT

TCAATCGACAATAAAGTGCTTACACGCTCGGATAAGAACCGAGGGAAAAG

TGACAATGTTCCAAGCGAGGAAGTCGTAAAGAAAATGAAGAACTATTGGC

GGCAGCTCCTAAATGCGAAACTGATAACGCAAAGAAAGTTCGATAACTTA

ACTAAAGCTGAGAGGGGTGGCTTGTCTGAACTTGACAAGGCCGGATTTAT

TAAACGTCAGCTCGTGGAAACCCGCCAAATCACAAAGCATGTTGCACAGA

TACTAGATTCCCGAATGAATACGAAATACGACGAGAACGATAAGCTGATT

CGGGAAGTCAAAGTAATCACTTTAAAGTCAAAATTGGTGTCGGACTTCAG

AAAGGATTTTCAATTCTATAAAGTTAGGGAGATAAATAACTACCACCATG

CGCACGACGCTTATCTTAATGCCGTCGTAGGGACCGCACTCATTAAGAAA

TACCCGAAGCTAGAAAGTGAGTTTGTGTATGGTGATTACAAAGTTTATGA

CGTCCGTAAGATGATCGCGAAAAGCGAACAGGAGATAGGCAAGGCTACAG

CCAAATACTTCTTTTATTCTAACATTATGAATTTCTTTAAGACGGAAATC

ACTCTGGCAAACGGAGAGATACGCAAACGACCTTTAATTGAAACCAATGG

GGAGACAGGTGAAATCGTATGGGATAAGGGCCGGGACTTCGCGACGGTGA

GAAAAGTTTTGTCCATGCCCCAAGTCAACATAGTAAAGAAAACTGAGGTG

CAGACCGGAGGGTTTTCAAAGGAATCGATTCTTCCAAAAAGGAATAGTGA

TAAGCTCATCGCTCGTAAAAAGGACTGGGACCCGAAAAAGTACGGTGGCT

TCGATAGCCCTACAGTTGCCTATTCTGTCCTAGTAGTGGCAAAAGTTGAG

AAGGGAAAATCCAAGAAACTGAAGTCAGTCAAAGAATTATTGGGGATAAC

GATTATGGAGCGCTCGTCTTTTGAAAAGAACCCCATCGACTTCCTTGAGG

CGAAAGGTTACAAGGAAGTAAAAAAGGATCTCATAATTAAACTACCAAAG

TATAGTCTGTTTGAGTTAGAAAATGGCCGAAAACGGATGTTGGCTAGCGC

CGGAGAGCTTCAAAAGGGGAACGAACTCGCACTACCGTCTAAATACGTGA

ATTTCCTGTATTTAGCGTCCCATTACGAGAAGTTGAAAGGTTCACCTGAA

GATAACGAACAGAAGCAACTTTTTGTTGAGCAGCACAAACATTATCTCGA

CGAAATCATAGAGCAAATTTCGGAATTCAGTAAGAGAGTCATCCTAGCTG

ATGCCAATCTGGACAAAGTATTAAGCGCATACAACAAGCACAGGGATAAA

CCCATACGTGAGCAGGCGGAAAATATTATCCATTTGTTTACTCTTACCAA

-continued

CCTCGGCGCTCCAGCCGCATTCAAGTATTTTGACACAACGATAGATCGCA

AACGATACACTTCTACCAAGGAGGTGCTAGACGCGACACTGATTCACCAA

TCCATCACGGGATTATATGAAACTCGGATAGATTTGTCACAGCTTGGGGG

TGACGGATCCCCCAAGAAGAAGAGGAAAGTCTCGAGCGACTACAAAGACC

ATGACGGTGATTATAAAGATCATGACATCGATTACAAGGATGACGATGAC

AAGGCTGCAGGATCAGGTGGAAGTGGCGGCAGCGGAGGTTCTGGATCCCA

ACTAGTCAAAAGTGAACTGGAGGAGAAGAAATCTGAACTTCGTCATAAAT

TGAAATATGTGCCTCATGAATATATTGAATTAATTGAAATTGCCAGAAAT

TCCACTCAGGATAGAATTCTTGAAATGAAGGTAATGGAATTTTTTATGAA

AGTTTATGGATATAGAGGTAAACATTTGGGTGGATCAAGGAAACCGGACG

GAGCAATTTATACTGTCGGATCTCCTATTGATTACGGTGTGATCGTGGAT

ACTAAAGCTTATAGCGGAGGTTATAATCTGCCAATTGGCCAAGCAGATGA

AATGCAACGATATGTCGAAGAAAATCAAACACGAAACAAACATATCAACC

CTAATGAATGGTGGAAAGTCTATCCATCTTCTGTAACGGAATTTAAGTTT

TTATTTGTGAGTGGTCACTTTAAAGGAAACTACAAAGCTCAGCTTACACG

ATTAAATCATATCACTAATTGTAATGGAGCTGTTCTTAGTGTAGAAGAGC

TTTTAATTGGTGGAGAAATGATTAAAGCCGGCACATTAACCTTAGAGGAA

GTCAGACGGAAATTTAATAACGGCGAGATAAACTTT fCas9 (e.g., NLS-dCas9-GGS3linker-FokI):

(SEQ ID NO: 10)

ATGGACTACAAAGACCATGACGGTGATTATAAAGATCATGACATCGATTA

CAAGGATGACGATGACAAGATGGCCCCCAAGAAGAAGAGGAAGGTGGGCA

TTCACCGCGGGGTACCTATGGATAAAAAGTATTCTATTGGTTTAGCTATC

GGCACTAATTCCGTTGGATGGGCTGTCATAACCGATGAATACAAAGTACC

TTCAAAGAAATTTAAGGTGTTGGGGAACACAGACCGTCATTCGATTAAAA

AGAATCTTATCGGTGCCCTCCTATTCGATAGTGGCGAAACGGCAGAGGCG

ACTCGCCTGAAACGAACCGCTCGGAGAAGGTATACACGTCGCAAGAACCG

AATATGTTACTTACAAGAAATTTTTAGCAATGAGATGGCCAAAGTTGACG

ATTCTTTCTTTCACCGTTTGGAAGAGTCCTTCCTTGTCGAAGAGGACAAG

AAACATGAACGGCACCCCATCTTTGGAAACATAGTAGATGAGGTGGCATA

TCATGAAAAGTACCCAACGATTTATCACCTCAGAAAAAAGCTAGTTGACT

CAACTGATAAAGCGGACCTGAGGTTAATCTACTTGGCTCTTGCCCATATG

ATAAAGTTCCGTGGGCACTTTCTCATTGAGGGTGATCTAAATCCGGACAA

CTCGGATGTCGACAAACTGTTCATCCAGTTAGTACAAACCTATAATCAGT

TGTTTGAAGAGAACCCTATAAATGCAAGTGGCGTGGATGCGAAGGCTATT

CTTAGCGCCCGCCTCTCTAAATCCCGACGGCTAGAAAACCTGATCGCACA

ATTACCCGGAGAGAAGAAAAATGGGTTGTTCGGTAACCTTATAGCGCTCT

CACTAGGCCTGACACCAAATTTTAAGTCGAACTTCGACTTAGCTGAAGAT

GCCAAATTGCAGCTTAGTAAGGACACGTACGATGACGATCTCGACAATCT

ACTGGCACAAATTGGAGATCAGTATGCGGACTTATTTTTGGCTGCCAAAA

-continued

ACCTTAGCGATGCAATCCTCCTATCTGACATACTGAGAGTTAATACTGAG

ATTACCAAGGCGCCGTTATCCGCTTCAATGATCAAAAGGTACGATGAACA

TCACCAAGACTTGACACTTCTCAAGGCCCTAGTCCGTCAGCAACTGCCTG

AGAAATATAAGGAAATATTCTTTGATCAGTCGAAAAACGGGTACGCAGGT

TATATTGACGGCGGAGCGAGTCAAGAGGAATTCTACAAGTTTATCAAACC

CATATTAGAGAAGATGGATGGGACGGAAGAGTTGCTTGTAAAACTCAATC

GCGAAGATCTACTGCGAAAGCAGCGGACTTTCGACAACGGTAGCATTCCA

CATCAAATCCACTTAGGCGAATTGCATGCTATACTTAGAAGGCAGGAGGA

TTTTTATCCGTTCCTCAAAGACAATCGTGAAAAGATTGAGAAAATCCTAA

CCTTTCGCATACCTTACTATGTGGGACCCCTGGCCCGAGGGAACTCTCGG

TTCGCATGGATGACAAGAAAGTCCGAAGAAACGATTACTCCATGGAATTT

TGAGGAAGTTGTCGATAAAGGTGCGTCAGCTCAATCGTTCATCGAGAGGA

TGACCAACTTTGACAAGAATTTACCGAACGAAAAAGTATTGCCTAAGCAC

AGTTTACTTTACGAGTATTTCACAGTGTACAATGAACTCACGAAAGTTAA

GTATGTCACTGAGGGCATGCGTAAACCCGCCTTTCTAAGCGGAGAACAGA

AGAAAGCAATAGTAGATCTGTTATTCAAGACCAACCGCAAAGTGACAGTT

AAGCAATTGAAAGAGGACTACTTTAAGAAAATTGAATGCTTCGATTCTGT

CGAGATCTCCGGGGTAGAAGATCGATTTAATGCGTCACTTGGTACGTATC

ATGACCTCCTAAAGATAATTAAAGATAAGGACTTCCTGGATAACGAAGAG

AATGAAGATATCTTAGAAGATATAGTGTTGACTCTTACCCTCTTTGAAGA

TCGGGAAATGATTGAGGAAAGACTAAAAACATACGCTCACCTGTTCGACG

ATAAGGTTATGAAACAGTTAAAGAGGCGTCGCTATACGGGCTGGGGACGA

TTGTCGCGGAAACTTATCAACGGGATAAGAGACAAGCAAAGTGGTAAAAC

TATTCTCGATTTTCTAAAGAGCGACGGCTTCGCCAATAGGAACTTTATGC

AGCTGATCCATGATGACTCTTTAACCTTCAAAGAGGATATACAAAAGGCA

CAGGTTTCCGGACAAGGGGACTCATTGCACGAACATATTGCGAATCTTGC

TGGTTCGCCAGCCATCAAAAAGGGCATACTCCAGACAGTCAAAGTAGTGG

ATGAGCTAGTTAAGGTCATGGGACGTCACAAACCGGAAAACATTGTAATC

GAGATGGCACGCGAAAATCAAACGACTCAGAAGGGGCAAAAAAACAGTCG

AGAGCGGATGAAGAGAATAGAAGAGGGTATTAAAGAACTGGGCAGCCAGA

TCTTAAAGGAGCATCCTGTGGAAAATACCCAATTGCAGAACGAGAAACTT

TACCTCTATTACCTACAAAATGGAAGGGACATGTATGTTGATCAGGAACT

GGACATAAACCGTTTATCTGATTACGACGTCGATGCCATTGTACCCCAAT

CCTTTTTGAAGGACGATTCAATCGACAATAAAGTGCTTACACGCTCGGAT

AAGAACCGAGGGAAAAGTGACAATGTTCCAAGCGAGGAAGTCGTAAAGAA

AATGAAGAACTATTGGCGGCAGCTCCTAAATGCGAAACTGATAACGCAAA

GAAAGTTCGATAACTTAACTAAAGCTGAGAGGGGTGGCTTGTCTGAACTT

GACAAGGCCGGATTTATTAAACGTCAGCTCGTGGAAACCCGCCAAATCAC

AAAGCATGTTGCACAGATACTAGATTCCCGAATGAATACGAAATACGACG

AGAACGATAAGCTGATTCGGGAAGTCAAAGTAATCACTTTAAAGTCAAAA

TTGGTGTCGGACTTCAGAAAGGATTTTCAATTCTATAAAGTTAGGGAGAT

-continued

AAATAACTACCACCATGCGCACGACGCTTATCTTAATGCCGTCGTAGGGA

CCGCACTCATTAAGAAATACCCGAAGCTAGAAAGTGAGTTTGTGTATGGT

GATTACAAAGTTTATGACGTCCGTAAGATGATCGCGAAAAGCGAACAGGA

GATAGGCAAGGCTACAGCCAAATACTTCTTTTATTCTAACATTATGAATT

TCTTTAAGACGGAAATCACTCTGGCAAACGGAGAGATACGCAAACGACCT

TTAATTGAAACCAATGGGGAGACAGGTGAAATCGTATGGGATAAGGGCCG

GGACTTCGCGACGGTGAGAAAAGTTTTGTCCATGCCCCAAGTCAACATAG

TAAAGAAAACTGAGGTGCAGACCGGAGGGTTTTCAAAGGAATCGATTCTT

CCAAAAAGGAATAGTGATAAGCTCATCGCTCGTAAAAAGGACTGGGACCC

GAAAAAGTACGGTGGCTTCGATAGCCCTACAGTTGCCTATTCTGTCCTAG

TAGTGGCAAAAGTTGAGAAGGGAAAATCCAAGAAACTGAAGTCAGTCAAA

GAATTATTGGGGATAACGATTATGGAGCGCTCGTCTTTTGAAAAGAACCC

CATCGACTTCCTTGAGGCGAAAGGTTACAAGGAAGTAAAAAAGGATCTCA

TAATTAAACTACCAAAGTATAGTCTGTTTGAGTTAGAAAATGGCCGAAAA

CGGATGTTGGCTAGCGCCGGAGAGCTTCAAAAGGGGAACGAACTCGCACT

ACCGTCTAAATACGTGAATTTCCTGTATTTAGCGTCCCATTACGAGAAGT

TGAAAGGTTCACCTGAAGATAACGAACAGAAGCAACTTTTTGTTGAGCAG

CACAAACATTATCTCGACGAAATCATAGAGCAAATTTCGGAATTCAGTAA

GAGAGTCATCCTAGCTGATGCCAATCTGGACAAAGTATTAAGCGCATACA

ACAAGCACAGGGATAAACCCATACGTGAGCAGGCGGAAAATATTATCCAT

TTGTTTACTCTTACCAACCTCGGCGCTCCAGCCGCATTCAAGTATTTTGA

CACAACGATAGATCGCAAACGATACACTTCTACCAAGGAGGTGCTAGACG

CGACACTGATTCACCAATCCATCACGGGATTATATGAAACTCGGATAGAT

TTGTCACAGCTTGGGGGTGACTCAGGTGGAAGTGGCGGCAGCGGAGGTTC

TGGATCCCAACTAGTCAAAAGTGAACTGGAGGAGAAGAAATCTGAACTTC

GTCATAAATTGAAATATGTGCCTCATGAATATATTGAATTAATTGAAATT

GCCAGAAATTCCACTCAGGATAGAATTCTTGAAATGAAGGTAATGGAATT

TTTTATGAAAGTTTATGGATATAGAGGTAAACATTTGGGTGGATCAAGGA

AACCGGACGGAGCAATTTATACTGTCGGATCTCCTATTGATTACGGTGTG

ATCGTGGATACTAAAGCTTATAGCGGAGGTTATAATCTGCCAATTGGCCA

AGCAGATGAAATGCAACGATATGTCGAAGAAAATCAAACACGAAACAAAC

ATATCAACCCTAATGAATGGTGGAAAGTCTATCCATCTTCTGTAACGGAA

TTTAAGTTTTTATTTGTGAGTGGTCACTTTAAAGGAAACTACAAAGCTCA

GCTTACACGATTAAATCATATCACTAATTGTAATGGAGCTGTTCTTAGTG

TAGAAGAGCTTTTAATTGGTGGAGAAATGATTAAAGCCGGCACATTAACC

TTAGAGGAAGTCAGACGGAAATTTAATAACGGCGAGATAAACTTT fCas9 (e.g., FokI-GGS3linker-dCas9-NLS):

(SEQ ID NO: 11)

ATGGGATCCCAACTAGTCAAAAGTGAACTGGAGGAGAAGAAATCTGAACT

TCGTCATAAATTGAAATATGTGCCTCATGAATATATTGAATTAATTGAAA

-continued

TTGCCAGAAATTCCACTCAGGATAGAATTCTTGAAATGAAGGTAATGGAA
TTTTTTATGAAAGTTTATGGATATAGAGGTAAACATTTGGGTGGATCAAG
GAAACCGGACGGAGCAATTTATACTGTCGGATCTCCTATTGATTACGGTG
TGATCGTGGATACTAAAGCTTATAGCGGAGGTTATAATCTGCCAATTGGC
CAAGCAGATGAAATGCAACGATATGTCGAAGAAAATCAAACACGAAACAA
ACATATCAACCCTAATGAATGGTGGAAAGTCTATCCATCTTCTGTAACGG
AATTTAAGTTTTTATTTGTGAGTGGTCACTTTAAAGGAAACTACAAAGCT
CAGCTTACACGATTAAATCATATCACTAATTGTAATGGAGCTGTTCTTAG
TGTAGAAGAGCTTTTAATTGGTGGAGAAATGATTAAAGCCGGCACATTAA
CCTTAGAGGAAGTCAGACGGAAATTTAATAACGGCGAGATAAACTTTGGC
GGTAGTGGGGGATCTGGGGGAAGTATGGATAAAAAGTATTCTATTGGTTT
AGCTATCGGCACTAATTCCGTTGGATGGGCTGTCATAACCGATGAATACA
AAGTACCTTCAAAGAAATTTAAGGTGTTGGGGAACACAGACCGTCATTCG
ATTAAAAAGAATCTTATCGGTGCCCTCCTATTCGATAGTGGCGAAACGGC
AGAGGCGACTCGCCTGAAACGAACCGCTCGGAGAAGGTATACACGTCGCA
AGAACCGAATATGTTACTTACAAGAAATTTTTAGCAATGAGATGGCCAAA
GTTGACGATTCTTTCTTTCACCGTTTGGAAGAGTCCTTCCTTGTCGAAGA
GGACAAGAAACATGAACGGCACCCCATCTTTGGAAACATAGTAGATGAGG
TGGCATATCATGAAAAGTACCCAACGATTTATCACCTCAGAAAAAAGCTA
GTTGACTCAACTGATAAAGCGGACCTGAGGTTAATCTACTTGGCTCTTGC
CCATATGATAAAGTTCCGTGGGCACTTTCTCATTGAGGGTGATCTAAATC
CGGACAACTCGGATGTCGACAAACTGTTCATCCAGTTAGTACAAACCTAT
AATCAGTTGTTTGAAGAGAACCCTATAAATGCAAGTGGCGTGGATGCGAA
GGCTATTCTTAGCGCCCGCCTCTCTAAATCCCGACGGCTAGAAAACCTGA
TCGCACAATTACCCGGAGAGAAGAAAAATGGGTTGTTCGGTAACCTTATA
GCGCTCTCACTAGGCCTGACACCAAATTTTAAGTCGAACTTCGACTTAGC
TGAAGATGCCAAATTGCAGCTTAGTAAGGACACGTACGATGACGATCTCG
ACAATCTACTGGCACAAATTGGAGATCAGTATGCGGACTTATTTTTGGCT
GCCAAAAACCTTAGCGATGCAATCCTCCTATCTGACATACTGAGAGTTAA
TACTGAGATTACCAAGGCGCCGTTATCCGCTTCAATGATCAAAAGGTACG
ATGAACATCACCAAGACTTGACACTTCTCAAGGCCCTAGTCCGTCAGCAA
CTGCCTGAGAAATATAAGGAAATATTCTTTGATCAGTCGAAAAACGGGTA
CGCAGGTTATATTGACGGCGGAGCGAGTCAAGAGGAATTCTACAAGTTTA
TCAAACCCATATTAGAGAAGATGGATGGGACGGAAGAGTTGCTTGTAAAA
CTCAATCGCGAAGATCTACTGCGAAAGCAGCGGACTTTCGACAACGGTAG
CATTCCACATCAAATCCACTTAGGCGAATTGCATGCTATACTTAGAAGGC
AGGAGGATTTTTATCCGTTCCTCAAAGACAATCGTGAAAAGATTGAGAAA
ATCCTAACCTTTCGCATACCTTACTATGTGGGACCCCTGGCCCGAGGGAA
CTCTCGGTTCGCATGGATGACAAGAAAGTCCGAAGAAACGATTACTCCAT
GGAATTTTGAGGAAGTTGTCGATAAAGGTGCGTCAGCTCAATCGTTCATC

-continued

GAGAGGATGACCAACTTTGACAAGAATTTACCGAACGAAAAAGTATTGCC
TAAGCACAGTTTACTTTACGAGTATTTCACAGTGTACAATGAACTCACGA
AAGTTAAGTATGTCACTGAGGGCATGCGTAAACCCGCCTTTCTAAGCGGA
GAACAGAAGAAAGCAATAGTAGATCTGTTATTCAAGACCAACCGCAAAGT
GACAGTTAAGCAATTGAAAGAGGACTACTTTAAGAAAATTGAATGCTTCG
ATTCTGTCGAGATCTCCGGGGTAGAAGATCGATTTAATGCGTCACTTGGT
ACGTATCATGACCTCCTAAAGATAATTAAAGATAAGGACTTCCTGGATAA
CGAAGAGAATGAAGATATCTTAGAAGATATAGTGTTGACTCTTACCCTCT
TTGAAGATCGGGAAATGATTGAGGAAAGACTAAAAACATACGCTCACCTG
TTCGACGATAAGGTTATGAAACAGTTAAAGAGGCGTCGCTATACGGGCTG
GGGACGATTGTCGCGGAAACTTATCAACGGGATAAGAGACAAGCAAAGTG
GTAAAACTATTCTCGATTTTCTAAAGAGCGACGGCTTCGCCAATAGGAAC
TTTATGCAGCTGATCCATGATGACTCTTTAACCTTCAAAGAGGATATACA
AAAGGCACAGGTTTCCGGACAAGGGGACTCATTGCACGAACATATTGCGA
ATCTTGCTGGTTCGCCAGCCATCAAAAAGGGCATACTCCAGACAGTCAAA
GTAGTGGATGAGCTAGTTAAGGTCATGGGACGTCACAAACCGGAAAACAT
TGTAATCGAGATGGCACGCGAAAATCAAACGACTCAGAAGGGGCAAAAAA
ACAGTCGAGAGCGGATGAAGAGAATAGAAGAGGGTATTAAAGAACTGGGC
AGCCAGATCTTAAAGGAGCATCCTGTGGAAAATACCCAATTGCAGAACGA
GAAACTTTACCTCTATTACCTACAAAATGGAAGGGACATGTATGTTGATC
AGGAACTGGACATAAACCGTTTATCTGATTACGACGTCGATGCCATTGTA
CCCCAATCCTTTTTGAAGGACGATTCAATCGACAATAAAGTGCTTACACG
CTCGGATAAGAACCGAGGGAAAAGTGACAATGTTCCAAGCGAGGAAGTCG
TAAAGAAAATGAAGAACTATTGGCGGCAGCTCCTAAATGCGAAACTGATA
ACGCAAAGAAAGTTCGATAACTTAACTAAAGCTGAGAGGGGTGGCTTGTC
TGAACTTGACAAGGCCGGATTTATTAAACGTCAGCTCGTGGAAACCCGCC
AAATCACAAAGCATGTTGCACAGATACTAGATTCCCGAATGAATACGAAA
TACGACGAGAACGATAAGCTGATTCGGGAAGTCAAAGTAATCACTTTAAA
GTCAAAATTGGTGTCGGACTTCAGAAAGGATTTTCAATTCTATAAAGTTA
GGGAGATAAATAACTACCACCATGCGCACGACGCTTATCTTAATGCCGTC
GTAGGGACCGCACTCATTAAGAAATACCCGAAGCTAGAAAGTGAGTTTGT
GTATGGTGATTACAAAGTTTATGACGTCCGTAAGATGATCGCGAAAAGCG
AACAGGAGATAGGCAAGGCTACAGCCAAATACTTCTTTTATTCTAACATT
ATGAATTTCTTTAAGACGGAAATCACTCTGGCAAACGGAGAGATACGCAA
ACGACCTTTAATTGAAACCAATGGGGAGACAGGTGAAATCGTATGGGATA
AGGGCCGGGACTTCGCGACGGTGAGAAAAGTTTTGTCCATGCCCCAAGTC
AACATAGTAAAGAAAACTGAGGTGCAGACCGGAGGGTTTTCAAAGGAATC
GATTCTTCCAAAAAGGAATAGTGATAAGCTCATCGCTCGTAAAAAGGACT
GGGACCCGAAAAAGTACGGTGGCTTCGATAGCCCTACAGTTGCCTATTCT
GTCCTAGTAGTGGCAAAAGTTGAGAAGGGAAAATCCAAGAAACTGAAGTC
AGTCAAAGAATTATTGGGGATAACGATTATGGAGCGCTCGTCTTTTGAAA

-continued

AGAACCCCATCGACTTCCTTGAGGCGAAAGGTTACAAGGAAGTAAAAAAG
GATCTCATAATTAAACTACCAAAGTATAGTCTGTTTGAGTTAGAAAATGG
CCGAAAACGGATGTTGGCTAGCGCCGGAGAGCTTCAAAAGGGGAACGAAC
TCGCACTACCGTCTAAATACGTGAATTTCCTGTATTTAGCGTCCCATTAC
GAGAAGTTGAAAGGTTCACCTGAAGATAACGAACAGAAGCAACTTTTTGT
TGAGCAGCACAAACATTATCTCGACGAAATCATAGAGCAAATTTCGGAAT
TCAGTAAGAGAGTCATCCTAGCTGATGCCAATCTGGACAAAGTATTAAGC
GCATACAACAAGCACAGGGATAAACCCATACGTGAGCAGGCGGAAAATAT
TATCCATTTGTTTACTCTTACCAACCTCGGCGCTCCAGCCGCATTCAAGT
ATTTTGACACAACGATAGATCGCAAACGATACACTTCTACCAAGGAGGTG
CTAGACGCGACACTGATTCACCAATCCATCACGGGATTATATGAAACTCG
GATAGATTTGTCACAGCTTGGGGGTGACGGATCCCCCAAGAAGAAGAGGA
AAGTCTCGAGCGACTACAAAGACCATGACGGTGATTATAAAGATCATGAC
ATCGATTACAAGGATGACGATGACAAGGCTGCAGGA fCas9 (e.g., NLS-FokI-GGS3linker-dCas9):

(SEQ ID NO: 12)
ATGGACTACAAAGACCATGACGGTGATTATAAAGATCATGACATCGATTA
CAAGGATGACGATGACAAGATGGCCCCCAAGAAGAAGAGGAAGGTGGGCA
TTCACCGCGGGGTACCTGGAGGTTCTATGGGATCCCAACTAGTCAAAAGT
GAACTGGAGGAGAAGAAATCTGAACTTCGTCATAAATTGAAATATGTGCC
TCATGAATATATTGAATTAATTGAAATTGCCAGAAATTCCACTCAGGATA
GAATTCTTGAAATGAAGGTAATGGAATTTTTTATGAAAGTTTATGGATAT
AGAGGTAAACATTTGGGTGGATCAAGGAAACCGGACGGAGCAATTTATAC
TGTCGGATCTCCTATTGATTACGGTGTGATCGTGGATACTAAAGCTTATA
GCGGAGGTTATAATCTGCCAATTGGCCAAGCAGATGAAATGCAACGATAT
GTCGAAGAAAATCAAACACGAAACAAACATATCAACCCTAATGAATGGTG
GAAAGTCTATCCATCTTCTGTAACGGAATTTAAGTTTTTATTTGTGAGTG
GTCACTTTAAAGGAAACTACAAAGCTCAGCTTACACGATTAAATCATATC
ACTAATTGTAATGGAGCTGTTCTTAGTGTAGAAGAGCTTTTAATTGGTGG
AGAAATGATTAAAGCCGGCACATTAACCTTAGAGGAAGTCAGACGGAAAT
TTAATAACGGCGAGATAAACTTTGGCGGTAGTGGGGGATCTGGGGGAAGT
ATGGATAAAAAGTATTCTATTGGTTTAGCTATCGGCACTAATTCCGTTGG
ATGGGCTGTCATAACCGATGAATACAAAGTACCTTCAAAGAAATTTAAGG
TGTTGGGGAACACAGACCGTCATTCGATTAAAAAGAATCTTATCGGTGCC
CTCCTATTCGATAGTGGCGAAACGGCAGAGGCGACTCGCCTGAAACGAAC
CGCTCGGAGAAGGTATACACGTCGCAAGAACCGAATATGTTACTTACAAG
AAATTTTTAGCAATGAGATGGCCAAAGTTGACGATTCTTTCTTTCACCGT
TTGGAAGAGTCCTTCCTTGTCGAAGAGGACAAGAAACATGAACGGCACCC
CATCTTTGGAAACATAGTAGATGAGGTGGCATATCATGAAAAGTACCCAA
CGATTTATCACCTCAGAAAAAAGCTAGTTGACTCAACTGATAAAGCGGAC

-continued

CTGAGGTTAATCTACTTGGCTCTTGCCCATATGATAAAGTTCCGTGGGCA
CTTTCTCATTGAGGGTGATCTAAATCCGGACAACTCGGATGTCGACAAAC
TGTTCATCCAGTTAGTACAAACCTATAATCAGTTGTTTGAAGAGAACCCT
ATAAATGCAAGTGGCGTGGATGCGAAGGCTATTCTTAGCGCCCGCCTCTC
TAAATCCCGACGGCTAGAAAACCTGATCGCACAATTACCCGGAGAGAAGA
AAAATGGGTTGTTCGGTAACCTTATAGCGCTCTCACTAGGCCTGACACCA
AATTTTAAGTCGAACTTCGACTTAGCTGAAGATGCCAAATTGCAGCTTAG
TAAGGACACGTACGATGACGATCTCGACAATCTACTGGCACAAATTGGAG
ATCAGTATGCGGACTTATTTTTGGCTGCCAAAAACCTTAGCGATGCAATC
CTCCTATCTGACATACTGAGAGTTAATACTGAGATTACCAAGGCGCCGTT
ATCCGCTTCAATGATCAAAAGGTACGATGAACATCACCAAGACTTGACAC
TTCTCAAGGCCCTAGTCCGTCAGCAACTGCCTGAGAAATATAAGGAAATA
TTCTTTGATCAGTCGAAAAACGGGTACGCAGGTTATATTGACGGCGGAGC
GAGTCAAGAGGAATTCTACAAGTTTATCAAACCCATATTAGAGAAGATGG
ATGGGACGGAAGAGTTGCTTGTAAAACTCAATCGCGAAGATCTACTGCGA
AAGCAGCGGACTTTCGACAACGGTAGCATTCCACATCAAATCCACTTAGG
CGAATTGCATGCTATACTTAGAAGGCAGGAGGATTTTTATCCGTTCCTCA
AAGACAATCGTGAAAAGATTGAGAAAATCCTAACCTTTCGCATACCTTAC
TATGTGGGACCCCTGGCCCGAGGGAACTCTCGGTTCGCATGGATGACAAG
AAAGTCCGAAGAAACGATTACTCCATGGAATTTTGAGGAAGTTGTCGATA
AAGGTGCGTCAGCTCAATCGTTCATCGAGAGGATGACCAACTTTGACAAG
AATTTACCGAACGAAAAAGTATTGCCTAAGCACAGTTTACTTTACGAGTA
TTTCACAGTGTACAATGAACTCACGAAAGTTAAGTATGTCACTGAGGGCA
TGCGTAAACCCGCCTTTCTAAGCGGAGAACAGAAGAAAGCAATAGTAGAT
CTGTTATTCAAGACCAACCGCAAAGTGACAGTTAAGCAATTGAAAGAGGA
CTACTTTAAGAAAATTGAATGCTTCGATTCTGTCGAGATCTCCGGGGTAG
AAGATCGATTTAATGCGTCACTTGGTACGTATCATGACCTCCTAAAGATA
ATTAAAGATAAGGACTTCCTGGATAACGAAGAGAATGAAGATATCTTAGA
AGATATAGTGTTGACTCTTACCCTCTTTGAAGATCGGGAAATGATTGAGG
AAAGACTAAAAACATACGCTCACCTGTTCGACGATAAGGTTATGAAACAG
TTAAAGAGGCGTCGCTATACGGGCTGGGGACGATTGTCGCGGAAACTTAT
CAACGGGATAAGAGACAAGCAAAGTGGTAAAACTATTCTCGATTTTCTAA
AGAGCGACGGCTTCGCCAATAGGAACTTTATGCAGCTGATCCATGATGAC
TCTTTAACCTTCAAAGAGGATATACAAAAGGCACAGGTTTCCGGACAAGG
GGACTCATTGCACGAACATATTGCGAATCTTGCTGGTTCGCCAGCCATCA
AAAAGGGCATACTCCAGACAGTCAAAGTAGTGGATGAGCTAGTTAAGGTC
ATGGGACGTCACAAACCGGAAAACATTGTAATCGAGATGGCACGCGAAAA
TCAAACGACTCAGAAGGGGCAAAAAAACAGTCGAGAGCGGATGAAGAGAA
TAGAAGAGGGTATTAAAGAACTGGGCAGCCAGATCTTAAAGGAGCATCCT
GTGGAAAATACCCAATTGCAGAACGAGAAACTTTACCTCTATTACCTACA

-continued

AAATGGAAGGGACATGTATGTTGATCAGGAACTGGACATAAACCGTTTAT
CTGATTACGACGTCGATGCCATTGTACCCCAATCCTTTTTGAAGGACGAT
TCAATCGACAATAAAGTGCTTACACGCTCGGATAAGAACCGAGGGAAAAG
TGACAATGTTCCAAGCGAGGAAGTCGTAAAGAAAATGAAGAACTATTGGC
GGCAGCTCCTAAATGCGAAACTGATAACGCAAAGAAAGTTCGATAACTTA
ACTAAAGCTGAGAGGGGTGGCTTGTCTGAACTTGACAAGGCCGGATTTAT
TAAACGTCAGCTCGTGGAAACCCGCCAAATCACAAAGCATGTTGCACAGA
TACTAGATTCCCGAATGAATACGAAATACGACGAGAACGATAAGCTGATT
CGGGAAGTCAAAGTAATCACTTTAAAGTCAAAATTGGTGTCGGACTTCAG
AAAGGATTTTCAATTCTATAAAGTTAGGGAGATAAATAACTACCACCATG
CGCACGACGCTTATCTTAATGCCGTCGTAGGGACCGCACTCATTAAGAAA
TACCCGAAGCTAGAAAGTGAGTTTGTGTATGGTGATTACAAAGTTTATGA
CGTCCGTAAGATGATCGCGAAAAGCGAACAGGAGATAGGCAAGGCTACAG
CCAAATACTTCTTTTATTCTAACATTATGAATTTCTTTAAGACGGAAATC
ACTCTGGCAAACGGAGAGATACGCAAACGACCTTTAATTGAAACCAATGG
GGAGACAGGTGAAATCGTATGGGATAAGGGCCGGGACTTCGCGACGGTGA
GAAAAGTTTTGTCCATGCCCCAAGTCAACATAGTAAAGAAAACTGAGGTG
CAGACCGGAGGGTTTTCAAAGGAATCGATTCTTCCAAAAAGGAATAGTGA
TAAGCTCATCGCTCGTAAAAAGGACTGGGACCCGAAAAAGTACGGTGGCT
TCGATAGCCCTACAGTTGCCTATTCTGTCCTAGTAGTGGCAAAAGTTGAG
AAGGGAAAATCCAAGAAACTGAAGTCAGTCAAAGAATTATTGGGGATAAC
GATTATGGAGCGCTCGTCTTTTGAAAAGAACCCCATCGACTTCCTTGAGG
CGAAAGGTTACAAGGAAGTAAAAAAGGATCTCATAATTAAACTACCAAAG
TATAGTCTGTTTGAGTTAGAAAATGGCCGAAAACGGATGTTGGCTAGCGC
CGGAGAGCTTCAAAAGGGGAACGAACTCGCACTACCGTCTAAATACGTGA
ATTTCCTGTATTTAGCGTCCCATTACGAGAAGTTGAAAGGTTCACCTGAA
GATAACGAACAGAAGCAACTTTTTGTTGAGCAGCACAAACATTATCTCGA
CGAAATCATAGAGCAAATTTCGGAATTCAGTAAGAGAGTCATCCTAGCTG
ATGCCAATCTGGACAAAGTATTAAGCGCATACAACAAGCACAGGGATAAA
CCCATACGTGAGCAGGCGGAAAATATTATCCATTTGTTTACTCTTACCAA
CCTCGGCGCTCCAGCCGCATTCAAGTATTTTGACACAACGATAGATCGCA
AACGATACACTTCTACCAAGGAGGTGCTAGACGCGACACTGATTCACCAA
TCCATCACGGGATTATATGAAACTCGGATAGATTTGTCACAGCTTGGGGG
TGAC fCas9:

(SEQ ID NO: 319)
ATGGACTACAAAGACCATGACGGTGATTATAAAGATCATGACATCGATTA
CAAGGATGACGATGACAAGATGGCCCCCAAGAAGAAGAGGAAGGTGGGCA
TTCACCGCGGGGTACCTGGAGGTTCTGGATCCCAACTAGTCAAAAGTGAA
CTGGAGGAGAAGAAATCTGAACTTCGTCATAAATTGAAATATGTGCCTCA
TGAATATATTGAATTAATTGAAATTGCCAGAAATTCCACTCAGGATAGAA
TTCTTGAAATGAAGGTAATGGAATTTTTTATGAAAGTTTATGGATATAGA
GGTAAACATTTGGGTGGATCAAGGAAACCGGACGGAGCAATTTATACTGT
CGGATCTCCTATTGATTACGGTGTGATCGTGGATACTAAAGCTTATAGCG
GAGGTTATAATCTGCCAATTGGCCAAGCAGATGAAATGCAACGATATGTC
GAAGAAAATCAAACACGAAACAAACATATCAACCCTAATGAATGGTGGAA
AGTCTATCCATCTTCTGTAACGGAATTTAAGTTTTTATTTGTGAGTGGTC
ACTTTAAAGGAAACTACAAAGCTCAGCTTACACGATTAAATCATATCACT
AATTGTAATGGAGCTGTTCTTAGTGTAGAAGAGCTTTTAATTGGTGGAGA
AATGATTAAAGCCGGCACATTAACCTTAGAGGAAGTCAGACGGAAATTTA
ATAACGGCGAGATAAACTTTAGCGGCAGCGAGACTCCCGGGACCTCAGAG
TCCGCCACACCCGAAAGTGATAAAAAGTATTCTATTGGTTTAGCTATCGG
CACTAATTCCGTTGGATGGGCTGTCATAACCGATGAATACAAAGTACCTT
CAAAGAAATTTAAGGTGTTGGGGAACACAGACCGTCATTCGATTAAAAAG
AATCTTATCGGTGCCCTCCTATTCGATAGTGGCGAAACGGCAGAGGCGAC
TCGCCTGAAACGAACCGCTCGGAGAAGGTATACACGTCGCAAGAACCGAA
TATGTTACTTACAAGAAATTTTTAGCAATGAGATGGCCAAAGTTGACGAT
TCTTTCTTTCACCGTTTGGAAGAGTCCTTCCTTGTCGAAGAGGACAAGAA
ACATGAACGGCACCCCATCTTTGGAAACATAGTAGATGAGGTGGCATATC
ATGAAAAGTACCCAACGATTTATCACCTCAGAAAAAAGCTAGTTGACTCA
ACTGATAAAGCGGACCTGAGGTTAATCTACTTGGCTCTTGCCCATATGAT
AAAGTTCCGTGGGCACTTTCTCATTGAGGGTGATCTAAATCCGGACAACT
CGGATGTCGACAAACTGTTCATCCAGTTAGTACAAACCTATAATCAGTTG
TTTGAAGAGAACCCTATAAATGCAAGTGGCGTGGATGCGAAGGCTATTCT
TAGCGCCCGCCTCTCTAAATCCCGACGGCTAGAAAACCTGATCGCACAAT
TACCCGGAGAGAAGAAAAATGGGTTGTTCGGTAACCTTATAGCGCTCTCA
CTAGGCCTGACACCAAATTTTAAGTCGAACTTCGACTTAGCTGAAGATGC
CAAATTGCAGCTTAGTAAGGACACGTACGATGACGATCTCGACAATCTAC
TGGCACAAATTGGAGATCAGTATGCGGACTTATTTTTGGCTGCCAAAAAC
CTTAGCGATGCAATCCTCCTATCTGACATACTGAGAGTTAATACTGAGAT
TACCAAGGCGCCGTTATCCGCTTCAATGATCAAAAGGTACGATGAACATC
ACCAAGACTTGACACTTCTCAAGGCCCTAGTCCGTCAGCAACTGCCTGAG
AAATATAAGGAAATATTCTTTGATCAGTCGAAAAACGGGTACGCAGGTTA
TATTGACGGCGGAGCGAGTCAAGAGGAATTCTACAAGTTTATCAAACCCA
TATTAGAGAAGATGGATGGGACGGAAGAGTTGCTTGTAAAACTCAATCGC
GAAGATCTACTGCGAAAGCAGCGGACTTTCGACAACGGTAGCATTCCACA
TCAAATCCACTTAGGCGAATTGCATGCTATACTTAGAAGGCAGGAGGATT
TTTATCCGTTCCTCAAAGACAATCGTGAAAAGATTGAGAAAATCCTAACC
TTTCGCATACCTTACTATGTGGGACCCCTGGCCCGAGGGAACTCTCGGTT
CGCATGGATGACAAGAAAGTCCGAAGAAACGATTACTCCATGGAATTTTG
AGGAAGTTGTCGATAAAGGTGCGTCAGCTCAATCGTTCATCGAGAGGATG

-continued

ACCAACTTTGACAAGAATTTACCGAACGAAAAAGTATTGCCTAAGCACAG

TTTACTTTACGAGTATTTCACAGTGTACAATGAACTCACGAAAGTTAAGT

ATGTCACTGAGGGCATGCGTAAACCCGCCTTTCTAAGCGGAGAACAGAAG

AAAGCAATAGTAGATCTGTTATTCAAGACCAACCGCAAAGTGACAGTTAA

GCAATTGAAAGAGGACTACTTTAAGAAAATTGAATGCTTCGATTCTGTCG

AGATCTCCGGGGTAGAAGATCGATTTAATGCGTCACTTGGTACGTATCAT

GACCTCCTAAAGATAATTAAAGATAAGGACTTCCTGGATAACGAAGAGAA

TGAAGATATCTTAGAAGATATAGTGTTGACTCTTACCCTCTTTGAAGATC

GGGAAATGATTGAGGAAAGACTAAAAACATACGCTCACCTGTTCGACGAT

AAGGTTATGAAACAGTTAAAGAGGCGTCGCTATACGGGCTGGGGACGATT

GTCGCGGAAACTTATCAACGGGATAAGAGACAAGCAAAGTGGTAAAACTA

TTCTCGATTTTCTAAAGAGCGACGGCTTCGCCAATAGGAACTTTATGCAG

CTGATCCATGATGACTCTTTAACCTTCAAAGAGGATATACAAAAGGCACA

GGTTTCCGGACAAGGGGACTCATTGCACGAACATATTGCGAATCTTGCTG

GTTCGCCAGCCATCAAAAAGGGCATACTCCAGACAGTCAAAGTAGTGGAT

GAGCTAGTTAAGGTCATGGGACGTCACAAACCGGAAAACATTGTAATCGA

GATGGCACGCGAAAATCAAACGACTCAGAAGGGGCAAAAAAACAGTCGAG

AGCGGATGAAGAGAATAGAAGAGGGTATTAAAGAACTGGGCAGCCAGATC

TTAAAGGAGCATCCTGTGGAAAATACCCAATTGCAGAACGAGAAACTTTA

CCTCTATTACCTACAAAATGGAAGGGACATGTATGTTGATCAGGAACTGG

ACATAAACCGTTTATCTGATTACGACGTCGATGCCATTGTACCCCAATCC

TTTTTGAAGGACGATTCAATCGACAATAAAGTGCTTACACGCTCGGATAA

GAACCGAGGGAAAAGTGACAATGTTCCAAGCGAGGAAGTCGTAAAGAAAA

TGAAGAACTATTGGCGGCAGCTCCTAAATGCGAAACTGATAACGCAAAGA

AAGTTCGATAACTTAACTAAAGCTGAGAGGGGTGGCTTGTCTGAACTTGA

CAAGGCCGGATTTATTAAACGTCAGCTCGTGGAAACCCGCCAAATCACAA

AGCATGTTGCACAGATACTAGATTCCCGAATGAATACGAAATACGACGAG

AACGATAAGCTGATTCGGGAAGTCAAAGTAATCACTTTAAAGTCAAAATT

GGTGTCGGACTTCAGAAAGGATTTTCAATTCTATAAAGTTAGGGAGATAA

ATAACTACCACCATGCGCACGACGCTTATCTTAATGCCGTCGTAGGGACC

GCACTCATTAAGAAATACCCGAAGCTAGAAAGTGAGTTTGTGTATGGTGA

TTACAAAGTTTATGACGTCCGTAAGATGATCGCGAAAAGCGAACAGGAGA

TAGGCAAGGCTACAGCCAAATACTTCTTTTATTCTAACATTATGAATTTC

TTTAAGACGGAAATCACTCTGGCAAACGGAGAGATACGCAAACGACCTTT

AATTGAAACCAATGGGGAGACAGGTGAAATCGTATGGGATAAGGGCCGGG

ACTTCGCGACGGTGAGAAAAGTTTTGTCCATGCCCCAAGTCAACATAGTA

AAGAAAACTGAGGTGCAGACCGGAGGGTTTTCAAAGGAATCGATTCTTCC

AAAAAGGAATAGTGATAAGCTCATCGCTCGTAAAAAGGACTGGGACCCGA

AAAAGTACGGTGGCTTCGATAGCCCTACAGTTGCCTATTCTGTCCTAGTA

GTGGCAAAAGTTGAGAAGGGAAAATCCAAGAAACTGAAGTCAGTCAAAGA

-continued

ATTATTGGGGATAACGATTATGGAGCGCTCGTCTTTTGAAAAGAACCCCA

TCGACTTCCTTGAGGCGAAAGGTTACAAGGAAGTAAAAAAGGATCTCATA

ATTAAACTACCAAAGTATAGTCTGTTTGAGTTAGAAAATGGCCGAAAACG

GATGTTGGCTAGCGCCGGAGAGCTTCAAAAGGGGAACGAACTCGCACTAC

CGTCTAAATACGTGAATTTCCTGTATTTAGCGTCCCATTACGAGAAGTTG

AAAGGTTCACCTGAAGATAACGAACAGAAGCAACTTTTTGTTGAGCAGCA

CAAACATTATCTCGACGAAATCATAGAGCAAATTTCGGAATTCAGTAAGA

GAGTCATCCTAGCTGATGCCAATCTGGACAAAGTATTAAGCGCATACAAC

AAGCACAGGGATAAACCCATACGTGAGCAGGCGGAAAATATTATCCATTT

GTTTACTCTTACCAACCTCGGCGCTCCAGCCGCATTCAAGTATTTTGACA

CAACGATAGATCGCAAACGATACACTTCTACCAAGGAGGTGCTAGACGCG

ACACTGATTCACCAATCCATCACGGGATTATATGAAACTCGGATAGATTT

GTCACAGCTTGGGGGTGAC

In some embodiments, an inventive fusion protein (e.g., fCas9) corresponds to or is encoded by a homologue of any one of SEQ ID NO:9-12 or SEQ ID NO:319.

In some embodiments, an inventive fusion protein (e.g., fCas9) comprises, in part of in whole, one or more of the amino acid sequences set forth as SEQ ID NO:5, SEQ ID NO:320, SEQ ID NO:6, SEQ ID NO:16, SEQ ID NO:318, and SEQ ID NO:321, as provided herein and shown below. The various domains corresponding to SEQ ID NO:5, SEQ ID NO:320, SEQ ID NO:6, SEQ ID NO:16, SEQ ID NO:318, and SEQ ID NO:321 may be arranged in any order with respect to each other. For example, in some embodiments, a dCas9 domain (e.g., SEQ ID NO:5 or SEQ ID NO:320) is at the amino or carboxy terminus, or is somewhere in between the amino and carboxy termini. Similarly, each of the other domains corresponding to SEQ ID NO:6, SEQ ID NO:16, SEQ ID NO:318, and SEQ ID NO:321 may be at the amino or carboxy terminus, or somewhere in between the amino and carboxy termini of an inventive fusion protein (e.g., fCas9). Examples of inventive fusion proteins having various domain arrangements include the inventive fusion proteins corresponding to SEQ ID NOs:9-12 and SEQ ID NO:319. In some embodiments, an inventive fusion protein comprises additional or other domains, such as other linkers, other NLS domains, other nuclease domains, or other Cas9 domains, which may be in addition to or substituted for any of the domains as provided herein.

FokI Cleavage Domain:

(SEQ ID NO: 6)

GSQLVKSELEEKKSELRHKLKYVPHEYIELIEIARNSTQDRILEMKVMEF

FMKVYGYRGKHLGGSRKPDGAIYTVGSPIDYGVIVDTKAYSGGYNLPIGQ

ADEMQRYVEENQTRNKHINPNEWWKVYPSSVTEFKFLFVSGHFKGNYKAQ

LTRLNHITNCNGAVLSVEELLIGGEMIKAGTLTLEEVRRKFNNGEINF dCas9:

(SEQ ID NO: 320)

DKKYSIGLAIGTNSVGWAVITDEYKVPSKKFKVLGNTDRHSIKKNLIGAL

LFDSGETAEATRLKRTARRRYTRRKNRICYLQEIFSNEMAKVDDSFFHRL

-continued

```
EESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYY

VGPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVDL

LFKTNRKVTVKQLKEDYFKKIECFDSVEISGVEDRFNASLGTYHDLLKII

KDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDAIVPQSFLKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKRYTSTKEVLDATLIHQS

ITGLYETRIDLSQLGGD
```

3×FLAG TAG:

(SEQ ID NO: 321)

MDYKDHDGDYKDHDIDYKDDDDK

NLS Domain:

(SEQ ID NO: 318)

MAPKKKRKVGIHRGVP

XTEN Linker:

(SEQ ID NO: 16)

SGSETPGTSESATPES

Figure 1B:
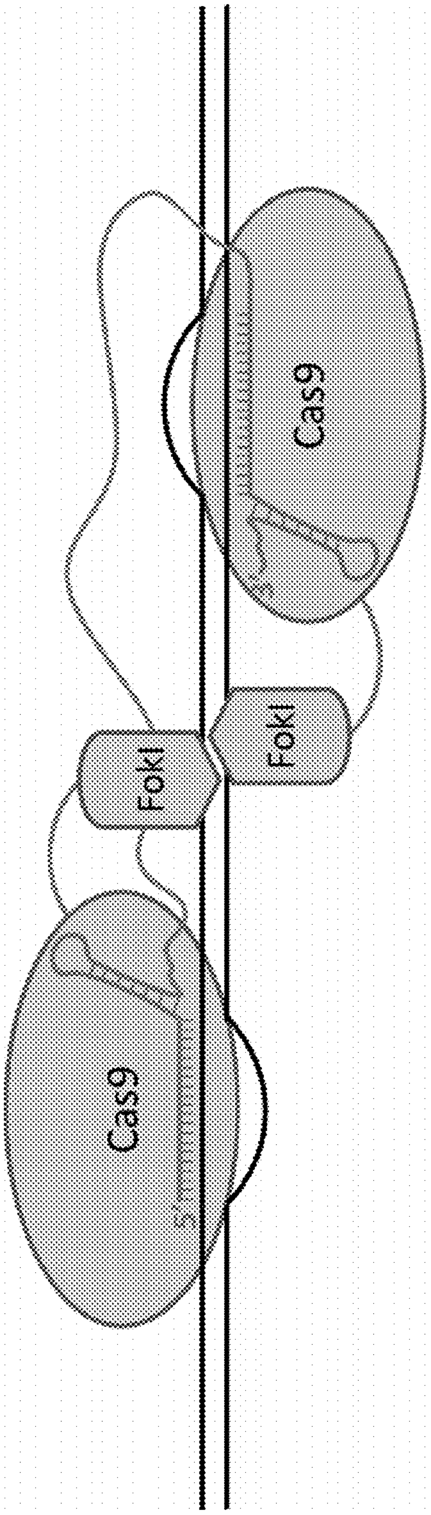

In some embodiments, the fusion proteins forming the dimer are coordinated through the action of a single extended gRNA (e.g., as opposed to two separate gRNAs, each binding a monomer of the fusion protein dimer). Thus, in some aspects, the single extended gRNA contains at least two portions, separated by a linker sequence, that complement the target nucleic acid (e.g., bind the target nucleic acid at two distinct sites), and the gRNA is able to bind at least two fusion proteins, as described herein. This is exemplified by the schematic shown in FIG. 1B. In some embodiments, the linker sequence separating the two portions in the extended gRNA has complementarity with the target sequence. In some embodiments, the extended gRNA is at least 50, at least 60, at least 70, at least 80, at least 90, at least 100, at least 125, at least 150, at least 175, at least 200, at least 250, at least 300, at least 350, at least 400, at least 500, at least 600, at least 700, at least 800, at least 900, or at least 1000 or more nucleotides in length. Whether the fusion proteins are coordinated through separate or a single gRNA, to form dimers that can cleave a target nucleic acid, it is expected that the specificity of such cleavage is enhanced (e.g., reduced or no off-target cleavage) as compared to nucleases having a single target nucleic acid binding site. Methods for determining the specificity of a nuclease are known (see e.g., published PCT Application, WO 2013/066438; pending provisional application U.S. 61/864,289; and Pattanayak, V., Ramirez, C. L., Joung, J. K. & Liu, D. R. Revealing off-target cleavage specificities of zinc-finger nucleases by in vitro selection. *Nature Methods* 8, 765-770 (2011), the entire contents of each of which are incorporated herein by reference).

Figure 4:
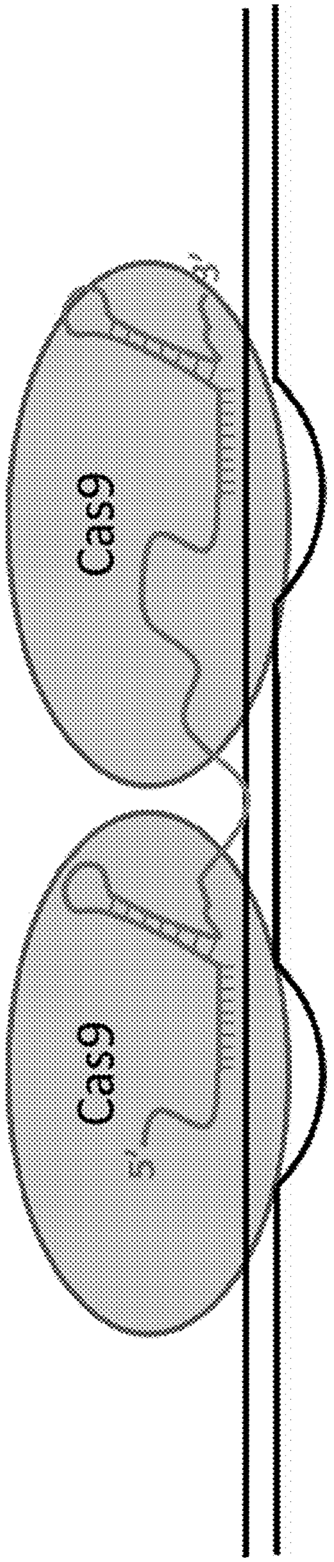
FIG. 4 shows how two Cas9 proteins can be coordinated through the action of a single extended RNA containing two distinct gRNA motifs. Each gRNA targeting region is shortened, such that a single Cas9:gRNA unit cannot bind efficiently by itself. The normal 20 nt targeting sequence has been altered so that some portion (e.g., the 5' initial 10 nt) has been changed to some non-specific linker sequence, such as AAAAAAAAAA (SEQ ID NO:13), with only 10 nt of the gRNA remaining to direct target binding (alternatively this 5' 10 nt is truncated entirely). This "low-affinity" gRNA unit exists as part of a tandem gRNA construct with a second, distinct low-affinity gRNA unit downstream, separated by a linker sequence. In some embodiments, there are more than two low-affinity gRNA units (e.g., at least 3, at least 4, at least 5, etc.). In some embodiments, the linker comprises a target nucleic acid complementary sequence (e.g., as depicted by the linker region contacting the DNA target).

According to another embodiment, dimers of Cas9 protein are provided. In some embodiments, the dimers are coordinated through the action of a single extended gRNA that comprises at least two portions that complement the target nucleic acid. In some embodiments, the portions complementary to the target nucleic acid comprise no more than 25, no more than 24, no more than 23, no more than 22, no more than 21, no more than 20, no more than 19, no more than 18, no more than 17, no more than 16, no more than 15, no more than 14, no more than 13, no more than 12, no more than 11, no more than 10, no more than 9, no more than 8, no more than 7, no more than 6, or no more than 5 nucleotides that complement the target nucleic acid. In some embodiments, the portions complementary to the target nucleic acid comprise 5-30, 5-25, or 5-20 nucleotides. In some embodiments, the portions complementary to the target nucleic acid comprise 15-25, 19-21, or 20 nucleotides. In some embodiments, the portions comprise the same number of nucleotides that complement the target nucleic acid. In some embodiments, the portions comprise different numbers of nucleotides that complement the target nucleic acid. For example, in some embodiments, the extended gRNA comprises two portions that complement (e.g., and hybridize to) the target nucleic acid, each portion comprising 5-19, 10-15, or 10 nucleotides that complement the target nucleic acid. Without wishing to be bound by any particular theory, having the portions comprise fewer than approximately 20 nucleotides typical of gRNAs (e.g., having the portions comprise approximately 5-19, 10-15, or 10 complementary nucleotides), ensures that a single Cas9:gRNA unit cannot bind efficiently by itself. Thus the cooperative binding between Cas9 proteins coordinated by such an extended gRNA improves the specificity and cleavage of intended target nucleic acids. In some embodiments, the linker sequence separating the two portions of the extended gRNA has complementarity with the target sequence. For example, in some embodiments, the linker sequence has at least 5, at least 6, at least 7, at least 8, at least 9, at least 10, at least 11, at least 12, at least 13, at least 14, at least 15, at least 20, at least 25, at least 30, at least 40, or at least 50 nucleotides that complement the target nucleic acid. Without wishing to be bound by any particular theory, it is believed that having an extended gRNA that comprises multiple binding sites (e.g., multiple low-affinity binding sites), including those that are bound by a Cas9 protein as well as those in the linker sequence, provides for increased specificity by promoting cooperative binding. Certain aspects of this embodiment are shown in FIG. 4. In some embodiments, any of the Cas9 proteins described herein may be coordinated through a single extended gRNA.

Figure 2A:
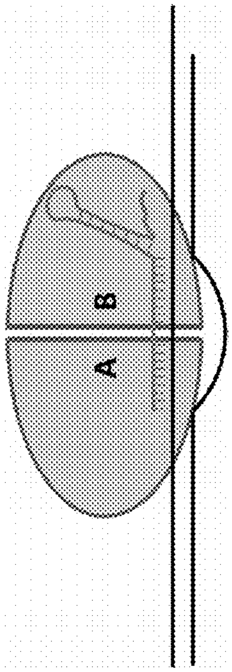
FIG. 2 is a schematic detailing certain embodiments of the invention. (A) In this embodiment, dimeric split Cas9 separates A) gRNA-binding ability from B) dsDNA cleavage. DNA cleavage occurs when both halves of the protein are co-localized to associate and refold into a nuclease-active state. (B) In this embodiment, nuclease-inactivated Cas9 mutant is fused to the A-half (or in some embodiments, the B-half) of the split Cas9 nuclease. Upon binding of both the Cas9-A-half (or Cas9-B-half) fusion and the inactive gRNA-binding Cas9 B-half (or A-half, respectively) at the target site, dsDNA is enabled following split protein reassembly. This split Cas9-pairing can use two distinct gRNA-binding Cas9 proteins to ensure the split nuclease-active Cas9 reassembles only on the correct target sequence. (C) In this embodiment, nuclease-inactivated Cas9 mutant is fused to the A-half of the split Cas9 nuclease. A separate nuclease-inactivated Cas9 mutant is fused to the B-half of the split Cas9 nuclease. Upon binding of one nuclease-inactivated Cas9 mutant to a gRNA target site and binding of the other nuclease-inactivated Cas9 mutant to a second gRNA target site, the split Cas9 halves can dimerize and bind a third gRNA target to become a fully active Cas9 nuclease that can cleave dsDNA. This split Cas9-pairing uses three distinct gRNA-binding Cas9 proteins to ensure the split nuclease-active Cas9 reassembles only on the correct target sequence. Any other DNA-binding domain in place of the inactive Cas9 (zinc fingers, TALE proteins, etc.) can be used to complete the reassembly of the split Cas9 nuclease.

In another embodiment, proteins comprising a fragment of an RNA-programmable nuclease (e.g., Cas9) are provided. For example, in some embodiments, a protein comprising the gRNA binding domain of Cas9 is provided. In some embodiments, the protein comprising the gRNA binding domain of Cas9 does not comprise a DNA cleavage domain (referred to herein as the "A-half" of Cas9). In other embodiments, proteins comprising the DNA cleavage domain(s) (e.g., the HNH, RuvC1 subdomains) of Cas9 are provided. In some embodiments, the "DNA cleavage domain" refers collectively to the portions of Cas9 required for double-stranded DNA cleavage (e.g., the HNH, RuvC1 subdomains). In some embodiments, the protein comprising the DNA cleavage domain of Cas9 does not comprise a gRNA binding domain (referred to herein as the "B-half" of Cas9). In some embodiments, dimers are provided that comprise (i) a protein comprising the gRNA binding domain of Cas9 (e.g., the A-half), and (ii) a protein comprising the DNA cleavage domain of Cas9 (e.g., the B-half). In some embodiments, the dimer is bound by a gRNA. For example, such dimers are expected to recapitulate the binding and cleaving activities of a full length Cas9 protein. In some embodiments, such dimers are referred to herein as "dimeric split Cas9." Using a dimeric split Cas9 to cleave a target nucleic acid is expected to provide for increased specificity as compared to a single full length Cas9 protein because both halves of the protein must be co-localized to associate and re-fold into a nuclease-active state. This strategy is shown in the schematic of FIG. 2A.

In some embodiments, fusion proteins comprising two domains are provided: (i) a protein capable of specifically binding a target nucleic acid (e.g., a nuclease-inactivated RNA programmable nuclease, such as a nuclease-inactivated Cas9, as described herein) fused or linked to (ii) a fragment of an RNA-programmable nuclease (e.g., the A- or B-half of Cas9, as described herein). In some embodiments, domain (i) of the aforementioned fusion protein comprises a DNA binding domain, for example, a DNA binding domain of a zinc finger or TALE protein. In some embodiments, the fusion protein comprises (i) a nuclease-inactivated Cas9, and (ii) a gRNA binding domain of Cas9 (e.g., Cas9 A-half). In some embodiments, domain (ii) of the fusion protein does not include a DNA cleavage domain. In other embodiments, the fusion protein comprises (i) a nuclease-inactivated Cas9, and (ii) a DNA cleavage domain (e.g., Cas9 B-half). In some embodiments, domain (ii) of the fusion protein does not include a gRNA binding domain.

Figure 2B:
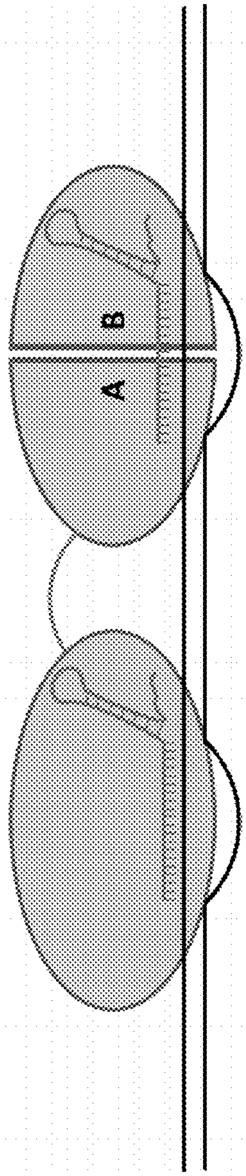

In some embodiments, dimers are provided that comprise two proteins: (i) a fusion protein comprising a nuclease-inactivated Cas9 and a gRNA binding domain of Cas9 (e.g., nuclease-inactivated Cas9 fused to Cas9 A-half), and (ii) a protein comprising the DNA cleavage domain of Cas9 (e.g., Cas9 B-half). In other embodiments, the dimer comprises (i) a fusion protein comprising a nuclease-inactivated Cas9 and a DNA cleavage domain of Cas9 (e.g., nuclease-inactivated Cas9 fused to Cas9 B-half), and (ii) a protein comprising the gRNA binding domain of Cas9 (e.g., Cas9 A-half). In some embodiments, the protein dimers include one or more gRNAs. For example, in some embodiments, the dimers include two gRNAs: one bound by the nuclease-inactivated Cas9 domain of the fusion protein; the other bound by the A-half domain (e.g., either the A-half of the fusion protein, or the A-half of the dimer not part of the fusion protein). Such a dimer (e.g., associated with two gRNAs having sequences binding separate regions of a target nucleic acid) is expected to have improved specificity compared to e.g., a Cas9 protein having a single gRNA. This strategy is shown in FIG. 2B.

Figure 2C:
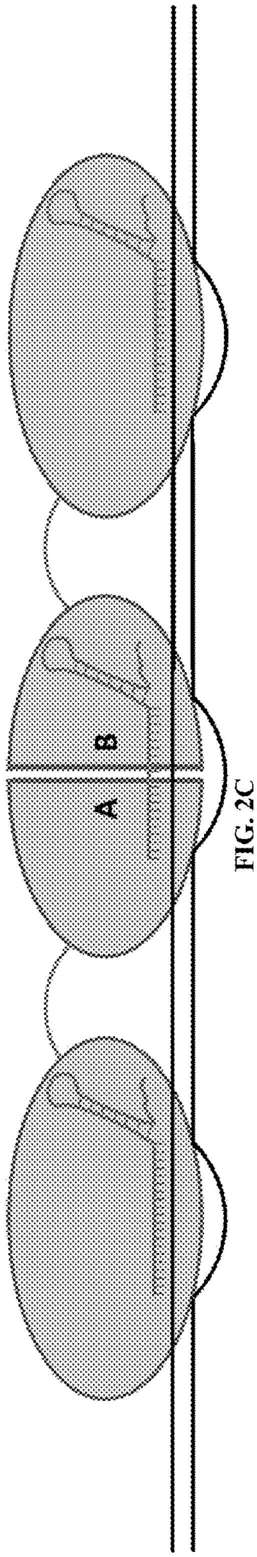
Figure 3:
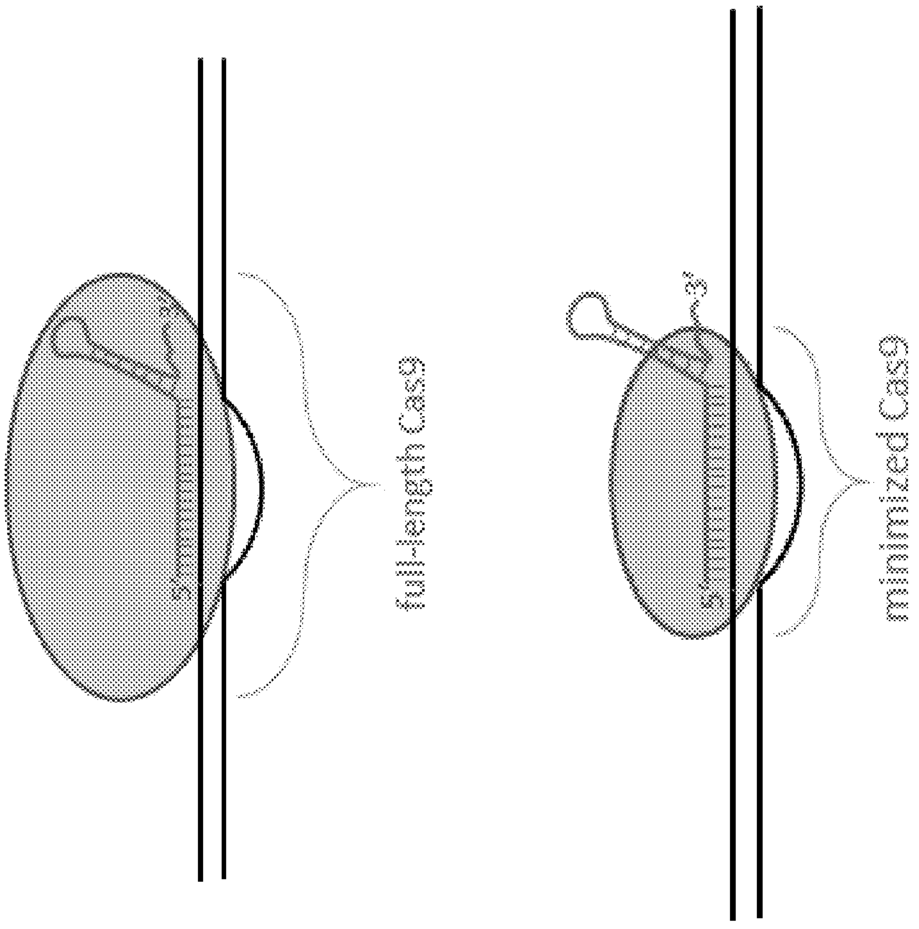
FIG. 3 shows schematically a minimal Cas9 protein that comprises the essential domains for Cas9 activity. Full-length Cas9 is a 4.1 kb gene which results in a protein of >150 kDa. Specific deletions and/or truncations decrease the size of Cas9 without affecting its activity (e.g., gRNA binding and DNA cleavage activity). The minimized Cas9 protein increases the efficacy of, for example, delivery to cells using viral vectors such as AAV (accommodating sequences ~<4700 bp) or lentivirus (accommodating sequences ~<9 kb), or when pursuing multiplexed gRNA/Cas9 approaches.

In some embodiments, a protein dimer is provided that comprises two fusion proteins: (i) a fusion protein comprising a nuclease-inactivated Cas9 and a gRNA binding domain of Cas9 (e.g., a nuclease-inactivated Cas9 fused to a Cas9 A-half), and (ii) a fusion protein comprising a nuclease-inactivated Cas9 and a DNA cleavage domain (e.g., a nuclease-inactivated Cas9 fused to a Cas9 B-half). In some embodiments, the dimer is associated with (e.g., binds) one or more distinct gRNAs. For example, in some embodiments, the dimer is associated with two or three gRNAs. In some embodiments, the dimer is associated with three gRNAs. For example, upon binding of one nuclease-inactivated Cas9:gRNA to a region of a nucleic acid target, and binding of the other nuclease-inactivated Cas9:gRNA to a second region of the nucleic acid target, the split Cas9 halves (e.g., A-half and B-half of the fusion proteins) can dimerize and bind a third gRNA complementary to a third region of the nucleic acid target, to become a fully active Cas9 nuclease, which can cleave dsDNA. This strategy is illustrated in FIG. 2C.

According to another aspect of the invention, minimized Cas9 proteins are provided. By "minimized," it is meant that the Cas9 protein comprises amino acid deletions and/or truncations, as compared to the wild type protein, but retains gRNA binding activity, DNA cleavage activity, or both. Any of the embodiments herein describing Cas9 proteins (e.g., split Cas9 proteins, Cas9 A-half, Cas9 B-half, nuclease-inactivated Cas9 fusion proteins, etc.) can utilize a minimized Cas9 protein. In some embodiments, minimized Cas9 proteins comprising N-terminal deletions and/or truncations are provided. In some embodiments, minimized Cas9 proteins comprising C-terminal deletions and/or truncations are provided. In some embodiments, minimized Cas9 proteins are provided that comprise N- and/or C-terminal deletions and/or truncations. In some embodiments, the minimized Cas9 protein retains both gRNA binding and DNA cleavage activities. In some embodiments, the minimized Cas9 protein comprises an N-terminal truncation that removes at least 5, at least 10, at least 15, at least 20, at least 25, at least 40, at least 40, at least 50, at least 75, at least 100, at least 150, at least 200, at least 250, at least 300, at least 350, at least 400, at least 450, or at least 500 amino acids. In some embodiments, the minimized Cas9 protein comprises a C-terminal truncation that removes at least 5, at least 10, at least 15, at least 20, at least 25, at least 40, at least 40, at least 50, at least 75, at least 100, at least 150, at least 200, at least 250, at least 300, at least 350, at least 400, at least 450, or at least 500 amino acids. In some embodiments, deletions are made within Cas9, for example in regions not affecting gRNA binding and/or DNA cleavage. In some embodiments, the minimized Cas9 protein is associated with one or more gRNAs. In certain embodiments, the minimized Cas9 protein is associated with one gRNA.

Recombinases

Some aspects of this disclosure provide RNA-guided recombinase fusion proteins that are designed using the methods and strategies described herein. Some embodiments of this disclosure provide nucleic acids encoding such recombinases. Some embodiments of this disclosure provide expression constructs comprising such encoding nucleic acids. For example, in some embodiments an isolated recombinase is provided that has been engineered to recombine a desired target site (e.g., a site targeted by one or more gRNAs bound to one or more of the engineered recombinases) within a genome, e.g., with another site in the genome or with an exogenous nucleic acid. In some embodiments, the isolated recombinase comprises a variant of an RNA-programmable nuclease, such as a Cas9 nuclease. In some embodiments, the Cas9 variant is a nuclease-inactivated Cas9 (e.g., dCas9). In some embodiments, dCas9 is encoded by a nucleotide sequence comprising in part or in whole, SEQ ID NO:5 or SEQ ID NO:320. In some embodiments, dCas9 is encoded by a nucleotide sequence comprising a variant of SEQ ID NO:5 or SEQ ID NO:320.

In one embodiment, an RNA-guided recombinase fusion protein is provided. Typically, the fusion protein comprises two or more domains. In some embodiments, the fusion protein comprises two domains. In some embodiments, one of the two or more domains is a nuclease-inactivated Cas9 (or fragment thereof, e.g., Cas9 A-half), for example, those described herein (e.g., dCas9). The Cas9 domain of the recombinase fusion protein is capable of binding one or more gRNAs, and thereby directs or targets the recombinase fusion protein(s) to a target nucleic acid, e.g., as described herein. Another domain of the two or more domains is a recombinase, or a fragment thereof, e.g., a catalytic domain of a recombinase. By "catalytic domain of a recombinase," it is meant that a fusion protein includes a domain comprising an amino acid sequence of (e.g., derived from) a recombinase, such that the domain is sufficient to induce recombination when contacted with a target nucleic acid (either alone or with additional factors including other recombinase catalytic domains which may or may not form part of the fusion protein). In some embodiments, a catalytic domain of a recombinase excludes a DNA binding domain of the recombinase. In some embodiments, the catalytic domain of a recombinase includes part or all of a recombinase, e.g., the catalytic domain may include a recombinase domain and a DNA binding domain, or parts thereof, or the catalytic domain may include a recombinase domain and a DNA binding domain that is mutated or truncated to abolish DNA binding activity. Recombinases and catalytic domains of recombinases are known to those of skill in the art, and include, for example, those described herein. In some embodiments, the catalytic domain is derived from any recombinase. In some embodiments, the recombinase catalytic domain is a catalytic domain of a Tn3 resolvase, a Hin recombinase, or a Gin recombinase. In some embodiments, the catalytic domain comprises a Tn3 resolvase (e.g., Stark Tn3 recombinase) that is encoded by a nucleotide sequence comprising, in part or in whole, SEQ ID NO:322, as provided below. In some embodiments, a Tn3 catalytic domain is encoded by a variant of SEQ ID NO:322. In some embodiments, a Tn3 catalytic domain is encoded by a polynucleotide (or a variant thereof) that encodes the polypeptide corresponding to SEQ ID NO:325. In some embodiments, the catalytic domain comprises a Hin recombinase that is encoded by a nucleotide sequence comprising, in part or in whole, SEQ ID NO:323, as provided below. In some embodiments, a Hin catalytic domain is encoded by a variant of SEQ ID NO:323. In some embodiments, a Hin catalytic domain is encoded by a polynucleotide (or a variant thereof) that encodes the polypeptide corresponding to SEQ ID NO:326. In some embodiments, the catalytic domain comprises a Gin recombinase (e.g., Gin beta recombinase) that is encoded by a nucleotide sequence comprising, in part or in whole, SEQ ID NO:324, as provided below. In some embodiments, a Gin catalytic domain is encoded by a variant of SEQ ID NO:324. In some embodiments, a Gin catalytic domain is encoded by a polynucleotide (or a variant thereof) that encodes the polypeptide corresponding to SEQ ID NO:327.

Stark Tn3 Recombinase (Nucleotide: SEQ ID NO:322; Amino Acid: SEQ ID NO:325):

(SEQ ID NO: 322)
ATGGCCCTGTTTGGCTACGCACGCGTGTCTACCAGTCAACAGTCACTCGA
TTTGCAAGTGAGGGCTCTTAAAGATGCCGGAGTGAAGGCAAACAGAATTT
TTACTGATAAGGCCAGCGGAAGCAGCACAGACAGAGAGGGGCTGGATCTC
CTGAGAATGAAGGTAAAGGAGGGTGATGTGATCTTGGTCAAAAAATTGGA
TCGACTGGGGAGAGACACAGCTGATATGCTTCAGCTTATTAAAGAGTTTG
ACGCTCAGGGTGTTGCCGTGAGGTTTATCGATGACGGCATCTCAACCGAC
TCCTACATTGGTCTTATGTTTGTGACAATTTTGTCCGCTGTGGCTCAGGC
TGAGCGGAGAAGGATTCTCGAAAGGACGAATGAGGGACGGCAAGCAGCTA
AGTTGAAAGGTATCAAATTTGGCAGACGAAGG (SEQ ID NO: 325)
MALFGYARVSTSQQSLDLQVRALKDAGVKANRIFTDKASGSSTDREGLDL
LRMKVKEGDVILVKKLDRLGRDTADMLQLIKEFDAQGVAVRFIDDGISTD
SYIGLMFVTILSAVAQAERRRILERTNEGRQAAKLKGIKFGRRR

Hin Recombinase (Nucleotide: SEQ ID NO:323; Amino Acid: SEQ ID NO:326):

(SEQ ID NO: 323)
ATGGCAACCATTGGCTACATAAGGGTGTCTACCATCGACCAAAATATCGA
CCTGCAGCGCAACGCTCTGACATCCGCCAACTGCGATCGGATCTTCGAGG
ATAGGATCAGTGGCAAGATCGCCAACCGGCCCGGTCTGAAGCGGGCTCTG
AAGTACGTGAATAAGGGCGATACTCTGGTTGTGTGGAAGTTGGATCGCTT
GGGTAGATCAGTGAAGAATCTCGTAGCCCTGATAAGCGAGCTGCACGAGA
GGGGTGCACATTTCCATTCTCTGACCGATTCCATCGATACGTCTAGCGCC
ATGGGCCGATTCTTCTTTTACGTCATGTCCGCCCTCGCTGAAATGGAGCG
CGAACTTATTGTTGAACGGACTTTGGCTGGACTGGCAGCGGCTAGAGCAC
AGGGCCGACTTGGA (SEQ ID NO: 326)
MATIGYIRVSTIDQNIDLQRNALTSANCDRIFEDRISGKIANRPGLKRAL
KYVNKGDTLVVWKLDRLGRSVKNLVALISELHERGAHFHSLTDSIDTSSA
MGRFFFYVMSALAEMERELIVERTLAGLAAARAQGRLG

Gin Beta Recombinase (Nucleotide: SEQ ID NO:324; Amino Acid: SEQ ID NO:327):

(SEQ ID NO: 324)
ATGCTCATTGGCTATGTAAGGGTCAGCACCAATGACCAAAACACAGACTT
GCAACGCAATGCTTTGGTTTGCGCCGGATGTGAACAGATATTTGAAGATA
AACTGAGCGGCACTCGGACAGACAGACCTGGGCTTAAGAGAGCACTGAAA
AGACTGCAGAAGGGGGACACCCTGGTCGTCTGGAAACTGGATCGCCTCGG
ACGCAGCATGAAACATCTGATTAGCCTGGTTGGTGAGCTTAGGGAGAGAG
GAATCAACTTCAGAAGCCTGACCGACTCCATCGACACCAGTAGCCCCATG
GGACGATTCTTCTTCTATGTGATGGGAGCACTTGCTGAGATGGAAAGAGA
GCTTATTATCGAAAGAACTATGGCTGGTATCGCTGCTGCCCGGAACAAAG
GCAGACGGTTCGGCAGACCGCCGAAGAGCGGC (SEQ ID NO: 327)
MLIGYVRVSTNDQNTDLQRNALVCAGCEQIFEDKLSGTRTDRPGLKRALK
RLQKGDTLVVWKLDRLGRSMKHLISLVGELRERGINFRSLTDSIDTSSPM
GRFFFYVMGALAEMERELIIERTMAGIAAARNKGRRFGRPPKSG

In some embodiments, the recombinase catalytic domain is fused to the N-terminus, the C-terminus, or somewhere in between the N- and C-termini of a Cas9 protein (e.g., sCas9). In some embodiments, the fusion protein further comprises a nuclear localization signal (NLS; e.g., any of those provided herein). For example, in some embodiments, the general architecture of exemplary RNA-guided recombinase fusion proteins (e.g., Cas9-recombinase fusions) comprise one of the following structures:

[$NH_2$]-[Cas9]-[recombinase]-[COOH],
[NH2]-[recombinase]-[Cas9],
[$NH_2$]-[NLS]-[Cas9]-[recombinase]-[COOH],
[$NH_2$]-[NLS]-[recombinase]-[Cas9]-[COOH],
[$NH_2$]-[Cas9]-[NLS]-[recombinase]-[COOH],
[$NH_2$]-[recombinase]-[NLS]-[Cas9]-[COOH],
[$NH_2$]-[Cas9]-[recombinase]-[NLS]-[COOH], or
[$NH_2$]-[recombinase]-[Cas9]-[NLS]-[COOH]

wherein NLS is a nuclear localization signal, $NH_2$ is the N-terminus of the fusion protein, and COOH is the C-terminus of the fusion protein. In some embodiments, a linker is inserted between the Cas9 domain and the recombinase domain, e.g., any linker provided herein. Additional features, such as sequence tags (e.g., any of those provided herein), may also be present.

Pharmaceutical Compositions

In some embodiments, any of the nucleases (e.g., fusion proteins comprising nucleases or nuclease domains) and recombinases (e.g., fusion proteins comprising recombinases or recombinase catalytic domains) described herein are provided as part of a pharmaceutical composition. For example, some embodiments provide pharmaceutical compositions comprising a nuclease and/or recombinase as provided herein, or a nucleic acid encoding such a nuclease and/or recombinase, and a pharmaceutically acceptable excipient. Pharmaceutical compositions may optionally comprise one or more additional therapeutically active substances.

In some embodiments, compositions provided herein are administered to a subject, for example, to a human subject, in order to effect a targeted genomic modification within the subject. In some embodiments, cells are obtained from the subject and are contacted with a nuclease and/or recombinase ex vivo. In some embodiments, cells removed from a subject and contacted ex vivo with an inventive nuclease and/or recombinase are re-introduced into the subject, optionally after the desired genomic modification has been effected or detected in the cells. Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, domesticated animals, pets, and commercially relevant mammals such as cattle, pigs, horses, sheep, cats, dogs, mice, and/or rats; and/or birds, including commercially relevant birds such as chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient, and then, if necessary and/or desirable, shaping and/or packaging the product into a desired single- or multi-dose unit.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy,* $21^{st}$ Edition, A. R. Gennaro (Lippincott, Williams & Wilkins, Baltimore, Md., 2006; incorporated in its entirety herein by reference) discloses various excipients used in formulating pharmaceutical compositions and known techniques for the preparation thereof. See also PCT application PCT/US2010/055131, incorporated in its entirety herein by reference, for additional suitable methods, reagents, excipients and solvents for producing pharmaceutical compositions comprising a nuclease. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this disclosure.

In some embodiments, compositions in accordance with the present invention may be used for treatment of any of a variety of diseases, disorders, and/or conditions, including but not limited to one or more of the following: autoimmune disorders (e.g. diabetes, lupus, multiple sclerosis, psoriasis, rheumatoid arthritis); inflammatory disorders (e.g. arthritis, pelvic inflammatory disease); infectious diseases (e.g. viral infections (e.g., HIV, HCV, RSV), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc.

Methods for Site-Specific Nucleic Acid Cleavage

In another embodiment of this disclosure, methods for site-specific nucleic acid (e.g., DNA) cleavage are provided. In some embodiments, the methods comprise contacting a DNA with any of the Cas9:gRNA complexes described herein. For example, in some embodiments, the method comprises contacting a DNA with a fusion protein (e.g., fCas9) that comprises two domains: (i) a nuclease-inactivated Cas9 (dCas9); and (ii) a nuclease (e.g., a FokI DNA cleavage domain), wherein the wherein the inactive Cas9 domain binds a gRNA that hybridizes to a region of the DNA. In some embodiments, the method further comprises contacting the DNA with a second fusion protein described herein (e.g., fCas9), wherein the nuclease-inactivated Cas9 (dCas9) domain of the second fusion protein binds a second gRNA that hybridizes to a second region of DNA, wherein the binding of the fusion proteins results in the dimerization of the nuclease domains of the fusion proteins, such that the DNA is cleaved in a region between the bound fusion proteins. See e.g., FIGS. 1A, 6D. In some embodiments, the gRNAs bound to each fusion protein hybridize to the same strand of the DNA, or they hybridize to opposing strands of the DNA. In some embodiments, the gRNAs hybridize to regions of the DNA that are no more than 10, no more than 15, no more than 20, no more than 25, no more than 30, no more than 40, 50, no more than 60, no more than 70, no more than 80, no more than 90, or no more than 100 base pairs apart. The region between the bound Cas9:gRNA complexes may be referred to as the "spacer sequence," which is typically where the target nucleic acid is cleaved. See, e.g., FIGS. 6C-D. In some embodiments, the spacer sequence is at least 5, at least 10, at least 15, at least 20, at least 25, at least 30 at least 35, at least 40, at least 45, at least 50, at least 60, at least 70, at least 80, at least 90, or at least 100 base pairs in length. In some embodiments, the spacer sequence is between about 5 and about 50 base pairs, about 10 and about 40, or about 15 and about 30 base pairs in length. In some embodiments, the spacer sequence is about 15 to about 25 base pairs in length. In some embodiments, the spacer sequence is about 15, about 20, or about 25 base pairs in length. In some embodiments, the Cas9:gRNA complexes are bound in the A orientation, as described herein. In some embodiments, the Cas9:gRNA complexes are bound in the B orientation, as described herein. In some embodiments, the method has an on-target:off-target modification ratio that is at least 2-fold, at least 5-fold, at least 10-fold, at least 20-fold, at least 30-fold, at least 40-fold, at least 50-fold, at least 60-fold, at least 70-fold, at least 80-fold, at least 90-fold, at least 100-fold, at least 110-fold, at least 120-fold, at least 130-fold, at least 140-fold, at least 150-fold, at least 175-fold, at least 200-fold, or at least 250-fold or more higher than the on-target:off-target modification ratio of methods utilizing a wild type Cas9 or other Cas9 variant. In some embodiments, the method has an on-target:off-target modification ratio that is between about 60-to about 180-fold, between about 80- to about 160-fold, between about 100- to about 150-fold, or between about 120- to about 140-fold higher than the on-target:off-target modification ratio of methods utilizing a wild type Cas9 or other Cas9 variant. Methods for determining on-target:off-target modification ratios are known, and include those described in the Examples. In some embodiments, the fusion proteins are coordinated or associated through a single gRNA, e.g., as described herein.

In some embodiments, the method comprises contacting a nucleic acid with a dimer of Cas9 proteins (or fragments thereof) coordinated with (e.g., bound by) a single gRNA as described herein. In some embodiments, the single gRNA comprises at least two portions that hybridize to the nucleic acid. In some embodiments, the portions comprise at least 5, at least 10, at least 15, or at least 19 complementary nucleotides. In some embodiments, the portions comprise fewer than 20 complementary nucleotides. In some embodiments, a linker sequence separates the portions, wherein the linker sequence also comprises nucleotides complementary to the target nucleic acid (e.g., but are not bound by a Cas9 protein). In some embodiments, the linker sequence does not hybridize to the target nucleic acid.

In some embodiments, the methods comprise contacting a DNA with a protein dimer of fusion proteins described herein, wherein the fusion proteins are bound by one or more gRNAs. For example, in some embodiments, one fusion protein of the dimer comprises a gRNA binding domain of Cas9 (e.g., Cas9 A-half), wherein the protein does not comprise a DNA cleavage domain (e.g., Cas9 B-half); and the other fusion protein of the dimer comprises a DNA cleavage domain of Cas9 (e.g., Cas9 B-half), wherein the protein does not comprise a gRNA binding domain (e.g., Cas9 A-half). Thus, in some embodiments, the binding of a gRNA (e.g., that hybridizes to a target nucleic acid) to one or both of the monomers of the dimer co-localizes the dimer to the target nucleic acid, allowing the dimer to re-fold into a nuclease-active state and cleave the target nucleic acid.

In some embodiments, the method comprises contacting a nucleic acid with protein dimers comprising two proteins: (i) a fusion protein comprising a nuclease-inactivated Cas9 and a gRNA binding domain of Cas9 (e.g., nuclease-inactivated Cas9 fused to Cas9 A-half), and (ii) a protein comprising the DNA cleavage domain of Cas9 (e.g., Cas9 B-half). In other embodiments, the dimer comprises (i) a fusion protein comprising a nuclease-inactivated Cas9 and a DNA cleavage domain of Cas9 (e.g., nuclease-inactivated Cas9 fused to Cas9 B-half), and (ii) a protein comprising the gRNA binding domain of Cas9 (e.g., Cas9 A-half). In some embodiments, the protein dimers are associated with one or more gRNAs. For example, in some embodiments, the dimers are associated with two gRNAs: one bound by the nuclease-inactivated Cas9 domain of the fusion protein; the other bound by the A-half domain (e.g., either the A-half of the fusion protein, or the A-half of the dimer not part of the fusion protein). In some embodiments, the protein dimer comprises (i) a fusion protein comprising a nuclease-inactivated Cas9 and a gRNA binding domain of Cas9 (e.g., a nuclease-inactivated Cas9 fused to a Cas9 A-half), and (ii) a fusion protein comprising a nuclease-inactivated Cas9 and a DNA cleavage domain (e.g., a nuclease-inactivated Cas9 fused to a Cas9 B-half). In some embodiments, the dimer is associated with one or more distinct gRNAs. For example, in some embodiments, the dimer is associated with two or three gRNAs. In some embodiments, the dimer is associated with three gRNAs. For example, upon binding of one nuclease-inactivated Cas9:gRNA to a region of a nucleic acid target, and binding of the other nuclease-inactivated Cas9:gRNA to a second region of the nucleic acid target, the split Cas9 halves (e.g., A-half and B-half of the fusion proteins) dimerize and bind a third gRNA complementary to a third region of the nucleic acid target, to become a fully active Cas9 nuclease leading to cleave of the target DNA.

In some embodiments, a method for site-specific cleavage of a nucleic acid comprises contacting a nucleic acid (e.g., DNA) with a minimized Cas9 protein (e.g., as described herein) associated with a gRNA.

In some embodiments, any of the methods provided herein can be performed on DNA in a cell, for example a bacterium, a yeast cell, or a mammalian cell. In some embodiments, the DNA contacted by any Cas9 protein provided herein is in a eukaryotic cell. In some embodiments, the methods can be performed on a cell or tissue in vitro or ex vivo. In some embodiments, the eukaryotic cell is in an individual, such as a patient or research animal. In some embodiments, the individual is a human.

Methods for Site-Specific Recombination

Figure 5A:
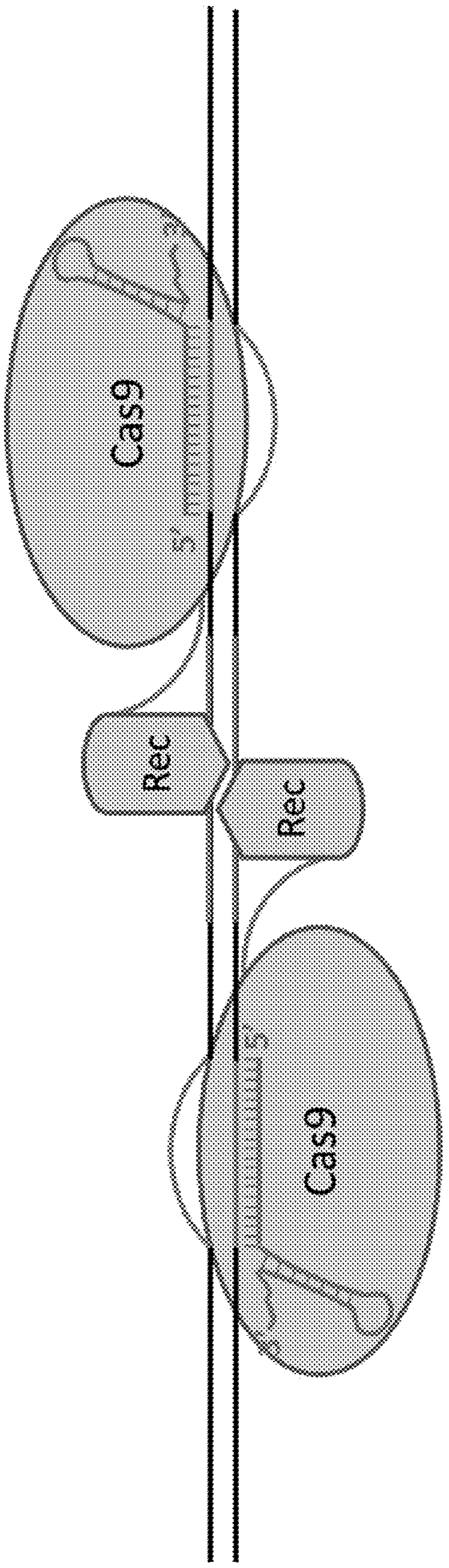
FIG. 5 shows schematically, how Cas9-recombinase fusions can be coordinated through gRNAs to bind and recombine target DNAs at desired sequences (sites). (A, B) Nuclease-inactivated Cas9 (dCas9) protein is fused to a monomer of a recombinase domain (Rec). Site-specific recombination is achieved through dimerization (A) of the recombinase catalytic domain monomers at the target site, and then tetramerization (B) of two dimers assembled on separate Cas9-recombination sites. The fusion to dCas9:gRNA complexes determines the sequence identity of the flanking target sites while the recombinase catalytic domain determines the identity of the core sequence (the sequence between the two dCas9-binding sites). (B) Recombination proceeds through strand cleavage, exchange, and re-ligation within the dCas9-recombinase tetramer complex.

In another embodiment of this disclosure, methods for site-specific nucleic acid (e.g., DNA) recombination are provided. In some embodiments, the methods are useful for inducing recombination of or between two or more regions of two or more nucleic acid (e.g., DNA) molecules. In other embodiments, the methods are useful for inducing recombination of or between two or more regions in a single nucleic acid molecule (e.g., DNA). In some embodiments, the recombination of one or more target nucleic acid molecules requires the formation of a tetrameric complex at the target site. Typically, the tetramer comprises four (4) inventive RNA-guided recombinase fusion proteins (e.g., a complex of any four inventive recombinase fusion protein provided herein). In some embodiments, each recombinase fusion protein of the tetramer targets a particular DNA sequence via a distinct gRNA bound to each recombinase fusion protein (See, e.g., FIG. 5).

In some embodiments, the method for site-specific recombination between two DNA molecules comprises (a) contacting a first DNA with a first RNA-guided recombinase fusion protein, wherein the nuclease-inactivated Cas9 domain binds a first gRNA that hybridizes to a region of the first DNA; (b) contacting the first DNA with a second RNA-guided recombinase fusion protein, wherein the nuclease-inactivated Cas9 domain of the second fusion protein binds a second gRNA that hybridizes to a second region of the first DNA; (c) contacting a second DNA with a third RNA-guided recombinase fusion protein, wherein the nuclease-inactivated Cas9 domain of the third fusion protein binds a third gRNA that hybridizes to a region of the second DNA; and (d) contacting the second DNA with a fourth RNA-guided recombinase fusion protein, wherein the nuclease-inactivated Cas9 domain of the fourth fusion protein binds a fourth gRNA that hybridizes to a second region of the second DNA. The binding of the fusion proteins in steps (a)-(d) results in the tetramerization of the recombinase catalytic domains of the fusion proteins, such that the DNAs are recombined. In some embodiments, the gRNAs of steps (a) and (b) hybridize to opposing strands of the first DNA, and the gRNAs of steps (c) and (d) hybridize to opposing strands of the second DNA. In some embodiments, the target sites of the gRNAs of steps (a)-(d) are spaced to allow for tetramerization of the recombinase catalytic domains. For example, in some embodiments, the target sites of the gRNAs of steps (a)-(d) are no more than 10, no more 15, no more than 20, no more than 25, no more than 30, no more than 40, no more than 50, no more than 60, no more than 70, no more than 80, no more than 90, or no more than 100 base pairs apart. In some embodiments, the two regions of the two DNA molecules being recombined share homology, such that the regions being recombined are at least 80%, at least 90%, at least 95%, at least 98%, or are 100% homologous.

In another embodiment, methods for site-specific recombination between two regions of a single DNA molecule are provided. In some embodiments, the methods comprise (a) contacting a DNA with a first RNA-guided recombinase fusion protein, wherein the nuclease-inactivated Cas9 domain binds a first gRNA that hybridizes to a region of the DNA; (b) contacting the DNA with a second RNA-guided recombinase fusion protein, wherein the nuclease-inactivated Cas9 domain of the second fusion protein binds a second gRNA that hybridizes to a second region of the DNA; (c) contacting the DNA with a third RNA-guided recombinase fusion protein, wherein the nuclease-inactivated Cas9 domain of the third fusion protein binds a third gRNA that hybridizes to a third region of the DNA; and (d) contacting the DNA with a fourth RNA-guided recombinase fusion protein, wherein the nuclease-inactivated Cas9 domain of the fourth fusion protein binds a fourth gRNA that hybridizes to a fourth region of the DNA. The binding of the fusion proteins in steps (a)-(d) results in the tetramerization of the recombinase catalytic domains of the fusion proteins, such that the DNA is recombined. In some embodiments, two of the gRNAs of steps (a)-(d) hybridize to the same strand of the DNA, and the other two gRNAs of steps (a)-(d) hybridize to the opposing strand of the DNA. In some embodiments, the gRNAs of steps (a) and (b) hybridize to regions of the DNA that are no more 10, no more than 15, no more than 20, no more than 25, no more than 30, no more than 40, no more than 50, no more than 60, no more than 70, no more than 80, no more than 90, or no more than 100 base pairs apart, and the gRNAs of steps (c) and (d) hybridize to regions of the DNA that are no more than 10, no more 15, no more than 20, no more than 25, no more than 30, no more than 40, no more than 50, no more than 60, no more than 70, no more than 80, no more than 90, or no more than 100 base pairs apart. In some embodiments, the two regions of the DNA molecule being recombined share homology, such that the regions being recombined are at least 80%, at least 90%, at least 95%, at least 98%, or are 100% homologous.

In some embodiments, any of the inventive methods for site-specific recombination are amenable for inducing recombination, such that the recombination results in excision (e.g., a segment of DNA is excised from a target DNA molecule), insertion (e.g., a segment of DNA is inserted into a target DNA molecule), inversion (e.g., a segment of DNA is inverted in a target DNA molecule), or translocation (e.g., the exchange of DNA segments between one or more target DNA molecule(s)). In some embodiments, the particular recombination event (e.g., excision, insertion, inversion, translocation, etc.) depends, inter alia, on the orientation (e.g., with respect to the target DNA molecule(s)) of the bound RNA-guided recombinase fusion protein(s). In some embodiments, the orientation, or direction, in which a RNA-guided recombinase fusion protein binds a target nucleic acid can be controlled, e.g., by the particular sequence of the gRNA bound to the RNA-guided recombinase fusion protein(s). Methods for controlling or directing a particular recombination event are known in the art, and include, for example, those described by Turan and Bode, "Site-specific recombinases: from tag-and-target-to tag-and-exchange-based genomic modifications." *FASEB J.* 2011; December; 25(12):4088-107, the entire contents of which are hereby incorporated by reference.

In some embodiments, any of the methods for site-specific recombination can be performed in vivo or in vitro. In some embodiments, any of the methods for site-specific recombination are performed in a cell (e.g., recombine genomic DNA in a cell). The cell can be prokaryotic or eukaryotic. The cell, such as a eukaryotic cell, can be in an individual, such as a subject, as described herein (e.g., a human subject). The methods described herein are useful for the genetic modification of cells in vitro and in vivo, for example, in the context of the generation of transgenic cells, cell lines, or animals, or in the alteration of genomic sequence, e.g., the correction of a genetic defect, in a cell in or obtained from a subject. In some embodiments, a cell obtained from a subject and modified according to the methods provided herein, is re-introduced into a subject (e.g., the same subject), e.g., to treat a disease, or for the production of genetically modified organisms in agriculture or biological research.

In applications in which it is desirable to recombine two or more nucleic acids so as to insert a nucleic acid sequence into a target nucleic acid, a nucleic acid comprising a donor sequence to be inserted is also provided, e.g., to a cell. By a "donor sequence" it is meant a nucleic acid sequence to be inserted at the target site induced by one or more RNA-guided recombinase fusion protein(s). In some embodiments, e.g., in the context of genomic modifications, the donor sequence will share homology to a genomic sequence at the target site, e.g., 1%, 2%, 3%, 4%, 5%, 10%, 20%, 30%, 40%, 50%, 60%, 70%, 80%, 85%, 90%, 95%, or 100% homology with the nucleotide sequences flanking the target site, e.g., within about 100 bases or less of the target site, e.g. within about 90 bases, within about 80 bases, within about 70 bases, within about 60 bases, within about 50 bases, within about 40 bases, within about 30 bases, within about 15 bases, within about 10 bases, within about 5 bases, or immediately flanking the target site. In some embodiments, the donor sequence does not share any homology with the target nucleic acid, e.g., does not share homology to a genomic sequence at the target site. Donor sequences can be of any length, e.g., 10 nucleotides or more, 50 nucleotides or more, 100 nucleotides or more, 250 nucleotides or more, 500 nucleotides or more, 1000 nucleotides or more, 5000 nucleotides or more, 10000 nucleotides or more, 100000 nucleotides or more, etc.

Typically, the donor sequence is not identical to the target sequence that it replaces or is inserted into. In some embodiments, the donor sequence contains at least one or more single base changes, insertions, deletions, inversions or rearrangements with respect to the target sequence (e.g., target genomic sequence). In some embodiments, donor sequences also comprise a vector backbone containing sequences that are not homologous to the DNA region of interest and that are not intended for insertion into the DNA region of interest.

The donor sequence may comprise certain sequence differences as compared to the target (e.g., genomic) sequence, for example restriction sites, nucleotide polymorphisms, selectable markers (e.g., drug resistance genes, fluorescent proteins, enzymes etc.), which can be used to assess for successful insertion of the donor sequence at the target site or in some cases may be used for other purposes (e.g., to signify expression at the targeted genomic locus). In some embodiments, if located in a coding region, such nucleotide sequence differences will not change the amino acid sequence, or will make silent amino acid changes (e.g., changes which do not affect the structure or function of the protein). In some embodiments, these sequences differences may include flanking recombination sequences such as FLPs, loxP sequences, or the like, that can be activated at a later time for removal of e.g., a marker sequence.

The donor sequence may be provided to the cell as single-stranded DNA, single-stranded RNA, double-stranded DNA, or double-stranded RNA. It may be introduced into a cell in linear or circular form. If introduced in linear form, the ends of the donor sequence may be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, e.g., Chang et al., *Proc. Natl. Acad Sci USA.* 1987; 84:4959-4963; Nehls et al., *Science.* 1996; 272:886-889. In some embodiments, a donor sequence can be introduced into a cell as part of a vector molecule having additional sequences such as, for example, replication origins, promoters and genes encoding antibiotic resistance. In some embodiments, donor sequences can be introduced as naked nucleic acid, as nucleic acid complexed with an agent such as a liposome or poloxamer, or can be delivered by viruses (e.g., adenovirus, AAV, etc.).

Polynucleotides, Vectors, Cells, Kits

In another embodiment of this disclosure, polynucleotides encoding one or more of the inventive proteins and/or gRNAs are provided. For example, polynucleotides encoding any of the proteins described herein are provided, e.g., for recombinant expression and purification of isolated nucleases and recombinases, e.g., comprising Cas9 variants. In some embodiments, an isolated polynucleotide comprises one or more sequences encoding a Cas9 half site (e.g., A-half and/or B-half). In some embodiments, an isolated polynucleotide comprises one or more sequences encoding a Cas9 fusion protein, for example, any of the Cas9 fusion proteins described herein (e.g., those comprising a nuclease-inactivated Cas9). In some embodiments, an isolated polynucleotides comprises one or more sequences encoding a gRNA, alone or in combination with a sequence encoding any of the proteins described herein.

In some embodiments, vectors encoding any of the proteins described herein are provided, e.g., for recombinant expression and purification of Cas9 proteins, and/or fusions comprising Cas9 proteins (e.g., variants). In some embodiments, the vector comprises or is engineered to include an isolated polynucleotide, e.g., those described herein. In some embodiments, the vector comprises one or more sequences encoding a Cas9 protein (as described herein), a gRNA, or combinations thereof, as described herein. Typically, the vector comprises a sequence encoding an inventive protein operably linked to a promoter, such that the fusion protein is expressed in a host cell.

In some embodiments, cells are provided, e.g., for recombinant expression and purification of any of the Cas9 proteins provided herein. The cells include any cell suitable for recombinant protein expression, for example, cells comprising a genetic construct expressing or capable of expressing an inventive protein (e.g., cells that have been transformed with one or more vectors described herein, or cells having genomic modifications, for example, those that express a protein provided herein from an allele that has been incorporated in the cell's genome). Methods for transforming cells, genetically modifying cells, and expressing genes and proteins in such cells are well known in the art, and include those provided by, for example, Green and Sambrook, *Molecular Cloning: A Laboratory Manual* ($4^{th}$ ed., Cold Spring Harbor Laboratory Press, Cold Spring Harbor, N.Y. (2012)) and Friedman and Rossi, *Gene Transfer: Delivery and Expression of DNA and RNA, A Laboratory Manual* ($1^{st}$ ed., Cold Spring Harbor Laboratory Press, Cold Spring Harbor, N.Y. (2006)).

Some aspects of this disclosure provide kits comprising a Cas9 variant and/or nuclease and/or recombinase, as provided herein. In some embodiments, the kit comprises a polynucleotide encoding an inventive Cas9 variant, nuclease, and/or recombinase, e.g., as provided herein. In some embodiments, the kit comprises a vector for recombinant protein expression, wherein the vector comprises a polynucleotide encoding any of the proteins provided herein. In some embodiments, the kit comprises a cell (e.g., any cell suitable for expressing Cas9 proteins or fusions comprising Cas9 proteins, such as bacterial, yeast, or mammalian cells) that comprises a genetic construct for expressing any of the proteins provided herein. In some embodiments, any of the kits provided herein further comprise one or more gRNAs and/or vectors for expressing one or more gRNAs. In some embodiments, the kit comprises an excipient and instructions for contacting the nuclease and/or recombinase with the excipient to generate a composition suitable for contacting a nucleic acid with the nuclease and/or recombinase such that hybridization to and cleavage and/or recombination of a target nucleic acid occurs. In some embodiments, the composition is suitable for delivering a Cas9 protein to a cell. In some embodiments, the composition is suitable for delivering a Cas9 protein to a subject. In some embodiments, the excipient is a pharmaceutically acceptable excipient.

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

Example 1

Fusion of Inactivated Cas9 to FokI Nuclease Improves Genome Modification Specificity Methods:

Oligonucleotides and PCR

All oligonucleotides were purchased from Integrated DNA Technologies (IDT). Oligonucleotide sequences are listed in Table 1. PCR was performed with 0.4 μL of 2 U/μL Phusion Hot Start Flex DNA polymerase (NEB) in 50 μL with 1×HF Buffer, 0.2 mM dNTP mix (0.2 mM dATP, 0.2 mM dCTP, 0.2 mM dGTP, 0.2 mM dTTP) (NEB), 0.5 μM of each primer and a program of: 98° C., 1 min; 35 cycles of [98° C., 15 s; 65° C., 15 s; 72° C., 30 s] unless otherwise noted.

Construction of FokI-dCas9, Cas9 Nickase and gRNA Expression Plasmids

The human codon-optimized *streptococcus pyogenes* Cas9 nuclease with NLS and 3×FLAG tag (Addgene plasmid 43861)[2] was used as the wild-type Cas9 expression plasmid.

PCR (72° C., 3 min) products of wild-type Cas9 expression plasmid as template with Cas9_Exp primers listed in Table 1 below were assembled with Gibson Assembly Cloning Kit (New England Biolabs) to construct Cas9 and FokI-dCas9 variants. Expression plasmids encoding a single gRNA construct (gRNA G1 through G13) were cloned as previously described. Briefly, gRNA oligonucleotides listed in Table 1 containing the 20-bp protospacer target sequence were annealed and the resulting 4-bp overhangs were ligated into BsmBI-digested gRNA expression plasmid. gRNA expression plasmids encoding expression of two separate gRNA constructs from separate promoters on a single plasmid were cloned in a two-step process. First, one gRNA (gRNA E1, V1, C1, C3, H1, G1, G2 or G3) was cloned as above and used as template for PCR (72° C., 3 min) with PCR_Pla-fwd and PCR_Pla-rev primers, 1 μl DpnI (NEB) was added, and the reaction was incubated at 37° C. for 30 min and then subjected to QIAquick PCR Purification Kit (Qiagen) for the "1$^{st}$ gRNA+vector DNA". PCR (72° C., 3 min) of 100 pg of BsmBI-digested gRNA expression plasmid as template with PCR_gRNA-fwd1, PCR_gRNA-rev1, PCR_gRNA-rev2 and appropriate PCR_gRNA primer listed in Table 1 was DpnI treated and purified as above for the "2$^{nd}$ gRNA instert DNA". ~200 ng of "1$^{st}$ gRNA+vector DNA" and ~200 ng of "2$^{nd}$ gRNA instert DNA" were blunt-end ligated in 1×T4 DNA Ligase Buffer, 1 μl of T4 DNA Ligase (400 U/μl, NEB) in a total volume of 20 μl at room temperature (~21° C.) for 15 min. For all cloning, 1 μl of ligation or assembly reaction was transformed into Machl chemically competent cells (Life Technologies).

TABLE 1

Oligonucleotides. '/5Phos/' indicates 5' phosphorylated oligonucleotides.

| | |
|---|---|
| dCas9-NLS-FokI primers: | |
| Cas9_Exp_CNF_Fok1 + Plas-Fwd | CGGCGAGATAAACTTTTAA TGACCGGTCATCATCACCA (SEQ ID NO: 26) |
| Cas9_Exp_CNF_Cas9coD10-Rev | CCAACGGAATTAGTGCCGATAGCTAAACCAATAGAATACTTTTTATC (SEQ ID NO: 27) |
| Cas9_Exp_CNF_Cas9coD10-Fwd | GATAAAAAGTATTCTATTGGTTTAGCTATCGGCACTAATTCCGTTGG (SEQ ID NO: 28) |
| Cas9_Exp_CNF_Cas9coH850-Rev | TTCAAAAAGGATTGGGGTACAATGGCATCGACGTCGTAATCAGATAAAC (SEQ ID NO: 29) |
| Cas9_Exp_CNF_Cas9coH850-Fwd | GTTTATCTGATTACGACGTCGATGCCATTGTACCCCAATCCTTTTTGAA (SEQ ID NO: 30) |
| Cas9_Exp_CNF_(Cas9)NLS + GGS-Fok-Rev | TTGGGATCCAGAACCTCCTCCTGCAGCCTTGTCATCG (SEQ ID NO: 31) |
| Cas9_Exp_CNF_(Cas9)NLS + GGS3-Fok-Rev | TTGGGATCCAGAACCTCC GCTGCCGCCACTTCCACCTGA TCCTGCAGCCTTGTCATCG (SEQ ID NO: 32) |
| Cas9_Exp_CNF_(Cas9)NLS + GGS-Fok-Fwd | CGATGACAAGGCTGCAGGAGGAGGTTCTGGATCCCAA (SEQ ID NO: 33) |
| Cas9_Exp_CNF_(Cas9)NLS + GGS3-Fok-Fwd | CGATGACAAGGCTGCAGGA TCAGGTGGAAGTGGCGGCAGC GGAGGTTCTGGATCCCAA (SEQ ID NO: 34) |
| Cas9_Exp_CNF_Fok1 + Plas-Rev | TGGTGATGATGACCGGTCA TTAAAAGTTTATCTCGCCG (SEQ ID NO: 35) |
| NLS-dCas9-FokI primers: | |
| Cas9_Exp_NCF_Fok1 + Plas-Fwd | CGGCGAGATAAACTTTTAA TGACCGGTCATCATCACCA (SEQ ID NO: 36) |
| Cas9_Exp_NCF_PlasS + FLAG (NLS-Fok1-Rev | TAGGGAGAGCCGCCACCATGGACTACAAAGACCATGACGG (SEQ ID NO: 37) |
| Cas9_Exp_NCF_NLS + Cas9coD10-Rev | TAAACCAATAGAATACTTTTTATC CATAGGTACCCCGCGGTGAATG (SEQ ID NO: 38) |
| Cas9_Exp_NCF_Cas9coD10-Fwd | GATAAAAAGTATTCTATTGGTTTAGCTATCGGCACTAATTCCGTTGG (SEQ ID NO: 39) |
| Cas9_Exp_NCF_Cas9coH850-Rev | TTCAAAAAGGATTGGGGTACAATGGCATCGACGTCGTAATCAGATAAAC (SEQ ID NO: 40) |
| Cas9_Exp_NCF_Cas9coH850-Fwd | GTTTATCTGATTACGACGTCGATGCCATTGTACCCCAATCCTTTTTGAA (SEQ ID NO: 41) |
| Cas9_Exp_NCF_Cas9End + GGS-Fok-Rev | TTGGGATCCAGAACCTCCGTCACCCCCAAGCTGTG (SEQ ID NO: 42) |
| Cas9_Exp_NCF_Cas9End + GGS3-Fok-Rev | TTGGGATCCAGAACCTCC GCTGCCGCCACTTCCACCTGA GTCACCCCCAAGCTGTG (SEQ ID NO: 43) |

TABLE 1-continued

| Oligonucleotides. '/5Phos/' indicates 5' phosphorylated oligonucleotides. | |
|---|---|
| Cas9_Exp_NCF_Cas9End + GGS-Fok-Fwd | CACAGCTTGGGGGTGACGGAGGTTCTGGATCCCAA (SEQ ID NO: 44) |
| Cas9_Exp_NCF_Cas9End + GGS3-Fok-Fwd | CACAGCTTGGGGGTGAC TCAGGTGGAAGTGGCGGCAGC GGAGGTTCTGGATCCCAA (SEQ ID NO: 45) |
| Cas9_Exp_NCF_Fok1 + Plas-Rev | TGGTGATGATGACCGGTCA TTAAAAGTTTATCTCGCCG (SEQ ID NO: 46) |
| FokI-dCas9-NLS primers: | |
| Cas9_Exp_FCN_PlasS + Fok-Fwd | TAGGGAGAGCCGCCACCATGGGATCCCAACTAGTCAAAAG (SEQ ID NO: 47) |
| Cas9_Exp_FCN_Fok1GGS + Cas-Rev | ACCAATAGAATACTTTTTATCCATGCTGCCACCAAAGTTTATCTC (SEQ ID NO: 48) |
| Cas9_Exp_FCN_Fok1GGS3 + Cas-Rev | ACCAATAGAATACTTTTTATCCATGCTGCCGCCACTTCCACCTG (SEQ ID NO: 49) |
| Cas9_Exp_FCN_Cas9coD10-Fwd | GATAAAAAGTATTCTATTGGTTTAGCTATCGGCACTAATTCCGTTGG (SEQ ID NO: 50) |
| Cas9_Exp_FCN_Cas9coH850-Rev | CCAACGGAATTAGTGCCGATAGCTAAACCAATAGAATACTTTTTATC (SEQ ID NO: 51) |
| Cas9_Exp_FCN_Cas9coH850-Fwd | GTTTATCTGATTACGACGTCGATGCCATTGTACCCCAATCCTTTTTGAA (SEQ ID NO: 52) |
| Cas9_Exp_FCN_Cas9End + PlasmidEn-Rev | TGGTGATGATGACCGGTCA GTCACCCCCAAGCTGTG (SEQ ID NO: 53) |
| Cas9_Exp_FCN_Cas9End + PlasmidEn-Fwd | CACAGCTTGGGGGTGAC TGACCGGTCATCATCACCA (SEQ ID NO: 54) |
| Cas9_Exp_FCN_PlasS + Fok-Rev | CTTTTGACTAGTTGGGATCCCATGGTGGCGGCTCTCCCTA (SEQ ID NO: 55) |
| gRNA_G1-top | ACACCCCTCGAACTTCACCTCGGCGG (SEQ ID NO: 56) |
| gRNA_G2-top | ACACCGTCGCCCTCGAACTTCACCTG (SEQ ID NO: 57) |
| gRNA_G3-top | ACACCCAGCTCGATGCGGTTCACCAG (SEQ ID NO: 58) |
| gRNA_G4-top | ACACCGGTGAACCGCATCGAGCTGAG (SEQ ID NO: 59) |
| gRNA_G5-top | ACACCGCTGAAGGGCATCGACTTCAG (SEQ ID NO: 60) |
| gRNA_G6-top | ACACCGGCATCGACTTCAAGGAGGAG (SEQ ID NO: 61) |
| gRNA_G7-top | ACACCCAAGGAGGACGGCAACATCCG (SEQ ID NO: 62) |
| gRNA_G8-top | ACACCACCATCTTCTTCAAGGACGAG (SEQ ID NO: 63) |
| gRNA_G9-top | ACACCCAACTACAAGACCCGCGCCGG (SEQ ID NO: 64) |
| gRNA_G10-top | ACACCCCGCGCCGAGGTGAAGTTCGG (SEQ ID NO: 65) |
| gRNA_G11-top | ACACCGAAGTTCGAGGGCGACACCCG (SEQ ID NO: 66) |
| gRNA_G12-top | ACACCTTCGAACTTCACCTCGGCGCG (SEQ ID NO: 67) |
| gRNA_G13-top | ACACCTCAGCTCGATGCGGTTCACCG (SEQ ID NO: 68) |
| gRNA_G14-top | ACACCCGATGCCCTTCAGCTCGATGG (SEQ ID NO: 69) |
| gRNA_G1-bottom | AAAACCGCCGAGGTGAAGTTCGAGGG (SEQ ID NO: 70) |
| gRNA_G2-bottom | AAAACAGGTGAAGTTCGAGGGCGACG (SEQ ID NO: 71) |
| gRNA_G3-bottom | AAAACTGGTGAACCGCATCGAGCTGG (SEQ ID NO: 72) |
| gRNA_G4-bottom | AAAACTCAGCTCGATGCGGTTCACCG (SEQ ID NO: 73) |
| gRNA_G5-bottom | AAAACTGAAGTCGATGCCCTTCAGCG (SEQ ID NO: 74) |
| gRNA_G6-bottom | AAAACTCCTCCTTGAAGTCGATGCCG (SEQ ID NO: 75) |

TABLE 1-continued

| Oligonucleotides. '/5Phos/' indicates 5' phosphorylated oligonucleotides. | |
|---|---|
| gRNA_G7-bottom | AAAACGGATGTTGCCGTCCTCCTTGG (SEQ ID NO: 76) |
| gRNA_G8-bottom | AAAACTCGTCCTTGAAGAAGATGGTG (SEQ ID NO: 77) |
| gRNA_G9-bottom | AAAACCGGCGCGGGTCTTGTAGTTGG (SEQ ID NO: 78) |
| gRNA_G10-bottom | AAAACCGAACTTCACCTCGGCGCGGG (SEQ ID NO: 79) |
| gRNA_G11-bottom | AAAACGGGTGTCGCCCTCGAACTTCG (SEQ ID NO: 80) |
| gRNA_G12-bottom | AAAACGCGCCGAGGTGAAGTTCGAAG (SEQ ID NO: 81) |
| gRNA_G13-bottom | AAAACGGTGAACCGCATCGAGCTGAG (SEQ ID NO: 82) |
| gRNA_G14-bottom | AAAACCATCGAGCTGAAGGGCATCGG (SEQ ID NO: 83) |
| gRNA_C1-top | ACACCTGGCCTGCTTGCTAGACTTGG (SEQ ID NO: 84) |
| gRNA_C3-top | ACACCGCAGATGTAGTGTTTCCACAG (SEQ ID NO: 85) |
| gRNA_H1-top | ACACCCTTGCCCCACAGGGCAGTAAG (SEQ ID NO: 86) |
| gRNA_E1-top | ACACCGAGTCCGAGCAGAAGAAGAAG (SEQ ID NO: 87) |
| gRNA_V1-top | ACACCGGGTGGGGGGAGTTTGCTCCG (SEQ ID NO: 88) |
| gRNA_C1-bottom | AAAACCAAGTCTAGCAAGCAGGCCAG (SEQ ID NO: 89) |
| gRNA_C3-bottom | AAAACTGTGGAAACACTACATCTGCG (SEQ ID NO: 90) |
| gRNA_H1-bottom | AAAACTTCTTCTTCTGCTCGGACTCG (SEQ ID NO: 91) |
| gRNA_E1-bottom | AAAACTTACTGCCCTGTGGGGCAAGG (SEQ ID NO: 92) |
| gRNA_V1-bottom | AAAACGGAGCAAACTCCCCCCACCCG (SEQ ID NO: 93) |
| PCR_Pla-fwd | AGG AAA GAA CAT GTG AGC AAA AG (SEQ ID NO: 94) |
| PCR_Pla-rev | CAGCGAGTCAGTGAGCGA (SEQ ID NO: 95) |
| PCR_gRNA-fwd1 | CTGTACAAAAAAGCAGGCTTTA (SEQ ID NO: 96) |
| PCR_gRNA-rev1 | AACGTAGGTCTCTACCGCTGTACAAAAAAGCAGGCTTTA (SEQ ID NO: 97) |
| PCR_gRNA-rev2 | AAAAAAAGCACCGACTCGGTGCCACTTTTTCAAGTTGATAACGGACTAGCC TTATTTTAACTTGCTATTTCTAGCTCTAAAAC (SEQ ID NO: 98) |
| PCR_gRNA_G1 | TTGCTATTTCTAGCTCTAAAACCGCCGAGGTGAAGTTCGAGGGGTGTTTCG TCCTTTCCA (SEQ ID NO: 99) |
| PCR_gRNA_G2 | TTGCTATTTCTAGCTCTAAAACAGGTGAAGTTCGAGGGCGACGGTGTTTCG TCCTTTCCA (SEQ ID NO: 100) |
| PCR_gRNA_G3 | TTGCTATTTCTAGCTCTAAAACTGGTGAACCGCATCGAGCTGGGTGTTTCGT CCTTTCCA (SEQ ID NO: 101) |
| PCR_gRNA_G4 | TTGCTATTTCTAGCTCTAAAACTCAGCTCGATGCGGTTCACCGGTGTTTCGT CCTTTCCA (SEQ ID NO: 102) |
| PCR_gRNA_G5 | TTGCTATTTCTAGCTCTAAAACTGAAGTCGATGCCCTTCAGCGGTGTTTCGT CCTTTCCA (SEQ ID NO: 103) |
| PCR_gRNA_G6 | TTGCTATTTCTAGCTCTAAAACTCCTCCTTGAAGTCGATGCCGGTGTTTCGT CCTTTCCA (SEQ ID NO: 104) |
| PCR_gRNA_G7 | TTGCTATTTCTAGCTCTAAAACGGATGTTGCCGTCCTCCTTGGGTGTTTCGT CCTTTCCA (SEQ ID NO: 105) |
| PCR_gRNA_C2 | TTGCTATTTCTAGCTCTAAAACGCTTGAGGGAGATGAGGACTGGTGTTTCG TCCTTTCCA (SEQ ID NO: 106) |
| PCR_gRNA_C4 | TTGCTATTTCTAGCTCTAAAACATGACTGTGAAGAGCTTCACGGTGTTTCGT CCTTTCCA (SEQ ID NO: 107) |
| PCR_gRNA_E2 | TTGCTATTTCTAGCTCTAAAACGAGGACAAAGTACAAACGGCGGTGTTTCG TCCTTTCCA (SEQ ID NO: 108) |

TABLE 1-continued

| Oligonucleotides. '/5Phos/' indicates 5' phosphorylated oligonucleotides. | |
|---|---|
| PCR_gRNA_E3 | TTGCTATTTCTAGCTCTAAAACGAACCGGAGGACAAAGTACAGGTGTTTCG TCCTTTCCA (SEQ ID NO: 109) |
| PCR_gRNA_H2 | TTGCTATTTCTAGCTCTAAAACCACCACCAACTTCATCCACGGGTGTTTCGT CCTTTCCA (SEQ ID NO: 110) |
| PCR_gRNA_H3 | TTGCTATTTCTAGCTCTAAAACGGGCCTCACCACCAACTTCAGGTGTTTCGT CCTTTCCA (SEQ ID NO: 111) |
| PCR_gRNA_H4 | TTGCTATTTCTAGCTCTAAAACGCCCAGGGCCTCACCACCAAGGTGTTTCG TCCTTTCCA (SEQ ID NO: 112) |
| PCR_gRNA_H5 | TTGCTATTTCTAGCTCTAAAACACCTGCCCAGGGCCTCACCAGGTGTTTCGT CCTTTCCA (SEQ ID NO: 113) |
| PCR_gRNA_H6 | TTGCTATTTCTAGCTCTAAAACTGATACCAACCTGCCCAGGGGGTGTTTCGT CCTTTCCA (SEQ ID NO: 114) |
| PCR_gRNA_H7 | TTGCTATTTCTAGCTCTAAAACTAAACCTGTCTTGTAACCTTGGTGTTTCGT CCTTTCCA (SEQ ID NO: 115) |
| PCR_gRNA_V2 | TTGCTATTTCTAGCTCTAAAACGCTCTGGCTAAAGAGGGAATGGTGTTTCG TCCTTTCCA (SEQ ID NO: 116) |
| PCR_gRNA_V3 | TTGCTATTTCTAGCTCTAAAACCGGCTCTGGCTAAAGAGGGAGGTGTTTCG TCCTTTCCA (SEQ ID NO: 117) |
| PCR_gRNA_V4 | TTGCTATTTCTAGCTCTAAAACTCTGCACACCCCGGCTCTGGGGTGTTTCGT CCTTTCCA (SEQ ID NO: 118) |
| Survey_GFP-fwd | TACGGCAAGCTGACCCTGAA (SEQ ID NO: 119) |
| Survey_GFP-rev | GTCCATGCCGAGAGTGATCC (SEQ ID NO: 120) |
| Survye_CLTA-fwd | GCCAGGGGCTGTTATCTTGG (SEQ ID NO: 121) |
| Survye_CLTA-rev | ATGCACAGAAGCACAGGTTGA (SEQ ID NO: 122) |
| Survey_EMX-fwd | CTGTGTCCTCTTCCTGCCCT (SEQ ID NO: 123) |
| Survey_EMX-rev | CTCTCCGAGGAGAAGGCCAA (SEQ ID NO: 124) |
| Survey_HBB-fwd | GGTAGACCACCAGCAGCCTA (SEQ ID NO: 125) |
| Survey_HBB-rev | CAGTGCCAGAAGAGCCAAGG (SEQ ID NO: 126) |
| Survey_VEGF-fwd | CCACACAGCTTCCCGTTCTC (SEQ ID NO: 127) |
| Survey_VEGF-rev | GAGAGCCGTTCCCTCTTTGC (SEQ ID NO: 128) |
| HTS_EXM_ON-fwd | CCTCCCCATTGGCCTGCTTC (SEQ ID NO: 129) |
| HTS_EXM_Off1-fwd | TCGTCCTGCTCTCACTTAGAC (SEQ ID NO: 130) |
| HTS_EXM_Off2-fwd | TTTTGTGGCTTGGCCCCAGT (SEQ ID NO: 131) |
| HTS_EXM_Off3-fwd | TGCAGTCTCATGACTTGGCCT (SEQ ID NO: 132) |
| HTS_EXM_Off4-fwd | TTCTGAGGGCTGCTACCTGT (SEQ ID NO: 133) |
| HTS_VEFG_ON-fwd | ACATGAAGCAACTCCAGTCCCA (SEQ ID NO: 134) |
| HTS_EXM_Off1-fwd | AGCAGACCCACTGAGTCAACTG (SEQ ID NO: 135) |
| HTS_EXM_Off2-fwd | CCCGCCACAGTCGTGTCAT (SEQ ID NO: 136) |
| HTS_EXM_Off3-fwd | CGCCCCGGTACAAGGTGA (SEQ ID NO: 137) |
| HTS_EXM_Off4-fwd | GTACCGTACATTGTAGGATGTTT (SEQ ID NO: 138) |
| HTS_CLTA2_ON-fwd | CCTCATCTCCCTCAAGCAGGC (SEQ ID NO: 139) |
| HTS_CLTA2_Off1-fwd | ATTCTGCTCTTGAGGTTATTTGT (SEQ ID NO: 140) |
| HTS_CLTA2_Off2-fwd | CACCTCTGCCTCAAGAGCAGAAAA (SEQ ID NO: 141) |
| HTS_CLTA2_Off3-fwd | TGTGTGTGTGTGTGTGTAGGACT (SEQ ID NO: 142) |

TABLE 1-continued

| Oligonucleotides. '/5Phos/' indicates 5' phosphorylated oligonucleotides. | |
|---|---|
| HTS_EXM_ON-rev | TCATCTGTGCCCCTCCCTCC (SEQ ID NO: 143) |
| HTS_EXM_Off-rev | CGAGAAGGAGGTGCAGGAG (SEQ ID NO: 144) |
| HTS_EXM_Off-rev | CGGGAGCTGTTCAGAGGCTG (SEQ ID NO: 145) |
| HTS_EXM_Off-rev | CTCACCTGGGCGAGAAAGGT (SEQ ID NO: 146) |
| HTS_EXM_Off-rev | AAAACTCAAAGAAATGCCCAATCA (SEQ ID NO: 147) |
| HTS_VEFG_ON-rev | AGACGCTGCTCGCTCCATTC (SEQ ID NO: 148) |
| HTS_EXM_Off1-rev | ACAGGCATGAATCACTGCACCT (SEQ ID NO: 149) |
| HTS_EXM_Off2-rev | GCGGCAACTTCAGACAACCGA (SEQ ID NO: 150) |
| HTS_EXM_Off3-rev | GACCCAGGGGCACCAGTT (SEQ ID NO: 151) |
| HTS_EXM_Off4-rev | CTGCCTTCATTGCTTAAAAGTGGAT (SEQ ID NO: 152) |
| HTS_CLTA2_ON-rev | ACAGTTGAAGGAAGGAAACATGC (SEQ ID NO: 153) |
| HTS_CLTA2_Off1-rev | GCTGCATTTGCCCATTTCCA (SEQ ID NO: 154) |
| HTS_CLTA2_Off2-rev | GTTGGGGGAGGAGGAGCTTAT (SEQ ID NO: 155) |
| HTS_CLTA2_Off3-rev | CTAAGAGCTATAAGGGCAAATGACT (SEQ ID NO: 156) |

Modification of Genomic GFP

HEK293-GFP stable cells (GenTarget) were used as a cell line constitutively expressing an Emerald GFP gene (GFP) integrated on the genome. Cells were maintained in Dulbecco's modified Eagle medium (DMEM, Life Technologies) supplemented with 10% (vol/vol) fetal bovine serum (FBS, Life Technologies) and penicillin/streptomycin (1×, Amresco). $5\times10^4$ HEK293-GFP cells were plated on 48-well collagen coated Biocoat plates (Becton Dickinson). One day following plating, cells at ~75% confluence were transfected with Lipofecatmine 2000 (Life Technologies) according to the manufacturer's protocol. Briefly, 1.5 μL of Lipofecatmine 2000 was used to transfect 950 ng of total plasmid (Cas9 expression plasmid plus gRNA expression plasmids). 700 ng of Cas9 expression plasmid, 125 ng of one gRNA expression plasmid and 125 ng of the paired gRNA expression plasmid with the pairs of targeted gRNAs listed in FIG. 6D and FIG. 9A. Separate wells were transfected with 1 μg of a near-infrared iRFP670 (Addgene plasmid 45457)[32] as a transfection control. 3.5 days following transfection, cells were trypsinized and resuspended in DMEM supplemented with 10% FBS and analyzed on a C6 flow cytometer (Accuri) with a 488 nm laser excitation and 520 nm filter with a 20 nm band pass. For each sample, transfections and flow cytometry measurements were performed once.

T7 Endonuclease I Surveyor Assays of Genomic Modifications

HEK293-GFP stable cells were transfected with Cas9 expression and gRNA expression plasmids as described above. A single plasmid encoding two separate gRNAs was transfected. For experiments titrating the total amount of expression plasmids (Cas9 expression+gRNA expression plasmid), 700/250, 350/125, 175/62.5, 88/31 ng of Cas9 expression plasmid/ng of gRNA expression plasmid were combined with inert carrier plasmid, pUC19 (NEB), as necessary to reach a total of 950 ng transfected plasmid DNA.

Genomic DNA was isolated from cells 2 days after transfection using a genomic DNA isolation kit, DNAdvance Kit (Agencourt). Briefly, cells in a 48-well plate were incubated with 40 μL of tryspin for 5 min at 37° C. 160 uL of DNAdvance lysis solution was added and the solution incubated for 2 hr at 55° C. and the subsequent steps in the Agencourt DNAdvance kit protocol were followed. 40 ng of isolated genomic DNA was used as template to PCR amplify the targeted genomic loci with flanking Survey primer pairs specified in Table 1. PCR products were purified with a QIAquick PCR Purification Kit (Qiagen) and quantified with Quant-iT™ PicoGreen® dsDNA Kit (Life Technologies). 250 ng of purified PCR DNA was combined with 2 μL of NEBuffer 2 (NEB) in a total volume of 19 μL and denatured then re-annealed with thermocycling at 95° C. for 5 min, 95 to 85° C. at 2° C./s; 85 to 20° C. at 0.2° C./s. The re-annealed DNA was incubated with 1 μl of T7 Endonuclease I (10 U/μl, NEB) at 37° C. for 15 min. 10 μL of 50% glycerol was added to the T7 Endonuclease reaction and 12 μL was analyzed on a 5% TBE 18-well Criterion PAGE gel (Bio-Rad) electrophoresed for 30 min at 150 V, then stained with 1×SYBR Gold (Life Technologies) for 30 min. Cas9-induced cleavage bands and the uncleaved band were visualized on an AlphaImager HP (Alpha Innotech) and quantified using ImageJ software.[33] The peak intensities of the cleaved bands were divided by the total intensity of all bands (uncleaved+cleaved bands) to determine the fraction cleaved which was used to estimate gene modification levels as previously described.[28] For each sample, transfections and subsequent modification measurements were performed in triplicate on different days.

High-Throughput Sequencing of Genomic Modifications

HEK293-GFP stable cells were transfected with Cas9 expression and gRNA expression plasmids, 700 ng of Cas9 expression plasmid plus 250 ng of a single plasmid expression a pair of gRNAs were transfected (high levels) and for just Cas9 nuclease, 88 ng of Cas9 expression plasmid plus 31 ng of a single plasmid expression a pair of gRNAs were transfected (low levels). Genomic DNA was isolated as above and pooled from three biological replicates. 150 ng or 600 ng of pooled genomic DNA was used as template to amplify by PCR the on-target and off-target genomic sites with flanking HTS primer pairs specified in Table 1. Relative amounts of crude PCR products were quantified by gel electrophoresis and samples treated with different gRNA pairs or Cas9 nuclease types were separately pooled in equimolar concentrations before purification with the QIAquick PCR Purification Kit (Qiagen). ~500 ng of pooled DNA was run a 5% TBE 18-well Criterion PAGE gel (BioRad) for 30 min at 200 V and DNAs of length ~125 bp to ~300 bp were isolated and purified by QIAquick PCR Purification Kit (Qiagen). Purified DNA was PCR amplified with primers containing sequencing adaptors, purified and sequenced on a MiSeq high-throughput DNA sequencer (Illumina) as described previously.[1]

Data Analysis

Illumina sequencing reads were filtered and parsed with scripts written in Unix Bash. All scripts were written in bash.

The Patmatch program[38] was used to search the human genome (GRCh37/hg19 build) for pattern sequences corresponding to Cas9 binding sites (CCN $N^{20}$ spacer $N^{20}$NGG for Orientation A and $N^{20}$NGG spacer CCN $N^{20}$ for Orientation B). The steps for the identification of ingels in sequences of genomic sites can be found below:

1) Sequence reads were initially filtered removing reads of less than 50 bases and removing reads with greater than 10% of the Illumina base scores not being B-J:

Example SeqA-$1^{st}$Read:

(SEQ ID NO: 157)
TTCTGAGGGCTGCTACCTGTACATCTGCACAAGATTGCCTTTACTCCAT
GCCTTTCTTCTTCTGCTCTAACTCTGACAATCTGTCTTGCCATGCCATAA
GCCCCTATTCTTTCTGTAACCCCAAGATGGTATAAAAGCATCAATGATTG
GGC

Example SeqA-$2^{st}$Read:

(SEQ ID NO: 158)
AAAACTCAAAGAAATGCCCAATCATTGATGCTTTTATACCATCTTGGG
GTTACAGAAAGAATAGGGGCTTATGGCATGGCAAGACAGATTGTCAGAG
TTAGAGCAGAAGAAGAAAGGCATGGAGTAAAGGCAATCTTGTGCAGATG
TACAGGTAA

2) Find the first 20 bases four bases from the start of the reverse complement of SeqA-$2^{nd}$ read in SeqA-1stread allowing for 1 mismatch:

Reverse complement of SeqA-$2^{nd}$ read:

(SEQ ID NO: 159)
TTACCTGTACATCTGCACAAGATTGCCTTTACTCCATGCCTTTCTTCT
TCTGCTCTAACTCTGACAATCTGTCTTGCCATGCCATAAGCCCCTATT
CTTTCTGTAACCCCAAGATGGTATAAAAGCATCAATGATTGGGCATTT
CTTTGAGTTTT

Position in SeqA-$1^{st}$Read (SEQ ID NO: 160)
TTCTGAGGGCTGCTACCTGTACATCTGCACAAGATTGCCTTTACTCCATG
CCTTTCTTCTTCTGCTCTAACTCTGACAATCTGTCTTGCCATGCCATAAG
CCCCTATTCTTTCTGTAACCCCAAGATGGTATAAAAGCATCAATGATTGG
GC 3) Align and then combine sequences, removing any sequence with greater than 5% mismatches in the simple base pair alignment:

Combination of SeqA-$1^{st}$ Read and SeqA-$2^{nd}$Read:

(SEQ ID NO: 161)
TTCTGAGGGCTGCTACCTGTACATCTGCACAAGATTGCCTTTACTCCATG
CCTTTCTTCTTCTGCTCTAACTCTGACAATCTGTCTTGCCATGCCATAAG
CCCCTATTCTTTCTGTAACCCCAAGATGGTATAAAAGCATCAATGATTGG
GCATTTCTTTGAGTTTT

4) To identify the target site the flanking genomic sequences were searched for with the Patmatch program[38] allowing for varying amounts of bases from 1 to 300 between the flanking genomic sequences (Table 2):

TABLE 2

| Patmatch Sequences | | |
|---|---|---|
| Target Site | Downstream genomic sequence | Upstream genomic sequence |
| EMX_On | GGCCTGCTTCGTGGCAATGC (SEQ ID NO: 162) | ACCTGGGCCAGGGAGGGAGG (SEQ ID NO: 163) |
| EMX_Off1 | CTCACTTAGACTTTCTCTCC (SEQ ID NO: 164) | CTCGGAGTCTAGCTCCTGCA (SEQ ID NO: 165) |
| EMX_Off2 | TGGCCCCAGTCTCTCTTCTA (SEQ ID NO: 166) | CAGCCTCTGAACAGCTCCCG (SEQ ID NO: 167) |
| EMX_Off3 | TGACTTGGCCTTTGTAGGAA (SEQ ID NO: 168) | GAGGCTACTGAAACATAAGT (SEQ ID NO: 169) |
| EMX_Off4 | TGCTACCTGTACATCTGCAC (SEQ ID NO: 170) | CATCAATGATTGGGCATTTC (SEQ ID NO: 171) |
| VEG_On | ACTCCAGTCCCAAATATGTA (SEQ ID NO: 172) | ACTAGGGGGCGCTCGGCCAC (SEQ ID NO: 173) |
| VEG_Off1 | CTGAGTCAACTGTAAGCATT (SEQ ID NO: 174) | GGCCAGGTGCAGTGATTCAT (SEQ ID NO: 175) |
| VEG_Off2 | TCGTGTCATCTTGTTTGTGC (SEQ ID NO: 176) | GGCAGAGCCCAGCGGACACT (SEQ ID NO: 177) |

TABLE 2-continued

Patmatch Sequences

| Target Site | Downstream genomic sequence | Upstream genomic sequence |
|---|---|---|
| VEG_Off3 | CAAGGTGAGCCTGGGTCTGT (SEQ ID NO: 178) | ATCACTGCCCAAGAAGTGCA (SEQ ID NO: 179) |
| VEG_Off4 | TTGTAGGATGTTTAGCAGCA (SEQ ID NO: 180) | ACTTGCTCTCTTTAGAGAAC (SEQ ID NO: 181) |
| CLT2_On | CTCAAGCAGGCCCCGCTGGT (SEQ ID NO: 182) | TTTTGGACCAAACCTTTTTG (SEQ ID NO: 183) |
| CLT2_Off1 | TGAGGTTATTTGTCCATTGT (SEQ ID NO: 184) | TAAGGGGAGTATTTACACCA (SEQ ID NO: 185) |
| CLT2_Off2 | TCAAGAGCAGAAAATGTGAC (SEQ ID NO: 186) | CTTGCAGGGACCTTCTGATT (SEQ ID NO: 187) |
| CLT2_Off3 | TGTGTGTAGGACTAAACTCT (SEQ ID NO: 188) | GATAGCAGTATGACCTTGGG (SEQ ID NO: 189) |

Any target site sequences corresponding to the same size as the reference genomic site in the human genome (GRCh37/hg19 build) were considered unmodified and any sequences not the reference size were considered potential insertions or deletions. Sequences not the reference size were aligned with ClustalW[39] to the reference genomic site. Aligned sequences with more than one insertion or one deletion in the DNA spacer sequence in or between the two half-site sequences were considered indels. Since high-throughput sequencing can result in insertions or deletions of one base pairs (mis-phasing) at a low but relevant rates—indels of two by are more likely to arise from Cas9 induced modifications.

Sample sizes for sequencing experiments were maximized (within practical experimental considerations) to ensure greatest power to detect effects. Statistical analyses for Cas9-modified genomic sites in Table 3 were performed as previously described[34] with multiple comparison correction using the Bonferroni method.

Table 3, referred to in the Results below, shows (A) results from sequencing CLTA on-target and previously reported genomic off-target sites amplified from 150 ng genomic DNA isolated from human cells treated with a plasmid expressing either wild-type Cas9, Cas9 nickase, or fCas9 and a single plasmid expressing two gRNAs targeting the CLTA on-target site (gRNA C3 and gRNA C4). As a negative control, transfection and sequencing were performed as above, but using two gRNAs targeting the GFP gene on-target site (gRNA G1, G2 or G3 and gRNA G4, G5, G6 or G7. Indels: the number of observed sequences containing insertions or deletions consistent with any of the three Cas9 nuclease-induced cleavage. Total: total number of sequence counts while only the first 10,000 sequences were analyzed for the on-target site sequences. Modified: number of indels divided by total number of sequences as percentages. Upper limits of potential modification were calculated for sites with no observed indels by assuming there is less than one indel then dividing by the total sequence count to arrive at an upper limit modification percentage, or taking the theoretical limit of detection (1/49,500), whichever value was larger. P-values: For wild-type Cas9 nuclease, Cas9 nickase or fCas9 nuclease, P-values were calculated as previously reported[18] using a two-sided Fisher's exact test between each sample treated with two gRNAs targeting the CLTA on-target site and the control sample treated with two gRNAs targeting the GFP on-target site. P-values of <0.0045 were considered significant and shown based on conservative multiple comparison correction using the Bonferroni method. On:off specificity is the ratio of on-target to off-target genomic modification frequency for each site. (B) Shows experimental and analytic methods as in (A) applied to EMX target sites using a single plasmid expressing two gRNAs targeting the EMX on-target site (gRNA E1 and gRNA E2). (C) shows experimental and analytic methods as in (A) applied to VEGF target sites using a single plasmid expressing two gRNAs targeting the VEGF on-target site (gRNA V1 and gRNA v2). (D) shows experimental and analytic methods as in (A) applied to VEGF on-target and VEGF off-target site 1 amplified from 600 ng genomic DNA to increase detection sensitivity to 1/198,000.

TABLE 3

Cellular modification induced by wild-type Cas9, Cas9 nickase, and fCas9 at on-target and off-target genomic sites.

(A)

| Nuclease type: gRNA pair target: | wt Cas9 CLTA | wt Cas9 CLTA | Cas9 nickase CLTA | fCas9 CLTA | wt Cas9 GFP | Cas9 nickase GFP | fCas9 GFP |
|---|---|---|---|---|---|---|---|
| Total expression plasmids (ng): | 1000 | 125 | 1000 | 1000 | 1000 | 1000 | 1000 |
| CLTA Sites | | | | | | | |
| CLT2_On | | | | | | | |
| Indels | 3528 | 1423 | 3400 | 575 | 3 | 13 | 5 |
| Total | 10000 | 10000 | 10000 | 10000 | 10000 | 10000 | 10000 |
| Modified (%) | 35.280 | 14.230 | 34.000 | 5.750 | 0.030 | 0.130 | 0.050 |
| P-value | <1.0E−300 | <1.0E−300 | <1.0E−300 | 1.4E−163 | | | |
| On:off specificity | 1 | 1 | | 1 | | | |

TABLE 3-continued

Cellular modification induced by wild-type Cas9, Cas9 nickase, and fCas9 at on-target and off-target genomic sites.

| | | | | | | | |
|---|---|---|---|---|---|---|---|
| CLT2_Off1 | | | | | | | |
| Indels | 316 | 44 | 2 | 2 | 1 | 3 | 3 |
| Total | 60620 | 64755 | 71537 | 63079 | 93883 | 91306 | 82055 |
| Modified (%) | 0.521 | 0.068 | 0.003 | 0.003 | <0.002 | 0.003 | 0.004 |
| P-value | 1.3E−126 | 2.1E−16 | | | | | |
| On:off specificity | 68 | 209 | | >2850 | | | |
| CLT2_Off2 | | | | | | | |
| Indels | 11 | 5 | 3 | 1 | 1 | 1 | 2 |
| Total | 72596 | 51093 | 59632 | 35541 | 69114 | 64412 | 39978 |
| Modified (%) | 0.015 | 0.010 | 0.005 | 0.003 | <0.002 | <0.002 | 0.005 |
| P-value | 6.5E−03 | | | | | | |
| On:off specificity | 2328 | 1454 | | >2850 | | | |
| CLT2_Off3 | | | | | | | |
| Indels | 11 | 10 | 0 | 0 | 1 | 1 | 1 |
| Total | 52382 | 44212 | 54072 | 48668 | 55670 | 58707 | 54341 |
| Modified (%) | 0.021 | 0.023 | <0.002 | <0.002 | <0.002 | <0.002 | <0.002 |
| P-value | 2.7E−03 | 3.5E−03 | | | | | |
| On:off specificity | 1680 | 629 | | >2850 | | | |

(B)

| Nuclease type:<br>gRNA pair: | wt Cas9<br>EMX | wt Cas9<br>EMX | Cas9 nickase<br>EMX | fCas9<br>EMX | wt Cas9<br>GFP | Cas9 nickase<br>GFP | fCas9<br>GFP |
|---|---|---|---|---|---|---|---|
| Total expression plasmids (ng): | 1000 | 125 | 1000 | 1000 | 1000 | 1000 | 1000 |
| EMX Site | | | | | | | |
| EMX_On | | | | | | | |
| Indels | 5111 | 2683 | 2267 | 522 | 0 | 0 | 2 |
| Total | 10000 | 10000 | 10000 | 10000 | 10000 | 10000 | 10000 |
| Modified (%) | 51.110 | 26.830 | 22.670 | 5.220 | <0.002 | <0.002 | 0.020 |
| P-value | <1.0E−300 | <1.0E−300 | <1.0E−300 | 1.0E−154 | | | |
| On:off specificity | 1 | 1 | 1 | 1 | | | |
| EMX_Off1 | | | | | | | |
| Indels | 386 | 122 | 7 | 1 | 4 | 9 | 7 |
| Total | 109787 | 83420 | 124564 | 88424 | 102817 | 90020 | 96526 |
| Modified (%) | 0.352 | 0.146 | 0.006 | <0.002 | 0.004 | 0.010 | 0.007 |
| P-value | 1.3E−103 | 2.8E−37 | | | | | |
| On:off specificity | 145 | 183 | >11222 | >2584 | | | |
| EMX_Off2 | | | | | | | |
| Indels | 74 | 58 | 3 | 6 | 3 | 0 | 4 |
| Total | 98568 | 94108 | 105747 | 78871 | 81717 | 79469 | 79193 |
| Modified (%) | 0.075 | 0.062 | 0.003 | 0.008 | 0.004 | <0.002 | 0.005 |
| P-value | 3.2E−16 | 1.4E−12 | | | | | |
| On:off specificity | 681 | 435 | >11222 | >2584 | | | |
| EMX_Off3 | | | | | | | |
| Indels | 736 | 178 | 20 | 14 | 12 | 11 | 17 |
| Total | 72888 | 65139 | 82348 | 59593 | 74341 | 73408 | 75080 |
| Modified (%) | 1.010 | 0.273 | 0.024 | 0.023 | 0.016 | 0.015 | 0.023 |
| P-value | 2.5E−202 | 3.1E−44 | | | | | |
| On:off specificity | 51 | 98 | >11222 | >2584 | | | |
| EMX_Off4 | | | | | | | |
| Indels | 4149 | 620 | 3 | 3 | 6 | 7 | 5 |
| Total | 107537 | 91695 | 91368 | 91605 | 111736 | 119643 | 128088 |
| Modified (%) | 3.858 | 0.676 | 0.003 | 0.003 | 0.005 | 0.006 | 0.004 |
| P-value | <1.0E−300 | 1.9E−202 | | | | | |
| On:off specificity | 13 | 40 | >11222 | >2584 | | | |

(C)

| Nuclease type:<br>gRNA pair: | wt Cas9<br>VEGF | wt Cas9<br>VEGF | Cas9 nickase<br>VEGF | fCas9<br>VEGF | wt Cas9<br>GFP | Cas9 nickase<br>GFP | fCas9<br>GFP |
|---|---|---|---|---|---|---|---|
| Total expression plasmids (ng): | 1000 | 125 | 1000 | 1000 | 1000 | 1000 | 1000 |
| VEGF Sites | | | | | | | |

TABLE 3-continued

Cellular modification induced by wild-type Cas9, Cas9 nickase, and fCas9 at on-target and off-target genomic sites.

| | | | | | | | |
|---|---|---|---|---|---|---|---|
| VEG_On | | | | | | | |
| Indels | 5253 | 2454 | 1230 | 1041 | 8 | 0 | 1 |
| Total | 10000 | 10000 | 10000 | 10000 | 10000 | 10000 | 10000 |
| Modified (%) | 52.530 | 24.540 | 12.300 | 10.410 | 0.080 | <0.002 | 0.010 |
| P-value | <1.0E−300 | <1.0E−300 | <1.0E−300 | 6.6E−286 | | | |
| On:off specificity | 1 | 1 | 1 | 1 | | | |
| VEG_Off1 | | | | | | | |
| Indels | 2950 | 603 | 22 | 0 | 0 | 4 | 1 |
| Total | 82198 | 71163 | 90434 | 77557 | 74765 | 79738 | 74109 |
| Modified (%) | 3.589 | 0.847 | 0.024 | <0.002 | <0.002 | 0.005 | <0.002 |
| P-value | <1.0E−300 | 3.2E−188 | 2.5E−06 | | | | |
| On:off specificity | 15 | 29 | 506 | >5150 | | | |
| VEG_Off2 | | | | | | | |
| Indels | 863 | 72 | 3 | 3 | 0 | 2 | 1 |
| Total | 102501 | 49836 | 119702 | 65107 | 54247 | 65753 | 61556 |
| Modified (%) | 0.842 | 0.144 | 0.003 | 0.005 | <0.002 | 0.003 | <0.002 |
| P-value | 3.5E−159 | 9.6E−24 | | | | | |
| On:off specificity | 62 | 170 | >6090 | >5150 | | | |
| VEG_Off3 | | | | | | | |
| Indels | 260 | 33 | 3 | 2 | 3 | 1 | 0 |
| Total | 91277 | 83124 | 90063 | 84385 | 62126 | 68165 | 69811 |
| Modified (%) | 0.285 | 0.040 | 0.003 | 0.002 | 0.005 | <0.002 | <0.002 |
| P-value | 6.8E−54 | 1.0E−05 | | | | | |
| On:off specificity | 184 | 618 | >6090 | >5150 | | | |
| VEG_Off4 | | | | | | | |
| Indels | 1305 | 149 | 3 | 2 | 3 | 2 | 4 |
| Total | 59827 | 41203 | 65964 | 57828 | 60906 | 61219 | 62162 |
| Modified (%) | 2.181 | 0.362 | 0.005 | 0.003 | 0.005 | 0.003 | 0.006 |
| P-value | <1.0E−300 | 2.7E−54 | | | | | |
| On:off specificity | 24 | 68 | >6090 | >5150 | | | |

(D)

| Nuclease type: gRNA pair: | Cas9 nickase VEGF | fCas9 VEGF | Cas9 nickase GFP | fCas9 GFP |
|---|---|---|---|---|
| Total expression plasmids (ng): | 1000 | 1000 | 1000 | 1000 |
| VEGF Sites | | | | |
| VEG_On | | | | |
| Indels | 2717 | 2122 | 10 | 13 |
| Total | 10000 | 10000 | 10000 | 10000 |
| Modified (%) | 27.170 | 21.220 | 0.100 | 0.130 |
| P-value | <1.0E−300 | <1.0E−300 | | |
| On:off specificity | 1 | 1 | | |
| VEG_Off1 | | | | |
| Indels | 67 | 30 | 3 | 2 |
| Total | 302573 | 233567 | 204454 | 190240 |
| Modified (%) | 0.022 | 0.013 | | |
| P-value | 5.9E−12 | 2.5E−06 | | |
| On:off specificity | 1227 | 1652 | | |

Results

Recently engineered variants of Cas9 that cleave only one DNA strand ("nickases") enable double-stranded breaks to be specified by two distinct gRNA sequences,[5-7] but still suffer from off-target cleavage activity[6,8] arising from the ability of each monomeric nickase to remain active when individually bound to DNA.[9-11] In contrast, the development of a FokI nuclease fusion to a catalytically dead Cas9 that requires simultaneous DNA binding and association of two FokI-dCas9 monomers to cleave DNA is described here. Off-target DNA cleavage of the engineered FokI-dCas9 (fCas9) is further reduced by the requirement that only sites flanked by two gRNAs ~15 or 25 base pairs apart are cleaved, a much more stringent spacing requirement than nickases. In human cells, fCas9 modified target DNA sites with efficiency comparable to that of nickases, and with >140-fold higher specificity than wild-type Cas9. Target sites that conform to the substrate requirements of fCas9 are abundant in the human genome, occurring on average once every 34 bp.

In cells, Cas9:gRNA-induced double strand breaks can result in functional gene knockout through non-homologous end joining (NHEJ) or alteration of a target locus to virtually any sequence through homology-directed repair (HDR) with an exogenous DNA template.[9,15,16] Cas9 is an especially convenient genome editing platform,[17] as a genome editing agent for each new target site of interest can be accessed by simply generating the corresponding gRNA. This approach has been widely used to create targeted knockouts and gene insertions in cells and model organisms, and has also been recognized for its potential therapeutic relevance.

While Cas9:gRNA systems provide an unprecedented level of programmability and ease of use, studies[1-5] have reported the ability of Cas9 to cleave off-target genomic sites, resulting in modification of unintended loci that can limit the usefulness and safety of Cas9 as a research tool and as a potential therapeutic. It was hypothesized that engineering Cas9 variants to cleave DNA only when two simultaneous, adjacent Cas9:DNA binding events take place could substantially improve genome editing specificity since the likelihood of two adjacent off-target binding events is much smaller than the likelihood of a single off-target binding event (approximately $1/n^2$ vs. $1/n$). Such an approach is distinct from the recent development of mutant Cas9 proteins that cleave only a single strand of dsDNA, such as nickases. Nickases can be used to nick opposite strands of two nearby target sites, generating what is effectively a double strand break, and paired Cas9 nickases can effect substantial on-target DNA modification with reduced off-target modification.[5,6,8] Because each of the component Cas9 nickases remains catalytically active[9-11] and single-stranded DNA cleavage events are weakly mutagenic,[18,19] nickases can induce genomic modification even when acting as monomers.[5,7,16] Indeed, Cas9 nickases have been previously reported to induce off-target modifications in cells.[6,8] Moreover, since paired Cas9 nickases can efficiently induce dsDNA cleavage-derived modification events when bound up to ~100 bp apart,[6] the statistical number of potential off-target sites for paired nickases is larger than that of a more spatially constrained dimeric Cas9 cleavage system.

Figure 6A:
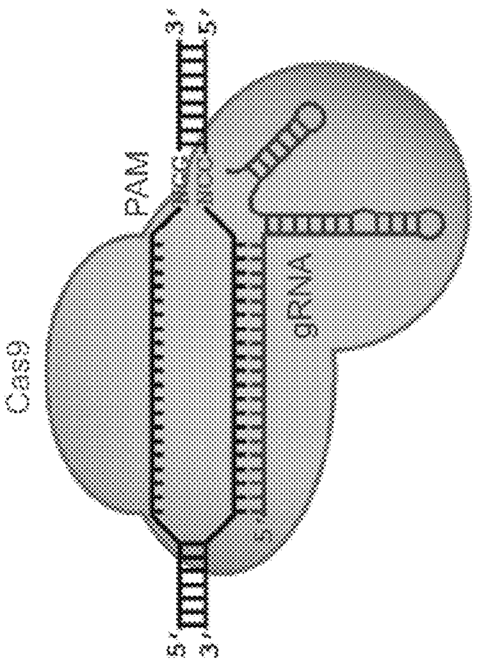
FIG. 6 shows architectures of Cas9 and FokI-dCas9 fusion variants. (A) Cas9 protein in complex with a guide RNA (gRNA) binds to target DNA. The *S. pyogenes* Cas9 protein recognizes the PAM sequence NGG, initiating unwinding of dsDNA and gRNA:DNA base pairing. (B) FokI-dCas9 fusion architectures tested. Four distinct configurations of NLS, FokI nuclease, and dCas9 were assembled. Seventeen (17) protein linker variants were also tested. (C) gRNA target sites tested within GFP. Seven gRNA target sites were chosen to test FokI-dCas9 activity in an orientation in which the PAM is distal from the cleaved spacer sequence (orientation A). Together, these seven gRNAs enabled testing of FokI-dCas9 fusion variants across spacer lengths ranging from 5 to 43 bp. See FIG. 9 for guide RNAs used to test orientation B, in which the PAM is adjacent to the spacer sequence. (D) Monomers of FokI nuclease fused to dCas9 bind to separate sites within the target locus. Only adjacently bound FokI-dCas9 monomers can assemble a catalytically active FokI nuclease dimer, triggering dsDNA cleavage. The sequences shown in (C) are identified as follows: "EmGFP (bp 326-415)" corresponds to SEQ ID NO:204; "G1" corresponds to SEQ ID NO:205; "G2" corresponds to SEQ ID NO:206; "G3" corresponds to SEQ ID NO:207; "G4" corresponds to SEQ ID NO:208; "G5" corresponds to SEQ ID NO:209; "G6" corresponds to SEQ ID NO:210; and "G7" corresponds to SEQ ID NO:211.
FIG. 6C), each gRNA individually, or no gRNAs. The Indel modification percentage is shown below each lane for samples with modification above the detection limit (~2%). (C-G) show graphs depicting Indel modification efficiency for (C) two pairs of gRNAs spaced 14 or 25 bp apart targeting the GFP site, (D) one pair of gRNAs spaced 19 bp apart targeting the CLTA site, (E) one pair of gRNAs spaced 23 bp apart targeting the EMX site, (F) one pair of gRNAs spaced 16 bp apart targeting the HBB site, and (G) two pairs of gRNAs spaced 14 or 16 bp apart targeting the VEGF site. Error bars reflect standard error of the mean from three biological replicates performed on different days.
Figure 6B:
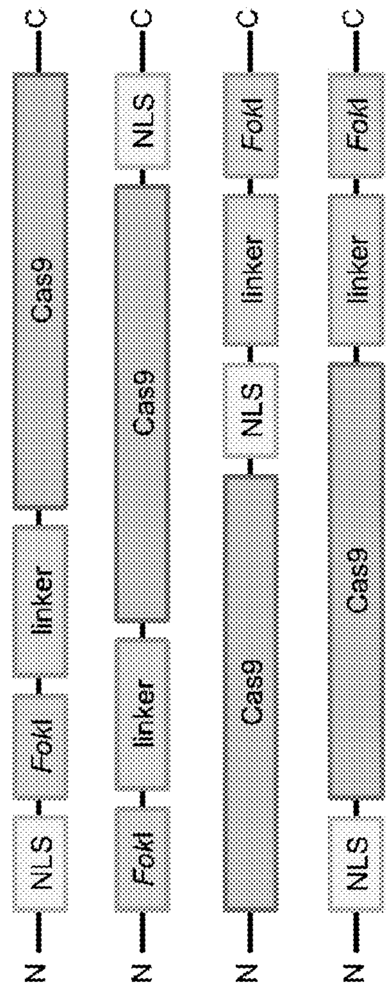
Figure 6D:
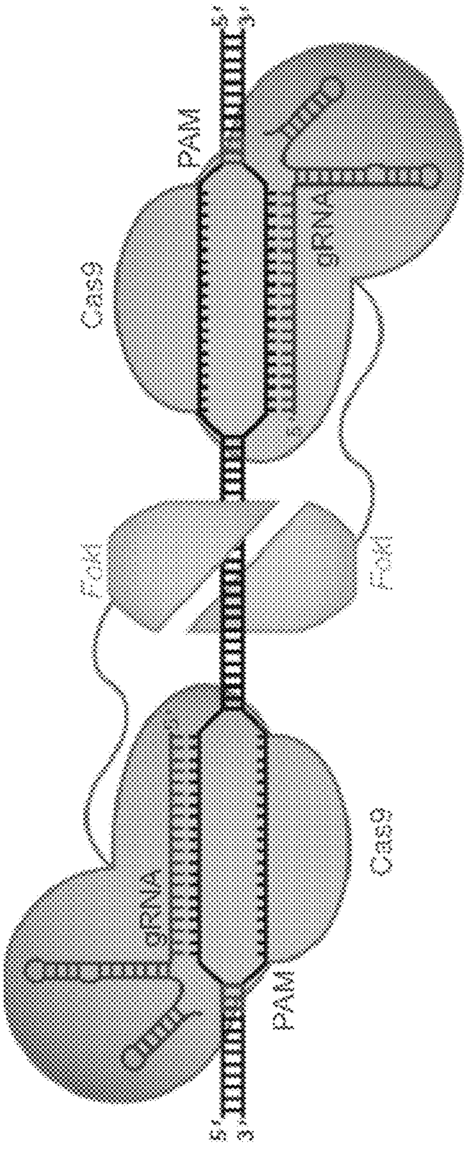

To further improve the specificity of the Cas9:gRNA system, an obligate dimeric Cas9 system is provided herein. In this example, fusing the FokI restriction endonuclease cleavage domain to a catalytically dead Cas9 (dCas9) created an obligate dimeric Cas9 that would cleave DNA only when two distinct FokI-dCas9:gRNA complexes bind to adjacent sites ("half-sites") with particular spacing constraints (FIG. 6D). In contrast with Cas9 nickases, in which single-stranded DNA cleavage by monomers takes place independently, the DNA cleavage of FokI-dCas9 requires simultaneous binding of two distinct FokI-dCas9 monomers because monomeric FokI nuclease domains are not catalytically competent.[21] This approach increased the specificity of DNA cleavage relative to wild-type Cas9 by doubling the number of specified target bases contributed by both monomers of the FokI-dCas9 dimer, and offered improved specificity compared to nickases due to inactivity of monomeric FokI-dCas9:gRNA complexes, and the more stringent spatial requirements for assembly of a FokI-dCas9 dimer.

While fusions of Cas9 to short functional peptide tags have been described to enable gRNA-programmed transcriptional regulation,[22] it is believed that no fusions of Cas9 with active enzyme domains have been previously reported. Therefore a wide variety of FokI-dCas9 fusion proteins were constructed and characterized with distinct configurations of a FokI nuclease domain, dCas9 containing inactivating mutations D10A and H840A, and a nuclear localization sequence (NLS). FokI was fused to either the N- or C-terminus of dCas9, and varied the location of the NLS to be at either terminus or between the two domains (FIG. 6B). The length of the linker sequence was varied as either one or three repeats of Gly-Gly-Ser (GGS) between the FokI and dCas9 domains. Since previously developed dimeric nuclease systems are sensitive to the length of the spacer sequence between half-sites,[23,24] a wide range of spacer sequence lengths was tested between two gRNA binding sites within a test target gene, Emerald GFP (referred to hereafter as GFP) (FIG. 6C and FIG. 9). Two sets of gRNA binding-site pairs with different orientations were chosen within GFP. One set placed the pair of NGG PAM sequences distal from the spacer sequence, with the 5' end of the gRNA adjacent to the spacer (orientation A) (FIG. 6C), while the other placed the PAM sequences immediately adjacent to the spacer (orientation B) (FIG. 9). In total, seven pairs of gRNAs were suitable for orientation A, and nine were suitable for orientation B. By pairwise combination of the gRNA targets, eight spacer lengths were tested in both dimer orientations, ranging from 5 to 43 bp in orientation A, and 4 to 42 bp in orientation B. In total, DNA constructs corresponding to 104 pairs of FokI-dCas9:gRNA complexes were generated and tested, exploring four fusion architectures, 17 protein linker variants (described below), both gRNA orientations and 13 spacer lengths between half-sites.

Figure 10A:
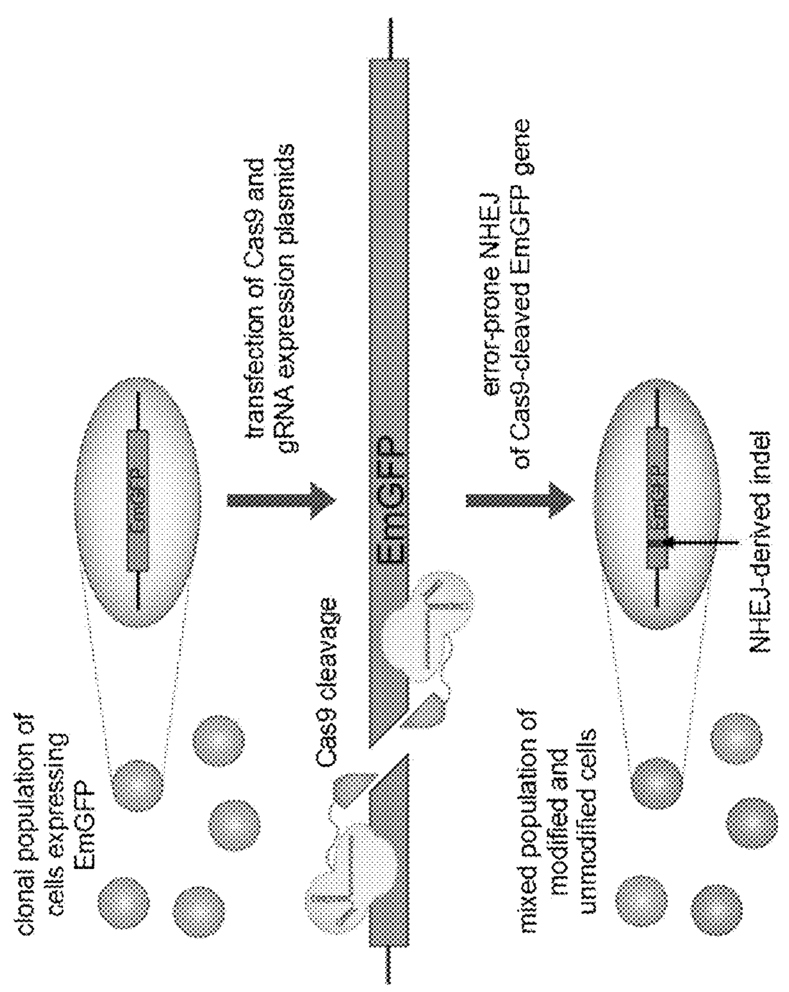
FIG. 10 shows a GFP disruption assay for measuring genomic DNA-modification activity. (A) depicts schematically a HEK293-derived cell line constitutively expressing a genomically integrated EmGFP gene used to test the activity of candidate FokI-dCas9 fusion constructs. Co-transfection of these cells with appropriate nuclease and gRNA expression plasmids leads to dsDNA cleavage within the EmGFP coding sequence, stimulating error-prone NHEJ and generating indels that can disrupt the expression of GFP, leading to loss of cellular fluorescence. The fraction of cells displaying a loss of GFP fluorescence is then quantitated by flow cytometry. (B) shows typical epifluorescence microscopy images at 200× magnification of EmGFP-HEK293 cells before and after co-transfection with wild-type Cas9 and gRNA expression plasmids.
Figure 10B:
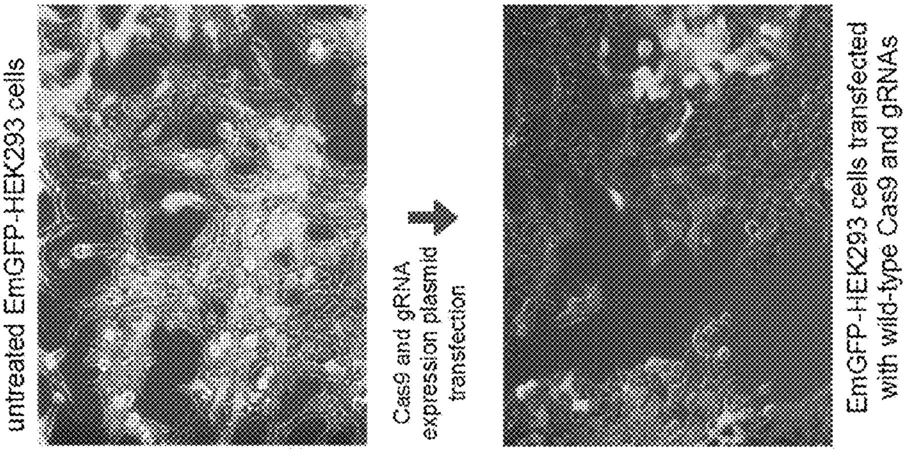

To assay the activities of these candidate FokI-dCas9: gRNA pairs, a previously described flow cytometry-based fluorescence assay[2,8] in which DNA cleavage and NHEJ of a stably integrated constitutively expressed GFP gene in HEK293 cells leads to loss of cellular fluorescence was used (FIG. 10). For comparison, the initial set of FokI-dCas9 variants were assayed side-by-side with the corresponding Cas9 nickases and wild-type Cas9 in the same expression plasmid across both gRNA spacer orientation sets A and B. Cas9 protein variants and gRNA were generated in cells by transient co-transfection of the corresponding Cas9 protein expression plasmids together with the appropriate pair of gRNA expression plasmids. The FokI-dCas9 variants, nickases, and wild-type Cas9 all targeted identical DNA sites using identical gRNAs.

Figure 11A:
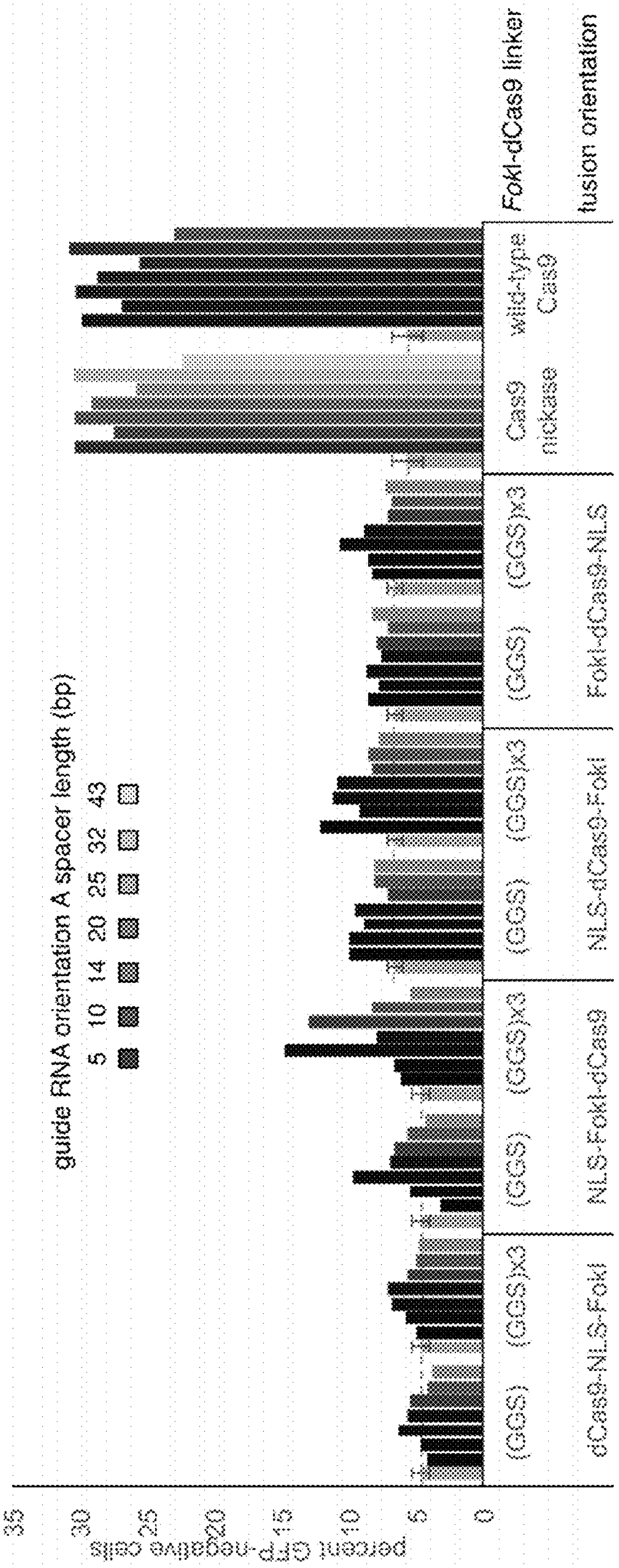
FIG. 11 shows a graph depicting the activities of FokI-dCas9 fusion candidates combined with gRNA pairs of different orientations and varying spacer lengths. The fusion architectures described in FIG. 6B were tested for functionality by flow cytometry using the GFP loss-of-function reporter across all (A) orientation A gRNA spacers and (B) orientation B gRNA spacers (FIG. 6C and FIG. 9). All FokI-dCas9 fusion data shown are the results of single trials. Wild-type Cas9 and Cas9 nickase data are the average of two replicates, while the 'no treatment' negative control data is the average of 6 replicates, with error bars representing one standard deviation. The grey dotted line across the Y-axis corresponds to the average of the 'no treatment' controls performed on the same day. The sequence shown as "(GGS)×3" corresponds to SEQ ID NO:14.
Figure 11B:
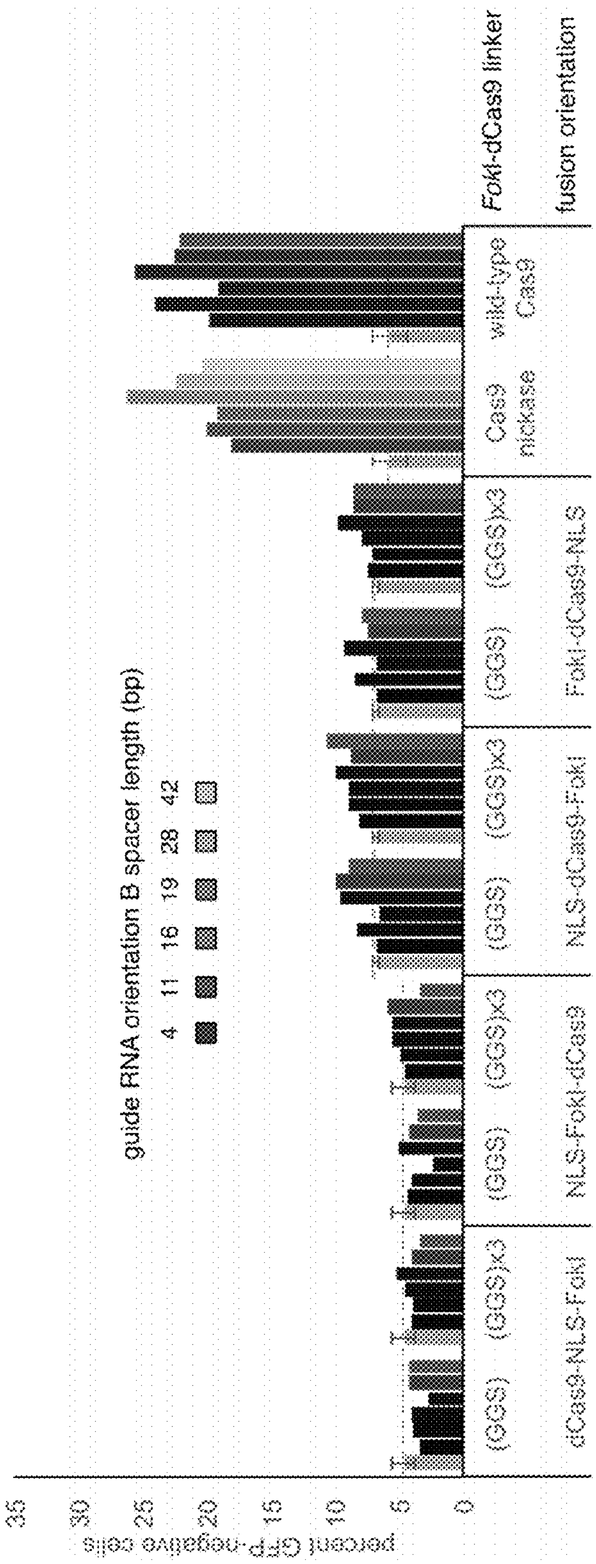

Most of the initial FokI-dCas9 fusion variants were inactive or very weakly active (FIG. 11). The NLS-FokI-dCas9 architecture (listed from N to C terminus), however, resulted in a 10% increase of GFP-negative cells above corresponding the no-gRNA control when used in orientation A, with PAMs distal from the spacer (FIG. 11A). In contrast, NLS-FokI-dCas9 activity was undetectable when used on gRNA pairs with PAMs adjacent to the spacer (FIG. 11B). Examination of the recently reported Cas9 structures[25,26] reveals that the Cas9 N-terminus protrudes from the RuvC1 domain, which contacts the 5' end of the gRNA:DNA duplex. Without wishing to be bound by any particular theory, it is speculated that this arrangement places an N-terminally fused FokI distal from the PAM, resulting in a preference for gRNA pairs with PAMs distal from the cleaved spacer (FIG. 6D). While other FokI-dCas9 fusion pairings and the other gRNA orientation in some cases showed modest activity (FIG. 11), NLS-FokI-dCas9 with gRNAs in orientation A were chosen for further development.

Figure 12B:
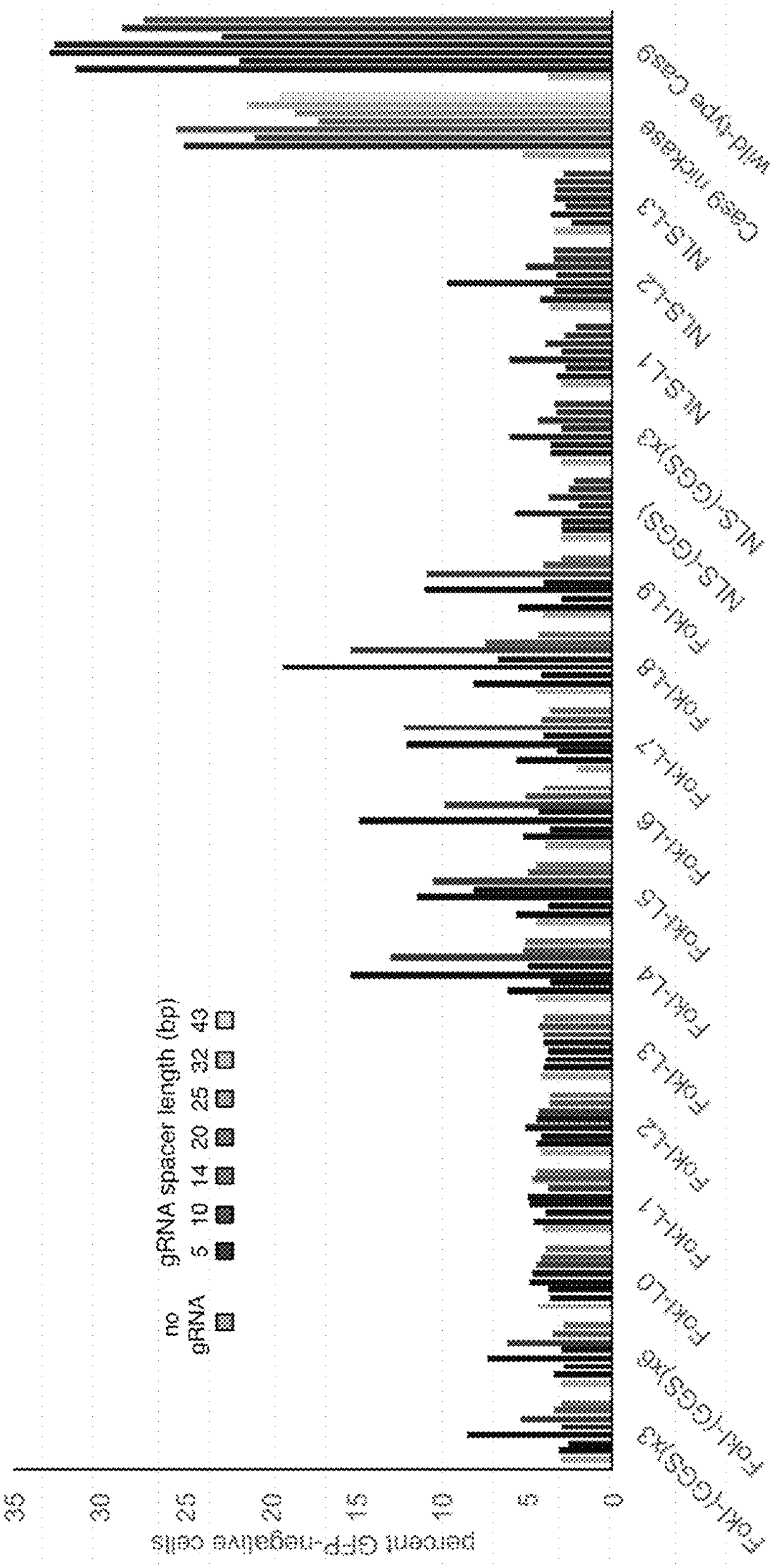
FIG. 12 shows the optimization of protein linkers in NLS-FokI-dCas9. (A) shows a table of all linker variants tested. Wild-type Cas9 and Cas9 nickase were included for comparison. The initial active construct NLS-FokI-dCas9 with a $(GGS)_3$ (SEQ ID NO:14) linker between FokI and dCas9 was tested across a range of alternate linkers. The final choice of linkers for fCas9 is highlighted. (B) shows a graph depicting the activity of FokI-dCas9 fusions with linker variants. Each variant was tested across a range of spacer lengths from 5 to 43 bp using gRNA pair orientation A. A control lacking gRNA ("no gRNA") was included for each separate fusion construct. NLS-FokI-dCas9 variant L8 showed the best activity, approaching the activity of Cas9 nickase. Variants L4 through L9 show peak activity with 14- and 25-bp spacer lengths, suggesting two optimal spacer lengths roughly one helical turn of dsDNA apart. The sequences shown in (A) are identified as follows: GGSGGSGGS corresponds to SEQ ID NO:14; GGSGGSGGSGGSGGSGGS corresponds to SEQ ID NO:15; MKIIEQLPSA corresponds to SEQ ID NO:22; VRHKLKRVGS corresponds to SEQ ID NO:23; VPFLLEPDNINGKTC corresponds to SEQ ID NO:19; GHGTGSTGSGSS corresponds to SEQ ID NO:24; MSRPDPA corresponds to SEQ ID NO:25; GSAGSAAGSGEF corresponds to SEQ ID NO:20; SGSETPGTSESA corresponds to SEQ ID NO:17; SGSETPGTSESATPES corresponds to SEQ ID NO:16; SGSETPGTSESATPEGGSGGS corresponds to SEQ ID NO:18; GGSM corresponds to SEQ ID NO:301; and SIVAQLSRPDPA corresponds to SEQ ID NO:21.

Next the protein linkers between the NLS and FokI domain, and between the FokI domain and dCas9 in the NLS-FokI-dCas9 architecture were optimized. 17 linkers with a wide range of amino acid compositions, predicted flexibilities, and lengths varying from 9 to 21 residues were tested (FIG. 12A). Between the FokI domain and dCas9 a flexible 18-residue linker, $(GGS)_6$ (SEQ ID NO:15), and a 16-residue "XTEN" linker (FokI-L8 in FIG. 12A) were identified based on a previously reported engineered protein with an open, extended conformation,[27] as supporting the highest levels of genomic GFP modification FIG. 12B).

The XTEN protein was originally designed to extend the serum half-life of translationally fused biologic drugs by increasing their hydrodynamic radius, acting as protein-based functional analog to chemical PEGylation.[35] Possessing a chemically stable, non-cationic, and non-hydrophobic primary sequence, and an extended conformation, it is hypothesized that a portion of XTEN could function as a stable, inert linker sequence for fusion proteins. The sequence of the XTEN protein tag from E-XTEN was analyzed, and repeating motifs within the amino acid sequence were aligned. The sequence used in the FokI-dCas9 fusion construct FokI-L8 (FIG. 12A) was derived from the consensus sequence of a common E-XTEN motif, and a 16 amino acid sequence was chosen from within this motif to test as a FokI-dCas9 linker.

Many of the FokI-dCas9 linkers tested including the optimal XTEN linker resulted in nucleases with a marked preference for spacer lengths of ~15 and ~25 bp between half-sites, with all other spacer lengths, including 20 bp, showing substantially lower activity (FIG. 12B). This pattern of linker preference is consistent with a model in which the FokI-dCas9 fusions must bind to opposite faces of the DNA double helix to cleave DNA, with optimal binding taking place ~1.5 or 2.5 helical turns apart. The variation of NLS-FokI linkers did not strongly affect nuclease performance, especially when combined with the XTEN FokI-dCas9 linker (FIG. 12B).

In addition to assaying linkers between the FokI domain and dCas9 in the NLS-FokI-dCas9 architecture, four linker variants between the N-terminal NLS and the FokI domain were also tested (FIG. 12A). Although a NLS-GSAGSAAGSGEF(SEQ ID NO:20)-FokI-dCas9 linker exhibited nearly 2-fold better GFP gene modification than the other NLS-FokI linkers tested when a simple GGS linker was used between the FokI and dCas9 domains (FIG. 12B), the GSAGSAAGSGEF (SEQ ID NO:20) linker did not perform substantially better when combined with the XTEN linker between the FokI and dCas9 domains.

Figure 7A:
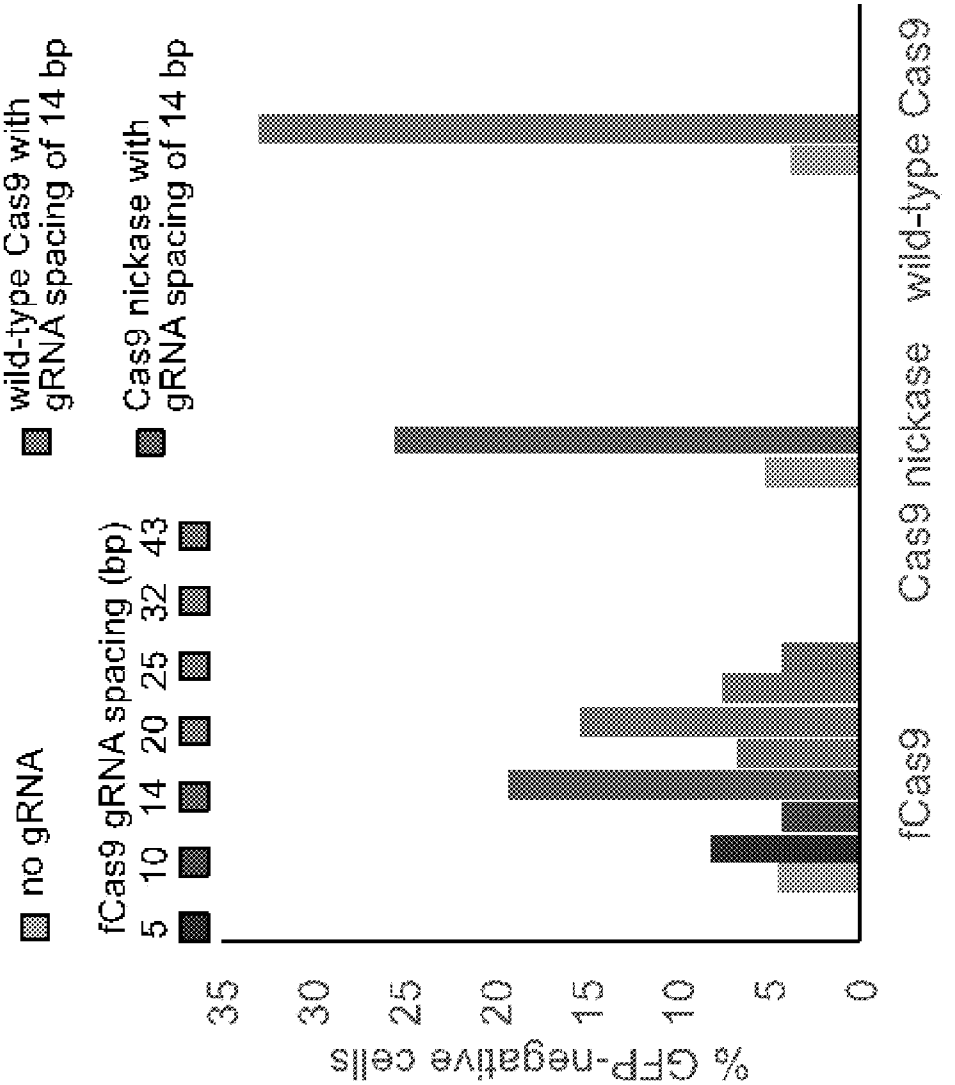
FIG. 7 shows genomic DNA modification by fCas9, Cas9 nickase, and wild-type Cas9. (A) shows a graph depicting GFP disruption activity of fCas9, Cas9 nickase, or wild-type Cas9 with either no gRNA, or gRNA pairs of variable spacer length targeting the GFP gene in orientation A. (B) is an image of a gel showing Indel modification efficiency from PAGE analysis of a Surveyor cleavage assay of renatured target-site DNA amplified from cells treated with fCas9, Cas9 nickase, or wild-type Cas9 and two gRNAs spaced 14 bp apart targeting the GFP site (gRNAs G3 and G7.

The NLS-GGS-FokI-XTEN-dCas9 construct consistently exhibited the highest activity among the tested candidates, inducing loss of GFP in ~15% of cells, compared to ~20% and ~30% for Cas9 nickases and wild-type Cas9 nuclease, respectively (FIG. 7A). All subsequent experiments were performed using this construct, hereafter referred to as fCas9. To confirm the ability of fCas9 to efficiently modify genomic target sites, the T7 endonuclease I Surveyor assay[28] was used to measure the amount of mutation at each of seven target sites within the integrated GFP gene in HEK293 cells treated with fCas9, Cas9 nickase, or wild-type Cas9 and either two distinct gRNAs in orientation A or no gRNAs as a negative control. Consistent with the flow cytometry-based studies, fCas9 was able to modify the GFP target sites with optimal spacer lengths of ~15 or ~25 bp at a rate of ~20%, comparable to the efficiency of nickase-induced modification and approximately two-thirds that of wild-type Cas9 (FIG. 7A-C).

Figure 13:
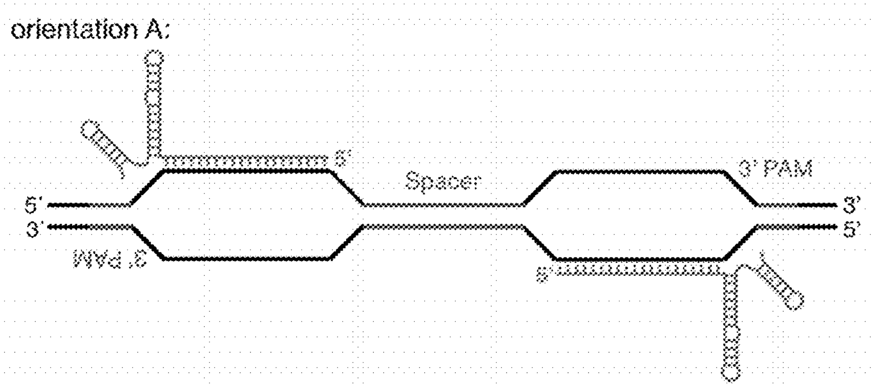
FIG. 13 shows target DNA sequences in endogenous human EMX, VEGF, CLTA, and HBB genes. The gRNA target sites tested within endogenous human EMX, VEGF, CLTA, and HBB genes are shown. Thirteen gRNA target sites were chosen to test the activity of the optimized fCas9 fusion in an orientation in which the PAM is distal from the cleaved spacer sequence (orientation A). Together, these 13 gRNAs enabled testing of fCas9 fusion variants across eight spacer lengths ranging from 5 to 47 bp. The sequences shown are identified as follows: “CLTA-1” corresponds to SEQ ID NO:220; “C1” corresponds to SEQ ID NO:221; “C2” corresponds to SEQ ID NO:222; “C3” corresponds to SEQ ID NO:224; “C4” corresponds to SEQ ID NO:225; “HBC” corresponds to SEQ ID NO:226; “H1” corresponds to SEQ ID NO:227; “H2” corresponds to SEQ ID NO:228; “H3” corresponds to SEQ ID NO:229; “H4” corresponds to SEQ ID NO:230; “H5” corresponds to SEQ ID NO:231; “H6” corresponds to SEQ ID NO:232; “H7” corresponds to SEQ ID NO:233; “EMX” corresponds to SEQ ID NO:234; “E1” corresponds to SEQ ID NO:235; “E2” corresponds to SEQ ID NO:236; “E3” corresponds to SEQ ID NO:237; “VEGF” corresponds to SEQ ID NO:238; “V1” corresponds to SEQ ID NO:239; “V2” corresponds to SEQ ID NO:240; “V3” corresponds to SEQ ID NO:241; and “V4” corresponds to SEQ ID NO:242.
Figure 14B:
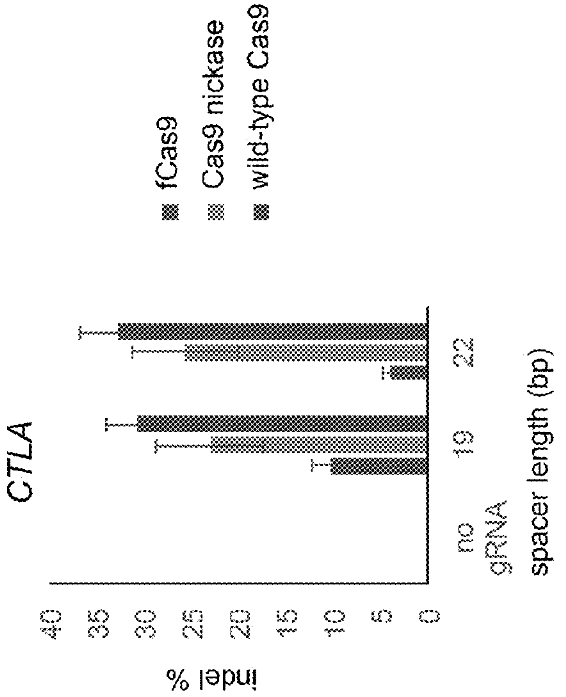
FIG. 14 shows graphs depicting spacer length preference of genomic DNA modification by fCas9, Cas9 nickase, and wild-type Cas9. Indel modification efficiency for (A) pairs of gRNAs targeting the GFP site, (B) pairs of gRNAs targeting the CLTA site, (C) pairs of gRNAs targeting the EMX site (D) pairs of gRNAs targeting the HBB site, and (E) pairs of gRNAs targeting the VEGF site. Error bars reflect standard error of the mean from three biological replicates performed on different days.
Figure 14A:
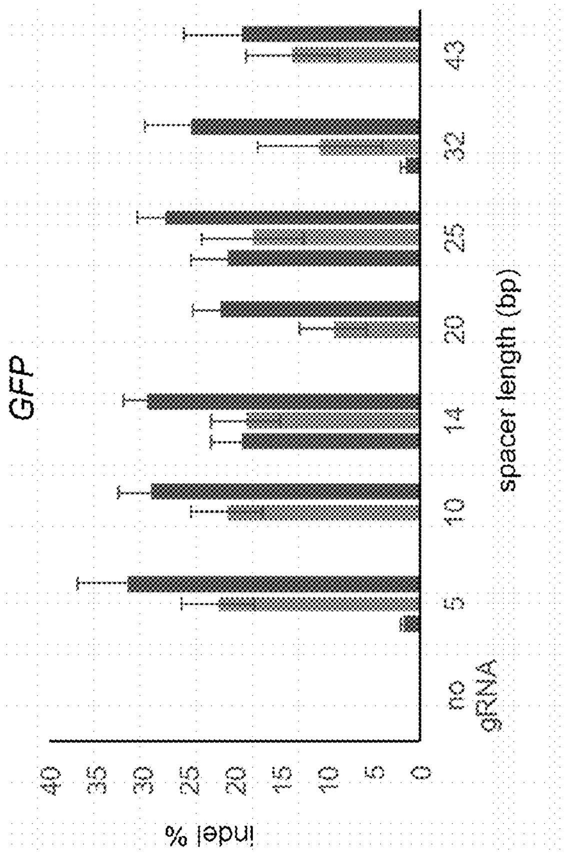
Figure 14E:
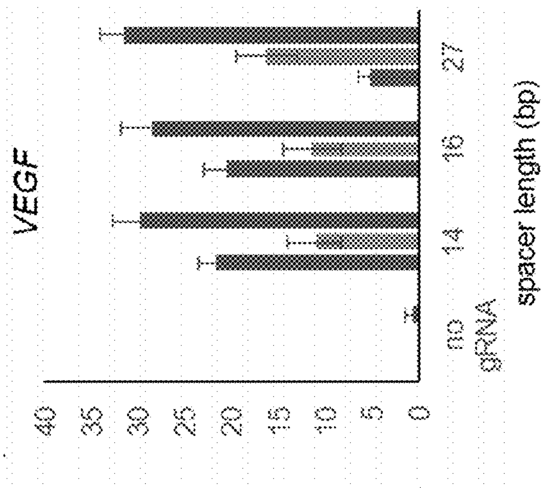
Figure 14D:
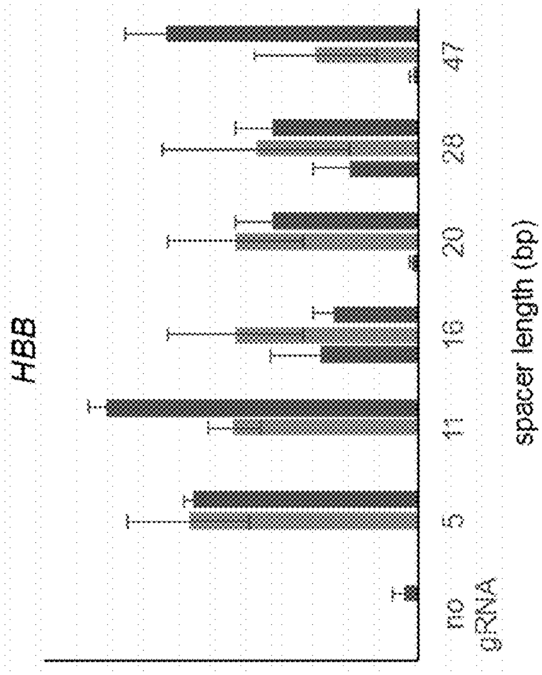
Figure 14C:
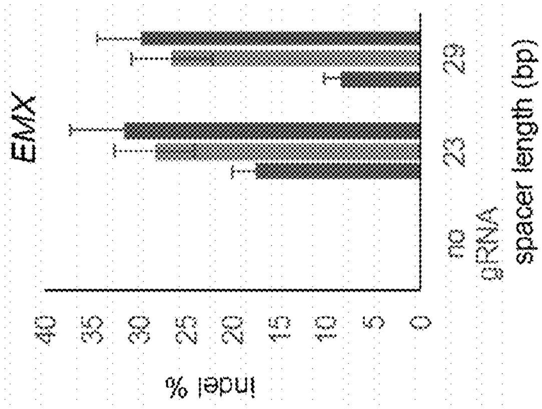
Figure 15A:
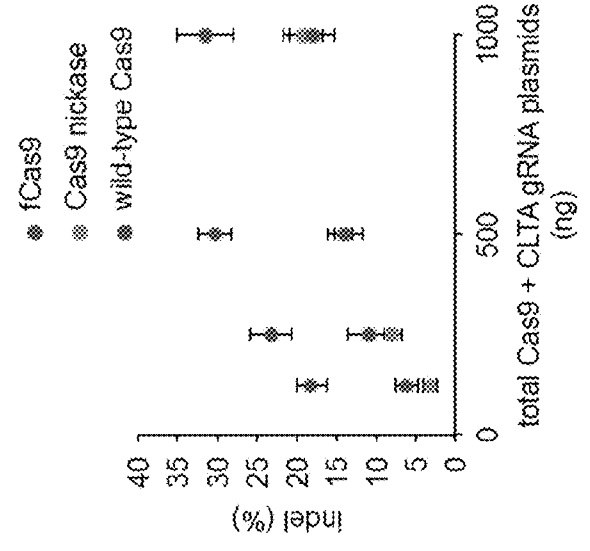
FIG. 15 shows graphs depicting the efficiency of genomic DNA modification by fCas9, Cas9 nickase, and wild-type Cas9 with varying amounts of Cas9 and gRNA expression plasmids. Indel modification efficiency from a Surveyor assay of renatured target-site DNA amplified from a population of cells treated with fCas9, Cas9 nickase, or wild-type Cas9 and two target site gRNAs. Either 700 ng of Cas9 expression plasmid with 250 ng of gRNA expression plasmid (950 ng total), 350 ng of Cas9 expression plasmid with 125 ng of gRNA expression plasmid (475 ng in total), 175 ng of Cas9 expression plasmid with 62.5 ng of gRNA expression plasmid (238 ng in total) or 88 ng of Cas9 expression plasmid with 31 ng of gRNA expression plasmid (119 ng in total) were transfected with an appropriate amount of inert, carrier plasmid to ensure uniform transfection of 950 ng of plasmid across all treatments. Indel modification efficiency for (A) gRNAs spaced 19-bp apart targeting the CLTA site, (B) gRNAs spaced 23 bp apart targeting the EMX site, and (C) gRNAs spaced 14 bp apart targeting the VEGF site. Error bars represent the standard error of the mean from three biological replicates performed on separate days.
Figure 15B:
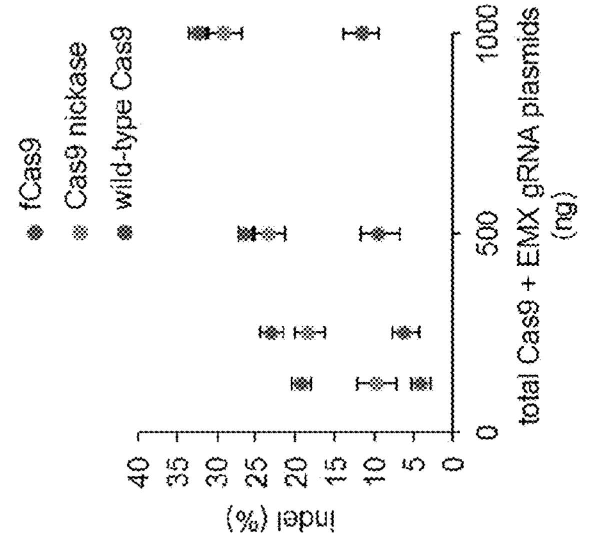
Figure 15C:
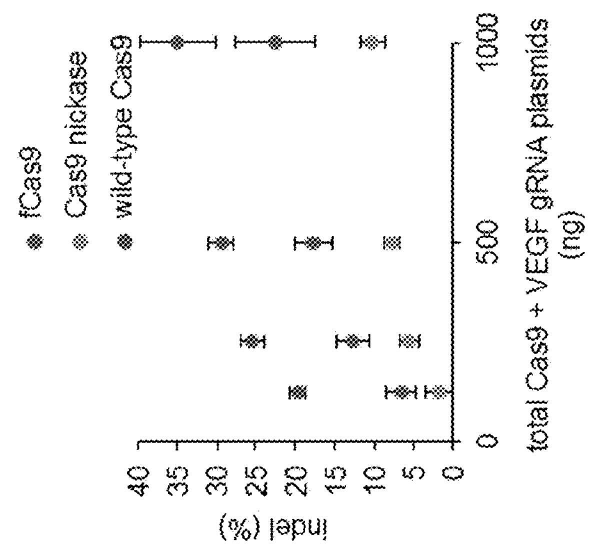

Next the ability of the optimized fCas9 to modify four distinct endogenous genomic loci by Surveyor assay was evaluated. CLTA (two sites), EMX (two sites), HBB (six sites) VEGF (three sites), and were targeted with two gRNAs per site in orientation A spaced at various lengths (FIG. 13). Consistent with the results of the experiments targeting GFP, at appropriately spaced target half-sites fCas9 induced efficient modification of all four genes, ranging from 8% to 22% target chromosomal site modification (FIG. 7D-G and FIG. 14). Among the gRNA spacer lengths resulting in the highest modification at each of the five genes targeted (including GFP), fCas9 induced on average 15.6% (±6.3% s.d.) modification, while Cas9 nickase and wild-type Cas9 induced on average 22.1% (±4.9% s.d.) and 30.4% (±3.1% s.d.) modification, respectively, from their optimal gRNA pairs for each gene. Because decreasing the amount of Cas9 expression plasmid and gRNA expression plasmid during transfection generally did not proportionally decrease genomic modification activity for Cas9 nickase and fCas9 (FIG. 15A-C), expression was likely not limiting under the conditions tested.

Figure 8B:
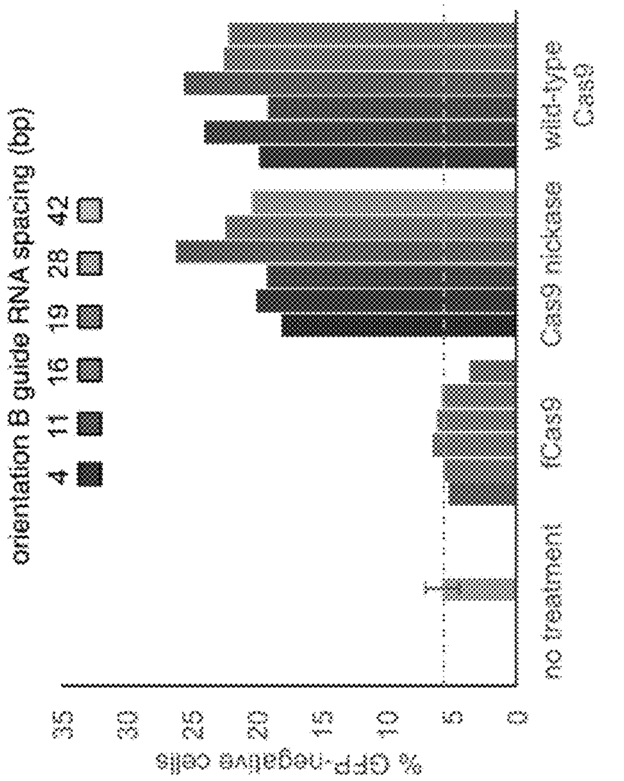
FIG. 8 shows the DNA modification specificity of fCas9, Cas9 nickase, and wild-type Cas9. (A) shows a graph depicting GFP gene disruption by wild-type Cas9, Cas9 nickase, and fCas9 using gRNA pairs in orientation A. High activity of fCas9 requires spacer lengths of ~15 and 25 bp, roughly one DNA helical turn apart. (B) shows a graph depicting GFP gene disruption using gRNA pairs in orientation B. Cas9 nickase, but not fCas9, accepts either orientation of gRNA pairs. (C) shows a graph depicting GFP gene disruption by fCas9, but not Cas9 nickase or wild-type Cas9, which depends on the presence of two gRNAs. Four single gRNAs were tested along with three gRNA pairs of varying spacer length. In the presence of gRNA pairs in orientation A with spacer lengths of 14 or 25 bp (gRNAs 1+5, and gRNAs 3+7, respectively), fCas9 is active, but not when a gRNA pair with a 10-bp spacer (gRNAs 1+4) is used. In (A-C), "no treatment" refers to cells receiving no plasmid DNA. (D-F) show graphs depicting the indel mutation frequency from high-throughput DNA sequencing of amplified genomic on-target sites and off-target sites from human cells treated with fCas9, Cas9 nickase, or wild-type Cas9 and (D) two gRNAs spaced 19 bp apart targeting the CLTA site (gRNAs C1 and C2), (E) two gRNAs spaced 23 bp apart targeting the EMX site (gRNAs E1 and E2), or (F, G) two gRNAs spaced 14 bp apart targeting the VEGF site (gRNAs V1 and V2). (G) shows a graph depicting two in-depth trials to measure genome modification at VEGF off-target site 1. Trial 1 used 150 ng of genomic input DNA and >$8\times10^5$ sequence reads for each sample; trial 2 used 600 ng of genomic input DNA and >$23\times10^5$ sequence reads for each sample. In (D-G), all significant (P value<0.005 Fisher's Exact Test) indel frequencies are shown. P values are listed in Table 3. For (D-F) each on- and off-target sample was sequenced once with >10,000 sequences analyzed per on-target sample and an average of 76,260 sequences analyzed per off-target sample (Table 3). The sequences shown in (C) are identified as follows, from top to bottom: the sequence found at the top of FIG. 8C corresponds to SEQ ID NO:204; "G1" corresponds to SEQ ID NO:205; "G3" corresponds to SEQ ID NO:207; "G5" corresponds to SEQ ID NO:209; "G7" corresponds to SEQ ID NO:211; "G1+4" corresponds to SEQ ID NO:205 and SEQ ID NO:208; "G1+5" corresponds to SEQ ID NO:205 and SEQ ID NO:209; "G3+7" corresponds to SEQ ID NO:207 and SEQ ID NO:211.
Figure 8A:
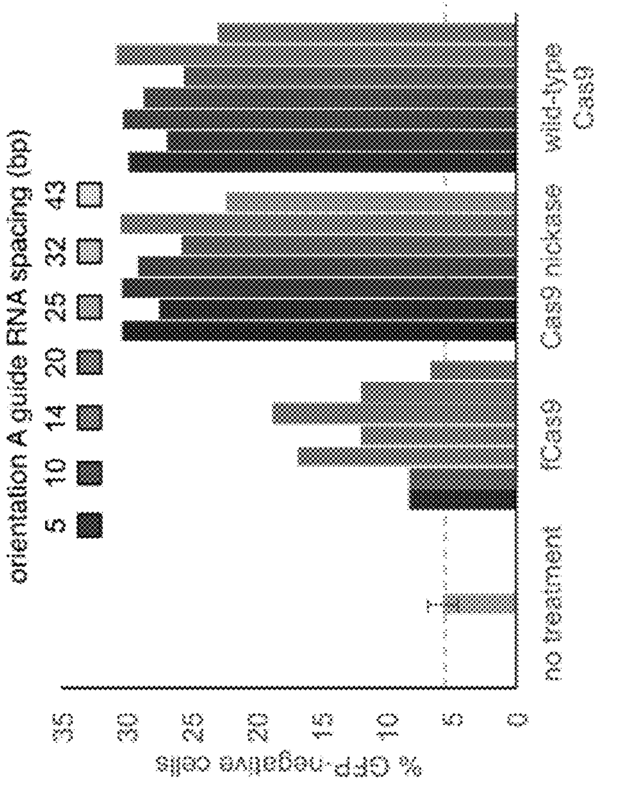

As the gRNA requirements of fCas9 potentially restricts the number of potential off-target substrates of fCas9, the effect of guide RNA orientation on the ability of fCas9, Cas9 nickase, and wild-type Cas9 to cleave target GFP sequences were compared. Consistent with previous reports,[5,6,17] Cas9 nickase efficiently cleaved targets when guide RNAs were bound either in orientation A or orientation B, similar to wild-type Cas9 (FIG. 8A, B). In contrast, fCas9 only cleaved the GFP target when guide RNAs were aligned in orientation A (FIG. 8A). This orientation requirement further limits opportunities for undesired off-target DNA cleavage.

Figure 7B:
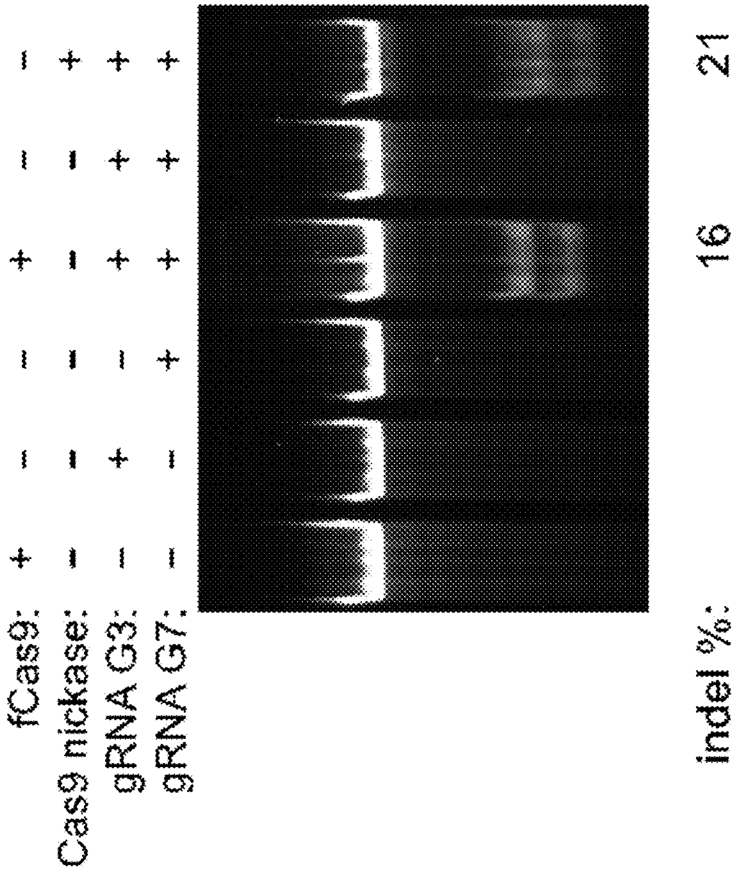
Figure 7E:
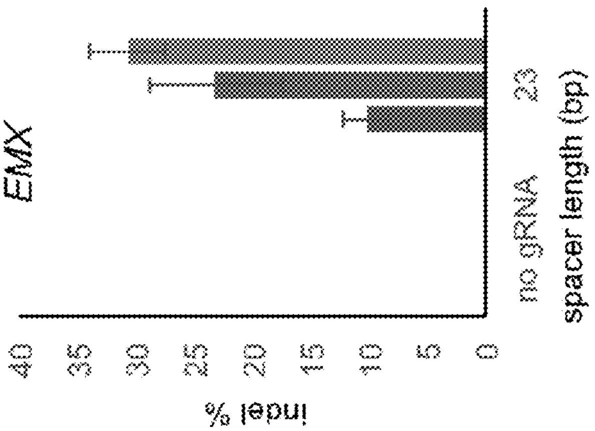
Figure 7D:
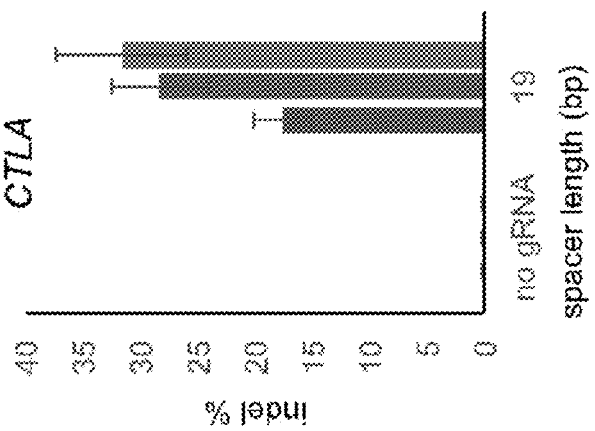
Figure 7C:
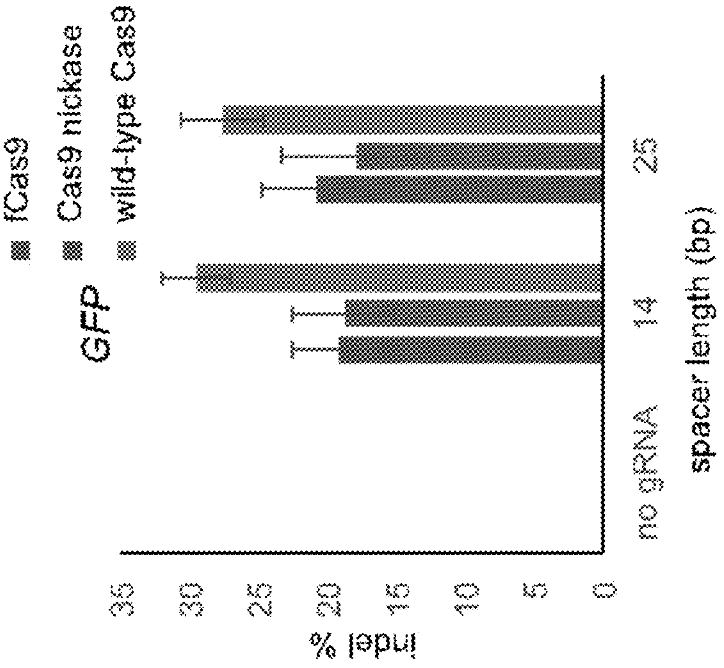
Figure 7F:
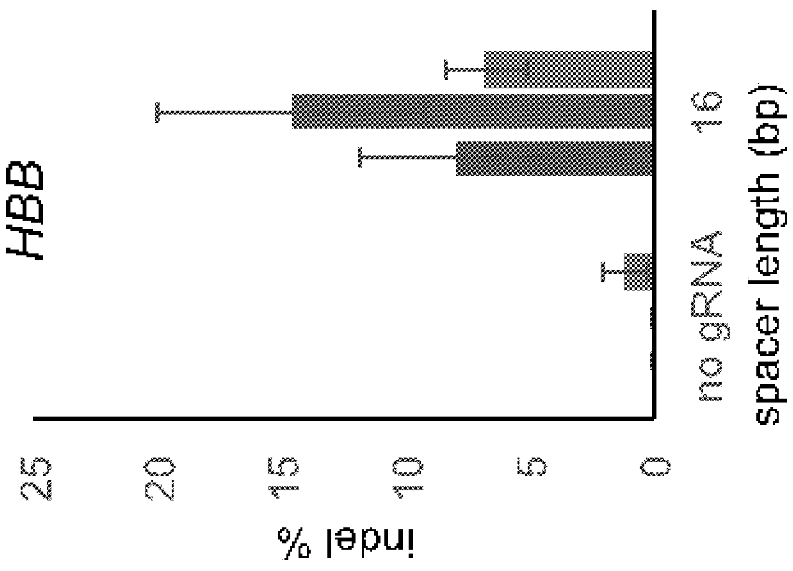
Figure 7G:
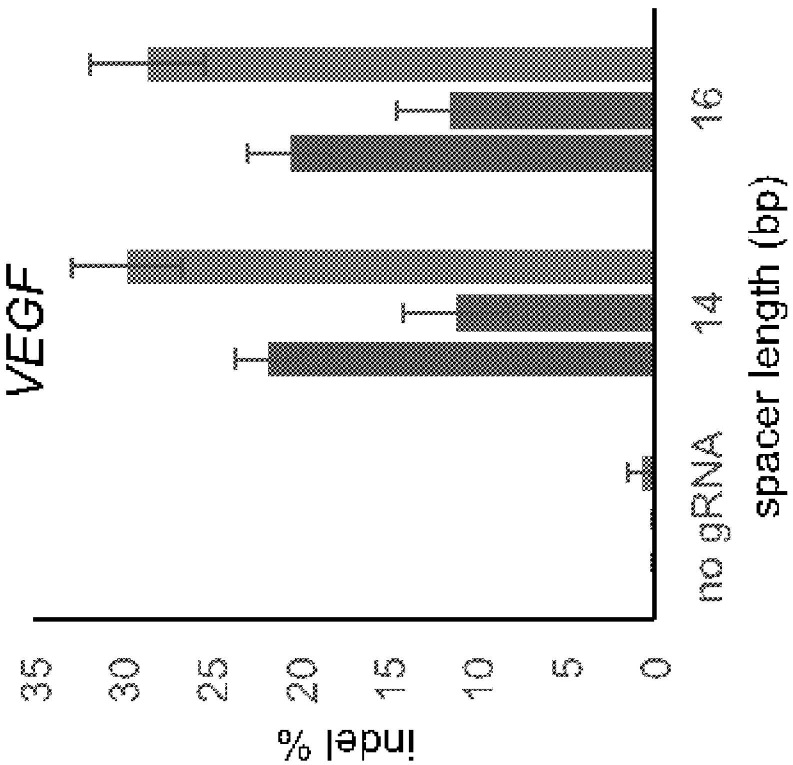
Figure 8C:
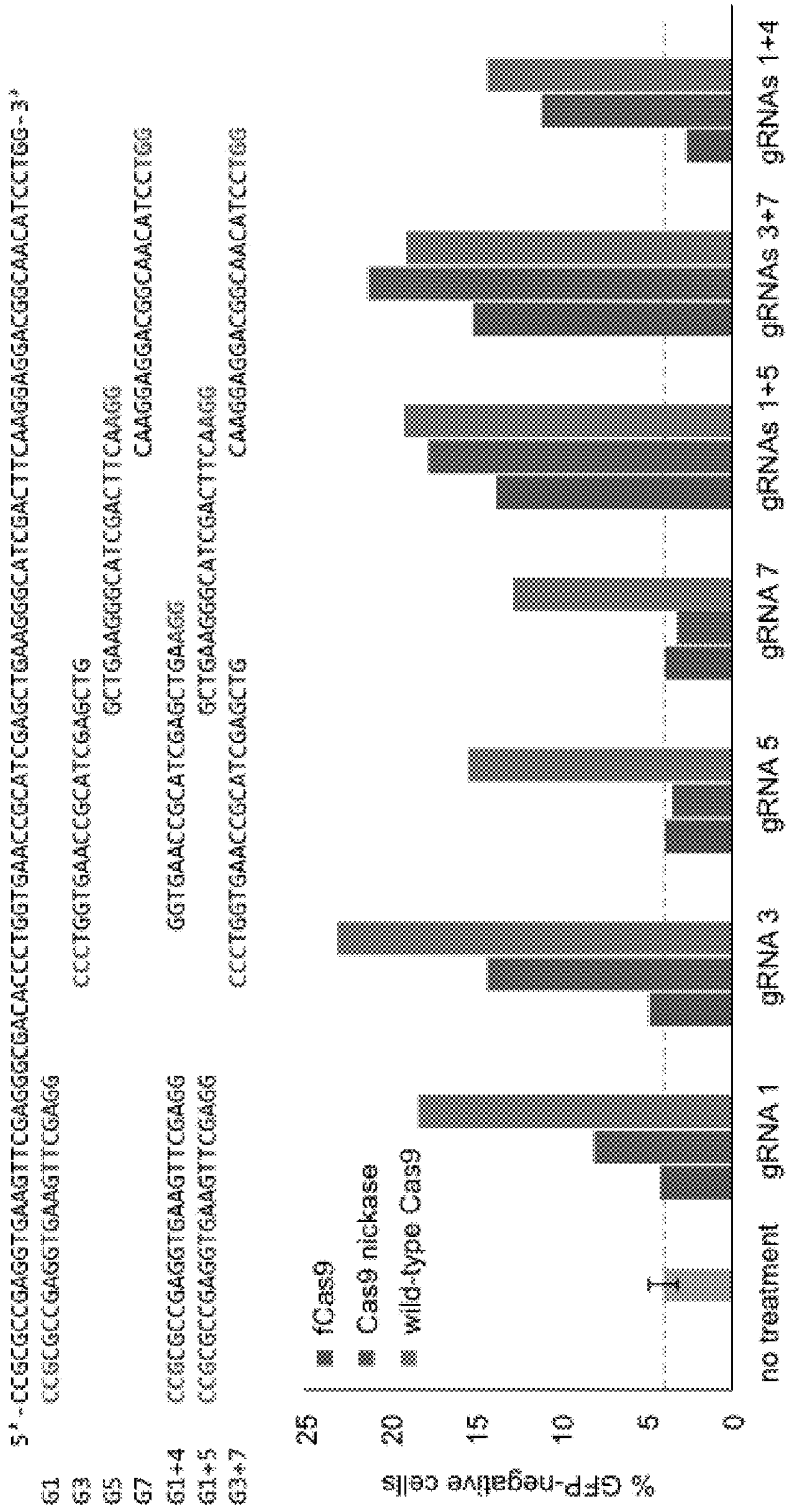
Figure 16A:
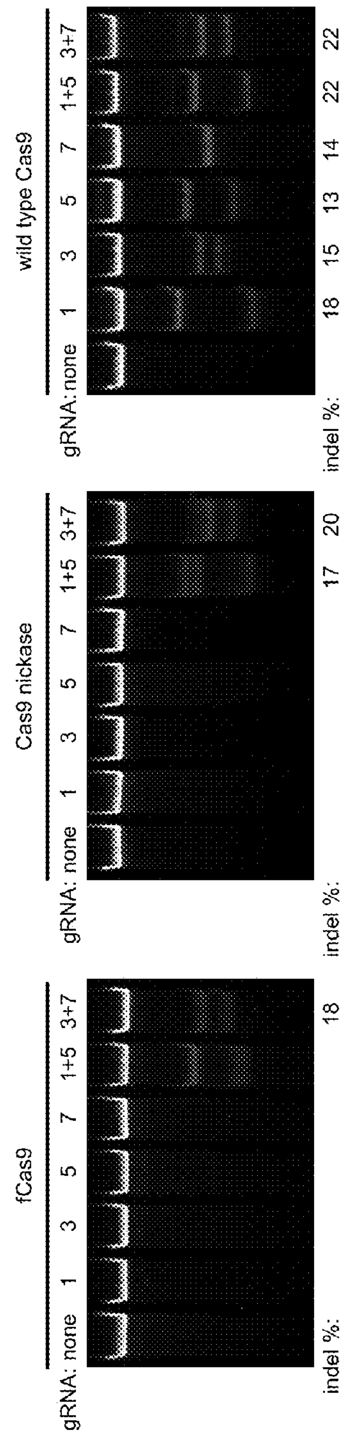
FIG. 16 shows the ability of fCas9, Cas9 nickase, and wild-type Cas9 to modify genomic DNA in the presence of a single gRNA. (A) shows images of gels depicting Surveyor assay of a genomic GFP target from DNA of cells treated with the indicated combination of Cas9 protein and gRNA(s). Single gRNAs do not induce genome modification at a detectable level (<2% modification) for both fCas9 and Cas9 nickase. Wild-type Cas9 effectively modifies the GFP target for all tested single and paired gRNAs. For both fCas9 and Cas9 nickase, appropriately paired gRNAs induce genome modification at levels comparable to those of wild-type Cas9. (B) shows a graph depicting the results from sequencing GFP on-target sites amplified from 150 ng genomic DNA isolated from human cells treated with a plasmid expressing either wild-type Cas9, Cas9 nickase, or fCas9 and either a single plasmid expressing a single gRNAs (G1, G3, G5 or G7), or two plasmids each expressing a different gRNA (G1+G5, or G3+G7). As a negative control, transfection and sequencing were performed in triplicate as above without any gRNA expression plasmids. Error bars represent s.d. Sequences with more than one insertion or deletion at the GFP target site (the start of the G1 binding site to the end of the G7 binding site) were considered indels. Indel percentages were calculated by dividing the number of indels by total number of sequences. While wild-type Cas9 produced indels across all gRNA treatments, fCas9 and Cas9 nickase produced indels efficiently (>1%) only when paired gRNAs were present. Indels induced by fCas9 and single gRNAs were not detected above the no-gRNA control, while Cas9 nickase and single gRNAs modified the target GFP sequence at an average rate of 0.12%.
Figure 16B:
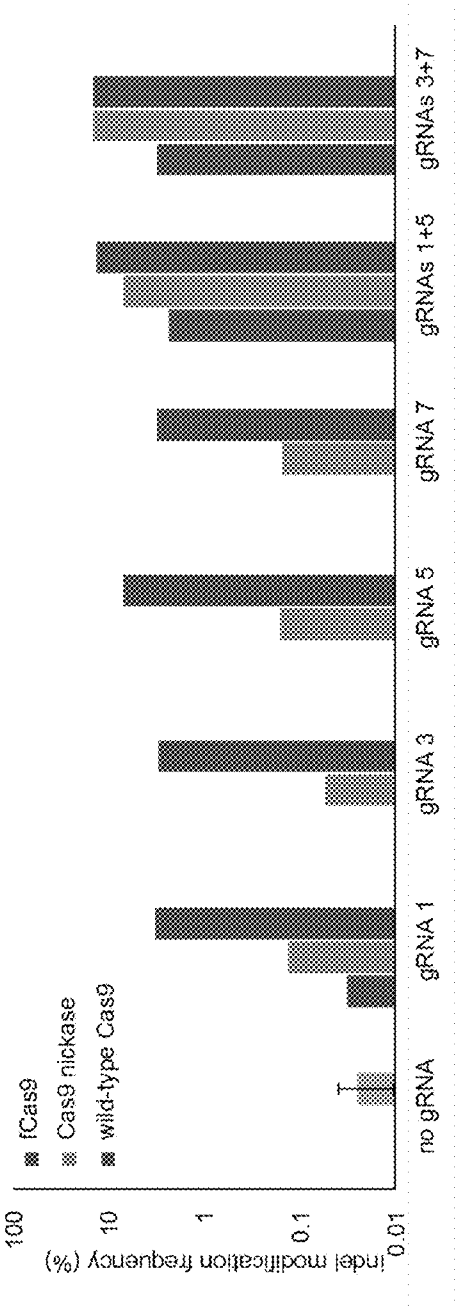
Figure 17:
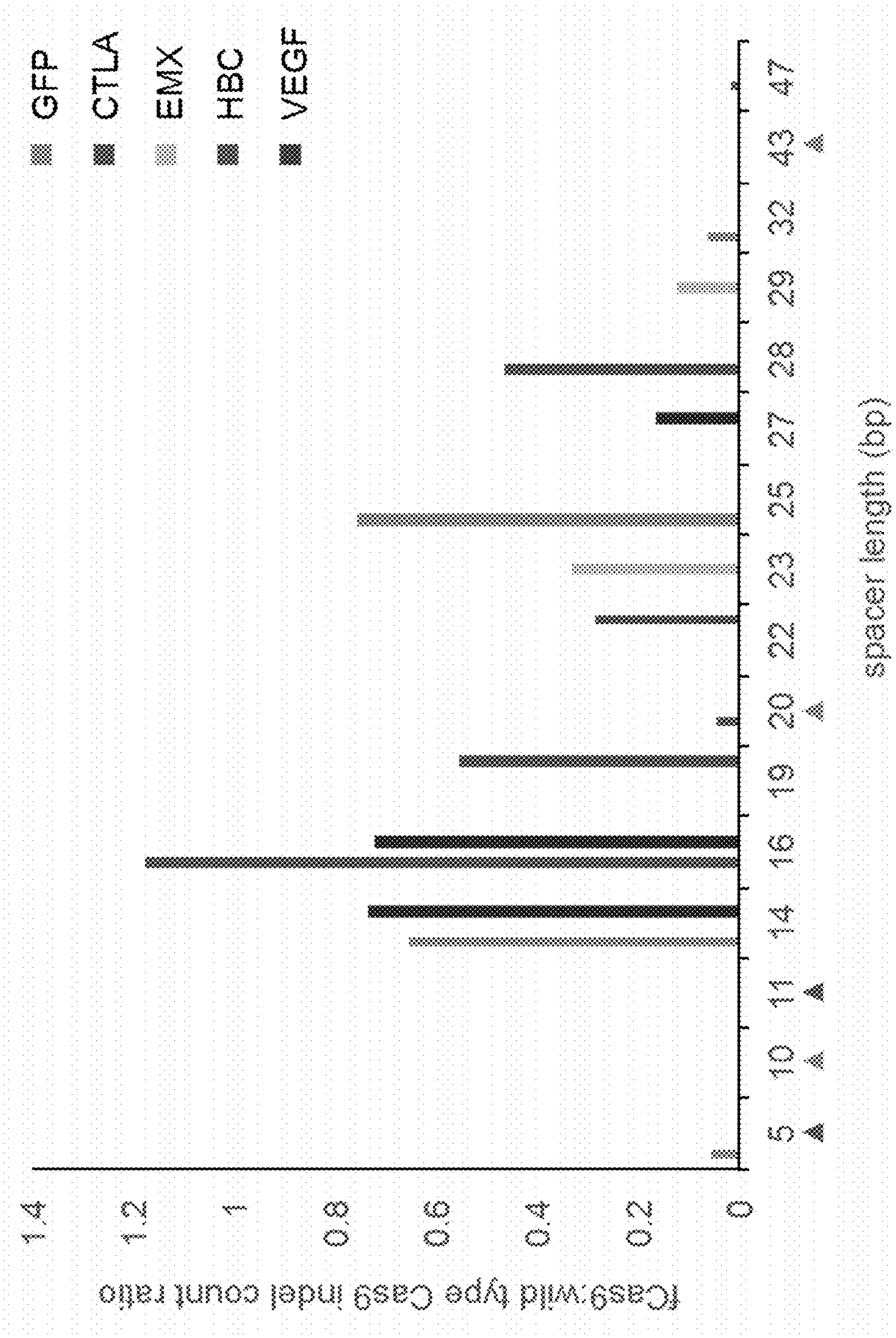
FIG. 17 shows a graph depicting how fCas9 indel frequency of genomic targets reflects gRNA pair spacer length preference. The graph shows the relationship between spacer length (number of by between two gRNAs) and the indel modification efficiency of fCas9 normalized to the indel modification efficiency of the same gRNAs co-expressed with wild-type Cas9 nuclease. Colored triangles below the X-axis denote spacer lengths that were tested but which yielded no detectable indels for the indicated target gene. These results suggest that fCas9 requires ~15 bp or ~25 bp between half-sites to efficiently cleave DNA.

Importantly, no modification was observed by GFP disruption or Surveyor assay when any of four single gRNAs were expressed individually with fCas9, as expected since two simultaneous binding events are required for FokI activity (FIG. 7B and FIG. 8C). In contrast, GFP disruption resulted from expression of any single gRNA with wild-type Cas9 (as expected) and, for two single gRNAs, with Cas9 nickase (FIG. 8C). Surprisingly, Surveyor assay revealed that although GFP was heavily modified by wild-type Cas9 with single gRNAs, neither fCas9 nor Cas9 nickase showed detectable modification (<~2%) in cells treated with single gRNAs (FIG. 16A). High-throughput sequencing to detect indels at the GFP target site in cells treated with a single gRNA and fCas9, Cas9 nickase, or wild-type Cas9 revealed the expected substantial level of modification by wild-type Cas9 (3-7% of sequence reads). Modification by fCas9 in the presence of any of the four single gRNAs was not detected above background (<~0.03% modification), consistent with the requirement of fCas9 to engage two gRNAs in order to cleave DNA. In contrast, Cas9 nickases in the presence of single gRNAs resulted in modification levels ranging from 0.05% to 0.16% at the target site (FIG. 16B). The detection of bona fide indels at target sites following Cas9 nickase treatment with single gRNAs confirms the mutagenic potential of genomic DNA nicking, consistent with previous reports.[5,7,18,19]

The observed rate of nickase-induced DNA modification, however, did not account for the much higher GFP disruption signal in the flow cytometry assay (FIG. 8C). Since the gRNAs that induced GFP signal loss with Cas9 nickase (gRNAs G1 and G3) both target the non-template strand of the GFP gene, and since targeting the non-template strand with dCas9 in the coding region of a gene is known to mediate efficient transcriptional repression,[29] it is speculated that Cas9 nickase combined with the G1 or G3 single guide RNAs induced substantial transcriptional repression, in addition to a low level of genome modification. The same effect was not seen for fCas9, suggesting that fCas9 may be more easily displaced from DNA by transcriptional machinery. Taken together, these results indicate that fCas9 can modify genomic DNA efficiently and in a manner that requires simultaneous engagement of two guide RNAs targeting adjacent sites, unlike the ability of wild-type Cas9 and Cas9 nickase to cleave DNA when bound to a single guide RNA.

The above results collectively reveal much more stringent spacer, gRNA orientation, and guide RNA pairing requirements for fCas9 compared with Cas9 nickase. In contrast with fCas9 (FIG. 17), Cas9 nickase cleaved sites across all spacers assayed (5- to 47-bp in orientation A and 4 to 42 bp in orientation B in this work) (FIG. 8A, B). These observations are consistent with previous reports of Cas9 nickases modifying sites targeted by gRNAs with spacer lengths up to 100 bp apart.[6] The more stringent spacer and gRNA orientation requirements of fCas9 compared with Cas9 nickase reduces the number of potential genomic off-target sites of the former by approximately 10-fold (Table 4). Although the more stringent spacer requirements of fCas9 also reduce the number of potential targetable sites, sequences that conform to the fCas9 spacer and dual PAM requirements exist in the human genome on average once every 34 bp ($9.2\times10^7$ sites in $3.1\times10^9$ bp) (Table 4). It is also anticipated that the growing number of Cas9 homologs with different PAM specificities[30] are amenable for use as described herein, and will further increase the number of targetable sites using the fCas9 approach.

In Table 4 (A) column 2 shows the number of sites in the human genome with paired gRNA binding sites in orientation A allowing for a spacer length from −8 bp to 25 bp (column 1) between the two gRNA binding sites. gRNA binding sites in orientation A have the NGG PAM sequences distal from the spacer sequence ($CCNN_{20}$-spacer-$N_{20}NGG$). Column 3 shows the number of sites in the human genome with paired gRNA binding sites in orientation B allowing for a spacer length from 4 to 25 bp (column 1) between the two gRNA binding sites. gRNA binding sites in orientation B have the NGG PAM sequences adjacent to the spacer sequence ($N_{20}NGG$ spacer $CCNN_{20}$). NC indicates the number of sites in the human genome was not calculated. Negative spacer lengths refer to target gRNA binding sites that overlap by the indicated number of base pairs. Table 4 (B) shows the sum of the number of paired gRNA binding sites in orientation A with spacer lengths of 13 to 19 bp, or 22 to 29 bp, the spacer preference of fCas9 (FIG. 16). Sum of the number of paired gRNA binding sites with spacer lengths of −8 bp to 100 bp in orientation A, or 4 to 42 bp in orientation B, the spacer preference of Cas9 nickases (4 to 42 bp in orientation B is based on FIG. 8B, C, and −8 bp to 100 bp in orientation A is based on previous reports[36,37]).

TABLE 4

Paired gRNA target site abundances for fCas9 and Cas9 nickase in the human genome.

(A)

| Spacer length (b) | Number of paired gRNA sites in orientation A | Number of paired gRNA sites in orientation B |
|---|---|---|
| −8 | 6874293 | NC |
| −7 | 6785996 | NC |
| −6 | 6984064 | NC |
| −5 | 7023260 | NC |
| −4 | 6487302 | NC |
| −3 | 6401348 | NC |
| −2 | 6981383 | NC |
| −1 | 7230098 | NC |
| 0 | 7055143 | NC |
| 1 | 6598582 | NC |
| 2 | 6877046 | NC |
| 3 | 6971447 | NC |
| 4 | 6505614 | 5542549 |
| 5 | 6098107 | 5663458 |
| 6 | 6254974 | 6819289 |
| 7 | 6680118 | 6061225 |
| 8 | 7687598 | 5702252 |
| 9 | 6755736 | 7306646 |
| 10 | 6544849 | 6387485 |
| 11 | 6918186 | 6172852 |
| 12 | 6241723 | 5799496 |
| 13 | 6233385 | 7092283 |
| 14 | 6298717 | 7882433 |
| 15 | 6181422 | 7472725 |
| 16 | 6266909 | 6294684 |
| 17 | 6647352 | 6825904 |
| 18 | 6103603 | 6973590 |
| 19 | 5896092 | 6349456 |
| 20 | 6000683 | 5835825 |
| 21 | 5858015 | 6056352 |
| 22 | 6116108 | 6531913 |
| 23 | 5991254 | 6941816 |
| 24 | 6114969 | 6572849 |
| 25 | 6135119 | 5671641 |

(B)

| Cas9 variant | Preferred spacer lengths (bp) | Total sites |
|---|---|---|
| fCas9 | 13 to 19, or 22 to 29, in orientation A | 92354891 |
| Cas9 nickase | −8 to 100 in orientation A<br>4 to 42 in orientation B | 953048977 |

To evaluate the DNA cleavage specificity of fCas9, the modification of known Cas9 off-target sites of CLTA, EMX, and VEGF genomic target sites were measured.[1,2,6,8] The target site and its corresponding known off-target sites (Table 5) were amplified from genomic DNA isolated from HEK293 cells treated with fCas9, Cas9 nickase, or wild-type Cas9 and two gRNAs spaced 19 bp apart targeting the CLTA site, two gRNAs spaced 23 bp apart targeting the EMX site, two gRNAs spaced 14 bp apart targeting the VEGF site, or two gRNAs targeting an unrelated site (GFP) as a negative control. In total 11 off-target sites were analyzed by high-throughput sequencing.

The sensitivity of the high-throughput sequencing method for detecting genomic off-target cleavage is limited by the amount genomic DNA (gDNA) input into the PCR amplification of each genomic target site. A 1 ng sample of human gDNA represents only ~330 unique genomes, and thus only ~330 unique copies of each genomic site are present. PCR amplification for each genomic target was performed on a total of 150 ng of input gDNA, which provides amplicons derived from at most 50,000 unique gDNA copies. Therefore, the high-throughput sequencing assay cannot detect rare genome modification events that occur at a frequency of less than 1 in 50,000, or 0.002%.

TABLE 5

Known off-target substrates of Cas9 target sites in EMX, VEGF, and CLTA. List of genomic on-target and off-targets sites of the EMX, VEGF, and CLTA are shown with mutations from on-target in lower case and bold. PAMs are shown in upper case bold.

| | Genomic target site |
|---|---|
| EMX_On | GAGTCCGAGCAGAAGAAGAA**GGG** (SEQ ID NO: 190) |
| EMX_Off1 | GAG**g**CCGAGCAGAAGAA**ag**A**CGG** (SEQ ID NO: 191) |
| EMX_Off2 | GAGTCC**t**AGCAG**g**AGAAGAA**GaG** (SEQ ID NO: 192) |
| EMX_Off3 | GAGTC**ta**AGCAGAAGAAGAA**GaG** (SEQ ID NO: 193) |
| EMX_Off4 | GAGT**ta**GAGCAGAAGAAGAA**AGG** (SEQ ID NO: 194) |

TABLE 5-continued

Known off-target substrates of Cas9 target sites in EMX, VEGF, and CLTA. List of genomic on-target and off-targets sites of the EMX, VEGF, and CLTA are shown with mutations from on-target in lower case and bold. PAMs are shown in upper case bold.

| | Genomic target site |
|---|---|
| VEG_On | GGGTGGGGGGAGTTTGCTCC**TGG** (SEQ ID NO: 195) |
| VEG_Off1 | GG**a**TGG**a**GGGAGTTTGCTCC**TGG** (SEQ ID NO: 196) |
| VEG_Off2 | GGG**a**GGG**t**GGAGTTTGCTCC**TGG** (SEQ ID NO: 197) |
| VEG_Off3 | **c**GG**g**GG**a**GGGAGTTTGCTCC**TGG** (SEQ ID NO: 198) |
| VEG_Off4 | GGG**ga**GGGG**a**AGTTTGCTCC**TGG** (SEQ ID NO: 199) |
| CLT2_On | GCAGATGTAGTGTTTCCACA**GGG** (SEQ ID NO: 200) |
| CLT2_Off1 | **a**CA**a**ATGTAGT**a**TTTCCACA**GGG** (SEQ ID NO: 201) |
| CLT2_Off2 | **c**CAGATGTAGT**a**TT**c**CCACA**GGG** (SEQ ID NO: 202) |
| CLT2_Off3 | **ct**AGATG**a**AGTG**c**TTCCACA**TGG** (SEQ ID NO: 203) |

Figure 8D:
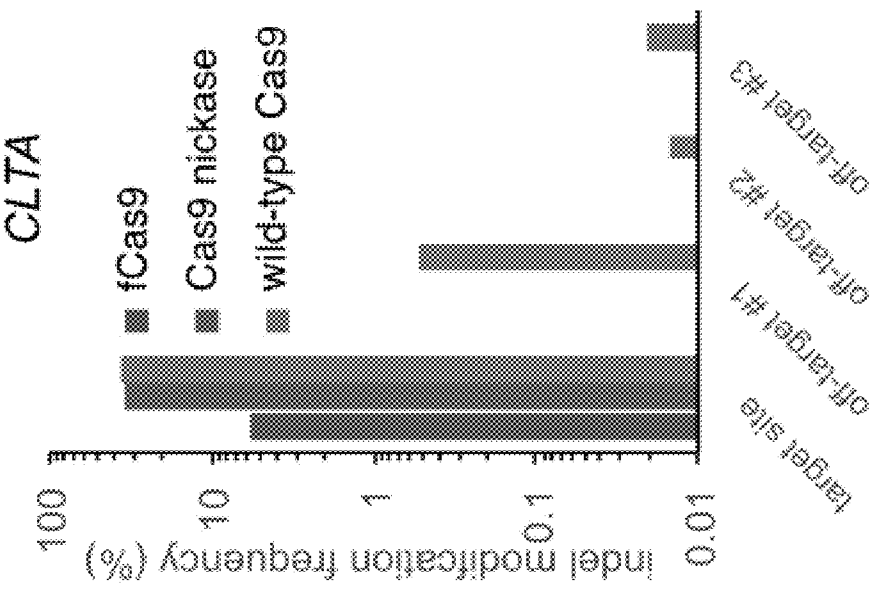
Figure 8E:
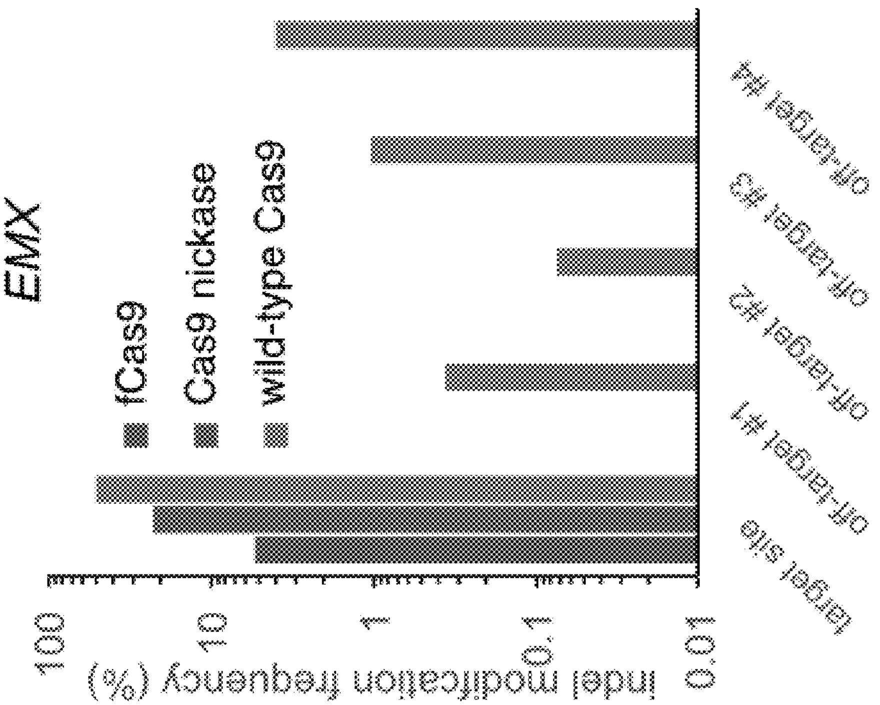
Figure 8G:
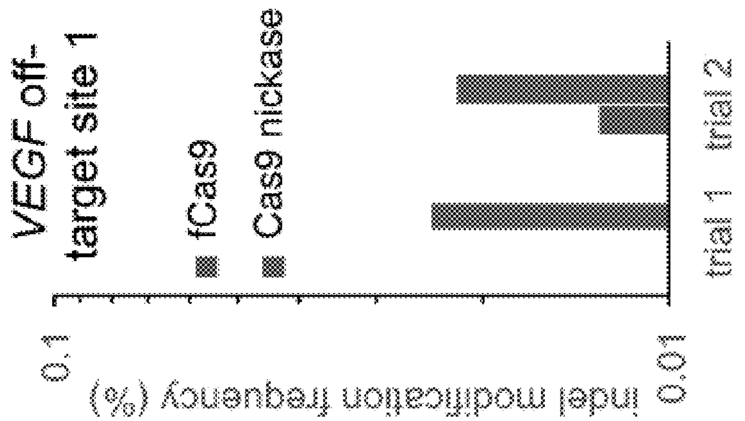
Figure 8F:
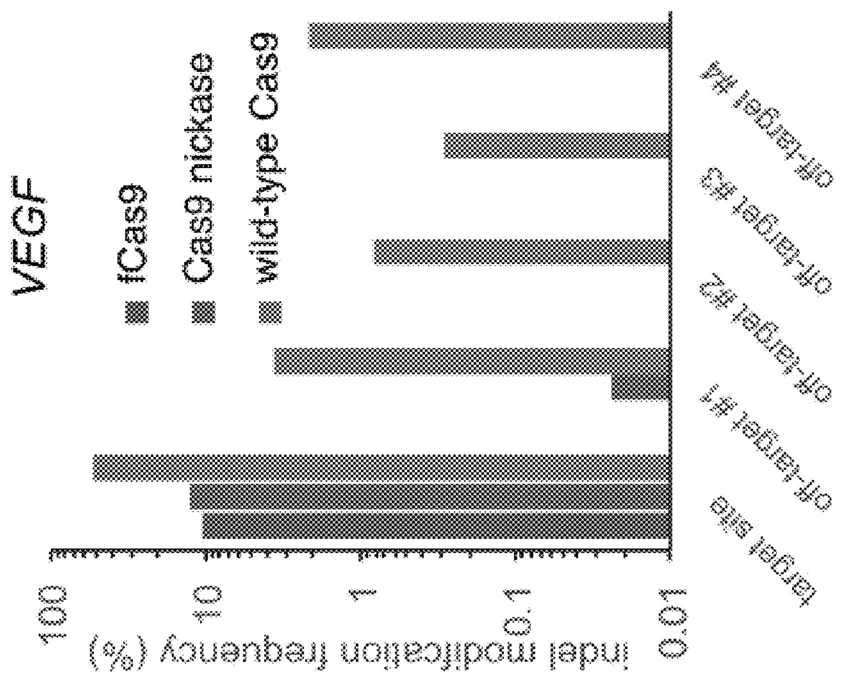

Sequences containing insertions or deletions of two or more base pairs in potential genomic off-target sites and present in significantly greater numbers (P value<0.005, Fisher's exact test) in the target gRNA-treated samples versus the control gRNA-treated samples were considered Cas9 nuclease-induced genome modifications. For 10 of the 11 off-target sites assayed, fCas9 did not result in any detectable genomic off-target modification within the sensitivity limit of the assay (<0.002%,), while demonstrating substantial on-target modification efficiencies of 5% to 10% (FIG. 8D-F and Table 3). The detailed inspection of fCas9-modified VEGF on-target sequences (FIG. 18A) revealed a prevalence of deletions ranging from two to dozens of base pairs consistent with cleavage occurring in the DNA spacer between the two target binding sites, similar to the effects of FokI nuclease domains fused to zinc finger or TALE DNA-binding domains.[31]

In contrast, genomic off-target DNA cleavage was observed for wild-type Cas9 at all 11 sites assayed. Using the detection limit of the assay as an upper bound for off-target fCas9 activity, it was calculated that fCas9 has a much lower off-target modification rate than wild-type Cas9 nuclease. At the 11 off-target sites modified by wild-type Cas9 nuclease, fCas9 resulted in on-target:off-target modification ratios at least 140-fold higher than that of wild-type Cas9 (FIG. 8D-F).

Consistent with previous reports,[5,6,8] Cas9 nickase also induced substantially fewer off-target modification events (1/11 off-target sites modified at a detectable rate) compared to wild-type Cas9. An initial high-throughput sequencing assay revealed significant (P value<$10^{-3}$, Fisher's Exact Test) modification induced by Cas9 nickases in 0.024% of sequences at VEGF off-target site 1. This genomic off-target site was not modified by fCas9 despite similar VEGF on-target modification efficiencies of 12.3% for Cas9 nickase and 10.4% for fCas9 (FIG. 8F and Table 3C). Because Cas9 nickase-induced modification levels were within an order of magnitude of the limit of detection and fCas9 modification levels were undetected, the experiment was repeated with a larger input DNA samples and a greater number of sequence reads (150 versus 600 ng genomic DNA and >$8\times10^5$ versus >$23\times10^5$ reads for the initial and repeated experiments, respectively) to detect off-target cleavage at this site by Cas9 nickase or fCas9. From this deeper interrogation, it was observed that Cas9 nickase and fCas9 both significantly modify (P value<$10^{-5}$, Fisher's Exact Test) VEGF off-target site 1 (FIG. 8G, Table 3D, FIG. 18B). For both experiments interrogating the modification rates at VEGF off-target site 1, fCas9 exhibited a greater on-target:off-target DNA modification ratio than that of Cas9 nickase (>5,150 and 1,650 for fCas9, versus 510 and 1,230 for Cas9 nickase, FIG. 8G).

Figure 18C:
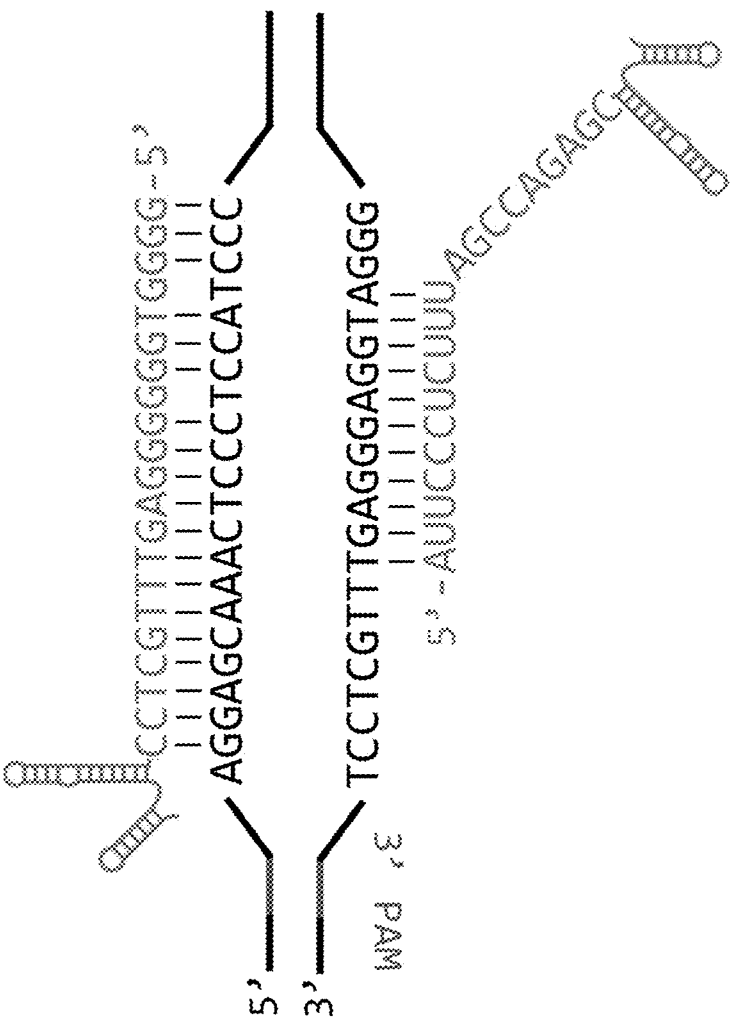
FIG. 18 shows modifications induced by Cas9 nuclease, Cas9 nickases, or fCas9 nucleases at endogenous loci. (A) shows examples of modified sequences at the VEGF on-target site with wild-type Cas9 nuclease, Cas9 nickases, or fCas9 nucleases and a single plasmid expressing two gRNAs targeting the VEGF on-target site (gRNA V1 and gRNA V2). For each example shown, the unmodified genomic site is the first sequence, followed by the top eight sequences containing deletions. The numbers before each sequence indicate sequencing counts. The gRNA target sites are bold and capitalized. (B) is an identical analysis as in (A) for VEGF off-target site 1VEG_Off1. (C) shows the potential binding mode of two gRNAs to VEGF off-target site 1. The top strand is bound in a canonical mode, while the bottom strand binds the second gRNA, gRNA V2, through gRNA:DNA base pairing that includes G:U base pairs. The sequences shown in (A) are identified, top to bottom, as follows: SEQ ID NO:243; SEQ ID NO:244; SEQ ID NO:245; SEQ ID NO:246; SEQ ID NO:247; SEQ ID NO:248; SEQ ID NO:249; SEQ ID NO:250; SEQ ID NO:251; SEQ ID NO:252; SEQ ID NO:253; SEQ ID NO:254; SEQ ID NO:255; SEQ ID NO:256; SEQ ID NO:257; SEQ ID NO:258; SEQ ID NO:259; SEQ ID NO:260; SEQ ID NO:261; SEQ ID NO:262; SEQ ID NO:263; SEQ ID NO:264; SEQ ID NO:265; SEQ ID NO:266; SEQ ID NO:267; SEQ ID NO:268; and SEQ ID NO:269. The sequences shown in (B) are identified, top to bottom, as follows: SEQ ID NO:270; SEQ ID NO:271; SEQ ID NO:272; SEQ ID NO:273; SEQ ID NO:274; SEQ ID NO:275; SEQ ID NO:276; SEQ ID NO:277; SEQ ID NO:278; SEQ ID NO:279; SEQ ID NO:280; SEQ ID NO:281; SEQ ID NO:282; SEQ ID NO:283; SEQ ID NO:284; SEQ ID NO:285; SEQ ID NO:286; SEQ ID NO:287; SEQ ID NO:288; SEQ ID NO:289; SEQ ID NO:290; SEQ ID NO:291; SEQ ID NO:292; SEQ ID NO:293; SEQ ID NO:294; SEQ ID NO:295; and SEQ ID NO:296. The sequences shown in (C) are identified, top to bottom, as follows: SEQ ID NO:297; SEQ ID NO:298; SEQ ID NO:299; and SEQ ID NO:300.

On either side of VEGF off-target site 1 there exist no other sites with six or fewer mutations from either of the two half-sites of the VEGF on-target sequence. The first 11 bases of one gRNA (V2) might hybridize to the single-stranded DNA freed by canonical Cas9:gRNA binding within VEGF off-target site 1 (FIG. 18C). Through this gRNA:DNA hybridization it is possible that a second Cas9 nickase or fCas9 could be recruited to modify this off-target site at a very low, but detectable level. Judicious gRNA pair design could eliminate this potential mode of off-target DNA cleavage, as VEGF off-target site 1 is highly unusual in its ability to form 11 consecutive potential base pairs with the second gRNA of a pair. In general, fCas9 was unable to modify the genomic off-target sites tested because of the absence of any adjacent second binding site required to dimerize and activate the FokI nuclease domain.

The optimized FokI-dCas9 fusion architecture developed in this work modified all five genomic loci targeted, demonstrating the generality of using fCas9 to induce genomic modification in human cells, although modification with fCas9 was somewhat less efficient than with wild-type Cas9. The use of fCas9 is straightforward, requiring only that PAM sequences be present with an appropriate spacing and orientation, and using the same gRNAs as wild-type Cas9 or Cas9 nickases. The observed low off-target:on-target modification ratios of fCas9, >140-fold lower than that of wild-type Cas9, likely arises from the distinct mode of action of dimeric FokI, in which DNA cleavage proceeds only if two DNA sites are occupied simultaneously by two FokI domains at a specified distance (here, ~15 bp or ~25 bp apart) and in a specific half-site orientation. The resulting unusually low off-target activity of fCas9 enable applications of Cas9:gRNA-based technologies that require a very high degree of target specificity, such as ex vivo or in vivo therapeutic modification of human cells.

REFERENCES

1. Pattanayak, V. et al. High-throughput profiling of off-target DNA cleavage reveals RNA-programmed Cas9 nuclease specificity. *Nat. Biotechnol.* 31, 839-843 (2013).
2. Fu, Y. et al. High-frequency off-target mutagenesis induced by CRISPR-Cas nucleases in human cells. *Nat. Biotechnol.* 31, 822-826 (2013).
3. Hsu, P. D. et al. DNA targeting specificity of RNA-guided Cas9 nucleases. *Nat. Biotechnol.* 31, 827-832 (2013).
4. Cradick, T. J., Fine, E. J., Antico, C. J. & Bao, G. CRISPR/Cas9 systems targeting-globin and CCR5 genes have substantial off-target activity. *Nucleic Acids Res.* 41, 9584-9592 (2013).
5. Cho, S. W. et al. Analysis of off-target effects of CRISPR/Cas-derived RNA-guided endonucleases and nickases. *Genome Res.* 24, 132-141 (2013).
6. Ran, F. A. et al. Double Nicking by RNA-Guided CRISPR Cas9 for Enhanced Genome Editing Specificity. *Cell* 154, 1380-1389 (2013).

7. Mali, P. et al. CAS9 transcriptional activators for target specificity screening and paired nickases for cooperative genome engineering. *Nat. Biotechnol.* 31, 833-838 (2013).
8. Fu, Y., Sander, J. D., Reyon, D., Cascio, V. M. & Joung, J. K. Improving CRISPR-Cas nuclease specificity using truncated guide RNAs. *Nat. Biotechnol.* (2014). doi: 10.1038/nbt.2808
9. Cong, L. et al. Multiplex Genome Engineering Using CRISPR/Cas Systems. *Science* 339, 819-823 (2013).
10. Jinek, M. et al. A Programmable Dual-RNA-Guided DNA Endonuclease in Adaptive Bacterial Immunity. *Science* 337, 816-821 (2012).
11. Gasiunas, G., Barrangou, R., Horvath, P. & Siksnys, V. Cas9-crRNA ribonucleoprotein complex mediates specific DNA cleavage for adaptive immunity in bacteria. *Proc. Natl. Acad. Sci.* 109, E2579-E2586 (2012).
12. Wang, T., Wei, J. J., Sabatini, D. M. & Lander, E. S. Genetic screens in human cells using the CRISPR-Cas9 system. *Science* 343, 80-84 (2014).
13. Shalem, O. et al. Genome-Scale CRISPR-Cas9 Knockout Screening in Human Cells. *Science* 343, 84-87 (2013).
14. Perez, E. E. et al. Establishment of HIV-1 resistance in CD4+ T cells by genome editing using zinc-finger nucleases. *Nat. Biotechnol.* 26, 808-816 (2008).
15. Jinek, M. et al. RNA-programmed genome editing in human cells. *eLife* 2, e00471-e00471 (2013).
16. Mali, P. et al. RNA-Guided Human Genome Engineering via Cas9. *Science* 339, 823-826 (2013).
17. Mali, P., Esvelt, K. M. & Church, G. M. Cas9 as a versatile tool for engineering biology. *Nat. Methods* 10, 957-963 (2013).
18. Ramirez, C. L. et al. Engineered zinc finger nickases induce homology-directed repair with reduced mutagenic effects. *Nucleic Acids Res.* 40, 5560-5568 (2012).
19. Wang, J. et al. Targeted gene addition to a predetermined site in the human genome using a ZFN-based nicking enzyme. *Genome Res.* 22, 1316-1326 (2012).
20. Gaj, T., Gersbach, C. A. & Barbas, C. F. ZFN, TALEN, and CRISPR/Cas-based methods for genome engineering. *Trends Biotechnol.* 31, 397-405 (2013).
21. Vanamee, É. S., Santagata, S. & Aggarwal, A. K. FokI requires two specific DNA sites for cleavage. *J. Mol. Biol.* 309, 69-78 (2001).
22. Maeder, M. L. et al. CRISPR RNA-guided activation of endogenous human genes. *Nat. Methods* 10, 977-979 (2013).
23. Pattanayak, V., Ramirez, C. L., Joung, J. K. & Liu, D. R. Revealing off-target cleavage specificities of zinc-finger nucleases by in vitro selection. *Nat. Methods* 8, 765-770 (2011).
24. Guilinger, J. P. et al. Broad specificity profiling of TALENs results in engineered nucleases with improved DNA-cleavage specificity. *Nat. Methods* (2014). doi:10.1038/nmeth.2845
25. Nishimasu, H. et al. Crystal Structure of Cas9 in Complex with Guide RNA and Target DNA. *Cell* (2014). doi: 10.1016/j.cell.2014.02.001
26. Jinek, M. et al. Structures of Cas9 Endonucleases Reveal RNA-Mediated Conformational Activation. *Science* (2014). doi:10.1126/science.1247997
27. Schellenberger, V. et al. A recombinant polypeptide extends the in vivo half-life of peptides and proteins in a tunable manner. *Nat. Biotechnol.* 27, 1186-1190 (2009).
28. Guschin, D. Y. et al. in *Eng. Zinc Finger Proteins* (Mackay, J. P. & Segal, D. J.) 649, 247-256 (Humana Press, 2010).
29. Qi, L. S. et al. Repurposing CRISPR as an RNA-guided platform for sequence-specific control of gene expression. *Cell* 152, 1173-1183 (2013).
30. Esvelt, K. M. et al. Orthogonal Cas9 proteins for RNA-guided gene regulation and editing. *Nat. Methods* 10, 1116-1121 (2013).
31. Kim, Y., Kweon, J. & Kim, J.-S. TALENs and ZFNs are associated with different mutation signatures. *Nat. Methods* 10, 185-185 (2013).
32. Shcherbakova, D. M. & Verkhusha, V. V. Near-infrared fluorescent proteins for multicolor in vivo imaging. *Nat. Methods* 10, 751-754 (2013).
33. Schneider, C. A., Rasband, W. S. & Eliceiri, K. W. NIH Image to ImageJ: 25 years of image analysis. *Nat. Methods* 9, 671-675 (2012).
34. Sander, J. D. et al. In silico abstraction of zinc finger nuclease cleavage profiles reveals an expanded landscape of off-target sites. *Nucleic Acids Res.* 41, e181-e181 (2013).
35. Schellenberger, V. et al. A recombinant polypeptide extends the in vivo half-life of peptides and proteins in a tunable manner. *Nat. Biotechnol.* 27, 1186-1190 (2009).
36. Mali, P. et al. CAS9 transcriptional activators for target specificity screening and paired nickases for cooperative genome engineering. *Nat. Biotechnol.* 31, 833-838 (2013).
37. Ran, F. A. et al. Double Nicking by RNA-Guided CRISPR Cas9 for Enhanced Genome Editing Specificity. *Cell* 154, 1380-1389 (2013).
38. Yan, T. et al. PatMatch: a program for finding patterns in peptide and nucleotide sequences. *Nucleic Acids Res.* 33, W262-W266 (2005).
39. Larkin, M. A. et al. Clustal W and Clustal X version 2.0. *Bioinformatics* 23, 2947-2948 (2007).

Example 2

Targeting CCR5 for Cas9 Variant-Mediated Inactivation

In addition to providing powerful research tools, site-specific nucleases also have potential as gene therapy agents, and site-specific zinc finger endonucleases have recently entered clinical trials: CCR5-2246, targeting a human CCR-5 allele as part of an anti-HIV therapeutic approach.

In a similar approach, the inventive Cas9 variants of the present disclosure may be used to inactivate CCR5, for example in autologous T cells obtained from a subject which, once modified by a Cas9 variant, are re-introduced into the subject for the treatment or prevention of HIV infection.

In this example, the CCR5 gene is targeted in T cells obtained from a subject. CCR5 protein is required for certain common types of HIV to bind to and enter T cells, thereby infecting them. T cells are one of the white blood cells used by the body to fight HIV.

Some people are born lacking CCR5 expression on their T cells and remain healthy and are resistant to infection with HIV. Others have low expression of CCR5 on their T cells, and their HIV disease is less severe and is slower to cause disease (AIDS).

In order to delete the CCR5 protein on the T cells, large numbers of T-cells are isolated from a subject. Cas9 variants (e.g., fCas9) and gRNA capable of inactivating CCR5 are then delivered to the isolated T cells using a viral vector, e.g., an adenoviral vector. Examples of suitable Cas9 variants include those inventive fusion proteins provided herein. Examples of suitable target sequences for gRNAs targeting the CCR5 allele include those described in FIG. 19, e.g., SEQ ID NOs:303-310 and 312-317. The viral vector(s) capable of expressing the Cas9 variant and gRNA is/are added to the isolated T cells to knock out the CCR5 protein. When the T cells are returned to subject, there is minimal adenovirus or Cas9 variant protein present. The removal of the CCR5 protein on the T cells subjects receive, however, is permanent.

The cells are then reintroduced to the subject for the treatment or prevention of HIV/AIDS.

Example 3

Cas9-Recombinase Fusion Proteins

Exemplary Cas9-Recombinase Fusion Proteins are Provided Below:

dCas9-NLS-GGS3linker-Tn3

(SEQ ID NO: 328)

MDKKYSIGLAIGTNSVGWAVITDEYKVPSKKFKVLGNTDRHSIKKNLIGA
LLFDSGETAEATRLKRTARRRYTRRKNRICYLQEIFSNEMAKVDDSFFHR
LEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENP
INASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQ
LKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVKV
MGRHKPENIVIEMARENQTTQKGQKNSRERMKRIEEGIKELGSQILKEHP
VENTQLQNEKLYLYYLQNGRDMYVDQELDINRLSDYDVDAIVPQSFLKDD
SIDNKVLTRSDKNRGKSDNVPSEEVVKKMKNYWRQLLNAKLITQRKFDNL
TKAERGGLSELDKAGFIKRQLVETRQITKHVAQILDSRMNTKYDENDKLI
REVKVITLKSKLVSDFRKDFQFYKVREINNYHHAHDAYLNAVVGTALIKK
YPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEV
QTGGFSKESILPKRNSDKLIARKKDWDPKKYGGFDSPTVAYSVLVVAKVE
KGKSKKLKSVKELLGITIMERSSFEKNPIDFLEAKGYKEVKKDLIIKLPK
YSLFELENGRKRMLASAGELQKGNELALPSKYVNFLYLASHYEKLKGSPE
DNEQKQLFVEQHKHYLDEIIEQISEFSKRVILADANLDKVLSAYNKHRDK
PIREQAENIIHLFTLTNLGAPAAFKYFDTTIDRKRYTSTKEVLDATLIHQ
SITGLYETRIDLSQLGGDMAPKKKRKVGIHRGVPGGSGGSGGSMALFGYA
RVSTSQQSLDLQVRALKDAGVKANRIFTDKASGSSTDREGLDLLRMKVKE
GDVILVKKLDRLGRDTADMLQLIKEFDAQGVAVRFIDDGISTDSYIGLMF
VTILSAVAQAERRRILERTNEGRQAAKLKGIKFGRRR (underline: nuclear localization signal; bold: linker sequence)

NLS-dCas9-GGS3linker-Tn3

(SEQ ID NO: 329)

MAPKKKRKVGIHRGVPMDKKYSIGLAIGTNSVGWAVITDEYKVPSKKFKV
LGNTDRHSIKKNLIGALLFDSGETAEATRLKRTARRRYTRRKNRICYLQE

-continued

IFSNEMAKVDDSFFHRLEESFLVEEDKKHERHPIFGNIVDEVAYHEKYPT
IYHLRKKLVDSTDKADLRLIYLALAHMIKFRGHFLIEGDLNPDNSDVDKL
FIQLVQTYNQLFEENPINASGVDAKAILSARLSKSRRLENLIAQLPGEKK
NGLFGNLIALSLGLTPNFKSNFDLAEDAKLQLSKDTYDDDLDNLLAQIGD
QYADLFLAAKNLSDAILLSDILRVNTEITKAPLSASMIKRYDEHHQDLTL
LKALVRQQLPEKYKEIFFDQSKNGYAGYIDGGASQEEFYKFIKPILEKMD
GTEELLVKLNREDLLRKQRTFDNGSIPHQIHLGELHAILRRQEDFYPFLK
DNREKIEKILTFRIPYYVGPLARGNSRFAWMTRKSEETITPWNFEEVVDK
GASAQSFIERMTNFDKNLPNEKVLPKHSLLYEYFTVYNELTKVKYVTEGM
RKPAFLSGEQKKAIVDLLFKTNRKVTVKQLKEDYFKKIECFDSVEISGVE
DRFNASLGTYHDLLKIIKDKDFLDNEENEDILEDIVLTLTLFEDREMIEE
RLKTYAHLFDDKVMKQLKRRRYTGWGRLSRKLINGIRDKQSGKTILDFLK
SDGFANRNFMQLIHDDSLTFKEDIQKAQVSGQGDSLHEHIANLAGSPAIK
KGILQTVKVVDELVKVMGRHKPENIVIEMARENQTTQKGQKNSRERMKRI
EEGIKELGSQILKEHPVENTQLQNEKLYLYYLQNGRDMYVDQELDINRLS
DYDVDAIVPQSFLKDDSIDNKVLTRSDKNRGKSDNVPSEEVVKKMKNYWR
QLLNAKLITQRKFDNLTKAERGGLSELDKAGFIKRQLVETRQITKHVAQI
LDSRMNTKYDENDKLIREVKVITLKSKLVSDFRKDFQFYKVREINNYHHA
HDAYLNAVVGTALIKKYPKLESEFVYGDYKVYDVRKMIAKSEQEIGKATA
KYFFYSNIMNFFKTEITLANGEIRKRPLIETNGETGEIVWDKGRDFATVR
KVLSMPQVNIVKKTEVQTGGFSKESILPKRNSDKLIARKKDWDPKKYGGF
DSPTVAYSVLVVAKVEKGKSKKLKSVKELLGITIMERSSFEKNPIDFLEA
KGYKEVKKDLIIKLPKYSLFELENGRKRMLASAGELQKGNELALPSKYVN
FLYLASHYEKLKGSPEDNEQKQLFVEQHKHYLDEIIEQISEFSKRVILAD
ANLDKVLSAYNKHRDKPIREQAENIIHLFTLTNLGAPAAFKYFDTTIDRK
RYTSTKEVLDATLIHQSITGLYETRIDLSQLGGDGGSGGSGGSMALFGYA
RVSTSQQSLDLQVRALKDAGVKANRIFTDKASGSSTDREGLDLLRMKVKE
GDVILVKKLDRLGRDTADMLQLIKEFDAQGVAVRFIDDGISTDSYIGLMF
VTILSAVAQAERRRILERTNEGRQAAKLKGIKFGRRR (underline: nuclear localization signal; bold: linker sequence)

Tn3-GGS3linker-dCas9-NLS (SEQ ID NO: 330)

MALFGYARVSTSQQSLDLQVRALKDAGVKANRIFTDKASGSSTDREGLDL
LRMKVKEGDVILVKKLDRLGRDTADMLQLIKEFDAQGVAVRFIDDGISTD
SYIGLMFVTILSAVAQAERRRILERTNEGRQAAKLKGIKFGRRRGGSGGS
GGSMDKKYSIGLAIGTNSVGWAVITDEYKVPSKKFKVLGNTDRHSIKKNL
IGALLFDSGETAEATRLKRTARRRYTRRKNRICYLQEIFSNEMAKVDDSF
FHRLEESFLVEEDKKHERHPIFGNIVDEVAYHEKYPTIYHLRKKLVDSTD
KADLRLIYLALAHMIKFRGHFLIEGDLNPDNSDVDKLFIQLVQTYNQLFE
ENPINASGVDAKAILSARLSKSRRLENLIAQLPGEKKNGLFGNLIALSLG

-continued

LTPNFKSNFDLAEDAKLQLSKDTYDDDLDNLLAQIGDQYADLFLAAKNLS
DAILLSDILRVNTEITKAPLSASMIKRYDEHHQDLTLLKALVRQQLPEKY
KEIFFDQSKNGYAGYIDGGASQEEFYKFIKPILEKMDGTEELLVKLNRED
LLRKQRTFDNGSIPHQIHLGELHAILRRQEDFYPFLKDNREKIEKILTFR
IPYYVGPLARGNSRFAWMTRKSEETITPWNFEEVVDKGASAQSFIERMTN
FDKNLPNEKVLPKHSLLYEYFTVYNELTKVKYVTEGMRKPAFLSGEQKKA
IVDLLFKTNRKVTVKQLKEDYFKKIECFDSVEISGVEDRFNASLGTYHDL
LKIIKDKDFLDNEENEDILEDIVLTLTLFEDREMIEERLKTYAHLFDDKV
MKQLKRRRYTGWGRLSRKLINGIRDKQSGKTILDFLKSDGFANRNFMQLI
HDDSLTFKEDIQKAQVSGQGDSLHEHIANLAGSPAIKKGILQTVKVVDEL
VKVMGRHKPENIVIEMARENQTTQKGQKNSRERMKRIEEGIKELGSQILK
EHPVENTQLQNEKLYLYYLQNGRDMYVDQELDINRLSDYDVDAIVPQSFL
KDDSIDNKVLTRSDKNRGKSDNVPSEEVVKKMKNYWRQLLNAKLITQRKF
DNLTKAERGGLSELDKAGFIKRQLVETRQITKHVAQILDSRMNTKYDEND
KLIREVKVITLKSKLVSDFRKDFQFYKVREINNYHHAHDAYLNAVVGTAL
IKKYPKLESEFVYGDYKVYDVRKMIAKSEQEIGKATAKYFFYSNIMNFFK
TEITLANGEIRKRPLIETNGETGEIVWDKGRDFATVRKVLSMPQVNIVKK
TEVQTGGFSKESILPKRNSDKLIARKKDWDPKKYGGFDSPTVAYSVLVVA
KVEKGKSKKLKSVKELLGITIMERSSFEKNPIDFLEAKGYKEVKKDLIIK
LPKYSLFELENGRKRMLASAGELQKGNELALPSKYVNFLYLASHYEKLKG
SPEDNEQKQLFVEQHKHYLDEIIEQISEFSKRVILADANLDKVLSAYNKH
RDKPIREQAENIIHLFTLTNLGAPAAFKYFDTTIDRKRYTSTKEVLDATL
IHQSITGLYETRIDLSQLGGDMAPKKKRKVGIHRGVP (underline: nuclear localization signal; bold: linker sequence)

NLS-Tn3-GGS3linker-dCas9

(SEQ ID NO: 331)

MAPKKKRKVGIHRGVPMALFGYARVSTSQQSLDLQVRALKDAGVKANRIF
TDKASGSSTDREGLDLLRMKVKEGDVILVKKLDRLGRDTADMLQLIKEFD
AQGVAVRFIDDGISTDSYIGLMFVTILSAVAQAERRRILERTNEGRQAAK
LKGIKFGRRRGGSGGSGGSMDKKYSIGLAIGTNSVGWAVITDEYKVPSKK
FKVLGNTDRHSIKKNLIGALLFDSGETAEATRLKRTARRRYTRRKNRICY
LQEIFSNEMAKVDDSFFHRLEESFLVEEDKKHERHPIFGNIVDEVAYHEK
YPTIYHLRKKLVDSTDKADLRLIYLALAHMIKFRGHFLIEGDLNPDNSDV
DKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQ
IGDQYADLFLAAKNLSDAILLSDILRVNTEITKAPLSASMIKRYDEHHQD
LTLLKALVRQQLPEKYKEIFFDQSKNGYAGYIDGGASQEEFYKFIKPILE
KMDGTEELLVKLNREDLLRKQRTFDNGSIPHQIHLGELHAILRRQEDFYP
FLKDNREKIEKILTFRIPYYVGPLARGNSRFAWMTRKSEETITPWNFEEV
VDKGASAQSFIERMTNFDKNLPNEKVLPKHSLLYEYFTVYNELTKVKYVT
EGMRKPAFLSGEQKKAIVDLLFKTNRKVTVKQLKEDYFKKIECFDSVEIS

-continued

GVEDRFNASLGTYHDLLKIIKDKDFLDNEENEDILEDIVLTLTLFEDREM
IEERLKTYAHLFDDKVMKQLKRRRYTGWGRLSRKLINGIRDKQSGKTILD
FLKSDGFANRNFMQLIHDDSLTFKEDIQKAQVSGQGDSLHEHIANLAGSP
AIKKGILQTVKVVDELVKVMGRHKPENIVIEMARENQTTQKGQKNSRERM
KRIEEGIKELGSQILKEHPVENTQLQNEKLYLYYLQNGRDMYVDQELDIN
RLSDYDVDAIVPQSFLKDDSIDNKVLTRSDKNRGKSDNVPSEEVVKKMKN
YWRQLLNAKLITQRKFDNLTKAERGGLSELDKAGFIKRQLVETRQITKHV
AQILDSRMNTKYDENDKLIREVKVITLKSKLVSDFRKDFQFYKVREINNY
HHAHDAYLNAVVGTALIKKYPKLESEFVYGDYKVYDVRKMIAKSEQEIGK
ATAKYFFYSNIMNFFKTEITLANGEIRKRPLIETNGETGEIVWDKGRDFA
TVRKVLSMPQVNIVKKTEVQTGGFSKESILPKRNSDKLIARKKDWDPKKY
GGFDSPTVAYSVLVVAKVEKGKSKKLKSVKELLGITIMERSSFEKNPIDF
LEAKGYKEVKKDLIIKLPKYSLFELENGRKRMLASAGELQKGNELALPSK
YVNFLYLASHYEKLKGSPEDNEQKQLFVEQHKHYLDEIIEQISEFSKRVI
LADANLDKVLSAYNKHRDKPIREQAENIIHLFTLTNLGAPAAFKYFDTTI
DRKRYTSTKEVLDATLIHQSITGLYETRIDLSQLGGD (underline: nuclear localization signal; bold: linker sequence)

dCas9-NLS-GGS3linker-Hin (SEQ ID NO: 332)

MDKKYSIGLAIGTNSVGWAVITDEYKVPSKKFKVLGNTDRHSIKKNLIGA
LLFDSGETAEATRLKRTARRRYTRRKNRICYLQEIFSNEMAKVDDSFFHR
LEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENP
INASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQ
LKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVKV
MGRHKPENIVIEMARENQTTQKGQKNSRERMKRIEEGIKELGSQILKEHP
VENTQLQNEKLYLYYLQNGRDMYVDQELDINRLSDYDVDAIVPQSFLKDD
SIDNKVLTRSDKNRGKSDNVPSEEVVKKMKNYWRQLLNAKLITQRKFDNL
TKAERGGLSELDKAGFIKRQLVETRQITKHVAQILDSRMNTKYDENDKLI
REVKVITLKSKLVSDFRKDFQFYKVREINNYHHAHDAYLNAVVGTALIKK
YPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEV

-continued

QTGGFSKESILPKRNSDKLIARKKDWDPKKYGGFDSPTVAYSVLVVAKVE
KGKSKKLKSVKELLGITIMERSSFEKNPIDFLEAKGYKEVKKDLIIKLPK
YSLFELENGRKRMLASAGELQKGNELALPSKYVNFLYLASHYEKLKGSPE
DNEQKQLFVEQHKHYLDEIIEQISEFSKRVILADANLDKVLSAYNKHRDK
PIREQAENIIHLFTLTNLGAPAAFKYFDTTIDRKRYTSTKEVLDATLIHQ
SITGLYETRIDLSQLGGDMAPKKKRKVGIHRGVPGGSGGSGGSMATIGYI
RVSTIDQNIDLQRNALTSANCDRIFEDRISGKIANRPGLKRALKYVNKGD
TLVVWKLDRLGRSVKNLVALISELHERGAHFHSLTDSIDTSSAMGRFFFY
VMSALAEMERELIVERTLAGLAAARAQGRLG (underline: nuclear localization signal; bold: linker sequence)
NLS-dCas9-GGS3linker-Hin (SEQ ID NO: 333)
MAPKKKRKVGIHRGVPMDKKYSIGLAIGTNSVGWAVITDEYKVPSKKFKV
LGNTDRHSIKKNLIGALLFDSGETAEATRLKRTARRRYTRRKNRICYLQE
IFSNEMAKVDDSFFHRLEESFLVEEDKKHERHPIFGNIVDEVAYHEKYPT
IYHLRKKLVDSTDKADLRLIYLALAHMIKFRGHFLIEGDLNPDNSDVDKL
FIQLVQTYNQLFEENPINASGVDAKAILSARLSKSRRLENLIAQLPGEKK
NGLFGNLIALSLGLTPNFKSNFDLAEDAKLQLSKDTYDDDLDNLLAQIGD
QYADLFLAAKNLSDAILLSDILRVNTEITKAPLSASMIKRYDEHHQDLTL
LKALVRQQLPEKYKEIFFDQSKNGYAGYIDGGASQEEFYKFIKPILEKMD
GTEELLVKLNREDLLRKQRTFDNGSIPHQIHLGELHAILRRQEDFYPFLK
DNREKIEKILTFRIPYYVGPLARGNSRFAWMTRKSEETITPWNFEEVVDK
GASAQSFIERMTNFDKNLPNEKVLPKHSLLYEYFTVYNELTKVKYVTEGM
RKPAFLSGEQKKAIVDLLFKTNRKVTVKQLKEDYFKKIECFDSVEISGVE
DRFNASLGTYHDLLKIIKDKDFLDNEENEDILEDIVLTLTLFEDREMIEE
RLKTYAHLFDDKVMKQLKRRRYTGWGRLSRKLINGIRDKQSGKTILDFLK
SDGFANRNFMQLIHDDSLTFKEDIQKAQVSGQGDSLHEHIANLAGSPAIK
KGILQTVKVVDELVKVMGRHKPENIVIEMARENQTTQKGQKNSRERMKRI
EEGIKELGSQILKEHPVENTQLQNEKLYLYYLQNGRDMYVDQELDINRLS
DYDVDAIVPQSFLKDDSIDNKVLTRSDKNRGKSDNVPSEEVVKKMKNYWR
QLLNAKLITQRKFDNLTKAERGGLSELDKAGFIKRQLVETRQITKHVAQI
LDSRMNTKYDENDKLIREVKVITLKSKLVSDFRKDFQFYKVREINNYHHA
HDAYLNAVVGTALIKKYPKLESEFVYGDYKVYDVRKMIAKSEQEIGKATA
KYFFYSNIMNFFKTEITLANGEIRKRPLIETNGETGEIVWDKGRDFATVR
KVLSMPQVNIVKKTEVQTGGFSKESILPKRNSDKLIARKKDWDPKKYGGF
DSPTVAYSVLVVAKVEKGKSKKLKSVKELLGITIMERSSFEKNPIDFLEA
KGYKEVKKDLIIKLPKYSLFELENGRKRMLASAGELQKGNELALPSKYVN
FLYLASHYEKLKGSPEDNEQKQLFVEQHKHYLDEIIEQISEFSKRVILAD
ANLDKVLSAYNKHRDKPIREQAENIIHLFTLTNLGAPAAFKYFDTTIDRK
RYTSTKEVLDATLIHQSITGLYETRIDLSQLGGDGGSGGSGGSMATIGYI
RVSTIDQNIDLQRNALTSANCDRIFEDRISGKIANRPGLKRALKYVNKGD -continued TLVVWKLDRLGRSVKNLVALISELHERGAHFHSLTDSIDTSSAMGRFFFY
VMSALAEMERELIVERTLAGLAAARAQGRLG (underline: nuclear localization signal; bold: linker sequence)
Hin-GGS3linker-dCas9-NLS (SEQ ID NO: 334)
MATIGYIRVSTIDQNIDLQRNALTSANCDRIFEDRISGKIANRPGLKRAL
KYVNKGDTLVVWKLDRLGRSVKNLVALISELHERGAHFHSLTDSIDTSSA
MGRFFFYVMSALAEMERELIVERTLAGLAAARAQGRLGGGSGGSGGSMDK
KYSIGLAIGTNSVGWAVITDEYKVPSKKFKVLGNTDRHSIKKNLIGALLF
DSGETAEATRLKRTARRRYTRRKNRICYLQEIFSNEMAKVDDSFFHRLEE
SFLVEEDKKHERHPIFGNIVDEVAYHEKYPTIYHLRKKLVDSTDKADLRL
IYLALAHMIKFRGHFLIEGDLNPDNSDVDKLFIQLVQTYNQLFEENPINA
SGVDAKAILSARLSKSRRLENLIAQLPGEKKNGLFGNLIALSLGLTPNFK
SNFDLAEDAKLQLSKDTYDDDLDNLLAQIGDQYADLFLAAKNLSDAILLS
DILRVNTEITKAPLSASMIKRYDEHHQDLTLLKALVRQQLPEKYKEIFFD
QSKNGYAGYIDGGASQEEFYKFIKPILEKMDGTEELLVKLNREDLLRKQR
TFDNGSIPHQIHLGELHAILRRQEDFYPFLKDNREKIEKILTFRIPYYVG
PLARGNSRFAWMTRKSEETITPWNFEEVVDKGASAQSFIERMTNFDKNLP
NEKVLPKHSLLYEYFTVYNELTKVKYVTEGMRKPAFLSGEQKKAIVDLLF
KTNRKVTVKQLKEDYFKKIECFDSVEISGVEDRFNASLGTYHDLLKIIKD
KDFLDNEENEDILEDIVLTLTLFEDREMIEERLKTYAHLFDDKVMKQLKR
RRYTGWGRLSRKLINGIRDKQSGKTILDFLKSDGFANRNFMQLIHDDSLT
FKEDIQKAQVSGQGDSLHEHIANLAGSPAIKKGILQTVKVVDELVKVMGR
HKPENIVIEMARENQTTQKGQKNSRERMKRIEEGIKELGSQILKEHPVEN
TQLQNEKLYLYYLQNGRDMYVDQELDINRLSDYDVDAIVPQSFLKDDSID
NKVLTRSDKNRGKSDNVPSEEVVKKMKNYWRQLLNAKLITQRKFDNLTKA
ERGGLSELDKAGFIKRQLVETRQITKHVAQILDSRMNTKYDENDKLIREV
KVITLKSKLVSDFRKDFQFYKVREINNYHHAHDAYLNAVVGTALIKKYPK
LESEFVYGDYKVYDVRKMIAKSEQEIGKATAKYFFYSNIMNFFKTEITLA
NGEIRKRPLIETNGETGEIVWDKGRDFATVRKVLSMPQVNIVKKTEVQTG
GFSKESILPKRNSDKLIARKKDWDPKKYGGFDSPTVAYSVLVVAKVEKGK
SKKLKSVKELLGITIMERSSFEKNPIDFLEAKGYKEVKKDLIIKLPKYSL
FELENGRKRMLASAGELQKGNELALPSKYVNFLYLASHYEKLKGSPEDNE
QKQLFVEQHKHYLDEIIEQISEFSKRVILADANLDKVLSAYNKHRDKPIR
EQAENIIHLFTLTNLGAPAAFKYFDTTIDRKRYTSTKEVLDATLIHQSIT
GLYETRIDLSQLGGDMAPKKKRKVGIHRGVP (underline: nuclear localization signal; bold: linker sequence)
NLS-Hin-GGS3linker-dCas9

(SEQ ID NO: 335)
MAPKKKRKVGIHRGVPMATIGYIRVSTIDQNIDLQRNALTSANCDRIFED
RISGKIANRPGLKRALKYVNKGDTLVVWKLDRLGRSVKNLVALISELHER
GAHFHSLTDSIDTSSAMGRFFFYVMSALAEMERELIVERTLAGLAAARAQ

-continued

GRLGGGSGGSGGSMDKKYSIGLAIGTNSVGWAVITDEYKVPSKKFKVLGN
TDRHSIKKNLIGALLFDSGETAEATRLKRTARRRYTRRKNRICYLQEIFS
NEMAKVDDSFFHRLEESFLVEEDKKHERHPIFGNIVDEVAYHEKYPTIYH
LRKKLVDSTDKADLRLIYLALAHMIKFRGHFLIEGDLNPDNSDVDKLFIQ
LVQTYNQLFEENPINASGVDAKAILSARLSKSRRLENLIAQLPGEKKNGL
FGNLIALSLGLTPNFKSNFDLAEDAKLQLSKDTYDDDLDNLLAQIGDQYA
DLFLAAKNLSDAILLSDILRVNTEITKAPLSASMIKRYDEHHQDLTLLKA
LVRQQLPEKYKEIFFDQSKNGYAGYIDGGASQEEFYKFIKPILEKMDGTE
ELLVKLNREDLLRKQRTFDNGSIPHQIHLGELHAILRRQEDFYPFLKDNR
EKIEKILTFRIPYYVGPLARGNSRFAWMTRKSEETITPWNFEEVVDKGAS
AQSFIERMTNFDKNLPNEKVLPKHSLLYEYFTVYNELTKVKYVTEGMRKP
AFLSGEQKKAIVDLLFKTNRKVTVKQLKEDYFKKIECFDSVEISGVEDRF
NASLGTYHDLLKIIKDKDFLDNEENEDILEDIVLTLTLFEDREMIEERLK
TYAHLFDDKVMKQLKRRRYTGWGRLSRKLINGIRDKQSGKTILDFLKSDG
FANRNFMQLIHDDSLTFKEDIQKAQVSGQGDSLHEHIANLAGSPAIKKGI
LQTVKVVDELVKVMGRHKPENIVIEMARENQTTQKGQKNSRERMKRIEEG
IKELGSQILKEHPVENTQLQNEKLYLYYLQNGRDMYVDQELDINRLSDYD
VDAIVPQSFLKDDSIDNKVLTRSDKNRGKSDNVPSEEVVKKMKNYWRQLL
NAKLITQRKFDNLTKAERGGLSELDKAGFIKRQLVETRQITKHVAQILDS
RMNTKYDENDKLIREVKVITLKSKLVSDFRKDFQFYKVREINNYHHAHDA
YLNAVVGTALIKKYPKLESEFVYGDYKVYDVRKMIAKSEQEIGKATAKYF
FYSNIMNFFKTEITLANGEIRKRPLIETNGETGEIVWDKGRDFATVRKVL
SMPQVNIVKKTEVQTGGFSKESILPKRNSDKLIARKKDWDPKKYGGFDSP
TVAYSVLVVAKVEKGKSKKLKSVKELLGITIMERSSFEKNPIDFLEAKGY
KEVKKDLIIKLPKYSLFELENGRKRMLASAGELQKGNELALPSKYVNFLY
LASHYEKLKGSPEDNEQKQLFVEQHKHYLDEIIEQISEFSKRVILADANL
DKVLSAYNKHRDKPIREQAENIIHLFTLTNLGAPAAFKYFDTTIDRKRYT
STKEVLDATLIHQSITGLYETRIDLSQLGGD (underline: nuclear localization signal; bold: linker sequence)
dCas9-NLS-GGS3linker-Gin (SEQ ID NO: 336)
MDKKYSIGLAIGTNSVGWAVITDEYKVPSKKFKVLGNTDRHSIKKNLIGA
LLFDSGETAEATRLKRTARRRYTRRKNRICYLQEIFSNEMAKVDDSFFHR
LEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENP
INASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQ
LKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVKV
MGRHKPENIVIEMARENQTTQKGQKNSRERMKRIEEGIKELGSQILKEHP
VENTQLQNEKLYLYYLQNGRDMYVDQELDINRLSDYDVDAIVPQSFLKDD
SIDNKVLTRSDKNRGKSDNVPSEEVVKKMKNYWRQLLNAKLITQRKFDNL
TKAERGGLSELDKAGFIKRQLVETRQITKHVAQILDSRMNTKYDENDKLI
REVKVITLKSKLVSDFRKDFQFYKVREINNYHHAHDAYLNAVVGTALIKK
YPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEV
QTGGFSKESILPKRNSDKLIARKKDWDPKKYGGFDSPTVAYSVLVVAKVE
KGKSKKLKSVKELLGITIMERSSFEKNPIDFLEAKGYKEVKKDLIIKLPK
YSLFELENGRKRMLASAGELQKGNELALPSKYVNFLYLASHYEKLKGSPE
DNEQKQLFVEQHKHYLDEIIEQISEFSKRVILADANLDKVLSAYNKHRDK
PIREQAENIIHLFTLTNLGAPAAFKYFDTTIDRKRYTSTKEVLDATLIHQ
SITGLYETRIDLSQLGGDMAPKKKRKVGIHRGVPGGSGGSGGSMLIGYVR
VSTNDQNTDLQRNALVCAGCEQIFEDKLSGTRTDRPGLKRALKRLQKGDT
LVVWKLDRLGRSMKHLISLVGELRERGINFRSLTDSIDTSSPMGRFFFYV
MGALAEMERELIIERTMAGIAAARNKGRRFGRPPKSG (underline: nuclear localization signal; bold: linker sequence)
NLS-dCas9-GGS3linker-Gin (SEQ ID NO: 337)
MAPKKKRKVGIHRGVPMDKKYSIGLAIGTNSVGWAVITDEYKVPSKKFKV
LGNTDRHSIKKNLIGALLFDSGETAEATRLKRTARRRYTRRKNRICYLQE
IFSNEMAKVDDSFFHRLEESFLVEEDKKHERHPIFGNIVDEVAYHEKYPT
IYHLRKKLVDSTDKADLRLIYLALAHMIKFRGHFLIEGDLNPDNSDVDKL
FIQLVQTYNQLFEENPINASGVDAKAILSARLSKSRRLENLIAQLPGEKK
NGLFGNLIALSLGLTPNFKSNFDLAEDAKLQLSKDTYDDDLDNLLAQIGD
QYADLFLAAKNLSDAILLSDILRVNTEITKAPLSASMIKRYDEHHQDLTL
LKALVRQQLPEKYKEIFFDQSKNGYAGYIDGGASQEEFYKFIKPILEKMD
GTEELLVKLNREDLLRKQRTFDNGSIPHQIHLGELHAILRRQEDFYPFLK
DNREKIEKILTFRIPYYVGPLARGNSRFAWMTRKSEETITPWNFEEVVDK
GASAQSFIERMTNFDKNLPNEKVLPKHSLLYEYFTVYNELTKVKYVTEGM
RKPAFLSGEQKKAIVDLLFKTNRKVTVKQLKEDYFKKIECFDSVEISGVE
DRFNASLGTYHDLLKIIKDKDFLDNEENEDILEDIVLTLTLFEDREMIEE
RLKTYAHLFDDKVMKQLKRRRYTGWGRLSRKLINGIRDKQSGKTILDFLK
SDGFANRNFMQLIHDDSLTFKEDIQKAQVSGQGDSLHEHIANLAGSPAIK
KGILQTVKVVDELVKVMGRHKPENIVIEMARENQTTQKGQKNSRERMKRI -continued EEGIKELGSQILKEHPVENTQLQNEKLYLYYLQNGRDMYVDQELDINRLS
DYDVDAIVPQSFLKDDSIDNKVLTRSDKNRGKSDNVPSEEVVKKMKNYWR
QLLNAKLITQRKFDNLTKAERGGLSELDKAGFIKRQLVETRQITKHVAQI
LDSRMNTKYDENDKLIREVKVITLKSKLVSDFRKDFQFYKVREINNYHHA
HDAYLNAVVGTALIKKYPKLESEFVYGDYKVYDVRKMIAKSEQEIGKATA
KYFFYSNIMNFFKTEITLANGEIRKRPLIETNGETGEIVWDKGRDFATVR
KVLSMPQVNIVKKTEVQTGGFSKESILPKRNSDKLIARKKDWDPKKYGGF
DSPTVAYSVLVVAKVEKGKSKKLKSVKELLGITIMERSSFEKNPIDFLEA
KGYKEVKKDLIIKLPKYSLFELENGRKRMLASAGELQKGNELALPSKYVN
FLYLASHYEKLKGSPEDNEQKQLFVEQHKHYLDEIIEQISEFSKRVILAD
ANLDKVLSAYNKHRDKPIREQAENIIHLFTLTNLGAPAAFKYFDTTIDRK
RYTSTKEVLDATLIHQSITGLYETRIDLSQLGGDGGSGGSGGSMLIGYVR
VSTNDQNTDLQRNALVCAGCEQIFEDKLSGTRTDRPGLKRALKRLQKGDT
LVVWKLDRLGRSMKHLISLVGELRERGINFRSLTDSIDTSSPMGRFFFYV
MGALAEMERELIIERTMAGIAAARNKGRRFGRPPKSG (underline: nuclear localization signal; bold: linker sequence)
Gin-GGS3linker-dCas9-NLS (SEQ ID NO: 338)

MLIGYVRVSTNDQNTDLQRNALVCAGCEQIFEDKLSGTRTDRPGLKRALK
RLQKGDTLVVWKLDRLGRSMKHLISLVGELRERGINFRSLTDSIDTSSPM
GRFFFYVMGALAEMERELIIERTMAGIAAARNKGRRFGRPPKSGGGSGGS
GGSMDKKYSIGLAIGTNSVGWAVITDEYKVPSKKFKVLGNTDRHSIKKNL
IGALLFDSGETAEATRLKRTARRRYTRRKNRICYLQEIFSNEMAKVDDSF
FHRLEESFLVEEDKKHERHPIFGNIVDEVAYHEKYPTIYHLRKKLVDSTD
KADLRLIYLALAHMIKFRGHFLIEGDLNPDNSDVDKLFIQLVQTYNQLFE
ENPINASGVDAKAILSARLSKSRRLENLIAQLPGEKKNGLFGNLIALSLG
LTPNFKSNFDLAEDAKLQLSKDTYDDDLDNLLAQIGDQYADLFLAAKNLS
DAILLSDILRVNTEITKAPLSASMIKRYDEHHQDLTLLKALVRQQLPEKY
KEIFFDQSKNGYAGYIDGGASQEEFYKFIKPILEKMDGTEELLVKLNRED
LLRKQRTFDNGSIPHQIHLGELHAILRRQEDFYPFLKDNREKIEKILTFR
IPYYVGPLARGNSRFAWMTRKSEETITPWNFEEVVDKGASAQSFIERMTN
FDKNLPNEKVLPKHSLLYEYFTVYNELTKVKYVTEGMRKPAFLSGEQKKA
IVDLLFKTNRKVTVKQLKEDYFKKIECFDSVEISGVEDRFNASLGTYHDL
LKIIKDKDFLDNEENEDILEDIVLTLTLFEDREMIEERLKTYAHLFDDKV
MKQLKRRRYTGWGRLSRKLINGIRDKQSGKTILDFLKSDGFANRNFMQLI
HDDSLTFKEDIQKAQVSGQGDSLHEHIANLAGSPAIKKGILQTVKVVDEL
VKVMGRHKPENIVIEMARENQTTQKGQKNSRERMKRIEEGIKELGSQILK
EHPVENTQLQNEKLYLYYLQNGRDMYVDQELDINRLSDYDVDAIVPQSFL
KDDSIDNKVLTRSDKNRGKSDNVPSEEVVKKMKNYWRQLLNAKLITQRKF
DNLTKAERGGLSELDKAGFIKRQLVETRQITKHVAQILDSRMNTKYDEND

-continued

KLIREVKVITLKSKLVSDFRKDFQFYKVREINNYHHAHDAYLNAVVGTAL
IKKYPKLESEFVYGDYKVYDVRKMIAKSEQEIGKATAKYFFYSNIMNFFK
TEITLANGEIRKRPLIETNGETGEIVWDKGRDFATVRKVLSMPQVNIVKK
TEVQTGGFSKESILPKRNSDKLIARKKDWDPKKYGGFDSPTVAYSVLVVA
KVEKGKSKKLKSVKELLGITIMERSSFEKNPIDFLEAKGYKEVKKDLIIK
LPKYSLFELENGRKRMLASAGELQKGNELALPSKYVNFLYLASHYEKLKG
SPEDNEQKQLFVEQHKHYLDEIIEQISEFSKRVILADANLDKVLSAYNKH
RDKPIREQAENIIHLFTLTNLGAPAAFKYFDTTIDRKRYTSTKEVLDATL
IHQSITGLYETRIDLSQLGGDMAPKKKRKVGIHRGVP (underline: nuclear localization signal; bold: linker sequence)
NLS-Gin-GGS3linker-dCas9

(SEQ ID NO: 339)

MAPKKKRKVGIHRGVPMLIGYVRVSTNDQNTDLQRNALVCAGCEQIFEDK
LSGTRTDRPGLKRALKRLQKGDTLVVWKLDRLGRSMKHLISLVGELRERG
INFRSLTDSIDTSSPMGRFFFYVMGALAEMERELIIERTMAGIAAARNKG
RRFGRPPKSGGGSGGSGGSMDKKYSIGLAIGTNSVGWAVITDEYKVPSKK
FKVLGNTDRHSIKKNLIGALLFDSGETAEATRLKRTARRRYTRRKNRICY
LQEIFSNEMAKVDDSFFHRLEESFLVEEDKKHERHPIFGNIVDEVAYHEK
YPTIYHLRKKLVDSTDKADLRLIYLALAHMIKFRGHFLIEGDLNPDNSDV
DKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQ
IGDQYADLFLAAKNLSDAILLSDILRVNTEITKAPLSASMIKRYDEHHQD
LTLLKALVRQQLPEKYKEIFFDQSKNGYAGYIDGGASQEEFYKFIKPILE
KMDGTEELLVKLNREDLLRKQRTFDNGSIPHQIHLGELHAILRRQEDFYP
FLKDNREKIEKILTFRIPYYVGPLARGNSRFAWMTRKSEETITPWNFEEV
VDKGASAQSFIERMTNFDKNLPNEKVLPKHSLLYEYFTVYNELTKVKYVT
EGMRKPAFLSGEQKKAIVDLLFKTNRKVTVKQLKEDYFKKIECFDSVEIS
GVEDRFNASLGTYHDLLKIIKDKDFLDNEENEDILEDIVLTLTLFEDREM
IEERLKTYAHLFDDKVMKQLKRRRYTGWGRLSRKLINGIRDKQSGKTILD
FLKSDGFANRNFMQLIHDDSLTFKEDIQKAQVSGQGDSLHEHIANLAGSP
AIKKGILQTVKVVDELVKVMGRHKPENIVIEMARENQTTQKGQKNSRERM
KRIEEGIKELGSQILKEHPVENTQLQNEKLYLYYLQNGRDMYVDQELDIN
RLSDYDVDAIVPQSFLKDDSIDNKVLTRSDKNRGKSDNVPSEEVVKKMKN
YWRQLLNAKLITQRKFDNLTKAERGGLSELDKAGFIKRQLVETRQITKHV
AQILDSRMNTKYDENDKLIREVKVITLKSKLVSDFRKDFQFYKVREINNY
HHAHDAYLNAVVGTALIKKYPKLESEFVYGDYKVYDVRKMIAKSEQEIGK
ATAKYFFYSNIMNFFKTEITLANGEIRKRPLIETNGETGEIVWDKGRDFA
TVRKVLSMPQVNIVKKTEVQTGGFSKESILPKRNSDKLIARKKDWDPKKY
GGFDSPTVAYSVLVVAKVEKGKSKKLKSVKELLGITIMERSSFEKNPIDF
LEAKGYKEVKKDLIIKLPKYSLFELENGRKRMLASAGELQKGNELALPSK
YVNFLYLASHYEKLKGSPEDNEQKQLFVEQHKHYLDEIIEQISEFSKRVI

-continued

LADANLDKVLSAYNKHRDKPIREQAENIIHLFTLTNLGAPAAFKYFDTTI

DRKRYTSTKEVLDATLIHQSITGLYETRIDLSQLGGD (underline: nuclear localization signal; bold: linker sequence)

Example 4

Figure 5B:
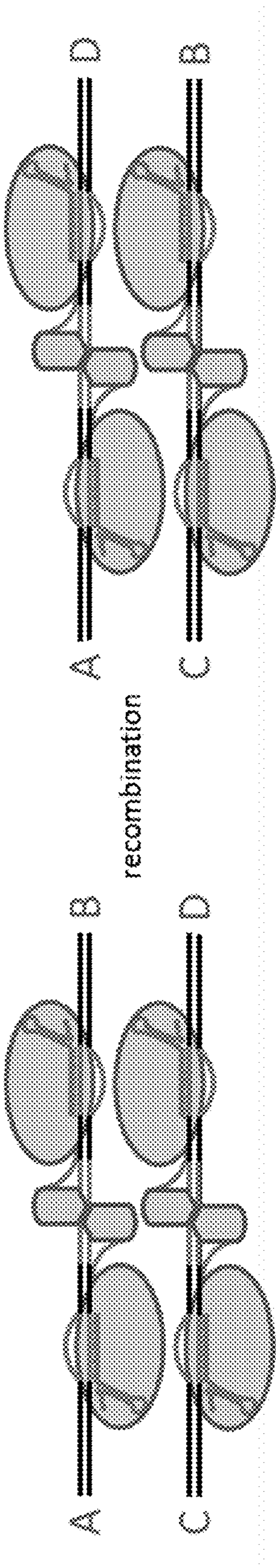

Introduction of a Marker Gene by Homologous Recombination Using Cas9-Recombinase Fusion Proteins A vector carrying a green fluorescent protein (GFP) marker gene flanked by genomic sequence of a host cell gene is introduced into a cell, along with an expression construct encoding a dCas9-recombinase fusion protein (any one of SEQ ID NO:328-339) and four appropriately designed gRNAs targeting the GFP marker gene and the genomic locus into which the GFP marker is recombined. Four dCas9-recombinase fusion proteins are coordinated at the genomic locus along with the GFP marker gene through the binding of the gRNAs (FIG. 5B). The four recombinase domains of the fusion proteins tetramerize, and the recombinase activity of the recombinase domains of the fusion protein results in the recombination between the gemomic locus and the marker gene, thereby introducing the marker gene into the genomic locus. Introduction of the marker gene is confirmed by GFP expression and/or by PCR.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

What is claimed is:

1. A dimer or tetramer of a fusion protein wherein the fusion protein comprises two domains: (i) a nuclease-inactivated Cas9 (dCas9); and (ii) a recombinase catalytic domain;

wherein the nuclease-inactivated Cas9 domain is bound to a guide RNA (gRNA); and wherein the dimer or the tetramer is bound to a nucleic acid.

2. The dimer or tetramer of a fusion protein of claim 1, wherein the recombinase catalytic domain is a monomer of the recombinase catalytic domain of Hin recombinase, Gin recombinase, or Tn3 recombinase.

3. The dimer or tetramer of a fusion protein of claim 1, further comprising a nuclear localization signal (NLS) domain.

4. The dimer or tetramer of a fusion protein of claim 3, wherein one or more domains of the fusion protein are separated by a peptide linker or a non-peptide linker.

5. The dimer or tetramer of a fusion protein of claim 4, wherein the peptide linker comprises an XTEN linker, an amino acid sequence comprising one or more repeats of the tri-peptide GGS, or any sequence as provided in FIG. 12A (SEQ ID NOs: 14-25 and 301).

6. The dimer of the fusion protein of claim 1, wherein each fusion protein of the dimer is bound to opposite strands of the nucleic acid.

7. A kit comprising a dimer or tetramer of a fusion protein of claim 1.

* * * * *

SEQUENCE LISTING

<160> NUMBER OF SEQ ID NOS: 339

<210> SEQ ID NO 1
<211> LENGTH: 4104
<212> TYPE: DNA
<213> ORGANISM: Streptococcus pyogenes

<400> SEQUENCE: 1

-continued

```
atggataaga aatactcaat aggcttagat atcggcacaa atagcgtcgg atgggcggtg     60
atcactgatg attataaggt tccgtctaaa aagttcaagg ttctgggaaa tacagaccgc    120
cacagtatca aaaaaaatct tataggggct cttttatttg gcagtggaga gacagcggaa    180
gcgactcgtc tcaaacggac agctcgtaga aggtatacac gtcggaagaa tcgtatttgt    240
tatctacagg agattttttc aaatgagatg gcgaaagtag atgatagttt ctttcatcga    300
cttgaagagt cttttttggt ggaagaagac aagaagcatg aacgtcatcc tatttttgga    360
aatatagtag atgaagttgc ttatcatgag aaatatccaa ctatctatca tctgcgaaaa    420
aaattggcag attctactga taaagcggat ttgcgcttaa tctatttggc cttagcgcat    480
atgattaagt ttcgtggtca tttttttgatt gagggagatt taaatcctga taatagtgat    540
gtggacaaac tatttatcca gttggtacaa atctacaatc aattatttga agaaaaccct    600
attaacgcaa gtagagtaga tgctaaagcg attctttctg cacgattgag taaatcaaga    660
cgattagaaa atctcattgc tcagctcccc ggtgagaaga gaaatggctt gtttgggaat    720
ctcattgctt tgtcattggg attgacccct aattttaaat caaattttga tttggcagaa    780
gatgctaaat tacagctttc aaaagatact tacgatgatg atttagataa tttattggcg    840
caaattggag atcaatatgc tgatttgttt ttggcagcta agaatttatc agatgctatt    900
ttactttcag atatcctaag agtaaatagt gaaataacta aggctcccct atcagcttca    960
atgattaagc gctacgatga acatcatcaa gacttgactc ttttaaaagc tttagttcga   1020
caacaacttc cagaaaagta taaagaaatc ttttttgatc aatcaaaaaa cggatatgca   1080
ggttatattg atgggggagc tagccaagaa gaattttata aatttatcaa accaatttta   1140
gaaaaaatgg atggtactga ggaattattg gtgaaactaa atcgtgaaga tttgctgcgc   1200
aagcaacgga cctttgacaa cggctctatt ccccatcaaa ttcacttggg tgagctgcat   1260
gctattttga gaagacaaga agacttttat ccattttttaa aagacaatcg tgagaagatt   1320
gaaaaaatct tgacttttcg aattccttat tatgttggtc cattggcgcg tggcaatagt   1380
cgttttgcat ggatgactcg gaagtctgaa gaaacaatta ccccatggaa ttttgaagaa   1440
gttgtcgata aaggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaggt caaatatgtt actgagggaa tgcgaaaacc agcatttctt   1620
tcaggtgaac agaagaaagc cattgttgat ttactcttca aaacaaatcg aaaagtaacc   1680
gttaagcaat taaaagaaga ttatttcaaa aaaatagaat gttttgatag tgttgaaatt   1740
tcaggagttg aagatagatt taatgcttca ttaggcgcct accatgattt gctaaaaatt   1800
attaaagata aagatttttt ggataatgaa gaaaatgaag atatcttaga ggatattgtt   1860
ttaacattga ccttatttga agatagggggg atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gatttttttga aatcagatgg ttttgccaat cgcaatttta tgcagctgat ccatgatgat   2100
agtttgacat ttaaagaaga tattcaaaaa gcacaggtgt ctggacaagg ccatagttta   2160
catgaacaga ttgctaactt agctggcagt cctgctatta aaaaaggtat tttacagact   2220
gtaaaaattg ttgatgaact ggtcaaagta atggggcata agccagaaaa tatcgttatt   2280
gaaatggcac gtgaaaatca gacaactcaa aagggccaga aaaattcgcg agagcgtatg   2340
```

-continued

```
aaacgaatcg aagaaggtat caaagaatta ggaagtcaga ttcttaaaga gcatcctgtt   2400
gaaaatactc aattgcaaaa tgaaaagctc tatctctatt atctacaaaa tggaagagac   2460
atgtatgtgg accaagaatt agatattaat cgtttaagtg attatgatgt cgatcacatt   2520
gttccacaaa gtttcattaa agacgattca atagacaata aggtactaac gcgttctgat   2580
aaaaatcgtg gtaaatcgga taacgttcca agtgaagaag tagtcaaaaa gatgaaaaac   2640
tattggagac aacttctaaa cgccaagtta atcactcaac gtaagtttga taatttaacg   2700
aaagctgaac gtggaggttt gagtgaactt gataaagctg gttttatcaa acgccaattg   2760
gttgaaactc gccaaatcac taagcatgtg gcacaaattt tggatagtcg catgaatact   2820
aaatacgatg aaaatgataa acttattcga gaggttaaag tgattacctt aaaatctaaa   2880
ttagtttctg acttccgaaa agatttccaa ttctataaag tacgtgagat taacaattac   2940
catcatgccc atgatgcgta tctaaatgcc gtcgttggaa ctgctttgat taagaaatat   3000
ccaaaacttg aatcggagtt tgtctatggt gattataaag tttatgatgt tcgtaaaatg   3060
attgctaagt ctgagcaaga aataggcaaa gcaaccgcaa aatatttctt ttactctaat   3120
atcatgaact tcttcaaaac agaaattaca cttgcaaatg gagagattcg caaacgccct   3180
ctaatcgaaa ctaatgggga aactggagaa attgtctggg ataaagggcg agattttgcc   3240
acagtgcgca aagtattgtc catgccccaa gtcaatattg tcaagaaaac agaagtacag   3300
acaggcggat tctccaagga gtcaatttta ccaaaaagaa attcggacaa gcttattgct   3360
cgtaaaaaag actgggatcc aaaaaaatat ggtggttttg atagtccaac ggtagcttat   3420
tcagtcctag tggttgctaa ggtggaaaaa gggaaatcga agaagttaaa atccgttaaa   3480
gagttactag ggatcacaat tatggaaaga agttcctttg aaaaaaatcc gattgacttt   3540
ttagaagcta aaggatataa ggaagttaaa aaagacttaa tcattaaact acctaaatat   3600
agtctttttg agttagaaaa cggtcgtaaa cggatgctgg ctagtgccgg agaattacaa   3660
aaaggaaatg agctggctct gccaagcaaa tatgtgaatt ttttatattt agctagtcat   3720
tatgaaaagt tgaagggtag tccagaagat aacgaacaaa aacaattgtt tgtggagcag   3780
cataagcatt atttagatga gattattgag caaatcagtg aattttctaa gcgtgttatt   3840
ttagcagatg ccaatttaga taaagttctt agtgcatata acaaacatag agacaaacca   3900
atacgtgaac aagcagaaaa tattattcat ttatttacgt tgacgaatct tggagctccc   3960
gctgctttta aatattttga tacaacaatt gatcgtaaac gatatacgtc tacaaaagaa   4020
gttttagatg ccactcttat ccatcaatcc atcactggtc tttatgaaac acgcattgat   4080
ttgagtcagc taggaggtga ctga                                          4104
```

<210> SEQ ID NO 2
<211> LENGTH: 1367
<212> TYPE: PRT
<213> ORGANISM: Streptococcus pyogenes

<400> SEQUENCE: 2

```
Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Gly Ser Gly Glu Thr Ala Glu Ala Thr Arg Leu
    50                  55                  60
```

```
Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Ala Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Ile Tyr
            180                 185                 190

Asn Gln Leu Phe Glu Glu Asn Pro Ile Asn Ala Ser Arg Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Arg Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Ser Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480
```

-continued

```
Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Ala Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Gly Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly His Ser Leu
705                 710                 715                 720

His Glu Gln Ile Ala Asn Leu Ala Gly Ser Pro Ala Ile Lys Lys Gly
                725                 730                 735

Ile Leu Gln Thr Val Lys Ile Val Asp Glu Leu Val Lys Val Met Gly
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Ile Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
```

-continued 900 905 910

Ala Gly Phe Ile Lys Arg Gln Leu Val Glu Thr Arg Gln Ile Thr Lys
915 920 925

His Val Ala Gln Ile Leu Asp Ser Arg Met Asn Thr Lys Tyr Asp Glu
930 935 940

Asn Asp Lys Leu Ile Arg Glu Val Lys Val Ile Thr Leu Lys Ser Lys
945 950 955 960

Leu Val Ser Asp Phe Arg Lys Asp Phe Gln Phe Tyr Lys Val Arg Glu
965 970 975

Ile Asn Asn Tyr His His Ala His Asp Ala Tyr Leu Asn Ala Val Val
980 985 990

Gly Thr Ala Leu Ile Lys Lys Tyr Pro Lys Leu Glu Ser Glu Phe Val
995 1000 1005

Tyr Gly Asp Tyr Lys Val Tyr Asp Val Arg Lys Met Ile Ala Lys
1010 1015 1020

Ser Glu Gln Glu Ile Gly Lys Ala Thr Ala Lys Tyr Phe Phe Tyr
1025 1030 1035

Ser Asn Ile Met Asn Phe Phe Lys Thr Glu Ile Thr Leu Ala Asn
1040 1045 1050

Gly Glu Ile Arg Lys Arg Pro Leu Ile Glu Thr Asn Gly Glu Thr
1055 1060 1065

Gly Glu Ile Val Trp Asp Lys Gly Arg Asp Phe Ala Thr Val Arg
1070 1075 1080

Lys Val Leu Ser Met Pro Gln Val Asn Ile Val Lys Lys Thr Glu
1085 1090 1095

Val Gln Thr Gly Gly Phe Ser Lys Glu Ser Ile Leu Pro Lys Arg
1100 1105 1110

Asn Ser Asp Lys Leu Ile Ala Arg Lys Lys Asp Trp Asp Pro Lys
1115 1120 1125

Lys Tyr Gly Gly Phe Asp Ser Pro Thr Val Ala Tyr Ser Val Leu
1130 1135 1140

Val Val Ala Lys Val Glu Lys Gly Lys Ser Lys Lys Leu Lys Ser
1145 1150 1155

Val Lys Glu Leu Leu Gly Ile Thr Ile Met Glu Arg Ser Ser Phe
1160 1165 1170

Glu Lys Asn Pro Ile Asp Phe Leu Glu Ala Lys Gly Tyr Lys Glu
1175 1180 1185

Val Lys Lys Asp Leu Ile Ile Lys Leu Pro Lys Tyr Ser Leu Phe
1190 1195 1200

Glu Leu Glu Asn Gly Arg Lys Arg Met Leu Ala Ser Ala Gly Glu
1205 1210 1215

Leu Gln Lys Gly Asn Glu Leu Ala Leu Pro Ser Lys Tyr Val Asn
1220 1225 1230

Phe Leu Tyr Leu Ala Ser His Tyr Glu Lys Leu Lys Gly Ser Pro
1235 1240 1245

Glu Asp Asn Glu Gln Lys Gln Leu Phe Val Glu Gln His Lys His
1250 1255 1260

Tyr Leu Asp Glu Ile Ile Glu Gln Ile Ser Glu Phe Ser Lys Arg
1265 1270 1275

Val Ile Leu Ala Asp Ala Asn Leu Asp Lys Val Leu Ser Ala Tyr
1280 1285 1290

Asn Lys His Arg Asp Lys Pro Ile Arg Glu Gln Ala Glu Asn Ile
1295 1300 1305

```
Ile His  Leu Phe Thr Leu Thr  Asn Leu Gly Ala Pro  Ala Ala Phe
    1310                 1315                 1320

Lys Tyr  Phe Asp Thr Thr Ile  Asp Arg Lys Arg Tyr  Thr Ser Thr
    1325                 1330                 1335

Lys Glu  Val Leu Asp Ala Thr  Leu Ile His Gln Ser  Ile Thr Gly
    1340                 1345                 1350

Leu Tyr  Glu Thr Arg Ile Asp  Leu Ser Gln Leu Gly  Gly Asp
    1355                 1360                 1365


<210> SEQ ID NO 3
<211> LENGTH: 4212
<212> TYPE: DNA
<213> ORGANISM: Artificial Sequence
<220> FEATURE:
<223> OTHER INFORMATION: Synthetic Polynucleotide

<400> SEQUENCE: 3

atggataaaa agtattctat tggtttagac atcggcacta attccgttgg atgggctgtc     60

ataaccgatg aatacaaagt accttcaaag aaatttaagg tgttggggaa cacagaccgt    120

cattcgatta aaaagaatct tatcggtgcc ctcctattcg atagtggcga aacggcagag    180

gcgactcgcc tgaaacgaac cgctcggaga aggtatacac gtcgcaagaa ccgaatatgt    240

tacttacaag aaatttttag caatgagatg gccaaagttg acgattcttt ctttcaccgt    300

ttggaagagt ccttccttgt cgaagaggac aagaaacatg aacggcaccc catctttgga    360

aacatagtag atgaggtggc atatcatgaa aagtacccaa cgatttatca cctcagaaaa    420

aagctagttg actcaactga taaagcggac ctgaggttaa tctacttggc tcttgcccat    480

atgataaagt tccgtgggca ctttctcatt gagggtgatc taaatccgga caactcggat    540

gtcgacaaac tgttcatcca gttagtacaa acctataatc agttgtttga agagaaccct    600

ataaatgcaa gtggcgtgga tgcgaaggct attcttagcg cccgcctctc taaatcccga    660

cggctagaaa acctgatcgc acaattaccc ggagagaaga aaaatgggtt gttcggtaac    720

cttatagcgc tctcactagg cctgacacca aattttaagt cgaacttcga cttagctgaa    780

gatgccaaat tgcagcttag taaggacacg tacgatgacg atctcgacaa tctactggca    840

caaattggag atcagtatgc ggacttattt ttggctgcca aaaaccttag cgatgcaatc    900

ctcctatctg acatactgag agttaatact gagattacca aggcgccgtt atccgcttca    960

atgatcaaaa ggtacgatga acatcaccaa gacttgacac ttctcaaggc cctagtccgt   1020

cagcaactgc ctgagaaata taaggaaata ttctttgatc agtcgaaaaa cgggtacgca   1080

ggttatattg acggcggagc gagtcaagag gaattctaca agtttatcaa acccatatta   1140

gagaagatgg atgggacgga agagttgctt gtaaaactca atcgcgaaga tctactgcga   1200

aagcagcgga ctttcgacaa cggtagcatt ccacatcaaa tccacttagg cgaattgcat   1260

gctatactta gaaggcagga ggatttttat ccgttcctca aagacaatcg tgaaaagatt   1320

gagaaaatcc taacctttcg cataccttac tatgtgggac ccctggcccg agggaactct   1380

cggttcgcat ggatgacaag aaagtccgaa gaaacgatta ctccatggaa ttttgaggaa   1440

gttgtcgata aaggtgcgtc agctcaatcg ttcatcgaga ggatgaccaa ctttgacaag   1500

aatttaccga acgaaaaagt attgcctaag cacagtttac tttacgagta tttcacagtg   1560

tacaatgaac tcacgaaagt taagtatgtc actgagggca tgcgtaaacc cgcctttcta   1620

agcggagaac agaagaaagc aatagtagat ctgttattca agaccaaccg caaagtgaca   1680
```

-continued

```
gttaagcaat tgaaagagga ctactttaag aaaattgaat gcttcgattc tgtcgagatc   1740
tccggggtag aagatcgatt taatgcgtca cttggtacgt atcatgacct cctaaagata   1800
attaaagata aggacttcct ggataacgaa gagaatgaag atatcttaga agatatagtg   1860
ttgactctta ccctctttga agatcgggaa atgattgagg aaagactaaa aacatacgct   1920
cacctgttcg acgataaggt tatgaaacag ttaaagaggc gtcgctatac gggctgggga   1980
cgattgtcgc ggaaacttat caacgggata agagacaagc aaagtggtaa aactattctc   2040
gattttctaa agagcgacgg cttcgccaat aggaacttta tgcagctgat ccatgatgac   2100
tctttaacct tcaaagagga tatacaaaag gcacaggttt ccggacaagg ggactcattg   2160
cacgaacata ttgcgaatct tgctggttcg ccagccatca aaaagggcat actccagaca   2220
gtcaaagtag tggatgagct agttaaggtc atgggacgtc acaaaccgga aaacattgta   2280
atcgagatgg cacgcgaaaa tcaaacgact cagaaggggc aaaaaaacag tcgagagcgg   2340
atgaagagaa tagaagaggg tattaaagaa ctgggcagcc agatcttaaa ggagcatcct   2400
gtggaaaata cccaattgca gaacgagaaa ctttacctct attacctaca aaatggaagg   2460
gacatgtatg ttgatcagga actggacata aaccgtttat ctgattacga cgtcgatcac   2520
attgtacccc aatccttttt gaaggacgat tcaatcgaca ataaagtgct tacacgctcg   2580
gataagaacc gagggaaaag tgacaatgtt ccaagcgagg aagtcgtaaa gaaaatgaag   2640
aactattggc ggcagctcct aaatgcgaaa ctgataacgc aaagaaagtt cgataactta   2700
actaaagctg agaggggtgg cttgtctgaa cttgacaagg ccggatttat taaacgtcag   2760
ctcgtggaaa cccgccaaat cacaaagcat gttgcacaga tactagattc ccgaatgaat   2820
acgaaatacg acgagaacga taagctgatt cgggaagtca aagtaatcac tttaaagtca   2880
aaattggtgt cggacttcag aaaggatttt caattctata aagttaggga gataaataac   2940
taccaccatg cgcacgacgc ttatcttaat gccgtcgtag ggaccgcact cattaagaaa   3000
tacccgaagc tagaaagtga gtttgtgtat ggtgattaca aagtttatga cgtccgtaag   3060
atgatcgcga aaagcgaaca ggagataggc aaggctacag ccaaatactt cttttattct   3120
aacattatga atttctttaa gacggaaatc actctggcaa acggagagat acgcaaacga   3180
cctttaattg aaaccaatgg ggagacaggt gaaatcgtat gggataaggg ccgggacttc   3240
gcgacggtga gaaaagtttt gtccatgccc caagtcaaca tagtaaagaa aactgaggtg   3300
cagaccggag ggttttcaaa ggaatcgatt cttccaaaaa ggaatagtga taagctcatc   3360
gctcgtaaaa aggactggga cccgaaaaag tacggtggct tcgatagccc tacagttgcc   3420
tattctgtcc tagtagtggc aaaagttgag aagggaaaat ccaagaaact gaagtcagtc   3480
aaagaattat tggggataac gattatggag cgctcgtctt ttgaaaagaa ccccatcgac   3540
ttccttgagg cgaaaggtta caaggaagta aaaaaggatc tcataattaa actaccaaag   3600
tatagtctgt ttgagttaga aaatggccga aaacggatgt tggctagcgc cggagagctt   3660
caaaagggga acgaactcgc actaccgtct aaatacgtga atttcctgta tttagcgtcc   3720
cattacgaga agttgaaagg ttcacctgaa gataacgaac agaagcaact ttttgttgag   3780
cagcacaaac attatctcga cgaaatcata gagcaaattt cggaattcag taagagagtc   3840
atcctagctg atgccaatct ggacaaagta ttaagcgcat acaacaagca cagggataaa   3900
cccatacgtg agcaggcgga aaatattatc catttgttta ctcttaccaa cctcggcgct   3960
ccagccgcat tcaagtattt tgacacaacg atagatcgca aacgatacac ttctaccaag   4020
gaggtgctag acgcgacact gattcaccaa tccatcacgg gattatatga aactcggata   4080
```

```
gatttgtcac agcttggggg tgacggatcc cccaagaaga agaggaaagt ctcgagcgac   4140

tacaaagacc atgacggtga ttataaagat catgacatcg attacaagga tgacgatgac   4200

aaggctgcag ga                                                       4212


<210> SEQ ID NO 4
<211> LENGTH: 1368
<212> TYPE: PRT
<213> ORGANISM: Artificial Sequence
<220> FEATURE:
<223> OTHER INFORMATION: Synthetic Polypeptide

<400> SEQUENCE: 4

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335
```

```
Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750
```

```
Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
```

```
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365


<210> SEQ ID NO 5
<211> LENGTH: 1368
<212> TYPE: PRT
<213> ORGANISM: Artificial Sequence
<220> FEATURE:
<223> OTHER INFORMATION: Synthetic Polypeptide

<400> SEQUENCE: 5

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
```

-continued

```
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575
```

```
Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990
```

-continued

```
Val Gly Thr Ala Leu Ile Lys Lys  Tyr Pro Lys Leu Glu  Ser Glu Phe
        995                 1000                 1005

Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 6
<211> LENGTH: 198
<212> TYPE: PRT

<213> ORGANISM: Artificial Sequence
<220> FEATURE:
<223> OTHER INFORMATION: Synthetic Polypeptide

<400> SEQUENCE: 6

```
Gly Ser Gln Leu Val Lys Ser Glu Leu Glu Glu Lys Lys Ser Glu Leu
1               5                   10                  15

Arg His Lys Leu Lys Tyr Val Pro His Glu Tyr Ile Glu Leu Ile Glu
            20                  25                  30

Ile Ala Arg Asn Ser Thr Gln Asp Arg Ile Leu Glu Met Lys Val Met
        35                  40                  45

Glu Phe Phe Met Lys Val Tyr Gly Tyr Arg Gly Lys His Leu Gly Gly
    50                  55                  60

Ser Arg Lys Pro Asp Gly Ala Ile Tyr Thr Val Gly Ser Pro Ile Asp
65                  70                  75                  80

Tyr Gly Val Ile Val Asp Thr Lys Ala Tyr Ser Gly Gly Tyr Asn Leu
                85                  90                  95

Pro Ile Gly Gln Ala Asp Glu Met Gln Arg Tyr Val Glu Glu Asn Gln
            100                 105                 110

Thr Arg Asn Lys His Ile Asn Pro Asn Glu Trp Trp Lys Val Tyr Pro
        115                 120                 125

Ser Ser Val Thr Glu Phe Lys Phe Leu Phe Val Ser Gly His Phe Lys
    130                 135                 140

Gly Asn Tyr Lys Ala Gln Leu Thr Arg Leu Asn His Ile Thr Asn Cys
145                 150                 155                 160

Asn Gly Ala Val Leu Ser Val Glu Glu Leu Leu Ile Gly Gly Glu Met
                165                 170                 175

Ile Lys Ala Gly Thr Leu Thr Leu Glu Glu Val Arg Arg Lys Phe Asn
            180                 185                 190

Asn Gly Glu Ile Asn Phe
        195
```

<210> SEQ ID NO 7
<211> LENGTH: 4221
<212> TYPE: DNA
<213> ORGANISM: Artificial Sequence
<220> FEATURE:
<223> OTHER INFORMATION: Synthetic Polynucleotide

<400> SEQUENCE: 7

```
atggactata aggaccacga cggagactac aaggatcatg atattgatta caaagacgat      60

gacgataaga tggccccaaa gaagaagcgg aaggtcggta tccacggagt cccagcagcc     120

gataaaaagt attctattgg tttagctatc ggcactaatt ccgttggatg ggctgtcata     180

accgatgaat acaaagtacc ttcaaagaaa tttaaggtgt tggggaacac agaccgtcat     240

tcgattaaaa agaatcttat cggtgccctc ctattcgata gtggcgaaac ggcagaggcg     300

actcgcctga aacgaaccgc tcggagaagg tatacacgtc gcaagaaccg aatatgttac     360

ttacaagaaa tttttagcaa tgagatggcc aaagttgacg attctttctt tcaccgtttg     420

gaagagtcct tccttgtcga agaggacaag aaacatgaac ggcaccccat ctttggaaac     480

atagtagatg aggtggcata tcatgaaaag tacccaacga tttatcacct cagaaaaaag     540

ctagttgact caactgataa agcggacctg aggttaatct acttggctct tgcccatatg     600

ataaagttcc gtgggcactt tctcattgag ggtgatctaa atccggacaa ctcggatgtc     660

gacaaactgt tcatccagtt agtacaaacc tataatcagt tgtttgaaga gaaccctata     720
```

-continued

```
aatgcaagtg gcgtggatgc gaaggctatt cttagcgccc gcctctctaa atcccgacgg    780
ctagaaaacc tgatcgcaca attacccgga gagaagaaaa atgggttgtt cggtaacctt    840
atagcgctct cactaggcct gacaccaaat tttaagtcga acttcgactt agctgaagat    900
gccaaattgc agcttagtaa ggacacgtac gatgacgatc tcgacaatct actggcacaa    960
attggagatc agtatgcgga cttatttttg gctgccaaaa accttagcga tgcaatcctc   1020
ctatctgaca tactgagagt taatactgag attaccaagg cgccgttatc cgcttcaatg   1080
atcaaaaggt acgatgaaca tcaccaagac ttgacacttc tcaaggccct agtccgtcag   1140
caactgcctg agaaatataa ggaaatattc tttgatcagt cgaaaaacgg gtacgcaggt   1200
tatattgacg gcggagcgag tcaagaggaa ttctacaagt ttatcaaacc catattagag   1260
aagatggatg ggacggaaga gttgcttgta aaactcaatc gcgaagatct actgcgaaag   1320
cagcggactt tcgacaacgg tagcattcca catcaaatcc acttaggcga attgcatgct   1380
atacttagaa ggcaggagga tttttatccg ttcctcaaag acaatcgtga aaagattgag   1440
aaaatcctaa cctttcgcat accttactat gtgggacccc tggcccgagg gaactctcgg   1500
ttcgcatgga tgacaagaaa gtccgaagaa acgattactc catggaattt tgaggaagtt   1560
gtcgataaag gtgcgtcagc tcaatcgttc atcgagagga tgaccaactt tgacaagaat   1620
ttaccgaacg aaaaagtatt gcctaagcac agtttacttt acgagtattt cacagtgtac   1680
aatgaactca cgaaagttaa gtatgtcact gagggcatgc gtaaacccgc ctttctaagc   1740
ggagaacaga agaaagcaat agtagatctg ttattcaaga ccaaccgcaa agtgacagtt   1800
aagcaattga aagaggacta ctttaagaaa attgaatgct tcgattctgt cgagatctcc   1860
ggggtagaag atcgatttaa tgcgtcactt ggtacgtatc atgacctcct aaagataatt   1920
aaagataagg acttcctgga taacgaagag aatgaagata tcttagaaga tatagtgttg   1980
actcttaccc tctttgaaga tcgggaaatg attgaggaaa gactaaaaac atacgctcac   2040
ctgttcgacg ataaggttat gaaacagtta aagaggcgtc gctatacggg ctggggacga   2100
ttgtcgcgga aacttatcaa cgggataaga gacaagcaaa gtggtaaaac tattctcgat   2160
tttctaaaga gcgacggctt cgccaatagg aactttatgc agctgatcca tgatgactct   2220
ttaaccttca aagaggatat acaaaaggca caggtttccg gacaagggga ctcattgcac   2280
gaacatattg cgaatcttgc tggttcgcca gccatcaaaa agggcatact ccagacagtc   2340
aaagtagtgg atgagctagt taaggtcatg ggacgtcaca aaccggaaaa cattgtaatc   2400
gagatggcac gcgaaaatca aacgactcag aaggggcaaa aaaacagtcg agagcggatg   2460
aagagaatag aagagggtat taaagaactg ggcagccaga tcttaaagga gcatcctgtg   2520
gaaaataccc aattgcagaa cgagaaactt tacctctatt acctacaaaa tggaagggac   2580
atgtatgttg atcaggaact ggacataaac cgtttatctg attacgacgt cgatcacatt   2640
gtaccccaat cctttttgaa ggacgattca atcgacaata aagtgcttac acgctcggat   2700
aagaaccgag ggaaaagtga caatgttcca agcgaggaag tcgtaaagaa aatgaagaac   2760
tattggcggc agctcctaaa tgcgaaactg ataacgcaaa gaaagttcga taacttaact   2820
aaagctgaga ggggtggctt gtctgaactt gacaaggccg gatttattaa acgtcagctc   2880
gtggaaaccc gccaaatcac aaagcatgtt gcacagatac tagattcccg aatgaatacg   2940
aaatacgacg agaacgataa gctgattcgg gaagtcaaag taatcacttt aaagtcaaaa   3000
ttggtgtcgg acttcagaaa ggattttcaa ttctataaag ttagggagat aaataactac   3060
caccatgcgc acgacgctta tcttaatgcc gtcgtaggga ccgcactcat taagaaatac   3120
```

-continued ccgaagctag aaagtgagtt tgtgtatggt gattacaaag tttatgacgt ccgtaagatg 3180
atcgcgaaaa gcgaacagga gataggcaag gctacagcca aatacttctt ttattctaac 3240
attatgaatt tctttaagac ggaaatcact ctggcaaacg gagagatacg caaacgacct 3300
ttaattgaaa ccaatgggga gacaggtgaa atcgtatggg ataagggccg ggacttcgcg 3360
acggtgagaa aagttttgtc catgccccaa gtcaacatag taaagaaaac tgaggtgcag 3420
accggagggt tttcaaagga atcgattctt ccaaaaagga atagtgataa gctcatcgct 3480
cgtaaaaagg actgggaccc gaaaaagtac ggtggcttcg atagccctac agttgcctat 3540
tctgtcctag tagtggcaaa agttgagaag ggaaaatcca agaaactgaa gtcagtcaaa 3600
gaattattgg ggataacgat tatggagcgc tcgtcttttg aaaagaaccc catcgacttc 3660
cttgaggcga aaggttacaa ggaagtaaaa aaggatctca taattaaact accaaagtat 3720
agtctgtttg agttagaaaa tggccgaaaa cggatgttgg ctagcgccgg agagcttcaa 3780
aaggggaacg aactcgcact accgtctaaa tacgtgaatt tcctgtattt agcgtcccat 3840
tacgagaagt tgaaaggttc acctgaagat aacgaacaga agcaactttt tgttgagcag 3900
cacaaacatt atctcgacga aatcatagag caaatttcgg aattcagtaa gagagtcatc 3960
ctagctgatg ccaatctgga caaagtatta agcgcataca acaagcacag ggataaaccc 4020
atacgtgagc aggcggaaaa tattatccat ttgtttactc ttaccaacct cggcgctcca 4080
gccgcattca agtattttga cacaacgata gatcgcaaac gatacacttc taccaaggag 4140
gtgctagacg cgacactgat tcaccaatcc atcacgggat tatatgaaac tcggatagat 4200
ttgtcacagc ttgggggtga c 4221

<210> SEQ ID NO 8
<211> LENGTH: 1368
<212> TYPE: PRT
<213> ORGANISM: Artificial Sequence
<220> FEATURE:
<223> OTHER INFORMATION: Synthetic Polypeptide

<400> SEQUENCE: 8

Met Asp Lys Lys Tyr Ser Ile Gly Leu Ala Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

-continued

```
Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
```

```
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005
```

Val Tyr Gly Asp Tyr Lys Val Tyr Asp Val Arg Lys Met Ile Ala
1010 1015 1020

Lys Ser Glu Gln Glu Ile Gly Lys Ala Thr Ala Lys Tyr Phe Phe
1025 1030 1035

Tyr Ser Asn Ile Met Asn Phe Phe Lys Thr Glu Ile Thr Leu Ala
1040 1045 1050

Asn Gly Glu Ile Arg Lys Arg Pro Leu Ile Glu Thr Asn Gly Glu
1055 1060 1065

Thr Gly Glu Ile Val Trp Asp Lys Gly Arg Asp Phe Ala Thr Val
1070 1075 1080

Arg Lys Val Leu Ser Met Pro Gln Val Asn Ile Val Lys Lys Thr
1085 1090 1095

Glu Val Gln Thr Gly Gly Phe Ser Lys Glu Ser Ile Leu Pro Lys
1100 1105 1110

Arg Asn Ser Asp Lys Leu Ile Ala Arg Lys Lys Asp Trp Asp Pro
1115 1120 1125

Lys Lys Tyr Gly Gly Phe Asp Ser Pro Thr Val Ala Tyr Ser Val
1130 1135 1140

Leu Val Val Ala Lys Val Glu Lys Gly Lys Ser Lys Lys Leu Lys
1145 1150 1155

Ser Val Lys Glu Leu Leu Gly Ile Thr Ile Met Glu Arg Ser Ser
1160 1165 1170

Phe Glu Lys Asn Pro Ile Asp Phe Leu Glu Ala Lys Gly Tyr Lys
1175 1180 1185

Glu Val Lys Lys Asp Leu Ile Ile Lys Leu Pro Lys Tyr Ser Leu
1190 1195 1200

Phe Glu Leu Glu Asn Gly Arg Lys Arg Met Leu Ala Ser Ala Gly
1205 1210 1215

Glu Leu Gln Lys Gly Asn Glu Leu Ala Leu Pro Ser Lys Tyr Val
1220 1225 1230

Asn Phe Leu Tyr Leu Ala Ser His Tyr Glu Lys Leu Lys Gly Ser
1235 1240 1245

Pro Glu Asp Asn Glu Gln Lys Gln Leu Phe Val Glu Gln His Lys
1250 1255 1260

His Tyr Leu Asp Glu Ile Ile Glu Gln Ile Ser Glu Phe Ser Lys
1265 1270 1275

Arg Val Ile Leu Ala Asp Ala Asn Leu Asp Lys Val Leu Ser Ala
1280 1285 1290

Tyr Asn Lys His Arg Asp Lys Pro Ile Arg Glu Gln Ala Glu Asn
1295 1300 1305

Ile Ile His Leu Phe Thr Leu Thr Asn Leu Gly Ala Pro Ala Ala
1310 1315 1320

Phe Lys Tyr Phe Asp Thr Thr Ile Asp Arg Lys Arg Tyr Thr Ser
1325 1330 1335

Thr Lys Glu Val Leu Asp Ala Thr Leu Ile His Gln Ser Ile Thr
1340 1345 1350

Gly Leu Tyr Glu Thr Arg Ile Asp Leu Ser Gln Leu Gly Gly Asp
1355 1360 1365

<210> SEQ ID NO 9
<211> LENGTH: 4836
<212> TYPE: DNA
<213> ORGANISM: Artificial Sequence
<220> FEATURE:

<223> OTHER INFORMATION: Synthetic Polynucleotide

<400> SEQUENCE: 9

```
atggataaaa agtattctat tggtttagct atcggcacta attccgttgg atgggctgtc     60
ataaccgatg aatacaaagt accttcaaag aaatttaagg tgttggggaa cacagaccgt    120
cattcgatta aaaagaatct tatcggtgcc ctcctattcg atagtggcga aacggcagag    180
gcgactcgcc tgaaacgaac cgctcggaga aggtatacac gtcgcaagaa ccgaatatgt    240
tacttacaag aaatttttag caatgagatg gccaaagttg acgattcttt ctttcaccgt    300
ttggaagagt ccttccttgt cgaagaggac aagaaacatg aacggcaccc catctttgga    360
aacatagtag atgaggtggc atatcatgaa aagtacccaa cgatttatca cctcagaaaa    420
aagctagttg actcaactga taaagcggac ctgaggttaa tctacttggc tcttgcccat    480
atgataaagt tccgtgggca ctttctcatt gagggtgatc taaatccgga caactcggat    540
gtcgacaaac tgttcatcca gttagtacaa acctataatc agttgtttga agagaaccct    600
ataaatgcaa gtggcgtgga tgcgaaggct attcttagcg cccgcctctc taaatcccga    660
cggctagaaa acctgatcgc acaattaccc ggagagaaga aaaatgggtt gttcggtaac    720
cttatagcgc tctcactagg cctgacacca aattttaagt cgaacttcga cttagctgaa    780
gatgccaaat tgcagcttag taaggacacg tacgatgacg atctcgacaa tctactggca    840
caaattggag atcagtatgc ggacttattt ttggctgcca aaaaccttag cgatgcaatc    900
ctcctatctg acatactgag agttaatact gagattacca aggcgccgtt atccgcttca    960
atgatcaaaa ggtacgatga acatcaccaa gacttgacac ttctcaaggc cctagtccgt   1020
cagcaactgc ctgagaaata taaggaaata ttctttgatc agtcgaaaaa cgggtacgca   1080
ggttatattg acggcggagc gagtcaagag gaattctaca agtttatcaa acccatatta   1140
gagaagatgg atgggacgga agagttgctt gtaaaactca atcgcgaaga tctactgcga   1200
aagcagcgga ctttcgacaa cggtagcatt ccacatcaaa tccacttagg cgaattgcat   1260
gctatactta gaaggcagga ggatttttat ccgttcctca aagacaatcg tgaaaagatt   1320
gagaaaatcc taacctttcg cataccttac tatgtgggac ccctggcccg agggaactct   1380
cggttcgcat ggatgacaag aaagtccgaa gaaacgatta ctccatggaa ttttgaggaa   1440
gttgtcgata aaggtgcgtc agctcaatcg ttcatcgaga ggatgaccaa ctttgacaag   1500
aatttaccga acgaaaaagt attgcctaag cacagtttac tttacgagta tttcacagtg   1560
tacaatgaac tcacgaaagt taagtatgtc actgagggca tgcgtaaacc cgcctttcta   1620
agcggagaac agaagaaagc aatagtagat ctgttattca agaccaaccg caaagtgaca   1680
gttaagcaat tgaaagagga ctactttaag aaaattgaat gcttcgattc tgtcgagatc   1740
tccggggtag aagatcgatt taatgcgtca cttggtacgt atcatgacct cctaaagata   1800
attaaagata aggacttcct ggataacgaa gagaatgaag atatcttaga agatatagtg   1860
ttgactctta ccctctttga agatcgggaa atgattgagg aaagactaaa aacatacgct   1920
cacctgttcg acgataaggt tatgaaacag ttaaagaggc gtcgctatac gggctgggga   1980
cgattgtcgc ggaaacttat caacgggata agagacaagc aaagtggtaa aactattctc   2040
gattttctaa agagcgacgg cttcgccaat aggaacttta tgcagctgat ccatgatgac   2100
tctttaacct tcaaagagga tatacaaaag gcacaggttt ccggacaagg ggactcattg   2160
cacgaacata ttgcgaatct tgctggttcg ccagccatca aaaagggcat actccagaca   2220
gtcaaagtag tggatgagct agttaaggtc atgggacgtc acaaaccgga aaacattgta   2280
```

atcgagatgg cacgcgaaaa tcaaacgact cagaaggggc aaaaaaacag tcgagagcgg 2340
atgaagagaa tagaagaggg tattaaagaa ctgggcagcc agatcttaaa ggagcatcct 2400
gtggaaaata cccaattgca gaacgagaaa ctttacctct attacctaca aaatggaagg 2460
gacatgtatg ttgatcagga actggacata aaccgtttat ctgattacga cgtcgatgcc 2520
attgtacccc aatccttttt gaaggacgat tcaatcgaca ataaagtgct tacacgctcg 2580
gataagaacc gagggaaaag tgacaatgtt ccaagcgagg aagtcgtaaa gaaaatgaag 2640
aactattggc ggcagctcct aaatgcgaaa ctgataacgc aaagaaagtt cgataactta 2700
actaaagctg agaggggtgg cttgtctgaa cttgacaagg ccggatttat taaacgtcag 2760
ctcgtggaaa cccgccaaat cacaaagcat gttgcacaga tactagattc ccgaatgaat 2820
acgaaatacg acgagaacga taagctgatt cgggaagtca aagtaatcac tttaaagtca 2880
aaattggtgt cggacttcag aaaggatttt caattctata aagttaggga gataaataac 2940
taccaccatg cgcacgacgc ttatcttaat gccgtcgtag ggaccgcact cattaagaaa 3000
tacccgaagc tagaaagtga gtttgtgtat ggtgattaca aagtttatga cgtccgtaag 3060
atgatcgcga aaagcgaaca ggagataggc aaggctacag ccaaatactt cttttattct 3120
aacattatga atttctttaa gacggaaatc actctggcaa acggagagat acgcaaacga 3180
cctttaattg aaaccaatgg ggagacaggt gaaatcgtat gggataaggg ccgggacttc 3240
gcgacggtga gaaaagtttt gtccatgccc caagtcaaca tagtaaagaa aactgaggtg 3300
cagaccggag ggttttcaaa ggaatcgatt cttccaaaaa ggaatagtga taagctcatc 3360
gctcgtaaaa aggactggga cccgaaaaag tacggtggct tcgatagccc tacagttgcc 3420
tattctgtcc tagtagtggc aaaagttgag aagggaaaat ccaagaaact gaagtcagtc 3480
aaagaattat tggggataac gattatggag cgctcgtctt ttgaaaagaa ccccatcgac 3540
ttccttgagg cgaaaggtta caaggaagta aaaaaggatc tcataattaa actaccaaag 3600
tatagtctgt ttgagttaga aaatggccga aaacggatgt tggctagcgc cggagagctt 3660
caaaagggga acgaactcgc actaccgtct aaatacgtga atttcctgta tttagcgtcc 3720
cattacgaga agttgaaagg ttcacctgaa gataacgaac agaagcaact tttgttgag 3780 cagcacaaac attatctcga cgaaatcata gagcaaattt cggaattcag taagagagtc 3840
atcctagctg atgccaatct ggacaaagta ttaagcgcat acaacaagca cagggataaa 3900
cccatacgtg agcaggcgga aaatattatc catttgttta ctcttaccaa cctcggcgct 3960
ccagccgcat tcaagtattt tgacacaacg atagatcgca aacgatacac ttctaccaag 4020
gaggtgctag acgcgacact gattcaccaa tccatcacgg gattatatga aactcggata 4080
gatttgtcac agcttggggg tgacggatcc cccaagaaga agaggaaagt ctcgagcgac 4140
tacaaagacc atgacggtga ttataaagat catgacatcg attacaagga tgacgatgac 4200
aaggctgcag gatcaggtgg aagtggcggc agcggaggtt ctggatccca actagtcaaa 4260
agtgaactgg aggagaagaa atctgaactt cgtcataaat tgaaatatgt gcctcatgaa 4320
tatattgaat taattgaaat tgccagaaat tccactcagg atagaattct tgaaatgaag 4380
gtaatggaat tttttatgaa agtttatgga tatagaggta aacatttggg tggatcaagg 4440
aaaccggacg gagcaattta tactgtcgga tctcctattg attacggtgt gatcgtggat 4500
actaaagctt atagcggagg ttataatctg ccaattggcc aagcagatga aatgcaacga 4560
tatgtcgaag aaaatcaaac acgaaacaaa catatcaacc ctaatgaatg gtggaaagtc 4620
tatccatctt ctgtaacgga atttaagttt ttatttgtga gtggtcactt taaaggaaac 4680
tacaaagctc agcttacacg attaaatcat atcactaatt gtaatggagc tgttcttagt 4740
gtagaagagc ttttaattgg tggagaaatg attaaagccg gcacattaac cttagaggaa 4800
gtcagacgga aatttaataa cggcgagata aacttt 4836

<210> SEQ ID NO 10
<211> LENGTH: 4845
<212> TYPE: DNA
<213> ORGANISM: Artificial Sequence
<220> FEATURE:
<223> OTHER INFORMATION: Synthetic Polynucleotide

<400> SEQUENCE: 10
atggactaca aagaccatga cggtgattat aaagatcatg acatcgatta caaggatgac 60
gatgacaaga tggcccccaa gaagaagagg aaggtgggca ttcaccgcgg ggtacctatg 120
gataaaaagt attctattgg tttagctatc ggcactaatt ccgttggatg ggctgtcata 180
accgatgaat acaaagtacc ttcaaagaaa tttaaggtgt tggggaacac agaccgtcat 240
tcgattaaaa agaatcttat cggtgccctc ctattcgata gtggcgaaac ggcagaggcg 300
actcgcctga aacgaaccgc tcggagaagg tatacacgtc gcaagaaccg aatatgttac 360
ttacaagaaa tttttagcaa tgagatggcc aaagttgacg attctttctt tcaccgtttg 420
gaagagtcct tccttgtcga agaggacaag aaacatgaac ggcaccccat ctttggaaac 480
atagtagatg aggtggcata tcatgaaaag tacccaacga tttatcacct cagaaaaaag 540
ctagttgact caactgataa agcggacctg aggttaatct acttggctct tgcccatatg 600
ataaagttcc gtgggcactt tctcattgag ggtgatctaa atccggacaa ctcggatgtc 660
gacaaactgt tcatccagtt agtacaaacc tataatcagt tgtttgaaga gaaccctata 720
aatgcaagtg gcgtggatgc gaaggctatt cttagcgccc gcctctctaa atcccgacgg 780
ctagaaaacc tgatcgcaca attacccgga gagaagaaaa atgggttgtt cggtaacctt 840
atagcgctct cactaggcct gacaccaaat tttaagtcga acttcgactt agctgaagat 900
gccaaattgc agcttagtaa ggacacgtac gatgacgatc tcgacaatct actggcacaa 960
attggagatc agtatgcgga cttatttttg gctgccaaaa accttagcga tgcaatcctc 1020
ctatctgaca tactgagagt taatactgag attaccaagg cgccgttatc cgcttcaatg 1080
atcaaaaggt acgatgaaca tcaccaagac ttgacacttc tcaaggccct agtccgtcag 1140
caactgcctg agaaatataa ggaaatattc tttgatcagt cgaaaaacgg gtacgcaggt 1200
tatattgacg gcggagcgag tcaagaggaa ttctacaagt ttatcaaacc catattagag 1260
aagatggatg ggacggaaga gttgcttgta aaactcaatc gcgaagatct actgcgaaag 1320
cagcggactt tcgacaacgg tagcattcca catcaaatcc acttaggcga attgcatgct 1380
atacttagaa ggcaggagga tttttatccg ttcctcaaag acaatcgtga aaagattgag 1440
aaaatcctaa cctttcgcat accttactat gtgggacccc tggcccgagg gaactctcgg 1500
ttcgcatgga tgacaagaaa gtccgaagaa acgattactc catggaattt tgaggaagtt 1560
gtcgataaag gtgcgtcagc tcaatcgttc atcgagagga tgaccaactt tgacaagaat 1620
ttaccgaacg aaaaagtatt gcctaagcac agtttacttt acgagtattt cacagtgtac 1680
aatgaactca cgaaagttaa gtatgtcact gagggcatgc gtaaacccgc ctttctaagc 1740
ggagaacaga agaaagcaat agtagatctg ttattcaaga ccaaccgcaa agtgacagtt 1800
aagcaattga aagaggacta ctttaagaaa attgaatgct tcgattctgt cgagatctcc 1860

-continued

```
ggggtagaag atcgatttaa tgcgtcactt ggtacgtatc atgacctcct aaagataatt   1920
aaagataagg acttcctgga taacgaagag aatgaagata tcttagaaga tatagtgttg   1980
actcttaccc tctttgaaga tcgggaaatg attgaggaaa gactaaaaac atacgctcac   2040
ctgttcgacg ataaggttat gaaacagtta aagaggcgtc gctatacggg ctggggacga   2100
ttgtcgcgga aacttatcaa cgggataaga gacaagcaaa gtggtaaaac tattctcgat   2160
tttctaaaga gcgacggctt cgccaatagg aactttatgc agctgatcca tgatgactct   2220
ttaaccttca aagaggatat acaaaaggca caggtttccg gacaagggga ctcattgcac   2280
gaacatattg cgaatcttgc tggttcgcca gccatcaaaa agggcatact ccagacagtc   2340
aaagtagtgg atgagctagt taaggtcatg ggacgtcaca aaccggaaaa cattgtaatc   2400
gagatggcac gcgaaaatca aacgactcag aaggggcaaa aaaacagtcg agagcggatg   2460
aagagaatag aagagggtat taaagaactg ggcagccaga tcttaaagga gcatcctgtg   2520
gaaaataccc aattgcagaa cgagaaactt tacctctatt acctacaaaa tggaagggac   2580
atgtatgttg atcaggaact ggacataaac cgtttatctg attacgacgt cgatgccatt   2640
gtaccccaat cctttttgaa ggacgattca atcgacaata aagtgcttac acgctcggat   2700
aagaaccgag ggaaaagtga caatgttcca agcgaggaag tcgtaaagaa aatgaagaac   2760
tattggcggc agctcctaaa tgcgaaactg ataacgcaaa gaaagttcga taacttaact   2820
aaagctgaga ggggtggctt gtctgaactt gacaaggccg gatttattaa acgtcagctc   2880
gtggaaaccc gccaaatcac aaagcatgtt gcacagatac tagattcccg aatgaatacg   2940
aaatacgacg agaacgataa gctgattcgg gaagtcaaag taatcacttt aaagtcaaaa   3000
ttggtgtcgg acttcagaaa ggattttcaa ttctataaag ttagggagat aaataactac   3060
caccatgcgc acgacgctta tcttaatgcc gtcgtaggga ccgcactcat taagaaatac   3120
ccgaagctag aaagtgagtt tgtgtatggt gattacaaag tttatgacgt ccgtaagatg   3180
atcgcgaaaa gcgaacagga gataggcaag gctacagcca aatacttctt ttattctaac   3240
attatgaatt tctttaagac ggaaatcact ctggcaaacg gagagatacg caaacgacct   3300
ttaattgaaa ccaatgggga gacaggtgaa atcgtatggg ataagggccg ggacttcgcg   3360
acggtgagaa aagttttgtc catgccccaa gtcaacatag taaagaaaac tgaggtgcag   3420
accggagggt tttcaaagga atcgattctt ccaaaaagga atagtgataa gctcatcgct   3480
cgtaaaaagg actgggaccc gaaaaagtac ggtggcttcg atagccctac agttgcctat   3540
tctgtcctag tagtggcaaa agttgagaag ggaaaatcca agaaactgaa gtcagtcaaa   3600
gaattattgg ggataacgat tatggagcgc tcgtcttttg aaaagaaccc catcgacttc   3660
cttgaggcga aaggttacaa ggaagtaaaa aaggatctca taattaaact accaaagtat   3720
agtctgtttg agttagaaaa tggccgaaaa cggatgttgg ctagcgccgg agagcttcaa   3780
aaggggaacg aactcgcact accgtctaaa tacgtgaatt tcctgtattt agcgtcccat   3840
tacgagaagt tgaaaggttc acctgaagat aacgaacaga agcaactttt tgttgagcag   3900
cacaaacatt atctcgacga aatcatagag caaatttcgg aattcagtaa gagagtcatc   3960
ctagctgatg ccaatctgga caaagtatta agcgcataca acaagcacag ggataaaccc   4020
atacgtgagc aggcggaaaa tattatccat ttgtttactc ttaccaacct cggcgctcca   4080
gccgcattca agtattttga cacaacgata gatcgcaaac gatacacttc taccaaggag   4140
gtgctagacg cgacactgat tcaccaatcc atcacgggat tatatgaaac tcggatagat   4200
```

ttgtcacagc ttgggggtga ctcaggtgga agtggcggca gcggaggttc tggatcccaa 4260
ctagtcaaaa gtgaactgga ggagaagaaa tctgaacttc gtcataaatt gaaatatgtg 4320
cctcatgaat atattgaatt aattgaaatt gccagaaatt ccactcagga tagaattctt 4380
gaaatgaagg taatggaatt ttttatgaaa gtttatggat atagaggtaa acatttgggt 4440
ggatcaagga aaccggacgg agcaatttat actgtcggat ctcctattga ttacggtgtg 4500
atcgtggata ctaaagctta tagcggaggt tataatctgc caattggcca agcagatgaa 4560
atgcaacgat atgtcgaaga aaatcaaaca cgaaacaaac atatcaaccc taatgaatgg 4620
tggaaagtct atccatcttc tgtaacggaa tttaagtttt tatttgtgag tggtcacttt 4680
aaaggaaact acaaagctca gcttacacga ttaaatcata tcactaattg taatggagct 4740
gttcttagtg tagaagagct tttaattggt ggagaaatga ttaaagccgg cacattaacc 4800
ttagaggaag tcagacggaa atttaataac ggcgagataa acttt 4845

<210> SEQ ID NO 11
<211> LENGTH: 4836
<212> TYPE: DNA
<213> ORGANISM: Artificial Sequence
<220> FEATURE:
<223> OTHER INFORMATION: Synthetic Polynucleotide

<400> SEQUENCE: 11
atgggatccc aactagtcaa aagtgaactg gaggagaaga aatctgaact tcgtcataaa 60
ttgaaatatg tgcctcatga atatattgaa ttaattgaaa ttgccagaaa ttccactcag 120
gatagaattc ttgaaatgaa ggtaatggaa tttttatga aagtttatgg atatagaggt 180
aaacatttgg gtggatcaag gaaaccggac ggagcaattt atactgtcgg atctcctatt 240
gattacggtg tgatcgtgga tactaaagct tatagcggag gttataatct gccaattggc 300
caagcagatg aaatgcaacg atatgtcgaa gaaaatcaaa cacgaaacaa acatatcaac 360
cctaatgaat ggtggaaagt ctatccatct tctgtaacgg aatttaagtt tttatttgtg 420
agtggtcact ttaaaggaaa ctacaaagct cagcttacac gattaaatca tatcactaat 480
tgtaatggag ctgttcttag tgtagaagag cttttaattg gtggagaaat gattaaagcc 540
ggcacattaa ccttagagga agtcagacgg aaatttaata acggcgagat aaactttggc 600
ggtagtgggg gatctggggg aagtatggat aaaaagtatt ctattggttt agctatcggc 660
actaattccg ttggatgggc tgtcataacc gatgaataca aagtaccttc aaagaaattt 720
aaggtgttgg ggaacacaga ccgtcattcg attaaaaaga atcttatcgg tgccctccta 780
ttcgatagtg gcgaaacggc agaggcgact cgcctgaaac gaaccgctcg gagaaggtat 840
acacgtcgca agaaccgaat atgttactta caagaaattt ttagcaatga gatggccaaa 900
gttgacgatt ctttctttca ccgtttggaa gagtccttcc ttgtcgaaga ggacaagaaa 960
catgaacggc accccatctt tggaaacata gtagatgagg tggcatatca tgaaaagtac 1020
ccaacgattt atcacctcag aaaaaagcta gttgactcaa ctgataaagc ggacctgagg 1080
ttaatctact tggctcttgc ccatatgata aagttccgtg ggcactttct cattgagggt 1140
gatctaaatc cggacaactc ggatgtcgac aaactgttca tccagttagt acaaacctat 1200
aatcagttgt ttgaagagaa ccctataaat gcaagtggcg tggatgcgaa ggctattctt 1260
agcgcccgcc tctctaaatc ccgacggcta gaaaacctga tcgcacaatt acccggagag 1320
aagaaaaatg ggttgttcgg taaccttata gcgctctcac taggcctgac accaaatttt 1380
aagtcgaact tcgacttagc tgaagatgcc aaattgcagc ttagtaagga cacgtacgat 1440

-continued

```
gacgatctcg acaatctact ggcacaaatt ggagatcagt atgcggactt atttttggct   1500
gccaaaaacc ttagcgatgc aatcctccta tctgacatac tgagagttaa tactgagatt   1560
accaaggcgc cgttatccgc ttcaatgatc aaaaggtacg atgaacatca ccaagacttg   1620
acacttctca aggccctagt ccgtcagcaa ctgcctgaga aatataagga aatattcttt   1680
gatcagtcga aaaacgggta cgcaggttat attgacggcg gagcgagtca agaggaattc   1740
tacaagttta tcaaacccat attagagaag atggatggga cggaagagtt gcttgtaaaa   1800
ctcaatcgcg aagatctact gcgaaagcag cggactttcg acaacggtag cattccacat   1860
caaatccact taggcgaatt gcatgctata cttagaaggc aggaggattt ttatccgttc   1920
ctcaaagaca atcgtgaaaa gattgagaaa atcctaacct ttcgcatacc ttactatgtg   1980
ggacccctgg cccgagggaa ctctcggttc gcatggatga caagaaagtc cgaagaaacg   2040
attactccat ggaattttga ggaagttgtc gataaaggtg cgtcagctca atcgttcatc   2100
gagaggatga ccaactttga caagaattta ccgaacgaaa aagtattgcc taagcacagt   2160
ttactttacg agtatttcac agtgtacaat gaactcacga aagttaagta tgtcactgag   2220
ggcatgcgta aacccgcctt tctaagcgga gaacagaaga aagcaatagt agatctgtta   2280
ttcaagacca accgcaaagt gacagttaag caattgaaag aggactactt taagaaaatt   2340
gaatgcttcg attctgtcga gatctccggg gtagaagatc gatttaatgc gtcacttggt   2400
acgtatcatg acctcctaaa gataattaaa gataaggact tcctggataa cgaagagaat   2460
gaagatatct tagaagatat agtgttgact cttaccctct ttgaagatcg ggaaatgatt   2520
gaggaaagac taaaaacata cgctcacctg ttcgacgata aggttatgaa acagttaaag   2580
aggcgtcgct atacgggctg gggacgattg tcgcggaaac ttatcaacgg gataagagac   2640
aagcaaagtg gtaaaactat tctcgatttt ctaaagagcg acggcttcgc caataggaac   2700
tttatgcagc tgatccatga tgactcttta accttcaaag aggatataca aaaggcacag   2760
gtttccggac aaggggactc attgcacgaa catattgcga atcttgctgg ttcgccagcc   2820
atcaaaaagg gcatactcca gacagtcaaa gtagtggatg agctagttaa ggtcatggga   2880
cgtcacaaac cggaaaacat tgtaatcgag atggcacgcg aaaatcaaac gactcagaag   2940
gggcaaaaaa acagtcgaga gcggatgaag agaatagaag agggtattaa agaactgggc   3000
agccagatct taaaggagca tcctgtggaa aatacccaat tgcagaacga gaaactttac   3060
ctctattacc tacaaaatgg aagggacatg tatgttgatc aggaactgga cataaaccgt   3120
ttatctgatt acgacgtcga tgccattgta ccccaatcct tttgaagga cgattcaatc    3180
gacaataaag tgcttacacg ctcggataag aaccgaggga aaagtgacaa tgttccaagc   3240
gaggaagtcg taaagaaaat gaagaactat tggcggcagc tcctaaatgc gaaactgata   3300
acgcaaagaa agttcgataa cttaactaaa gctgagaggg gtggcttgtc tgaacttgac   3360
aaggccggat ttattaaacg tcagctcgtg gaaacccgcc aaatcacaaa gcatgttgca   3420
cagatactag attcccgaat gaatacgaaa tacgacgaga acgataagct gattcgggaa   3480
gtcaaagtaa tcactttaaa gtcaaaattg gtgtcggact tcagaaagga ttttcaattc   3540
tataaagtta gggagataaa taactaccac catgcgcacg acgcttatct taatgccgtc   3600
gtagggaccg cactcattaa gaaatacccg aagctagaaa gtgagtttgt gtatggtgat   3660
tacaaagttt atgacgtccg taagatgatc gcgaaaagcg aacaggagat aggcaaggct   3720
acagccaaat acttctttta ttctaacatt atgaatttct ttaagacgga aatcactctg   3780
```

gcaaacggag agatacgcaa acgaccttta attgaaacca atggggagac aggtgaaatc 3840
gtatgggata agggccggga cttcgcgacg gtgagaaaag ttttgtccat gccccaagtc 3900
aacatagtaa agaaaactga ggtgcagacc ggagggtttt caaaggaatc gattcttcca 3960
aaaaggaata gtgataagct catcgctcgt aaaaaggact gggacccgaa aaagtacggt 4020
ggcttcgata gccctacagt tgcctattct gtcctagtag tggcaaaagt tgagaaggga 4080
aaatccaaga aactgaagtc agtcaaagaa ttattgggga taacgattat ggagcgctcg 4140
tcttttgaaa agaaccccat cgacttcctt gaggcgaaag gttacaagga agtaaaaaag 4200
gatctcataa ttaaactacc aaagtatagt ctgtttgagt tagaaaatgg ccgaaaacgg 4260
atgttggcta gcgccggaga gcttcaaaag gggaacgaac tcgcactacc gtctaaatac 4320
gtgaatttcc tgtatttagc gtcccattac gagaagttga aaggttcacc tgaagataac 4380
gaacagaagc aactttttgt tgagcagcac aaacattatc tcgacgaaat catagagcaa 4440
atttcggaat tcagtaagag agtcatccta gctgatgcca atctggacaa agtattaagc 4500
gcatacaaca agcacaggga taaacccata cgtgagcagg cggaaaatat tatccatttg 4560
tttactctta ccaacctcgg cgctccagcc gcattcaagt attttgacac aacgatagat 4620
cgcaaacgat acacttctac caaggaggtg ctagacgcga cactgattca ccaatccatc 4680
acgggattat atgaaactcg gatagatttg tcacagcttg gggtgacgg atcccccaag 4740 aagaagagga aagtctcgag cgactacaaa gaccatgacg gtgattataa agatcatgac 4800
atcgattaca aggatgacga tgacaaggct gcagga 4836

<210> SEQ ID NO 12
<211> LENGTH: 4854
<212> TYPE: DNA
<213> ORGANISM: Artificial Sequence
<220> FEATURE:
<223> OTHER INFORMATION: Synthetic Polynucleotide

<400> SEQUENCE: 12
atggactaca aagaccatga cggtgattat aaagatcatg acatcgatta caaggatgac 60
gatgacaaga tggcccccaa gaagaagagg aaggtgggca ttcaccgcgg ggtacctgga 120
ggttctatgg gatcccaact agtcaaaagt gaactggagg agaagaaatc tgaacttcgt 180
cataaattga aatatgtgcc tcatgaatat attgaattaa ttgaaattgc cagaaattcc 240
actcaggata gaattcttga aatgaaggta atggaatttt ttatgaaagt ttatggatat 300
agaggtaaac atttgggtgg atcaaggaaa ccggacggag caatttatac tgtcggatct 360
cctattgatt acggtgtgat cgtggatact aaagcttata gcggaggtta taatctgcca 420
attggccaag cagatgaaat gcaacgatat gtcgaagaaa atcaaacacg aaacaaacat 480
atcaacccta atgaatggtg gaaagtctat ccatcttctg taacggaatt taagttttta 540
tttgtgagtg gtcactttaa aggaaactac aaagctcagc ttacacgatt aaatcatatc 600
actaattgta atggagctgt tcttagtgta gaagagcttt taattggtgg agaaatgatt 660
aaagccggca cattaacctt agaggaagtc agacggaaat ttaataacgg cgagataaac 720
tttggcggta gtgggggatc tgggggaagt atggataaaa agtattctat tggtttagct 780
atcggcacta attccgttgg atgggctgtc ataaccgatg aatacaaagt accttcaaag 840
aaatttaagg tgttggggaa cacagaccgt cattcgatta aaaagaatct tatcggtgcc 900
ctcctattcg atagtggcga aacggcagag gcgactcgcc tgaaacgaac cgctcggaga 960
aggtatacac gtcgcaagaa ccgaatatgt tacttacaag aaatttttag caatgagatg 1020
gccaaagttg acgattcttt ctttcaccgt ttggaagagt ccttccttgt cgaagaggac 1080
aagaaacatg aacggcaccc catctttgga aacatagtag atgaggtggc atatcatgaa 1140
aagtacccaa cgatttatca cctcagaaaa aagctagttg actcaactga taaagcggac 1200
ctgaggttaa tctacttggc tcttgcccat atgataaagt tccgtgggca ctttctcatt 1260
gagggtgatc taaatccgga caactcggat gtcgacaaac tgttcatcca gttagtacaa 1320
acctataatc agttgtttga agagaaccct ataaatgcaa gtggcgtgga tgcgaaggct 1380
attcttagcg cccgcctctc taaatcccga cggctagaaa acctgatcgc acaattaccc 1440
ggagagaaga aaaatgggtt gttcggtaac cttatagcgc tctcactagg cctgacacca 1500
aattttaagt cgaacttcga cttagctgaa gatgccaaat tgcagcttag taaggacacg 1560
tacgatgacg atctcgacaa tctactggca caaattggag atcagtatgc ggacttattt 1620
ttggctgcca aaaaccttag cgatgcaatc ctcctatctg acatactgag agttaatact 1680
gagattacca aggcgccgtt atccgcttca atgatcaaaa ggtacgatga acatcaccaa 1740
gacttgacac ttctcaaggc cctagtccgt cagcaactgc ctgagaaata taaggaaata 1800
ttctttgatc agtcgaaaaa cgggtacgca ggttatattg acggcggagc gagtcaagag 1860
gaattctaca agtttatcaa acccatatta gagaagatgg atgggacgga agagttgctt 1920
gtaaaactca atcgcgaaga tctactgcga aagcagcgga ctttcgacaa cggtagcatt 1980
ccacatcaaa tccacttagg cgaattgcat gctatactta gaaggcagga ggatttttat 2040
ccgttcctca aagacaatcg tgaaaagatt gagaaaatcc taacctttcg cataccttac 2100
tatgtgggac ccctggcccg agggaactct cggttcgcat ggatgacaag aaagtccgaa 2160
gaaacgatta ctccatggaa ttttgaggaa gttgtcgata aaggtgcgtc agctcaatcg 2220
ttcatcgaga ggatgaccaa ctttgacaag aatttaccga acgaaaaagt attgcctaag 2280
cacagtttac tttacgagta tttcacagtg tacaatgaac tcacgaaagt taagtatgtc 2340
actgagggca tgcgtaaacc cgcctttcta agcggagaac agaagaaagc aatagtagat 2400
ctgttattca agaccaaccg caaagtgaca gttaagcaat tgaaagagga ctactttaag 2460
aaaattgaat gcttcgattc tgtcgagatc tccggggtag aagatcgatt taatgcgtca 2520
cttggtacgt atcatgacct cctaaagata attaaagata aggacttcct ggataacgaa 2580
gagaatgaag atatcttaga agatatagtg ttgactctta ccctctttga agatcgggaa 2640
atgattgagg aaagactaaa aacatacgct cacctgttcg acgataaggt tatgaaacag 2700
ttaaagaggc gtcgctatac gggctgggga cgattgtcgc ggaaacttat caacgggata 2760
agagacaagc aaagtggtaa aactattctc gattttctaa agagcgacgg cttcgccaat 2820
aggaacttta tgcagctgat ccatgatgac tctttaacct tcaaagagga tatacaaaag 2880
gcacaggttt ccggacaagg ggactcattg cacgaacata ttgcgaatct tgctggttcg 2940
ccagccatca aaaagggcat actccagaca gtcaaagtag tggatgagct agttaaggtc 3000
atgggacgtc acaaaccgga aaacattgta atcgagatgg cacgcgaaaa tcaaacgact 3060
cagaaggggc aaaaaaacag tcgagagcgg atgaagagaa tagaagaggg tattaaagaa 3120
ctgggcagcc agatcttaaa ggagcatcct gtggaaaata cccaattgca gaacgagaaa 3180
ctttacctct attacctaca aaatggaagg gacatgtatg ttgatcagga actggacata 3240
aaccgtttat ctgattacga cgtcgatgcc attgtacccc aatccttttt gaaggacgat 3300
tcaatcgaca ataaagtgct tacacgctcg gataagaacc gagggaaaag tgacaatgtt 3360
ccaagcgagg aagtcgtaaa gaaaatgaag aactattggc ggcagctcct aaatgcgaaa 3420
ctgataacgc aaagaaagtt cgataactta actaaagctg agaggggtgg cttgtctgaa 3480
cttgacaagg ccggatttat taaacgtcag ctcgtggaaa cccgccaaat cacaaagcat 3540
gttgcacaga tactagattc ccgaatgaat acgaaatacg acgagaacga taagctgatt 3600
cgggaagtca aagtaatcac tttaaagtca aaattggtgt cggacttcag aaaggatttt 3660
caattctata aagttaggga gataaataac taccaccatg cgcacgacgc ttatcttaat 3720
gccgtcgtag ggaccgcact cattaagaaa tacccgaagc tagaaagtga gtttgtgtat 3780
ggtgattaca aagtttatga cgtccgtaag atgatcgcga aaagcgaaca ggagataggc 3840
aaggctacag ccaaatactt cttttattct aacattatga atttctttaa gacggaaatc 3900
actctggcaa acggagagat acgcaaacga cctttaattg aaaccaatgg ggagacaggt 3960
gaaatcgtat gggataaggg ccgggacttc gcgacggtga gaaaagtttt gtccatgccc 4020
caagtcaaca tagtaaagaa aactgaggtg cagaccggag ggttttcaaa ggaatcgatt 4080
cttccaaaaa ggaatagtga taagctcatc gctcgtaaaa aggactggga cccgaaaaag 4140
tacggtggct tcgatagccc tacagttgcc tattctgtcc tagtagtggc aaaagttgag 4200
aagggaaaat ccaagaaact gaagtcagtc aaagaattat tggggataac gattatggag 4260
cgctcgtctt ttgaaaagaa ccccatcgac ttccttgagg cgaaaggtta caaggaagta 4320
aaaaaggatc tcataattaa actaccaaag tatagtctgt ttgagttaga aaatggccga 4380
aaacggatgt tggctagcgc cggagagctt caaaagggga acgaactcgc actaccgtct 4440
aaatacgtga atttcctgta tttagcgtcc cattacgaga agttgaaagg ttcacctgaa 4500
gataacgaac agaagcaact ttttgttgag cagcacaaac attatctcga cgaaatcata 4560
gagcaaattt cggaattcag taagagagtc atcctagctg atgccaatct ggacaaagta 4620
ttaagcgcat acaacaagca cagggataaa cccatacgtg agcaggcgga aaatattatc 4680
catttgttta ctcttaccaa cctcggcgct ccagccgcat tcaagtattt tgacacaacg 4740
atagatcgca aacgatacac ttctaccaag gaggtgctag acgcgacact gattcaccaa 4800
tccatcacgg gattatatga aactcggata gatttgtcac agcttggggg tgac 4854

<210> SEQ ID NO 13
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 13
aaaaaaaaaa 10

<210> SEQ ID NO 14
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 14

Gly Gly Ser Gly Gly Ser Gly Gly Ser
1 5

<210> SEQ ID NO 15
<211> LENGTH: 18
<212> TYPE: PRT

<213> ORGANISM: Artificial Sequence
<220> FEATURE:
<223> OTHER INFORMATION: Synthetic Polypeptide

<400> SEQUENCE: 15

Gly Gly Ser Gly Gly Ser Gly Gly Ser Gly Gly Ser Gly Gly Ser Gly
1 5 10 15

Gly Ser

<210> SEQ ID NO 16
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 16

Ser Gly Ser Glu Thr Pro Gly Thr Ser Glu Ser Ala Thr Pro Glu Ser
1 5 10 15

<210> SEQ ID NO 17
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 17

Ser Gly Ser Glu Thr Pro Gly Thr Ser Glu Ser Ala
1 5 10

<210> SEQ ID NO 18
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 18

Ser Gly Ser Glu Thr Pro Gly Thr Ser Glu Ser Ala Thr Pro Glu Gly
1 5 10 15

Gly Ser Gly Gly Ser
20

<210> SEQ ID NO 19
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 19

Val Pro Phe Leu Leu Glu Pro Asp Asn Ile Asn Gly Lys Thr Cys
1 5 10 15

<210> SEQ ID NO 20
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 20

Gly Ser Ala Gly Ser Ala Ala Gly Ser Gly Glu Phe
1 5 10

<210> SEQ ID NO 21
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 21

Ser Ile Val Ala Gln Leu Ser Arg Pro Asp Pro Ala
1 5 10

<210> SEQ ID NO 22
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 22

Met Lys Ile Ile Glu Gln Leu Pro Ser Ala
1 5 10

<210> SEQ ID NO 23
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 23

Val Arg His Lys Leu Lys Arg Val Gly Ser
1 5 10

<210> SEQ ID NO 24
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 24

Gly His Gly Thr Gly Ser Thr Gly Ser Gly Ser Ser
1 5 10

<210> SEQ ID NO 25
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 25

Met Ser Arg Pro Asp Pro Ala
1 5

<210> SEQ ID NO 26
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 26
cggcgagata aacttttaat gaccggtcat catcacca 38

<210> SEQ ID NO 27

<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 27
ccaacggaat tagtgccgat agctaaacca atagaatact ttttatc 47

<210> SEQ ID NO 28
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 28
gataaaaagt attctattgg tttagctatc ggcactaatt ccgttgg 47

<210> SEQ ID NO 29
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 29
ttcaaaaagg attggggtac aatggcatcg acgtcgtaat cagataaac 49

<210> SEQ ID NO 30
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 30
gtttatctga ttacgacgtc gatgccattg taccccaatc ctttttgaa 49

<210> SEQ ID NO 31
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 31
ttgggatcca gaacctcctc ctgcagcctt gtcatcg 37

<210> SEQ ID NO 32
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 32
ttgggatcca gaacctccgc tgccgccact tccacctgat cctgcagcct tgtcatcg 58

<210> SEQ ID NO 33
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 33
cgatgacaag gctgcaggag gaggttctgg atcccaa 37

<210> SEQ ID NO 34
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 34
cgatgacaag gctgcaggat caggtggaag tggcggcagc ggaggttctg gatcccaa 58

<210> SEQ ID NO 35
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 35
tggtgatgat gaccggtcat taaaagttta tctcgccg 38

<210> SEQ ID NO 36
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 36
cggcgagata aacttttaat gaccggtcat catcacca 38

<210> SEQ ID NO 37
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 37
tagggagagc cgccaccatg gactacaaag accatgacgg 40

<210> SEQ ID NO 38
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 38
taaaccaata gaatactttt tatccatagg taccccgcgg tgaatg 46

<210> SEQ ID NO 39
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 39
gataaaaagt attctattgg tttagctatc ggcactaatt ccgttgg 47

<210> SEQ ID NO 40
<211> LENGTH: 49
<212> TYPE: DNA

<213> ORGANISM: Artificial Sequence
<220> FEATURE:
<223> OTHER INFORMATION: Synthetic Polynucleotide

<400> SEQUENCE: 40
ttcaaaaagg attggggtac aatggcatcg acgtcgtaat cagataaac 49

<210> SEQ ID NO 41
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 41
gtttatctga ttacgacgtc gatgccattg taccccaatc ctttttgaa 49

<210> SEQ ID NO 42
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 42
ttgggatcca gaacctccgt cacccccaag ctgtg 35

<210> SEQ ID NO 43
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 43
ttgggatcca gaacctccgc tgccgccact tccacctgag tcacccccaa gctgtg 56

<210> SEQ ID NO 44
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 44
cacagcttgg gggtgacgga ggttctggat cccaa 35

<210> SEQ ID NO 45
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 45
cacagcttgg gggtgactca ggtggaagtg gcggcagcgg aggttctgga tcccaa 56

<210> SEQ ID NO 46
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 46
tggtgatgat gaccggtcat taaaagttta tctcgccg 38

<210> SEQ ID NO 47
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 47
tagggagagc cgccaccatg ggatcccaac tagtcaaaag 40

<210> SEQ ID NO 48
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 48
accaatagaa tactttttat ccatgctgcc accaaagttt atctc 45

<210> SEQ ID NO 49
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 49
accaatagaa tactttttat ccatgctgcc gccacttcca cctg 44

<210> SEQ ID NO 50
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 50
gataaaaagt attctattgg tttagctatc ggcactaatt ccgttgg 47

<210> SEQ ID NO 51
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 51
ccaacggaat tagtgccgat agctaaacca atagaatact ttttatc 47

<210> SEQ ID NO 52
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 52
gtttatctga ttacgacgtc gatgccattg taccccaatc ctttttgaa 49

<210> SEQ ID NO 53
<211> LENGTH: 36
<212> TYPE: DNA
<213> ORGANISM: Artificial Sequence
<220> FEATURE:

<223> OTHER INFORMATION: Synthetic Polynucleotide

<400> SEQUENCE: 53
tggtgatgat gaccggtcag tcacccccaa gctgtg         36

<210> SEQ ID NO 54
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 54
cacagcttgg gggtgactga ccggtcatca tcacca         36

<210> SEQ ID NO 55
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 55
cttttgacta gttgggatcc catggtggcg gctctcccta         40

<210> SEQ ID NO 56
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 56
acacccctcg aacttcacct cggcgg         26

<210> SEQ ID NO 57
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 57
acaccgtcgc cctcgaactt cacctg         26

<210> SEQ ID NO 58
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 58
acacccagct cgatgcggtt caccag         26

<210> SEQ ID NO 59
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 59
acaccggtga accgcatcga gctgag         26

<210> SEQ ID NO 60
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 60
acaccgctga agggcatcga cttcag 26

<210> SEQ ID NO 61
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 61
acaccggcat cgacttcaag gaggag 26

<210> SEQ ID NO 62
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 62
acacccaagg aggacggcaa catccg 26

<210> SEQ ID NO 63
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 63
acaccaccat cttcttcaag gacgag 26

<210> SEQ ID NO 64
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 64
acacccaact acaagacccg cgccgg 26

<210> SEQ ID NO 65
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 65
acaccccgcg ccgaggtgaa gttcgg 26

<210> SEQ ID NO 66
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 66
acaccgaagt tcgagggcga cacccg 26

<210> SEQ ID NO 67
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 67
acaccttcga acttcacctc ggcgcg 26

<210> SEQ ID NO 68
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 68
acacctcagc tcgatgcggt tcaccg 26

<210> SEQ ID NO 69
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 69
acacccgatg cccttcagct cgatgg 26

<210> SEQ ID NO 70
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 70
aaaaccgccg aggtgaagtt cgaggg 26

<210> SEQ ID NO 71
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 71
aaaacaggtg aagttcgagg gcgacg 26

<210> SEQ ID NO 72
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 72
aaaactggtg aaccgcatcg agctgg 26

<210> SEQ ID NO 73
<211> LENGTH: 26

<212> TYPE: DNA
<213> ORGANISM: Artificial Sequence
<220> FEATURE:
<223> OTHER INFORMATION: Synthetic Polynucleotide

<400> SEQUENCE: 73
aaaactcagc tcgatgcggt tcaccg 26

<210> SEQ ID NO 74
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 74
aaaactgaag tcgatgccct tcagcg 26

<210> SEQ ID NO 75
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 75
aaaactcctc cttgaagtcg atgccg 26

<210> SEQ ID NO 76
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 76
aaaacggatg ttgccgtcct ccttgg 26

<210> SEQ ID NO 77
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 77
aaaactcgtc cttgaagaag atggtg 26

<210> SEQ ID NO 78
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 78
aaaaccggcg cgggtcttgt agttgg 26

<210> SEQ ID NO 79
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 79
aaaaccgaac ttcacctcgg cgcggg 26

<210> SEQ ID NO 80
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 80
aaaacgggtg tcgccctcga acttcg 26

<210> SEQ ID NO 81
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 81
aaaacgcgcc gaggtgaagt tcgaag 26

<210> SEQ ID NO 82
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 82
aaaacggtga accgcatcga gctgag 26

<210> SEQ ID NO 83
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 83
aaaaccatcg agctgaaggg catcgg 26

<210> SEQ ID NO 84
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 84
acacctggcc tgcttgctag acttgg 26

<210> SEQ ID NO 85
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 85
acaccgcaga tgtagtgttt ccacag 26

<210> SEQ ID NO 86
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 86
acacccttgc cccacagggc agtaag 26

<210> SEQ ID NO 87
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 87
acaccgagtc cgagcagaag aagaag 26

<210> SEQ ID NO 88
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 88
acaccgggtg gggggagttt gctccg 26

<210> SEQ ID NO 89
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 89
aaaaccaagt ctagcaagca ggccag 26

<210> SEQ ID NO 90
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 90
aaaactgtgg aaacactaca tctgcg 26

<210> SEQ ID NO 91
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 91
aaaacttctt cttctgctcg gactcg 26

<210> SEQ ID NO 92
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 92
aaaacttact gccctgtggg gcaagg 26

<210> SEQ ID NO 93
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 93
aaaacggagc aaactccccc cacccg 26

<210> SEQ ID NO 94
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 94
aggaaagaac atgtgagcaa aag 23

<210> SEQ ID NO 95
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 95
cagcgagtca gtgagcga 18

<210> SEQ ID NO 96
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 96
ctgtacaaaa aagcaggctt ta 22

<210> SEQ ID NO 97
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 97
aacgtaggtc tctaccgctg tacaaaaaag caggcttta 39

<210> SEQ ID NO 98
<211> LENGTH: 83
<212> TYPE: DNA
<213> ORGANISM: Artificial Sequence
<220> FEATURE:
<223> OTHER INFORMATION: Synthetic Polynucleotide

<400> SEQUENCE: 98
aaaaaaagca ccgactcggt gccacttttt caagttgata acggactagc cttattttaa 60
cttgctattt ctagctctaa aac 83

<210> SEQ ID NO 99
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 99
ttgctatttc tagctctaaa accgccgagg tgaagttcga ggggtgtttc gtcctttcca 60

<210> SEQ ID NO 100
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 100
ttgctatttc tagctctaaa acaggtgaag ttcgagggcg acggtgtttc gtcctttcca 60

<210> SEQ ID NO 101
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 101
ttgctatttc tagctctaaa actggtgaac cgcatcgagc tgggtgtttc gtcctttcca 60

<210> SEQ ID NO 102
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 102
ttgctatttc tagctctaaa actcagctcg atgcggttca ccggtgtttc gtcctttcca 60

<210> SEQ ID NO 103
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 103
ttgctatttc tagctctaaa actgaagtcg atgcccttca gcggtgtttc gtcctttcca 60

<210> SEQ ID NO 104
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 104
ttgctatttc tagctctaaa actcctcctt gaagtcgatg ccggtgtttc gtcctttcca 60

<210> SEQ ID NO 105
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 105
ttgctatttc tagctctaaa acggatgttg ccgtcctcct tgggtgtttc gtcctttcca 60

<210> SEQ ID NO 106
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 106
ttgctatttc tagctctaaa acgcttgagg gagatgagga ctggtgtttc gtcctttcca 60

<210> SEQ ID NO 107
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 107
ttgctatttc tagctctaaa acatgactgt gaagagcttc acggtgtttc gtcctttcca 60

<210> SEQ ID NO 108
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 108
ttgctatttc tagctctaaa acgaggacaa agtacaaacg gcggtgtttc gtcctttcca 60

<210> SEQ ID NO 109
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 109
ttgctatttc tagctctaaa acgaaccgga ggacaaagta caggtgtttc gtcctttcca 60

<210> SEQ ID NO 110
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 110
ttgctatttc tagctctaaa accaccacca acttcatcca cgggtgtttc gtcctttcca 60

<210> SEQ ID NO 111
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 111
ttgctatttc tagctctaaa acgggcctca ccaccaactt caggtgtttc gtcctttcca 60

<210> SEQ ID NO 112
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 112
ttgctatttc tagctctaaa acgcccaggg cctcaccacc aaggtgtttc gtcctttcca    60

<210> SEQ ID NO 113
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 113
ttgctatttc tagctctaaa acacctgccc agggcctcac caggtgtttc gtcctttcca    60

<210> SEQ ID NO 114
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 114
ttgctatttc tagctctaaa actgatacca acctgcccag ggggtgtttc gtcctttcca    60

<210> SEQ ID NO 115
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 115
ttgctatttc tagctctaaa actaaacctg tcttgtaacc ttggtgtttc gtcctttcca    60

<210> SEQ ID NO 116
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 116
ttgctatttc tagctctaaa acgctctggc taaagaggga atggtgtttc gtcctttcca    60

<210> SEQ ID NO 117
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 117
ttgctatttc tagctctaaa accggctctg gctaaagagg gaggtgtttc gtcctttcca    60

<210> SEQ ID NO 118
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 118
ttgctatttc tagctctaaa actctgcaca ccccggctct ggggtgtttc gtcctttcca    60

<210> SEQ ID NO 119

<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 119
tacggcaagc tgaccctgaa 20

<210> SEQ ID NO 120
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 120
gtccatgccg agagtgatcc 20

<210> SEQ ID NO 121
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 121
gccaggggct gttatcttgg 20

<210> SEQ ID NO 122
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 122
atgcacagaa gcacaggttg a 21

<210> SEQ ID NO 123
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 123
ctgtgtcctc ttcctgccct 20

<210> SEQ ID NO 124
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 124
ctctccgagg agaaggccaa 20

<210> SEQ ID NO 125
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 125
ggtagaccac cagcagccta 20

<210> SEQ ID NO 126
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 126
cagtgccaga agagccaagg 20

<210> SEQ ID NO 127
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 127
ccacacagct tcccgttctc 20

<210> SEQ ID NO 128
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 128
gagagccgtt ccctctttgc 20

<210> SEQ ID NO 129
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 129
cctccccatt ggcctgcttc 20

<210> SEQ ID NO 130
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 130
tcgtcctgct ctcacttaga c 21

<210> SEQ ID NO 131
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 131
ttttgtggct tggccccagt 20

<210> SEQ ID NO 132
<211> LENGTH: 21
<212> TYPE: DNA

<213> ORGANISM: Artificial Sequence
<220> FEATURE:
<223> OTHER INFORMATION: Synthetic Polynucleotide

<400> SEQUENCE: 132
tgcagtctca tgacttggcc t 21

<210> SEQ ID NO 133
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 133
ttctgagggc tgctacctgt 20

<210> SEQ ID NO 134
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 134
acatgaagca actccagtcc ca 22

<210> SEQ ID NO 135
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 135
agcagaccca ctgagtcaac tg 22

<210> SEQ ID NO 136
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 136
cccgccacag tcgtgtcat 19

<210> SEQ ID NO 137
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 137
cgccccggta caaggtga 18

<210> SEQ ID NO 138
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 138
gtaccgtaca ttgtaggatg ttt 23

<210> SEQ ID NO 139
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 139
cctcatctcc ctcaagcagg c 21

<210> SEQ ID NO 140
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 140
attctgctct tgaggttatt tgt 23

<210> SEQ ID NO 141
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 141
cacctctgcc tcaagagcag aaaa 24

<210> SEQ ID NO 142
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 142
tgtgtgtgtg tgtgtgtagg act 23

<210> SEQ ID NO 143
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 143
tcatctgtgc ccctccctcc 20

<210> SEQ ID NO 144
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 144
cgagaaggag gtgcaggag 19

<210> SEQ ID NO 145
<211> LENGTH: 20
<212> TYPE: DNA
<213> ORGANISM: Artificial Sequence
<220> FEATURE:

<223> OTHER INFORMATION: Synthetic Polynucleotide

<400> SEQUENCE: 145
cgggagctgt tcagaggctg 20

<210> SEQ ID NO 146
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 146
ctcacctggg cgagaaaggt 20

<210> SEQ ID NO 147
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 147
aaaactcaaa gaaatgccca atca 24

<210> SEQ ID NO 148
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 148
agacgctgct cgctccattc 20

<210> SEQ ID NO 149
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 149
acaggcatga atcactgcac ct 22

<210> SEQ ID NO 150
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 150
gcggcaactt cagacaaccg a 21

<210> SEQ ID NO 151
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 151
gacccagggg caccagtt 18

<210> SEQ ID NO 152
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 152
ctgccttcat tgcttaaaag tggat 25

<210> SEQ ID NO 153
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 153
acagttgaag gaaggaaaca tgc 23

<210> SEQ ID NO 154
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 154
gctgcatttg cccatttcca 20

<210> SEQ ID NO 155
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 155
gttgggggag gaggagctta t 21

<210> SEQ ID NO 156
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 156
ctaagagcta taagggcaaa tgact 25

<210> SEQ ID NO 157
<211> LENGTH: 152
<212> TYPE: DNA
<213> ORGANISM: Artificial Sequence
<220> FEATURE:
<223> OTHER INFORMATION: Synthetic Polynucleotide

<400> SEQUENCE: 157
ttctgagggc tgctacctgt acatctgcac aagattgcct ttactccatg cctttcttct 60
tctgctctaa ctctgacaat ctgtcttgcc atgccataag cccctattct ttctgtaacc 120
ccaagatggt ataaaagcat caatgattgg gc 152

<210> SEQ ID NO 158
<211> LENGTH: 155
<212> TYPE: DNA

-continued

<213> ORGANISM: Artificial Sequence
<220> FEATURE:
<223> OTHER INFORMATION: Synthetic Polynucleotide

<400> SEQUENCE: 158
aaaactcaaa gaaatgccca atcattgatg cttttatacc atcttggggt tacagaaaga 60
ataggggctt atggcatggc aagacagatt gtcagagtta gagcagaaga agaaaggcat 120
ggagtaaagg caatcttgtg cagatgtaca ggtaa 155

<210> SEQ ID NO 159
<211> LENGTH: 155
<212> TYPE: DNA
<213> ORGANISM: Artificial Sequence
<220> FEATURE:
<223> OTHER INFORMATION: Synthetic Polynucleotide

<400> SEQUENCE: 159
ttacctgtac atctgcacaa gattgccttt actccatgcc tttcttcttc tgctctaact 60
ctgacaatct gtcttgccat gccataagcc cctattcttt ctgtaacccc aagatggtat 120
aaaagcatca atgattgggc atttctttga gtttt 155

<210> SEQ ID NO 160
<211> LENGTH: 152
<212> TYPE: DNA
<213> ORGANISM: Artificial Sequence
<220> FEATURE:
<223> OTHER INFORMATION: Synthetic Polynucleotide

<400> SEQUENCE: 160
ttctgagggc tgctacctgt acatctgcac aagattgcct ttactccatg cctttcttct 60
tctgctctaa ctctgacaat ctgtcttgcc atgccataag cccctattct ttctgtaacc 120
ccaagatggt ataaaagcat caatgattgg gc 152

<210> SEQ ID NO 161
<211> LENGTH: 167
<212> TYPE: DNA
<213> ORGANISM: Artificial Sequence
<220> FEATURE:
<223> OTHER INFORMATION: Synthetic Polynucleotide

<400> SEQUENCE: 161
ttctgagggc tgctacctgt acatctgcac aagattgcct ttactccatg cctttcttct 60
tctgctctaa ctctgacaat ctgtcttgcc atgccataag cccctattct ttctgtaacc 120
ccaagatggt ataaaagcat caatgattgg gcatttcttt gagtttt 167

<210> SEQ ID NO 162
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 162
ggcctgcttc gtggcaatgc 20

<210> SEQ ID NO 163
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 163
acctgggcca gggagggagg 20

<210> SEQ ID NO 164
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 164
ctcacttaga ctttctctcc 20

<210> SEQ ID NO 165
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 165
ctcggagtct agctcctgca 20

<210> SEQ ID NO 166
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 166
tggccccagt ctctcttcta 20

<210> SEQ ID NO 167
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 167
cagcctctga acagctcccg 20

<210> SEQ ID NO 168
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 168
tgacttggcc tttgtaggaa 20

<210> SEQ ID NO 169
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 169
gaggctactg aaacataagt 20

<210> SEQ ID NO 170

<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 170
tgctacctgt acatctgcac 20

<210> SEQ ID NO 171
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 171
catcaatgat tgggcatttc 20

<210> SEQ ID NO 172
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 172
actccagtcc caaatatgta 20

<210> SEQ ID NO 173
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 173
actagggggc gctcggccac 20

<210> SEQ ID NO 174
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 174
ctgagtcaac tgtaagcatt 20

<210> SEQ ID NO 175
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 175
ggccaggtgc agtgattcat 20

<210> SEQ ID NO 176
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 176
tcgtgtcatc ttgtttgtgc 20

<210> SEQ ID NO 177
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 177
ggcagagccc agcggacact 20

<210> SEQ ID NO 178
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 178
caaggtgagc ctgggtctgt 20

<210> SEQ ID NO 179
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 179
atcactgccc aagaagtgca 20

<210> SEQ ID NO 180
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 180
ttgtaggatg tttagcagca 20

<210> SEQ ID NO 181
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 181
acttgctctc tttagagaac 20

<210> SEQ ID NO 182
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 182
ctcaagcagg ccccgctggt 20

<210> SEQ ID NO 183
<211> LENGTH: 20
<212> TYPE: DNA

<213> ORGANISM: Artificial Sequence
<220> FEATURE:
<223> OTHER INFORMATION: Synthetic Polynucleotide

<400> SEQUENCE: 183
ttttggacca aaccttttg 20

<210> SEQ ID NO 184
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 184
tgaggttatt tgtccattgt 20

<210> SEQ ID NO 185
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 185
taaggggagt atttacacca 20

<210> SEQ ID NO 186
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 186
tcaagagcag aaaatgtgac 20

<210> SEQ ID NO 187
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 187
cttgcaggga ccttctgatt 20

<210> SEQ ID NO 188
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 188
tgtgtgtagg actaaactct 20

<210> SEQ ID NO 189
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 189
gatagcagta tgaccttggg 20

<210> SEQ ID NO 190
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 190
gagtccgagc agaagaagaa ggg 23

<210> SEQ ID NO 191
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 191
gaggccgagc agaagaaaga cgg 23

<210> SEQ ID NO 192
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 192
gagtcctagc aggagaagaa gag 23

<210> SEQ ID NO 193
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 193
gagtctaagc agaagaagaa gag 23

<210> SEQ ID NO 194
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 194
gagttagagc agaagaagaa agg 23

<210> SEQ ID NO 195
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 195
gggtgggggg agtttgctcc tgg 23

<210> SEQ ID NO 196
<211> LENGTH: 23
<212> TYPE: DNA
<213> ORGANISM: Artificial Sequence
<220> FEATURE:

<223> OTHER INFORMATION: Synthetic Polynucleotide

<400> SEQUENCE: 196
ggatggaggg agtttgctcc tgg 23

<210> SEQ ID NO 197
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 197
gggagggtgg agtttgctcc tgg 23

<210> SEQ ID NO 198
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 198
cgggggaggg agtttgctcc tgg 23

<210> SEQ ID NO 199
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 199
ggggagggga agtttgctcc tgg 23

<210> SEQ ID NO 200
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 200
gcagatgtag tgtttccaca ggg 23

<210> SEQ ID NO 201
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 201
acaaatgtag tatttccaca ggg 23

<210> SEQ ID NO 202
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 202
ccagatgtag tattcccaca ggg 23

<210> SEQ ID NO 203
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 203
ctagatgaag tgcttccaca tgg 23

<210> SEQ ID NO 204
<211> LENGTH: 89
<212> TYPE: DNA
<213> ORGANISM: Homo sapiens

<400> SEQUENCE: 204
ccgcgccgag gtgaagttcg agggcgacac cctggtgaac cgcatcgagc tgaagggcat 60
cgacttcaag gaggacggca acatcctgg 89

<210> SEQ ID NO 205
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 205
ccgcgccgag gtgaagttcg agg 23

<210> SEQ ID NO 206
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 206
ccgaggtgaa gttcgagggc gac 23

<210> SEQ ID NO 207
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 207
ccctggtgaa ccgcatcgag ctg 23

<210> SEQ ID NO 208
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 208
ggtgaaccgc atcgagctga agg 23

<210> SEQ ID NO 209
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 209
gctgaagggc atcgacttca agg 23

<210> SEQ ID NO 210
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 210
ggcatcgact tcaaggagga cgg 23

<210> SEQ ID NO 211
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 211
caaggaggac ggcaacatcc tgg 23

<210> SEQ ID NO 212
<211> LENGTH: 104
<212> TYPE: DNA
<213> ORGANISM: Homo sapiens

<400> SEQUENCE: 212
ggagcgcacc atcttcttca aggacgacgg caactacaag acccgcgccg aggtgaagtt 60
cgagggcgac accctggtga accgcatcga gctgaagggc atcg 104

<210> SEQ ID NO 213
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 213
accatcttct tcaaggacga cgg 23

<210> SEQ ID NO 214
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 214
caactacaag acccgcgccg agg 23

<210> SEQ ID NO 215
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 215
ccgcgccgag gtgaagttcg agg 23

<210> SEQ ID NO 216
<211> LENGTH: 23

<212> TYPE: DNA
<213> ORGANISM: Artificial Sequence
<220> FEATURE:
<223> OTHER INFORMATION: Synthetic Polynucleotide

<400> SEQUENCE: 216
gaagttcgag ggcgacaccc tgg 23

<210> SEQ ID NO 217
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 217
cccgcgccga ggtgaagttc gag 23

<210> SEQ ID NO 218
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 218
cctggtgaac cgcatcgagc tga 23

<210> SEQ ID NO 219
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 219
ccgcatcgag ctgaagggca tcg 23

<210> SEQ ID NO 220
<211> LENGTH: 68
<212> TYPE: DNA
<213> ORGANISM: Homo sapiens

<400> SEQUENCE: 220
ccccaagtct agcaagcagg ccaaagatgt ctcccgcatg cgctcagtcc tcatctccct 60
caagcagg 68

<210> SEQ ID NO 221
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 221
ccccaagtct agcaagcagg cca 23

<210> SEQ ID NO 222
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 222
agtcctcatc tccctcaagc agg 23

<210> SEQ ID NO 223
<211> LENGTH: 65
<212> TYPE: DNA
<213> ORGANISM: Homo sapiens

<400> SEQUENCE: 223
ccctgtggaa acactacatc tgcaatatct taatcctact cagtgaagct cttcacagtc 60
attgg 65

<210> SEQ ID NO 224
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 224
ccctgtggaa acactacatc tgc 23

<210> SEQ ID NO 225
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 225
gtgaagctct tcacagtcat tgg 23

<210> SEQ ID NO 226
<211> LENGTH: 93
<212> TYPE: DNA
<213> ORGANISM: Artificial Sequence
<220> FEATURE:
<223> OTHER INFORMATION: Synthetic Polynucleotide

<400> SEQUENCE: 226
ccgttactgc cctgtggggc aaggtgaacg tggatgaagt tggtggtgag gccctgggca 60
ggttggtatc aaggttacaa gacaggttta agg 93

<210> SEQ ID NO 227
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 227
ccgttactgc cctgtggggc aag 23

<210> SEQ ID NO 228
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 228
cgtggatgaa gttggtggtg gg 22

<210> SEQ ID NO 229
<211> LENGTH: 23

<212> TYPE: DNA
<213> ORGANISM: Artificial Sequence
<220> FEATURE:
<223> OTHER INFORMATION: Synthetic Polynucleotide

<400> SEQUENCE: 229
tgaagttggt ggtgaggccc tgg 23

<210> SEQ ID NO 230
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 230
ttggtggtga ggccctgggc agg 23

<210> SEQ ID NO 231
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 231
tggtgaggcc ctgggcaggt tgg 23

<210> SEQ ID NO 232
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 232
ccctgggcag gttggtatca agg 23

<210> SEQ ID NO 233
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 233
aaggttacaa gacaggttta agg 23

<210> SEQ ID NO 234
<211> LENGTH: 75
<212> TYPE: DNA
<213> ORGANISM: Artificial Sequence
<220> FEATURE:
<223> OTHER INFORMATION: Synthetic Polynucleotide

<400> SEQUENCE: 234
cccttcttct tctgctcgga ctcaggccct tcctcctcca gcttctgccg tttgtacttt 60
gtcctccggt tctgg 75

<210> SEQ ID NO 235
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 235
cccttcttct tctgctcgga ctc 23

<210> SEQ ID NO 236
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 236
gccgtttgta ctttgtcctc cgg 23

<210> SEQ ID NO 237
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 237
tgtactttgt cctccggttc tgg 23

<210> SEQ ID NO 238
<211> LENGTH: 73
<212> TYPE: DNA
<213> ORGANISM: Artificial Sequence
<220> FEATURE:
<223> OTHER INFORMATION: Synthetic Polynucleotide

<400> SEQUENCE: 238
ccaggagcaa actcccccca ccccctttcc aaagcccatt ccctctttag ccagagccgg 60
ggtgtgcaga cgg 73

<210> SEQ ID NO 239
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 239
ccaggagcaa actcccccca ccc 23

<210> SEQ ID NO 240
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 240
attccctctt tagccagagc cgg 23

<210> SEQ ID NO 241
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 241
tccctcttta gccagagccg ggg 23

<210> SEQ ID NO 242
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 242
ccagagccgg ggtgtgcaga cgg 23

<210> SEQ ID NO 243
<211> LENGTH: 106
<212> TYPE: DNA
<213> ORGANISM: Artificial Sequence
<220> FEATURE:
<223> OTHER INFORMATION: Synthetic Polynucleotide

<400> SEQUENCE: 243
gctgtttggg aggtcagaaa tagggggtcc aggagcaaac tccccccacc ccctttccaa 60
agcccattcc ctctttagcc agagccgggg tgtgcagacg gcagtc 106

<210> SEQ ID NO 244
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 244
gctgtttggg aggtcagaaa tagggggtcc aggaagccgg ggtgtgcaga cggcagtc 58

<210> SEQ ID NO 245
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 245
gctgtttggg aggtcagaaa tagggggtcc aggagcaaac tccccccacc ccctttccaa 60
agcccattcc ctctttagcc ggggtgtgca gacggcagtc 100

<210> SEQ ID NO 246
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 246
gctgtttggg aggtcagaaa tagggggtcc aggagagccg gggtgtgcag acggcagtc 59

<210> SEQ ID NO 247
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 247
gctgtttggg aggtcagaaa tagccggggt gtgcagacgg cagtc 45

<210> SEQ ID NO 248
<211> LENGTH: 57
<212> TYPE: DNA

<213> ORGANISM: Artificial Sequence
<220> FEATURE:
<223> OTHER INFORMATION: Synthetic Polynucleotide

<400> SEQUENCE: 248
gctgtttggg aggtcagaaa tagggggtcc aggagccggg gtgtgcagac ggcagtc 57

<210> SEQ ID NO 249
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 249
gctgtttggg aggtcagaaa tagggggtcc agccggggtg tgcagacggc agtc 54

<210> SEQ ID NO 250
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 250
gctgtttggg aggtcagaaa tagggggtcc aggagcaaac tccccccacc ccctttccaa 60
agcccattcc ctctttagcc agggtgtgca gacggcagtc 100

<210> SEQ ID NO 251
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 251
gctgtttggg aggtcagaaa tagggggtcc aggatagccg gggtgtgcag acggcagtc 59

<210> SEQ ID NO 252
<211> LENGTH: 106
<212> TYPE: DNA
<213> ORGANISM: Artificial Sequence
<220> FEATURE:
<223> OTHER INFORMATION: Synthetic Polynucleotide

<400> SEQUENCE: 252
gctgtttggg aggtcagaaa tagggggtcc aggagcaaac tccccccacc ccctttccaa 60
agcccattcc ctctttagcc agagccgggg tgtgcagacg gcagtc 106

<210> SEQ ID NO 253
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 253
gctgtttggg aggtcagaaa tagggggtcc agacggcagt c 41

<210> SEQ ID NO 254
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 254
gctgtttggg aggtcagaaa tagggggtcc aggagcaaac tccccccacc ccctttccaa 60
agccggggtg tgcagacggc agtc 84

<210> SEQ ID NO 255
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 255
gctgtttggg aggtcagaaa tagggggtcc aaagcccatt ccctctttag ccagagccgg 60
ggtggcagac ggcagtc 77

<210> SEQ ID NO 256
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 256
gctgtttggg aggtcagaaa tagggggtgt gcagacggca gtc 43

<210> SEQ ID NO 257
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 257
gctgtttggg aggtcagaaa tagggggtcc agccggggtg tgcagacggc agtc 54

<210> SEQ ID NO 258
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 258
gctgtttggg aggtcagaaa tagggggtcc agggtgtgca gacggcagtc 50

<210> SEQ ID NO 259
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 259
gctgtttggg aggtcagaaa gagggggtcc aggagccggg gtgtgcagac ggcagtc 57

<210> SEQ ID NO 260
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 260
gctgtttggg aggtcagaaa tagccggggt gtgcagacgg cagtc 45

<210> SEQ ID NO 261
<211> LENGTH: 106
<212> TYPE: DNA
<213> ORGANISM: Artificial Sequence
<220> FEATURE:
<223> OTHER INFORMATION: Synthetic Polynucleotide

<400> SEQUENCE: 261
gctgtttggg aggtcagaaa tagggggtcc aggagcaaac tccccccacc ccctttccaa 60
agcccattcc ctctttagcc agagccgggg tgtgcagacg gcagtc 106

<210> SEQ ID NO 262
<211> LENGTH: 94
<212> TYPE: DNA
<213> ORGANISM: Artificial Sequence
<220> FEATURE:
<223> OTHER INFORMATION: Synthetic Polynucleotide

<400> SEQUENCE: 262
gctgtttggg aggtcagaaa tagggggtcc aggagcaaac tccccccaag cccattccct 60
ctttagccag agccggggtg tgcagacggc agtc 94

<210> SEQ ID NO 263
<211> LENGTH: 95
<212> TYPE: DNA
<213> ORGANISM: Artificial Sequence
<220> FEATURE:
<223> OTHER INFORMATION: Synthetic Polynucleotide

<400> SEQUENCE: 263
gctgtttggg aggtcagaaa tagggggtcc aggagcaaac tccccccacc cccttttccc 60
tctttagcca gagccggggt gtgcagacgg cagtc 95

<210> SEQ ID NO 264
<211> LENGTH: 94
<212> TYPE: DNA
<213> ORGANISM: Artificial Sequence
<220> FEATURE:
<223> OTHER INFORMATION: Synthetic Polynucleotide

<400> SEQUENCE: 264
gctgtttggg aggtcagaaa tagggggtcc aggagcaaac tccccccacc ccctttccct 60
ctttagccag agccggggtg tgcagacggc agtc 94

<210> SEQ ID NO 265
<211> LENGTH: 93
<212> TYPE: DNA
<213> ORGANISM: Artificial Sequence
<220> FEATURE:
<223> OTHER INFORMATION: Synthetic Polynucleotide

<400> SEQUENCE: 265
gctgtttggg aggtcagaaa tagggggtcc aggagcaaac tccccccagc ccattccctc 60
tttagccaga gccggggtgt gcagacggca gtc 93

<210> SEQ ID NO 266
<211> LENGTH: 94
<212> TYPE: DNA
<213> ORGANISM: Artificial Sequence
<220> FEATURE:
<223> OTHER INFORMATION: Synthetic Polynucleotide

<400> SEQUENCE: 266
gctgtttggg aggtcagaaa tagggggtcc aggagcaaac tccccccacc cccattccct 60
ctttagccag agccggggtg tgcagacggc agtc 94

<210> SEQ ID NO 267
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 267
gctgtttggg aggtcagaaa tagggggtcc aggagcaaac tccccccacc ccctttagcc 60
agagccgggg tgtgcagacg gcagtc 86

<210> SEQ ID NO 268
<211> LENGTH: 103
<212> TYPE: DNA
<213> ORGANISM: Artificial Sequence
<220> FEATURE:
<223> OTHER INFORMATION: Synthetic Polynucleotide

<400> SEQUENCE: 268
gctgtttggg aggtcagaaa tagggggtcc aggagcaaac tccccccacc cccttaaagc 60
ccattccctc tttagccaga gccggggtgt gcagacggca gtc 103

<210> SEQ ID NO 269
<211> LENGTH: 93
<212> TYPE: DNA
<213> ORGANISM: Artificial Sequence
<220> FEATURE:
<223> OTHER INFORMATION: Synthetic Polynucleotide

<400> SEQUENCE: 269
gctgtttggg aggtcagaaa tagggggtcc aggagcaaac tcccccaagc ccattccctc 60
tttagccaga gccggggtgt gcagacggca gtc 93

<210> SEQ ID NO 270
<211> LENGTH: 132
<212> TYPE: DNA
<213> ORGANISM: Artificial Sequence
<220> FEATURE:
<223> OTHER INFORMATION: Synthetic Polynucleotide

<400> SEQUENCE: 270
cattcaacag atacttactg aatgctaatg tctcagacag gacattctga caccccagga 60
gcaaactccc tccatcccac aaatccgtcc ttagatgtgc acacccaacc tcctaagaaa 120
tagaaggatg at 132

<210> SEQ ID NO 271
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 271
cattcaacag atacttactg aatgctaatg tctcagacag gacattctga caccccaggc 60
aaactccctc catcccacaa atccgtcctt agatgtgcac acccaacctc ctaagaaata 120
gaaggatgat 130

<210> SEQ ID NO 272
<211> LENGTH: 123
<212> TYPE: DNA
<213> ORGANISM: Artificial Sequence
<220> FEATURE:
<223> OTHER INFORMATION: Synthetic Polynucleotide

<400> SEQUENCE: 272
cattcaacag atacttactg aatgctaatg tctcagacag gacattctga caccccatcc 60
ctccatccca caaatccgtc cttagatgtg cacacccaac ctcctaagaa atagaaggat 120
gat 123

<210> SEQ ID NO 273
<211> LENGTH: 129
<212> TYPE: DNA
<213> ORGANISM: Artificial Sequence
<220> FEATURE:
<223> OTHER INFORMATION: Synthetic Polynucleotide

<400> SEQUENCE: 273
cattcaacag atacttactg aatgctaatg tctcagacag gacattctga caccccagca 60
aactccctcc atcccacaaa tccgtcctta gatgtgcaca cccaacctcc taagaaatag 120
aaggatgat 129

<210> SEQ ID NO 274
<211> LENGTH: 110
<212> TYPE: DNA
<213> ORGANISM: Artificial Sequence
<220> FEATURE:
<223> OTHER INFORMATION: Synthetic Polynucleotide

<400> SEQUENCE: 274
cattcaacag atacttactg aatgctaatg tctcagacag gacattctga caccccacaa 60
atccgtcctt agatgtgcac acccaacctc ctaagaaata gaaggatgat 110

<210> SEQ ID NO 275
<211> LENGTH: 119
<212> TYPE: DNA
<213> ORGANISM: Artificial Sequence
<220> FEATURE:
<223> OTHER INFORMATION: Synthetic Polynucleotide

<400> SEQUENCE: 275
cattcaacag atacttactg aatgctaatg tctcagacag gacattctga cactccctcc 60
atcccacaaa tccgtcctta gatgtgcaca cccaacctcc taagaaatag aaggatgat 119

<210> SEQ ID NO 276
<211> LENGTH: 118
<212> TYPE: DNA
<213> ORGANISM: Artificial Sequence
<220> FEATURE:
<223> OTHER INFORMATION: Synthetic Polynucleotide

<400> SEQUENCE: 276
cattcaacag atacttactg aatgctaatg tctcagacag gacattctga cacccctcca 60
tcccacaaat ccgtccttag atgtgcacac ccaacctcct aagaaataga aggatgat 118

<210> SEQ ID NO 277
<211> LENGTH: 64

-continued

<212> TYPE: DNA
<213> ORGANISM: Artificial Sequence
<220> FEATURE:
<223> OTHER INFORMATION: Synthetic Polynucleotide

<400> SEQUENCE: 277
cattcaacag atacttactg aatgctaatg tctcagacag gacattctga caccccagga 60
tgat 64

<210> SEQ ID NO 278
<211> LENGTH: 117
<212> TYPE: DNA
<213> ORGANISM: Artificial Sequence
<220> FEATURE:
<223> OTHER INFORMATION: Synthetic Polynucleotide

<400> SEQUENCE: 278
cattcaacag atacttactg aatgctaatg tctcagacag gacattctga ctccctccat 60
cccacaaatc cgtccttaga tgtgcacacc caacctccta agaaatagaa ggatgat 117

<210> SEQ ID NO 279
<211> LENGTH: 132
<212> TYPE: DNA
<213> ORGANISM: Homo sapiens

<400> SEQUENCE: 279
cattcaacag atacttactg aatgctaatg tctcagacag gacattctga caccccagga 60
gcaaactccc tccatcccac aaatccgtcc ttagatgtgc acacccaacc tcctaagaaa 120
tagaaggatg at 132

<210> SEQ ID NO 280
<211> LENGTH: 111
<212> TYPE: DNA
<213> ORGANISM: Artificial Sequence
<220> FEATURE:
<223> OTHER INFORMATION: Synthetic Polynucleotide

<400> SEQUENCE: 280
cattcaacag atacttactg aatgctaatg tctcagacag gacattctga caccccagga 60
catccgtcct tagatgtgca cacccaacct cctaagaaat agaaggatga t 111

<210> SEQ ID NO 281
<211> LENGTH: 117
<212> TYPE: DNA
<213> ORGANISM: Artificial Sequence
<220> FEATURE:
<223> OTHER INFORMATION: Synthetic Polynucleotide

<400> SEQUENCE: 281
cattcaacag atacttactg aatgctaatg tctcagacag gacattctga ctccctccat 60
cccacaaatc cgtccttaga tgtgcacacc caacctccta agaaatagaa ggatgat 117

<210> SEQ ID NO 282
<211> LENGTH: 99
<212> TYPE: DNA
<213> ORGANISM: Artificial Sequence
<220> FEATURE:
<223> OTHER INFORMATION: Synthetic Polynucleotide

<400> SEQUENCE: 282
cattcaacag atacttactg aatgctaatg tctcagacag gacattctga tccgtcctta 60
gatgtgcaca cccaacctcc taagaaatag aaggatgat 99

<210> SEQ ID NO 283
<211> LENGTH: 121
<212> TYPE: DNA
<213> ORGANISM: Artificial Sequence
<220> FEATURE:
<223> OTHER INFORMATION: Synthetic Polynucleotide

<400> SEQUENCE: 283
cattcaacag atacttactg aatgctaatg tctcagacag gacattctga caccccagca 60
tctgatgaca aatccgtcct tagatgtgca cacccaacct cctaagaaat agaaggatga 120
t 121

<210> SEQ ID NO 284
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 284
cattcaacag atacttactg aatgctaatg tctcagacag gacattctga caccccagga 60
gcaaactccc tccatcccac aaatccgtcc ttagatgtgc acccaacctc ctaagaaata 120
gaaggatgat 130

<210> SEQ ID NO 285
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 285
cattcaacag atacttactg aatgctaatg tctcagacag gacattctga caccccagga 60
gcaaactccc tccatcccac aaatccgtcc ttatgtgcac acccaacctc ctaagaaata 120
gaaggatgat 130

<210> SEQ ID NO 286
<211> LENGTH: 132
<212> TYPE: DNA
<213> ORGANISM: Artificial Sequence
<220> FEATURE:
<223> OTHER INFORMATION: Synthetic Polynucleotide

<400> SEQUENCE: 286
cattcaacag atacttactg aatgctaatg tctcagacag gacattctga caccccagga 60
gcaaactccc tccatcccac aaatccgtcc ttagatgtgc acacccaacc tcctaagaaa 120
tagaaggatg at 132

<210> SEQ ID NO 287
<211> LENGTH: 101
<212> TYPE: DNA
<213> ORGANISM: Artificial Sequence
<220> FEATURE:
<223> OTHER INFORMATION: Synthetic Polynucleotide

<400> SEQUENCE: 287
cattcaacag atacttactg aatgctaatg tctcagacag gacattctga aatccgtcct 60
tagatgtgca cacccaacct cctaagaaat agaaggatga t 101

<210> SEQ ID NO 288
<211> LENGTH: 132
<212> TYPE: DNA
<213> ORGANISM: Artificial Sequence
<220> FEATURE:
<223> OTHER INFORMATION: Synthetic Polynucleotide

<400> SEQUENCE: 288
cattcaacag atacttactg aatgctaatg tctcagacag gacattctga caccccagga 60
gcaaactccc tccatcccac aaatccgtcc ttagatgtgc acacccaacc tcctaagaaa 120
tagaaggatg at 132

<210> SEQ ID NO 289
<211> LENGTH: 119
<212> TYPE: DNA
<213> ORGANISM: Artificial Sequence
<220> FEATURE:
<223> OTHER INFORMATION: Synthetic Polynucleotide

<400> SEQUENCE: 289
cattcaacag atacttactg aatgctaatg tctcagacag gacattctga caccccagga 60
gcaaactccc tccgtcctta gatgtgcaca cccaacctcc taagaaatag aaggatgat 119

<210> SEQ ID NO 290
<211> LENGTH: 121
<212> TYPE: DNA
<213> ORGANISM: Artificial Sequence
<220> FEATURE:
<223> OTHER INFORMATION: Synthetic Polynucleotide

<400> SEQUENCE: 290
cattcaacag atacttactg aatgctaatg tctcagacag gacattctga caccccagga 60
gcaaactccc tctccgtcct tagatgtgca cacccaacct cctaagaaat agaaggatga 120
t 121

<210> SEQ ID NO 291
<211> LENGTH: 124
<212> TYPE: DNA
<213> ORGANISM: Artificial Sequence
<220> FEATURE:
<223> OTHER INFORMATION: Synthetic Polynucleotide

<400> SEQUENCE: 291
cattcaacag atacttactg aatgctaatg tctcagacag gacattctga caccccagga 60
gcaaactccc tccattccgt ccttagatgt gcacacccaa cctcctaaga aatagaagga 120
tgat 124

<210> SEQ ID NO 292
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 292
cattcaacag atacttactg aatgctaatg tctcagacag gacattctga caccccagga 60
gcaaactccc tccatcccac aaatccgtcc ttagatgtgc acccaacctc ctaagaaata 120
gaaggatgat 130

<210> SEQ ID NO 293
<211> LENGTH: 122
<212> TYPE: DNA
<213> ORGANISM: Artificial Sequence
<220> FEATURE:
<223> OTHER INFORMATION: Synthetic Polynucleotide

<400> SEQUENCE: 293
cattcaacag atacttactg aatgctaatg tctcagacag gacattctga caccccagga 60
gcaaactccc tcctccgtcc ttagatgtgc acacccaacc tcctaagaaa tagaaggatg 120
at 122

<210> SEQ ID NO 294
<211> LENGTH: 123
<212> TYPE: DNA
<213> ORGANISM: Artificial Sequence
<220> FEATURE:
<223> OTHER INFORMATION: Synthetic Polynucleotide

<400> SEQUENCE: 294
cattcaacag atacttactg aatgctaatg tctcagacag gacattctga caccccagga 60
gcaaactccc tccatccgtc cttagatgtg cacacccaac ctcctaagaa atagaaggat 120
gat 123

<210> SEQ ID NO 295
<211> LENGTH: 128
<212> TYPE: DNA
<213> ORGANISM: Artificial Sequence
<220> FEATURE:
<223> OTHER INFORMATION: Synthetic Polynucleotide

<400> SEQUENCE: 295
cattcaacag atacttactg aatgctaatg tctcagacag gacattctga caccccagga 60
gcaaactccc tccatcccac aaatccgtcc ttagatgtgc acaccctcct aagaaataga 120
aggatgat 128

<210> SEQ ID NO 296
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 296
cattcaacag atacttactg aatgctaatg tctcagacag gacattctga caccccagga 60
gcaaactccc tccatcccac aaatccgtcc agatgtgcac acccaacctc ctaagaaata 120
gaaggatgat 130

<210> SEQ ID NO 297
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 297
ggggtggggg gagtttgctc c 21

<210> SEQ ID NO 298
<211> LENGTH: 22

-continued

<212> TYPE: DNA
<213> ORGANISM: Artificial Sequence
<220> FEATURE:
<223> OTHER INFORMATION: Synthetic Polynucleotide

<400> SEQUENCE: 298
aggagcaaac tccctccatc cc 22

<210> SEQ ID NO 299
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 299
gggatggagg gagtttgctc ct 22

<210> SEQ ID NO 300
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 300
auucccucuu uagccagagc 20

<210> SEQ ID NO 301
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 301

Gly Gly Ser Met
1

<210> SEQ ID NO 302
<211> LENGTH: 99
<212> TYPE: DNA
<213> ORGANISM: Artificial Sequence
<220> FEATURE:
<223> OTHER INFORMATION: Synthetic Polynucleotide

<400> SEQUENCE: 302
ccagcaagag gctcccgagc gagcaagctc agtttacacc cgatccactg gggagcagga 60
aatatctgtg ggcttgtgac acggactcaa gtgggctgg 99

<210> SEQ ID NO 303
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 303
ccagcaagag gctcccgagc gag 23

<210> SEQ ID NO 304
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 304
cccgagcgag caagctcagt tta 23

<210> SEQ ID NO 305
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 305
cccgatccac tggggagcag gaa 23

<210> SEQ ID NO 306
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 306
agtttacacc cgatccactg ggg 23

<210> SEQ ID NO 307
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 307
tggggagcag gaaatatctg tggg 24

<210> SEQ ID NO 308
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 308
atatctgtgg gcttgtgaca cgg 23

<210> SEQ ID NO 309
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 309
gcttgtgaca cggactcaag tgg 23

<210> SEQ ID NO 310
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 310
tgacacggac tcaagtgggc tgg 23

<210> SEQ ID NO 311

<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 311
cctggccatc tctgacctgt ttttccttct tactgtcccc ttctgggctc actatgctgc 60
cgcccagtgg gactttggaa atacaatgtg tcaactcttg acagggctct attttatagg 120

<210> SEQ ID NO 312
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 312
cctggccatc tctgacctgt ttt 23

<210> SEQ ID NO 313
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 313
ccccttctgg gctcactatg ctg 23

<210> SEQ ID NO 314
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 314
ccgcccagtg ggactttgga aat 23

<210> SEQ ID NO 315
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 315
tcactatgct gccgcccagt ggg 23

<210> SEQ ID NO 316
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 316
caatgtgtca actcttgaca ggg 23

<210> SEQ ID NO 317
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 317
ttgacagggc tctattttat agg 23

<210> SEQ ID NO 318
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 318

Met Ala Pro Lys Lys Lys Arg Lys Val Gly Ile His Arg Gly Val Pro
1 5 10 15

<210> SEQ ID NO 319
<211> LENGTH: 4869
<212> TYPE: DNA
<213> ORGANISM: Artificial Sequence
<220> FEATURE:
<223> OTHER INFORMATION: Synthetic Polynucleotide

<400> SEQUENCE: 319
atggactaca aagaccatga cggtgattat aaagatcatg acatcgatta caaggatgac 60
gatgacaaga tggcccccaa gaagaagagg aaggtgggca ttcaccgcgg ggtacctgga 120
ggttctggat cccaactagt caaaagtgaa ctggaggaga agaaatctga acttcgtcat 180
aaattgaaat atgtgcctca tgaatatatt gaattaattg aaattgccag aaattccact 240
caggatagaa ttcttgaaat gaaggtaatg gaatttttta tgaaagttta tggatataga 300
ggtaaacatt tgggtggatc aaggaaaccg gacggagcaa tttatactgt cggatctcct 360
attgattacg gtgtgatcgt ggatactaaa gcttatagcg gaggttataa tctgccaatt 420
ggccaagcag atgaaatgca acgatatgtc gaagaaaatc aaacacgaaa caaacatatc 480
aaccctaatg aatggtggaa agtctatcca tcttctgtaa cggaatttaa gtttttattt 540
gtgagtggtc actttaaagg aaactacaaa gctcagctta cacgattaaa tcatatcact 600
aattgtaatg gagctgttct tagtgtagaa gagcttttaa ttggtggaga aatgattaaa 660
gccggcacat taaccttaga ggaagtcaga cggaaattta ataacggcga gataaacttt 720
agcggcagcg agactcccgg gacctcagag tccgccacac ccgaaagtga taaaaagtat 780
tctattggtt tagctatcgg cactaattcc gttggatggg ctgtcataac cgatgaatac 840
aaagtacctt caaagaaatt taaggtgttg gggaacacag accgtcattc gattaaaaag 900
aatcttatcg gtgccctcct attcgatagt ggcgaaacgg cagaggcgac tcgcctgaaa 960
cgaaccgctc ggagaaggta tacacgtcgc aagaaccgaa tatgttactt acaagaaatt 1020
tttagcaatg agatggccaa agttgacgat tctttctttc accgtttgga agagtccttc 1080
cttgtcgaag aggacaagaa acatgaacgg caccccatct ttggaaacat agtagatgag 1140
gtggcatatc atgaaaagta cccaacgatt tatcacctca gaaaaaagct agttgactca 1200
actgataaag cggacctgag gttaatctac ttggctcttg cccatatgat aaagttccgt 1260
gggcactttc tcattgaggg tgatctaaat ccggacaact cggatgtcga caaactgttc 1320
atccagttag tacaaaccta taatcagttg tttgaagaga accctataaa tgcaagtggc 1380
gtggatgcga aggctattct tagcgcccgc ctctctaaat cccgacggct agaaaacctg 1440
atcgcacaat tacccggaga gaagaaaaat gggttgttcg gtaaccttat agcgctctca 1500
ctaggcctga caccaaattt taagtcgaac ttcgacttag ctgaagatgc caaattgcag 1560

```
cttagtaagg acacgtacga tgacgatctc gacaatctac tggcacaaat tggagatcag   1620
tatgcggact tatttttggc tgccaaaaac cttagcgatg caatcctcct atctgacata   1680
ctgagagtta atactgagat taccaaggcg ccgttatccg cttcaatgat caaaaggtac   1740
gatgaacatc accaagactt gacacttctc aaggccctag tccgtcagca actgcctgag   1800
aaatataagg aaatattctt tgatcagtcg aaaaacgggt acgcaggtta tattgacggc   1860
ggagcgagtc aagaggaatt ctacaagttt atcaaaccca tattagagaa gatggatggg   1920
acggaagagt tgcttgtaaa actcaatcgc gaagatctac tgcgaaagca gcggactttc   1980
gacaacggta gcattccaca tcaaatccac ttaggcgaat tgcatgctat acttagaagg   2040
caggaggatt tttatccgtt cctcaaagac aatcgtgaaa agattgagaa aatcctaacc   2100
tttcgcatac cttactatgt gggacccctg gcccgaggga actctcggtt cgcatggatg   2160
acaagaaagt ccgaagaaac gattactcca tggaattttg aggaagttgt cgataaaggt   2220
gcgtcagctc aatcgttcat cgagaggatg accaactttg acaagaattt accgaacgaa   2280
aaagtattgc ctaagcacag tttactttac gagtatttca cagtgtacaa tgaactcacg   2340
aaagttaagt atgtcactga gggcatgcgt aaacccgcct ttctaagcgg agaacagaag   2400
aaagcaatag tagatctgtt attcaagacc aaccgcaaag tgacagttaa gcaattgaaa   2460
gaggactact ttaagaaaat tgaatgcttc gattctgtcg agatctccgg ggtagaagat   2520
cgatttaatg cgtcacttgg tacgtatcat gacctcctaa agataattaa agataaggac   2580
ttcctggata acgaagagaa tgaagatatc ttagaagata tagtgttgac tcttaccctc   2640
tttgaagatc gggaaatgat tgaggaaaga ctaaaaacat acgctcacct gttcgacgat   2700
aaggttatga aacagttaaa gaggcgtcgc tatacgggct ggggacgatt gtcgcggaaa   2760
cttatcaacg ggataagaga caagcaaagt ggtaaaacta ttctcgattt tctaaagagc   2820
gacggcttcg ccaataggaa ctttatgcag ctgatccatg atgactcttt aaccttcaaa   2880
gaggatatac aaaaggcaca ggtttccgga caaggggact cattgcacga acatattgcg   2940
aatcttgctg gttcgccagc catcaaaaag ggcatactcc agacagtcaa agtagtggat   3000
gagctagtta aggtcatggg acgtcacaaa ccggaaaaca ttgtaatcga gatggcacgc   3060
gaaaatcaaa cgactcagaa ggggcaaaaa aacagtcgag agcggatgaa gagaatagaa   3120
gagggtatta aagaactggg cagccagatc ttaaaggagc atcctgtgga aaatacccaa   3180
ttgcagaacg agaaacttta cctctattac ctacaaaatg gaagggacat gtatgttgat   3240
caggaactgg acataaaccg tttatctgat tacgacgtcg atgccattgt accccaatcc   3300
tttttgaagg acgattcaat cgacaataaa gtgcttacac gctcggataa gaaccgaggg   3360
aaaagtgaca atgttccaag cgaggaagtc gtaaagaaaa tgaagaacta ttggcggcag   3420
ctcctaaatg cgaaactgat aacgcaaaga aagttcgata acttaactaa agctgagagg   3480
ggtggcttgt ctgaacttga caaggccgga tttattaaac gtcagctcgt ggaaacccgc   3540
caaatcacaa agcatgttgc acagatacta gattcccgaa tgaatacgaa atacgacgag   3600
aacgataagc tgattcggga agtcaaagta atcactttaa agtcaaaatt ggtgtcggac   3660
ttcagaaagg attttcaatt ctataaagtt agggagataa ataactacca ccatgcgcac   3720
gacgcttatc ttaatgccgt cgtagggacc gcactcatta agaaataccc gaagctagaa   3780
agtgagtttg tgtatggtga ttacaaagtt tatgacgtcc gtaagatgat cgcgaaaagc   3840
gaacaggaga taggcaaggc tacagccaaa tacttctttt attctaacat tatgaatttc   3900
```

-continued

```
tttaagacgg aaatcactct ggcaaacgga gagatacgca aacgaccttt aattgaaacc   3960

aatggggaga caggtgaaat cgtatgggat aagggccggg acttcgcgac ggtgagaaaa   4020

gttttgtcca tgccccaagt caacatagta aagaaaactg aggtgcagac cggagggttt   4080

tcaaaggaat cgattcttcc aaaaaggaat agtgataagc tcatcgctcg taaaaaggac   4140

tgggacccga aaaagtacgg tggcttcgat agccctacag ttgcctattc tgtcctagta   4200

gtggcaaaag ttgagaaggg aaaatccaag aaactgaagt cagtcaaaga attattgggg   4260

ataacgatta tggagcgctc gtcttttgaa aagaacccca tcgacttcct tgaggcgaaa   4320

ggttacaagg aagtaaaaaa ggatctcata attaaactac caaagtatag tctgtttgag   4380

ttagaaaatg gccgaaaacg gatgttggct agcgccggag agcttcaaaa ggggaacgaa   4440

ctcgcactac cgtctaaata cgtgaatttc ctgtatttag cgtcccatta cgagaagttg   4500

aaaggttcac ctgaagataa cgaacagaag caactttttg ttgagcagca caaacattat   4560

ctcgacgaaa tcatagagca aatttcggaa ttcagtaaga gagtcatcct agctgatgcc   4620

aatctggaca aagtattaag cgcatacaac aagcacaggg ataaacccat acgtgagcag   4680

gcggaaaata ttatccattt gtttactctt accaacctcg gcgctccagc cgcattcaag   4740

tattttgaca caacgataga tcgcaaacga tacacttcta ccaaggaggt gctagacgcg   4800

acactgattc accaatccat cacgggatta tatgaaactc ggatagattt gtcacagctt   4860

gggggtgac                                                           4869
```

<210> SEQ ID NO 320
<211> LENGTH: 1367
<212> TYPE: PRT
<213> ORGANISM: Artificial Sequence
<220> FEATURE:
<223> OTHER INFORMATION: Synthetic Polypeptide

<400> SEQUENCE: 320

```
Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190
```

-continued

```
Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605
```

```
Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp Ala Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Lys Leu Glu Ser  Glu Phe Val
        995                 1000                1005

Tyr Gly  Asp Tyr Lys Val Tyr  Asp Val Arg Lys Met  Ile Ala Lys
    1010                1015                1020

Ser Glu  Gln Glu Ile Gly Lys  Ala Thr Ala Lys Tyr  Phe Phe Tyr
```

```
    1025                1030                1035

Ser Asn  Ile Met Asn Phe Phe  Lys Thr Glu Ile Thr  Leu Ala Asn
    1040                1045                1050

Gly Glu  Ile Arg Lys Arg Pro  Leu Ile Glu Thr Asn  Gly Glu Thr
    1055                1060                1065

Gly Glu  Ile Val Trp Asp Lys  Gly Arg Asp Phe Ala  Thr Val Arg
    1070                1075                1080

Lys Val  Leu Ser Met Pro Gln  Val Asn Ile Val Lys  Lys Thr Glu
    1085                1090                1095

Val Gln  Thr Gly Gly Phe Ser  Lys Glu Ser Ile Leu  Pro Lys Arg
    1100                1105                1110

Asn Ser  Asp Lys Leu Ile Ala  Arg Lys Lys Asp Trp  Asp Pro Lys
    1115                1120                1125

Lys Tyr  Gly Gly Phe Asp Ser  Pro Thr Val Ala Tyr  Ser Val Leu
    1130                1135                1140

Val Val  Ala Lys Val Glu Lys  Gly Lys Ser Lys Lys  Leu Lys Ser
    1145                1150                1155

Val Lys  Glu Leu Leu Gly Ile  Thr Ile Met Glu Arg  Ser Ser Phe
    1160                1165                1170

Glu Lys  Asn Pro Ile Asp Phe  Leu Glu Ala Lys Gly  Tyr Lys Glu
    1175                1180                1185

Val Lys  Lys Asp Leu Ile Ile  Lys Leu Pro Lys Tyr  Ser Leu Phe
    1190                1195                1200

Glu Leu  Glu Asn Gly Arg Lys  Arg Met Leu Ala Ser  Ala Gly Glu
    1205                1210                1215

Leu Gln  Lys Gly Asn Glu Leu  Ala Leu Pro Ser Lys  Tyr Val Asn
    1220                1225                1230

Phe Leu  Tyr Leu Ala Ser His  Tyr Glu Lys Leu Lys  Gly Ser Pro
    1235                1240                1245

Glu Asp  Asn Glu Gln Lys Gln  Leu Phe Val Glu Gln  His Lys His
    1250                1255                1260

Tyr Leu  Asp Glu Ile Ile Glu  Gln Ile Ser Glu Phe  Ser Lys Arg
    1265                1270                1275

Val Ile  Leu Ala Asp Ala Asn  Leu Asp Lys Val Leu  Ser Ala Tyr
    1280                1285                1290

Asn Lys  His Arg Asp Lys Pro  Ile Arg Glu Gln Ala  Glu Asn Ile
    1295                1300                1305

Ile His  Leu Phe Thr Leu Thr  Asn Leu Gly Ala Pro  Ala Ala Phe
    1310                1315                1320

Lys Tyr  Phe Asp Thr Thr Ile  Asp Arg Lys Arg Tyr  Thr Ser Thr
    1325                1330                1335

Lys Glu  Val Leu Asp Ala Thr  Leu Ile His Gln Ser  Ile Thr Gly
    1340                1345                1350

Leu Tyr  Glu Thr Arg Ile Asp  Leu Ser Gln Leu Gly  Gly Asp
    1355                1360                1365


<210> SEQ ID NO 321
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 321

Met Asp Tyr Lys Asp His Asp Gly Asp Tyr Lys Asp His Asp Ile Asp
```

1 5 10 15

Tyr Lys Asp Asp Asp Asp Lys
20

<210> SEQ ID NO 322
<211> LENGTH: 432
<212> TYPE: DNA
<213> ORGANISM: Artificial Sequence
<220> FEATURE:
<223> OTHER INFORMATION: Synthetic Polynucleotide

<400> SEQUENCE: 322
atggccctgt ttggctacgc acgcgtgtct accagtcaac agtcactcga tttgcaagtg 60
agggctctta aagatgccgg agtgaaggca aacagaattt ttactgataa ggccagcgga 120
agcagcacag acagagaggg gctggatctc ctgagaatga aggtaaagga gggtgatgtg 180
atcttggtca aaaaattgga tcgactgggg agagacacag ctgatatgct tcagcttatt 240
aaagagtttg acgctcaggg tgttgccgtg aggtttatcg atgacggcat ctcaaccgac 300
tcctacattg gtcttatgtt tgtgacaatt ttgtccgctg tggctcaggc tgagcggaga 360
aggattctcg aaaggacgaa tgagggacgg caagcagcta agttgaaagg tatcaaattt 420
ggcagacgaa gg 432

<210> SEQ ID NO 323
<211> LENGTH: 414
<212> TYPE: DNA
<213> ORGANISM: Artificial Sequence
<220> FEATURE:
<223> OTHER INFORMATION: Synthetic Polynucleotide

<400> SEQUENCE: 323
atggcaacca ttggctacat aagggtgtct accatcgacc aaaatatcga cctgcagcgc 60
aacgctctga catccgccaa ctgcgatcgg atcttcgagg ataggatcag tggcaagatc 120
gccaaccggc ccggtctgaa gcgggctctg aagtacgtga ataagggcga tactctggtt 180
gtgtggaagt tggatcgctt gggtagatca gtgaagaatc tcgtagccct gataagcgag 240
ctgcacgaga ggggtgcaca tttccattct ctgaccgatt ccatcgatac gtctagcgcc 300
atgggccgat tcttctttta cgtcatgtcc gccctcgctg aaatggagcg cgaacttatt 360
gttgaacgga ctttggctgg actggcagcg gctagagcac agggccgact tgga 414

<210> SEQ ID NO 324
<211> LENGTH: 432
<212> TYPE: DNA
<213> ORGANISM: Artificial Sequence
<220> FEATURE:
<223> OTHER INFORMATION: Synthetic Polynucleotide

<400> SEQUENCE: 324
atgctcattg gctatgtaag ggtcagcacc aatgaccaaa acacagactt gcaacgcaat 60
gctttggttt gcgccggatg tgaacagata tttgaagata aactgagcgg cactcggaca 120
gacagacctg ggcttaagag agcactgaaa agactgcaga agggggacac cctggtcgtc 180
tggaaactgg atcgcctcgg acgcagcatg aaacatctga ttagcctggt tggtgagctt 240
agggagagag gaatcaactt cagaagcctg accgactcca tcgacaccag tagccccatg 300
ggacgattct tcttctatgt gatgggagca cttgctgaga tggaaagaga gcttattatc 360
gaaagaacta tggctggtat cgctgctgcc cggaacaaag gcagacggtt cggcagaccg 420
ccgaagagcg gc 432

<210> SEQ ID NO 325
<211> LENGTH: 144
<212> TYPE: PRT
<213> ORGANISM: Artificial Sequence
<220> FEATURE:
<223> OTHER INFORMATION: Synthetic Polypeptide

<400> SEQUENCE: 325

```
Met Ala Leu Phe Gly Tyr Ala Arg Val Ser Thr Ser Gln Gln Ser Leu
1               5                   10                  15

Asp Leu Gln Val Arg Ala Leu Lys Asp Ala Gly Val Lys Ala Asn Arg
            20                  25                  30

Ile Phe Thr Asp Lys Ala Ser Gly Ser Ser Thr Asp Arg Glu Gly Leu
        35                  40                  45

Asp Leu Leu Arg Met Lys Val Lys Glu Gly Asp Val Ile Leu Val Lys
    50                  55                  60

Lys Leu Asp Arg Leu Gly Arg Asp Thr Ala Asp Met Leu Gln Leu Ile
65                  70                  75                  80

Lys Glu Phe Asp Ala Gln Gly Val Ala Val Arg Phe Ile Asp Asp Gly
                85                  90                  95

Ile Ser Thr Asp Ser Tyr Ile Gly Leu Met Phe Val Thr Ile Leu Ser
            100                 105                 110

Ala Val Ala Gln Ala Glu Arg Arg Arg Ile Leu Glu Arg Thr Asn Glu
        115                 120                 125

Gly Arg Gln Ala Ala Lys Leu Lys Gly Ile Lys Phe Gly Arg Arg Arg
    130                 135                 140
```

<210> SEQ ID NO 326
<211> LENGTH: 138
<212> TYPE: PRT
<213> ORGANISM: Artificial Sequence
<220> FEATURE:
<223> OTHER INFORMATION: Synthetic Polypeptide

<400> SEQUENCE: 326

```
Met Ala Thr Ile Gly Tyr Ile Arg Val Ser Thr Ile Asp Gln Asn Ile
1               5                   10                  15

Asp Leu Gln Arg Asn Ala Leu Thr Ser Ala Asn Cys Asp Arg Ile Phe
            20                  25                  30

Glu Asp Arg Ile Ser Gly Lys Ile Ala Asn Arg Pro Gly Leu Lys Arg
        35                  40                  45

Ala Leu Lys Tyr Val Asn Lys Gly Asp Thr Leu Val Val Trp Lys Leu
    50                  55                  60

Asp Arg Leu Gly Arg Ser Val Lys Asn Leu Val Ala Leu Ile Ser Glu
65                  70                  75                  80

Leu His Glu Arg Gly Ala His Phe His Ser Leu Thr Asp Ser Ile Asp
                85                  90                  95

Thr Ser Ser Ala Met Gly Arg Phe Phe Phe Tyr Val Met Ser Ala Leu
            100                 105                 110

Ala Glu Met Glu Arg Glu Leu Ile Val Glu Arg Thr Leu Ala Gly Leu
        115                 120                 125

Ala Ala Ala Arg Ala Gln Gly Arg Leu Gly
    130                 135
```

<210> SEQ ID NO 327
<211> LENGTH: 144

<212> TYPE: PRT
<213> ORGANISM: Artificial Sequence
<220> FEATURE:
<223> OTHER INFORMATION: Synthetic Polypeptide

<400> SEQUENCE: 327

Met Leu Ile Gly Tyr Val Arg Val Ser Thr Asn Asp Gln Asn Thr Asp
1 5 10 15

Leu Gln Arg Asn Ala Leu Val Cys Ala Gly Cys Glu Gln Ile Phe Glu
20 25 30

Asp Lys Leu Ser Gly Thr Arg Thr Asp Arg Pro Gly Leu Lys Arg Ala
35 40 45

Leu Lys Arg Leu Gln Lys Gly Asp Thr Leu Val Val Trp Lys Leu Asp
50 55 60

Arg Leu Gly Arg Ser Met Lys His Leu Ile Ser Leu Val Gly Glu Leu
65 70 75 80

Arg Glu Arg Gly Ile Asn Phe Arg Ser Leu Thr Asp Ser Ile Asp Thr
85 90 95

Ser Ser Pro Met Gly Arg Phe Phe Phe Tyr Val Met Gly Ala Leu Ala
100 105 110

Glu Met Glu Arg Glu Leu Ile Ile Glu Arg Thr Met Ala Gly Ile Ala
115 120 125

Ala Ala Arg Asn Lys Gly Arg Arg Phe Gly Arg Pro Pro Lys Ser Gly
130 135 140

<210> SEQ ID NO 328
<211> LENGTH: 1537
<212> TYPE: PRT
<213> ORGANISM: Artificial Sequence
<220> FEATURE:
<223> OTHER INFORMATION: Synthetic Polypeptide

<400> SEQUENCE: 328

Met Asp Lys Lys Tyr Ser Ile Gly Leu Ala Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

-continued

```
Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605
```

```
Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                  1000                 1005

Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
```

```
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365

Met Ala  Pro Lys Lys Lys Arg  Lys Val Gly Ile His  Arg Gly Val
    1370                1375                1380

Pro Gly  Gly Ser Gly Gly Ser  Gly Gly Ser Met Ala  Leu Phe Gly
    1385                1390                1395

Tyr Ala  Arg Val Ser Thr Ser  Gln Gln Ser Leu Asp  Leu Gln Val
    1400                1405                1410

Arg Ala  Leu Lys Asp Ala Gly  Val Lys Ala Asn Arg  Ile Phe Thr
    1415                1420                1425
```

```
Asp Lys  Ala Ser Gly Ser Ser  Thr Asp Arg Glu Gly  Leu Asp Leu
    1430                 1435                 1440

Leu Arg  Met Lys Val Lys Glu  Gly Asp Val Ile Leu  Val Lys Lys
    1445                 1450                 1455

Leu Asp  Arg Leu Gly Arg Asp  Thr Ala Asp Met Leu  Gln Leu Ile
    1460                 1465                 1470

Lys Glu  Phe Asp Ala Gln Gly  Val Ala Val Arg Phe  Ile Asp Asp
    1475                 1480                 1485

Gly Ile  Ser Thr Asp Ser Tyr  Ile Gly Leu Met Phe  Val Thr Ile
    1490                 1495                 1500

Leu Ser  Ala Val Ala Gln Ala  Glu Arg Arg Arg Ile  Leu Glu Arg
    1505                 1510                 1515

Thr Asn  Glu Gly Arg Gln Ala  Ala Lys Leu Lys Gly  Ile Lys Phe
    1520                 1525                 1530

Gly Arg  Arg Arg
    1535


<210> SEQ ID NO 329
<211> LENGTH: 1537
<212> TYPE: PRT
<213> ORGANISM: Artificial Sequence
<220> FEATURE:
<223> OTHER INFORMATION: Synthetic Polypeptide

<400> SEQUENCE: 329

Met Ala Pro Lys Lys Lys Arg Lys Val Gly Ile His Arg Gly Val Pro
1               5                   10                  15

Met Asp Lys Lys Tyr Ser Ile Gly Leu Ala Ile Gly Thr Asn Ser Val
            20                  25                  30

Gly Trp Ala Val Ile Thr Asp Glu Tyr Lys Val Pro Ser Lys Lys Phe
        35                  40                  45

Lys Val Leu Gly Asn Thr Asp Arg His Ser Ile Lys Lys Asn Leu Ile
    50                  55                  60

Gly Ala Leu Leu Phe Asp Ser Gly Glu Thr Ala Glu Ala Thr Arg Leu
65                  70                  75                  80

Lys Arg Thr Ala Arg Arg Arg Tyr Thr Arg Arg Lys Asn Arg Ile Cys
                85                  90                  95

Tyr Leu Gln Glu Ile Phe Ser Asn Glu Met Ala Lys Val Asp Asp Ser
            100                 105                 110

Phe Phe His Arg Leu Glu Glu Ser Phe Leu Val Glu Glu Asp Lys Lys
        115                 120                 125

His Glu Arg His Pro Ile Phe Gly Asn Ile Val Asp Glu Val Ala Tyr
    130                 135                 140

His Glu Lys Tyr Pro Thr Ile Tyr His Leu Arg Lys Lys Leu Val Asp
145                 150                 155                 160

Ser Thr Asp Lys Ala Asp Leu Arg Leu Ile Tyr Leu Ala Leu Ala His
                165                 170                 175

Met Ile Lys Phe Arg Gly His Phe Leu Ile Glu Gly Asp Leu Asn Pro
            180                 185                 190

Asp Asn Ser Asp Val Asp Lys Leu Phe Ile Gln Leu Val Gln Thr Tyr
        195                 200                 205

Asn Gln Leu Phe Glu Glu Asn Pro Ile Asn Ala Ser Gly Val Asp Ala
    210                 215                 220

Lys Ala Ile Leu Ser Ala Arg Leu Ser Lys Ser Arg Arg Leu Glu Asn
225                 230                 235                 240
```

```
Leu Ile Ala Gln Leu Pro Gly Glu Lys Lys Asn Gly Leu Phe Gly Asn
                245                 250                 255

Leu Ile Ala Leu Ser Leu Gly Leu Thr Pro Asn Phe Lys Ser Asn Phe
            260                 265                 270

Asp Leu Ala Glu Asp Ala Lys Leu Gln Leu Ser Lys Asp Thr Tyr Asp
        275                 280                 285

Asp Asp Leu Asp Asn Leu Leu Ala Gln Ile Gly Asp Gln Tyr Ala Asp
    290                 295                 300

Leu Phe Leu Ala Ala Lys Asn Leu Ser Asp Ala Ile Leu Leu Ser Asp
305                 310                 315                 320

Ile Leu Arg Val Asn Thr Glu Ile Thr Lys Ala Pro Leu Ser Ala Ser
                325                 330                 335

Met Ile Lys Arg Tyr Asp Glu His His Gln Asp Leu Thr Leu Leu Lys
            340                 345                 350

Ala Leu Val Arg Gln Gln Leu Pro Glu Lys Tyr Lys Glu Ile Phe Phe
        355                 360                 365

Asp Gln Ser Lys Asn Gly Tyr Ala Gly Tyr Ile Asp Gly Gly Ala Ser
    370                 375                 380

Gln Glu Glu Phe Tyr Lys Phe Ile Lys Pro Ile Leu Glu Lys Met Asp
385                 390                 395                 400

Gly Thr Glu Glu Leu Leu Val Lys Leu Asn Arg Glu Asp Leu Leu Arg
                405                 410                 415

Lys Gln Arg Thr Phe Asp Asn Gly Ser Ile Pro His Gln Ile His Leu
            420                 425                 430

Gly Glu Leu His Ala Ile Leu Arg Arg Gln Glu Asp Phe Tyr Pro Phe
        435                 440                 445

Leu Lys Asp Asn Arg Glu Lys Ile Glu Lys Ile Leu Thr Phe Arg Ile
    450                 455                 460

Pro Tyr Tyr Val Gly Pro Leu Ala Arg Gly Asn Ser Arg Phe Ala Trp
465                 470                 475                 480

Met Thr Arg Lys Ser Glu Glu Thr Ile Thr Pro Trp Asn Phe Glu Glu
                485                 490                 495

Val Val Asp Lys Gly Ala Ser Ala Gln Ser Phe Ile Glu Arg Met Thr
            500                 505                 510

Asn Phe Asp Lys Asn Leu Pro Asn Glu Lys Val Leu Pro Lys His Ser
        515                 520                 525

Leu Leu Tyr Glu Tyr Phe Thr Val Tyr Asn Glu Leu Thr Lys Val Lys
    530                 535                 540

Tyr Val Thr Glu Gly Met Arg Lys Pro Ala Phe Leu Ser Gly Glu Gln
545                 550                 555                 560

Lys Lys Ala Ile Val Asp Leu Leu Phe Lys Thr Asn Arg Lys Val Thr
                565                 570                 575

Val Lys Gln Leu Lys Glu Asp Tyr Phe Lys Lys Ile Glu Cys Phe Asp
            580                 585                 590

Ser Val Glu Ile Ser Gly Val Glu Asp Arg Phe Asn Ala Ser Leu Gly
        595                 600                 605

Thr Tyr His Asp Leu Leu Lys Ile Ile Lys Asp Lys Asp Phe Leu Asp
    610                 615                 620

Asn Glu Glu Asn Glu Asp Ile Leu Glu Asp Ile Val Leu Thr Leu Thr
625                 630                 635                 640

Leu Phe Glu Asp Arg Glu Met Ile Glu Glu Arg Leu Lys Thr Tyr Ala
                645                 650                 655
```

```
His Leu Phe Asp Asp Lys Val Met Lys Gln Leu Lys Arg Arg Arg Tyr
            660                 665                 670

Thr Gly Trp Gly Arg Leu Ser Arg Lys Leu Ile Asn Gly Ile Arg Asp
        675                 680                 685

Lys Gln Ser Gly Lys Thr Ile Leu Asp Phe Leu Lys Ser Asp Gly Phe
    690                 695                 700

Ala Asn Arg Asn Phe Met Gln Leu Ile His Asp Asp Ser Leu Thr Phe
705                 710                 715                 720

Lys Glu Asp Ile Gln Lys Ala Gln Val Ser Gly Gln Gly Asp Ser Leu
                725                 730                 735

His Glu His Ile Ala Asn Leu Ala Gly Ser Pro Ala Ile Lys Lys Gly
            740                 745                 750

Ile Leu Gln Thr Val Lys Val Val Asp Glu Leu Val Lys Val Met Gly
        755                 760                 765

Arg His Lys Pro Glu Asn Ile Val Ile Glu Met Ala Arg Glu Asn Gln
    770                 775                 780

Thr Thr Gln Lys Gly Gln Lys Asn Ser Arg Glu Arg Met Lys Arg Ile
785                 790                 795                 800

Glu Glu Gly Ile Lys Glu Leu Gly Ser Gln Ile Leu Lys Glu His Pro
                805                 810                 815

Val Glu Asn Thr Gln Leu Gln Asn Glu Lys Leu Tyr Leu Tyr Tyr Leu
            820                 825                 830

Gln Asn Gly Arg Asp Met Tyr Val Asp Gln Glu Leu Asp Ile Asn Arg
        835                 840                 845

Leu Ser Asp Tyr Asp Val Asp Ala Ile Val Pro Gln Ser Phe Leu Lys
    850                 855                 860

Asp Asp Ser Ile Asp Asn Lys Val Leu Thr Arg Ser Asp Lys Asn Arg
865                 870                 875                 880

Gly Lys Ser Asp Asn Val Pro Ser Glu Glu Val Val Lys Lys Met Lys
                885                 890                 895

Asn Tyr Trp Arg Gln Leu Leu Asn Ala Lys Leu Ile Thr Gln Arg Lys
            900                 905                 910

Phe Asp Asn Leu Thr Lys Ala Glu Arg Gly Gly Leu Ser Glu Leu Asp
        915                 920                 925

Lys Ala Gly Phe Ile Lys Arg Gln Leu Val Glu Thr Arg Gln Ile Thr
    930                 935                 940

Lys His Val Ala Gln Ile Leu Asp Ser Arg Met Asn Thr Lys Tyr Asp
945                 950                 955                 960

Glu Asn Asp Lys Leu Ile Arg Glu Val Lys Val Ile Thr Leu Lys Ser
                965                 970                 975

Lys Leu Val Ser Asp Phe Arg Lys Asp Phe Gln Phe Tyr Lys Val Arg
            980                 985                 990

Glu Ile Asn Asn Tyr His His Ala  His Asp Ala Tyr Leu  Asn Ala Val
        995                 1000                 1005

Val Gly  Thr Ala Leu Ile Lys  Lys Tyr Pro Lys Leu  Glu Ser Glu
    1010                 1015                 1020

Phe Val  Tyr Gly Asp Tyr Lys  Val Tyr Asp Val Arg  Lys Met Ile
    1025                 1030                 1035

Ala Lys  Ser Glu Gln Glu Ile  Gly Lys Ala Thr Ala  Lys Tyr Phe
    1040                 1045                 1050

Phe Tyr  Ser Asn Ile Met Asn  Phe Phe Lys Thr Glu  Ile Thr Leu
    1055                 1060                 1065

Ala Asn  Gly Glu Ile Arg Lys  Arg Pro Leu Ile Glu  Thr Asn Gly
```

```
    1070                1075                1080

Glu Thr  Gly Glu Ile Val Trp  Asp Lys Gly Arg Asp  Phe Ala Thr
    1085                1090                1095

Val Arg  Lys Val Leu Ser Met  Pro Gln Val Asn Ile  Val Lys Lys
    1100                1105                1110

Thr Glu  Val Gln Thr Gly Gly  Phe Ser Lys Glu Ser  Ile Leu Pro
    1115                1120                1125

Lys Arg  Asn Ser Asp Lys Leu  Ile Ala Arg Lys Lys  Asp Trp Asp
    1130                1135                1140

Pro Lys  Lys Tyr Gly Gly Phe  Asp Ser Pro Thr Val  Ala Tyr Ser
    1145                1150                1155

Val Leu  Val Val Ala Lys Val  Glu Lys Gly Lys Ser  Lys Lys Leu
    1160                1165                1170

Lys Ser  Val Lys Glu Leu Leu  Gly Ile Thr Ile Met  Glu Arg Ser
    1175                1180                1185

Ser Phe  Glu Lys Asn Pro Ile  Asp Phe Leu Glu Ala  Lys Gly Tyr
    1190                1195                1200

Lys Glu  Val Lys Lys Asp Leu  Ile Ile Lys Leu Pro  Lys Tyr Ser
    1205                1210                1215

Leu Phe  Glu Leu Glu Asn Gly  Arg Lys Arg Met Leu  Ala Ser Ala
    1220                1225                1230

Gly Glu  Leu Gln Lys Gly Asn  Glu Leu Ala Leu Pro  Ser Lys Tyr
    1235                1240                1245

Val Asn  Phe Leu Tyr Leu Ala  Ser His Tyr Glu Lys  Leu Lys Gly
    1250                1255                1260

Ser Pro  Glu Asp Asn Glu Gln  Lys Gln Leu Phe Val  Glu Gln His
    1265                1270                1275

Lys His  Tyr Leu Asp Glu Ile  Ile Glu Gln Ile Ser  Glu Phe Ser
    1280                1285                1290

Lys Arg  Val Ile Leu Ala Asp  Ala Asn Leu Asp Lys  Val Leu Ser
    1295                1300                1305

Ala Tyr  Asn Lys His Arg Asp  Lys Pro Ile Arg Glu  Gln Ala Glu
    1310                1315                1320

Asn Ile  Ile His Leu Phe Thr  Leu Thr Asn Leu Gly  Ala Pro Ala
    1325                1330                1335

Ala Phe  Lys Tyr Phe Asp Thr  Thr Ile Asp Arg Lys  Arg Tyr Thr
    1340                1345                1350

Ser Thr  Lys Glu Val Leu Asp  Ala Thr Leu Ile His  Gln Ser Ile
    1355                1360                1365

Thr Gly  Leu Tyr Glu Thr Arg  Ile Asp Leu Ser Gln  Leu Gly Gly
    1370                1375                1380

Asp Gly  Gly Ser Gly Gly Ser  Gly Gly Ser Met Ala  Leu Phe Gly
    1385                1390                1395

Tyr Ala  Arg Val Ser Thr Ser  Gln Gln Ser Leu Asp  Leu Gln Val
    1400                1405                1410

Arg Ala  Leu Lys Asp Ala Gly  Val Lys Ala Asn Arg  Ile Phe Thr
    1415                1420                1425

Asp Lys  Ala Ser Gly Ser Ser  Thr Asp Arg Glu Gly  Leu Asp Leu
    1430                1435                1440

Leu Arg  Met Lys Val Lys Glu  Gly Asp Val Ile Leu  Val Lys Lys
    1445                1450                1455

Leu Asp  Arg Leu Gly Arg Asp  Thr Ala Asp Met Leu  Gln Leu Ile
    1460                1465                1470
```

```
Lys Glu  Phe Asp Ala Gln Gly  Val Ala Val Arg Phe  Ile Asp Asp
    1475                 1480                 1485

Gly Ile  Ser Thr Asp Ser Tyr  Ile Gly Leu Met Phe  Val Thr Ile
    1490                 1495                 1500

Leu Ser  Ala Val Ala Gln Ala  Glu Arg Arg Arg Ile  Leu Glu Arg
    1505                 1510                 1515

Thr Asn  Glu Gly Arg Gln Ala  Ala Lys Leu Lys Gly  Ile Lys Phe
    1520                 1525                 1530

Gly Arg  Arg Arg
    1535


<210> SEQ ID NO 330
<211> LENGTH: 1537
<212> TYPE: PRT
<213> ORGANISM: Artificial Sequence
<220> FEATURE:
<223> OTHER INFORMATION: Synthetic Polypeptide

<400> SEQUENCE: 330

Met Ala Leu Phe Gly Tyr Ala Arg Val Ser Thr Ser Gln Gln Ser Leu
1               5                   10                  15

Asp Leu Gln Val Arg Ala Leu Lys Asp Ala Gly Val Lys Ala Asn Arg
            20                  25                  30

Ile Phe Thr Asp Lys Ala Ser Gly Ser Ser Thr Asp Arg Glu Gly Leu
        35                  40                  45

Asp Leu Leu Arg Met Lys Val Lys Glu Gly Asp Val Ile Leu Val Lys
    50                  55                  60

Lys Leu Asp Arg Leu Gly Arg Asp Thr Ala Asp Met Leu Gln Leu Ile
65                  70                  75                  80

Lys Glu Phe Asp Ala Gln Gly Val Ala Val Arg Phe Ile Asp Asp Gly
                85                  90                  95

Ile Ser Thr Asp Ser Tyr Ile Gly Leu Met Phe Val Thr Ile Leu Ser
            100                 105                 110

Ala Val Ala Gln Ala Glu Arg Arg Arg Ile Leu Glu Arg Thr Asn Glu
        115                 120                 125

Gly Arg Gln Ala Ala Lys Leu Lys Gly Ile Lys Phe Gly Arg Arg Arg
    130                 135                 140

Gly Gly Ser Gly Gly Ser Gly Gly Ser Met Asp Lys Lys Tyr Ser Ile
145                 150                 155                 160

Gly Leu Ala Ile Gly Thr Asn Ser Val Gly Trp Ala Val Ile Thr Asp
                165                 170                 175

Glu Tyr Lys Val Pro Ser Lys Lys Phe Lys Val Leu Gly Asn Thr Asp
            180                 185                 190

Arg His Ser Ile Lys Lys Asn Leu Ile Gly Ala Leu Leu Phe Asp Ser
        195                 200                 205

Gly Glu Thr Ala Glu Ala Thr Arg Leu Lys Arg Thr Ala Arg Arg Arg
    210                 215                 220

Tyr Thr Arg Arg Lys Asn Arg Ile Cys Tyr Leu Gln Glu Ile Phe Ser
225                 230                 235                 240

Asn Glu Met Ala Lys Val Asp Asp Ser Phe Phe His Arg Leu Glu Glu
                245                 250                 255

Ser Phe Leu Val Glu Glu Asp Lys Lys His Glu Arg His Pro Ile Phe
            260                 265                 270

Gly Asn Ile Val Asp Glu Val Ala Tyr His Glu Lys Tyr Pro Thr Ile
        275                 280                 285
```

```
Tyr His Leu Arg Lys Lys Leu Val Asp Ser Thr Asp Lys Ala Asp Leu
    290                 295                 300

Arg Leu Ile Tyr Leu Ala Leu Ala His Met Ile Lys Phe Arg Gly His
305                 310                 315                 320

Phe Leu Ile Glu Gly Asp Leu Asn Pro Asp Asn Ser Asp Val Asp Lys
                325                 330                 335

Leu Phe Ile Gln Leu Val Gln Thr Tyr Asn Gln Leu Phe Glu Glu Asn
            340                 345                 350

Pro Ile Asn Ala Ser Gly Val Asp Ala Lys Ala Ile Leu Ser Ala Arg
        355                 360                 365

Leu Ser Lys Ser Arg Arg Leu Glu Asn Leu Ile Ala Gln Leu Pro Gly
    370                 375                 380

Glu Lys Lys Asn Gly Leu Phe Gly Asn Leu Ile Ala Leu Ser Leu Gly
385                 390                 395                 400

Leu Thr Pro Asn Phe Lys Ser Asn Phe Asp Leu Ala Glu Asp Ala Lys
                405                 410                 415

Leu Gln Leu Ser Lys Asp Thr Tyr Asp Asp Asp Leu Asp Asn Leu Leu
            420                 425                 430

Ala Gln Ile Gly Asp Gln Tyr Ala Asp Leu Phe Leu Ala Ala Lys Asn
        435                 440                 445

Leu Ser Asp Ala Ile Leu Leu Ser Asp Ile Leu Arg Val Asn Thr Glu
    450                 455                 460

Ile Thr Lys Ala Pro Leu Ser Ala Ser Met Ile Lys Arg Tyr Asp Glu
465                 470                 475                 480

His His Gln Asp Leu Thr Leu Leu Lys Ala Leu Val Arg Gln Gln Leu
                485                 490                 495

Pro Glu Lys Tyr Lys Glu Ile Phe Phe Asp Gln Ser Lys Asn Gly Tyr
            500                 505                 510

Ala Gly Tyr Ile Asp Gly Gly Ala Ser Gln Glu Glu Phe Tyr Lys Phe
        515                 520                 525

Ile Lys Pro Ile Leu Glu Lys Met Asp Gly Thr Glu Glu Leu Leu Val
    530                 535                 540

Lys Leu Asn Arg Glu Asp Leu Leu Arg Lys Gln Arg Thr Phe Asp Asn
545                 550                 555                 560

Gly Ser Ile Pro His Gln Ile His Leu Gly Glu Leu His Ala Ile Leu
                565                 570                 575

Arg Arg Gln Glu Asp Phe Tyr Pro Phe Leu Lys Asp Asn Arg Glu Lys
            580                 585                 590

Ile Glu Lys Ile Leu Thr Phe Arg Ile Pro Tyr Tyr Val Gly Pro Leu
        595                 600                 605

Ala Arg Gly Asn Ser Arg Phe Ala Trp Met Thr Arg Lys Ser Glu Glu
    610                 615                 620

Thr Ile Thr Pro Trp Asn Phe Glu Glu Val Val Asp Lys Gly Ala Ser
625                 630                 635                 640

Ala Gln Ser Phe Ile Glu Arg Met Thr Asn Phe Asp Lys Asn Leu Pro
                645                 650                 655

Asn Glu Lys Val Leu Pro Lys His Ser Leu Leu Tyr Glu Tyr Phe Thr
            660                 665                 670

Val Tyr Asn Glu Leu Thr Lys Val Lys Tyr Val Thr Glu Gly Met Arg
        675                 680                 685

Lys Pro Ala Phe Leu Ser Gly Glu Gln Lys Lys Ala Ile Val Asp Leu
    690                 695                 700
```

-continued

```
Leu Phe Lys Thr Asn Arg Lys Val Thr Val Lys Gln Leu Lys Glu Asp
705                 710                 715                 720

Tyr Phe Lys Lys Ile Glu Cys Phe Asp Ser Val Glu Ile Ser Gly Val
                725                 730                 735

Glu Asp Arg Phe Asn Ala Ser Leu Gly Thr Tyr His Asp Leu Leu Lys
            740                 745                 750

Ile Ile Lys Asp Lys Asp Phe Leu Asp Asn Glu Glu Asn Glu Asp Ile
        755                 760                 765

Leu Glu Asp Ile Val Leu Thr Leu Thr Leu Phe Glu Asp Arg Glu Met
    770                 775                 780

Ile Glu Glu Arg Leu Lys Thr Tyr Ala His Leu Phe Asp Asp Lys Val
785                 790                 795                 800

Met Lys Gln Leu Lys Arg Arg Arg Tyr Thr Gly Trp Gly Arg Leu Ser
                805                 810                 815

Arg Lys Leu Ile Asn Gly Ile Arg Asp Lys Gln Ser Gly Lys Thr Ile
            820                 825                 830

Leu Asp Phe Leu Lys Ser Asp Gly Phe Ala Asn Arg Asn Phe Met Gln
        835                 840                 845

Leu Ile His Asp Asp Ser Leu Thr Phe Lys Glu Asp Ile Gln Lys Ala
    850                 855                 860

Gln Val Ser Gly Gln Gly Asp Ser Leu His Glu His Ile Ala Asn Leu
865                 870                 875                 880

Ala Gly Ser Pro Ala Ile Lys Lys Gly Ile Leu Gln Thr Val Lys Val
                885                 890                 895

Val Asp Glu Leu Val Lys Val Met Gly Arg His Lys Pro Glu Asn Ile
            900                 905                 910

Val Ile Glu Met Ala Arg Glu Asn Gln Thr Thr Gln Lys Gly Gln Lys
        915                 920                 925

Asn Ser Arg Glu Arg Met Lys Arg Ile Glu Glu Gly Ile Lys Glu Leu
    930                 935                 940

Gly Ser Gln Ile Leu Lys Glu His Pro Val Glu Asn Thr Gln Leu Gln
945                 950                 955                 960

Asn Glu Lys Leu Tyr Leu Tyr Tyr Leu Gln Asn Gly Arg Asp Met Tyr
                965                 970                 975

Val Asp Gln Glu Leu Asp Ile Asn Arg Leu Ser Asp Tyr Asp Val Asp
            980                 985                 990

Ala Ile Val Pro Gln Ser Phe Leu  Lys Asp Asp Ser Ile  Asp Asn Lys
        995                 1000                1005

Val Leu  Thr Arg Ser Asp Lys  Asn Arg Gly Lys Ser  Asp Asn Val
    1010                1015                1020

Pro Ser  Glu Glu Val Val Lys  Lys Met Lys Asn Tyr  Trp Arg Gln
    1025                1030                1035

Leu Leu  Asn Ala Lys Leu Ile  Thr Gln Arg Lys Phe  Asp Asn Leu
    1040                1045                1050

Thr Lys  Ala Glu Arg Gly Gly  Leu Ser Glu Leu Asp  Lys Ala Gly
    1055                1060                1065

Phe Ile  Lys Arg Gln Leu Val  Glu Thr Arg Gln Ile  Thr Lys His
    1070                1075                1080

Val Ala  Gln Ile Leu Asp Ser  Arg Met Asn Thr Lys  Tyr Asp Glu
    1085                1090                1095

Asn Asp  Lys Leu Ile Arg Glu  Val Lys Val Ile Thr  Leu Lys Ser
    1100                1105                1110

Lys Leu  Val Ser Asp Phe Arg  Lys Asp Phe Gln Phe  Tyr Lys Val
```

```
    1115                1120                1125

Arg Glu  Ile Asn Asn Tyr His  His Ala His Asp Ala  Tyr Leu Asn
    1130                1135                1140

Ala Val  Val Gly Thr Ala Leu  Ile Lys Lys Tyr Pro  Lys Leu Glu
    1145                1150                1155

Ser Glu  Phe Val Tyr Gly Asp  Tyr Lys Val Tyr Asp  Val Arg Lys
    1160                1165                1170

Met Ile  Ala Lys Ser Glu Gln  Glu Ile Gly Lys Ala  Thr Ala Lys
    1175                1180                1185

Tyr Phe  Phe Tyr Ser Asn Ile  Met Asn Phe Phe Lys  Thr Glu Ile
    1190                1195                1200

Thr Leu  Ala Asn Gly Glu Ile  Arg Lys Arg Pro Leu  Ile Glu Thr
    1205                1210                1215

Asn Gly  Glu Thr Gly Glu Ile  Val Trp Asp Lys Gly  Arg Asp Phe
    1220                1225                1230

Ala Thr  Val Arg Lys Val Leu  Ser Met Pro Gln Val  Asn Ile Val
    1235                1240                1245

Lys Lys  Thr Glu Val Gln Thr  Gly Gly Phe Ser Lys  Glu Ser Ile
    1250                1255                1260

Leu Pro  Lys Arg Asn Ser Asp  Lys Leu Ile Ala Arg  Lys Lys Asp
    1265                1270                1275

Trp Asp  Pro Lys Lys Tyr Gly  Gly Phe Asp Ser Pro  Thr Val Ala
    1280                1285                1290

Tyr Ser  Val Leu Val Val Ala  Lys Val Glu Lys Gly  Lys Ser Lys
    1295                1300                1305

Lys Leu  Lys Ser Val Lys Glu  Leu Leu Gly Ile Thr  Ile Met Glu
    1310                1315                1320

Arg Ser  Ser Phe Glu Lys Asn  Pro Ile Asp Phe Leu  Glu Ala Lys
    1325                1330                1335

Gly Tyr  Lys Glu Val Lys Lys  Asp Leu Ile Ile Lys  Leu Pro Lys
    1340                1345                1350

Tyr Ser  Leu Phe Glu Leu Glu  Asn Gly Arg Lys Arg  Met Leu Ala
    1355                1360                1365

Ser Ala  Gly Glu Leu Gln Lys  Gly Asn Glu Leu Ala  Leu Pro Ser
    1370                1375                1380

Lys Tyr  Val Asn Phe Leu Tyr  Leu Ala Ser His Tyr  Glu Lys Leu
    1385                1390                1395

Lys Gly  Ser Pro Glu Asp Asn  Glu Gln Lys Gln Leu  Phe Val Glu
    1400                1405                1410

Gln His  Lys His Tyr Leu Asp  Glu Ile Ile Glu Gln  Ile Ser Glu
    1415                1420                1425

Phe Ser  Lys Arg Val Ile Leu  Ala Asp Ala Asn Leu  Asp Lys Val
    1430                1435                1440

Leu Ser  Ala Tyr Asn Lys His  Arg Asp Lys Pro Ile  Arg Glu Gln
    1445                1450                1455

Ala Glu  Asn Ile Ile His Leu  Phe Thr Leu Thr Asn  Leu Gly Ala
    1460                1465                1470

Pro Ala  Ala Phe Lys Tyr Phe  Asp Thr Thr Ile Asp  Arg Lys Arg
    1475                1480                1485

Tyr Thr  Ser Thr Lys Glu Val  Leu Asp Ala Thr Leu  Ile His Gln
    1490                1495                1500

Ser Ile  Thr Gly Leu Tyr Glu  Thr Arg Ile Asp Leu  Ser Gln Leu
    1505                1510                1515
```

```
Gly Gly  Asp Met Ala Pro Lys  Lys Lys Arg Lys Val  Gly Ile His
    1520                1525                1530

Arg Gly  Val Pro
    1535
```

<210> SEQ ID NO 331
<211> LENGTH: 1537
<212> TYPE: PRT
<213> ORGANISM: Artificial Sequence
<220> FEATURE:
<223> OTHER INFORMATION: Synthetic Polypeptide

<400> SEQUENCE: 331

```
Met Ala Pro Lys Lys Lys Arg Lys Val Gly Ile His Arg Gly Val Pro
1               5                   10                  15

Met Ala Leu Phe Gly Tyr Ala Arg Val Ser Thr Ser Gln Gln Ser Leu
            20                  25                  30

Asp Leu Gln Val Arg Ala Leu Lys Asp Ala Gly Val Lys Ala Asn Arg
        35                  40                  45

Ile Phe Thr Asp Lys Ala Ser Gly Ser Ser Thr Asp Arg Glu Gly Leu
    50                  55                  60

Asp Leu Leu Arg Met Lys Val Lys Glu Gly Asp Val Ile Leu Val Lys
65                  70                  75                  80

Lys Leu Asp Arg Leu Gly Arg Asp Thr Ala Asp Met Leu Gln Leu Ile
                85                  90                  95

Lys Glu Phe Asp Ala Gln Gly Val Ala Val Arg Phe Ile Asp Asp Gly
            100                 105                 110

Ile Ser Thr Asp Ser Tyr Ile Gly Leu Met Phe Val Thr Ile Leu Ser
        115                 120                 125

Ala Val Ala Gln Ala Glu Arg Arg Arg Ile Leu Glu Arg Thr Asn Glu
    130                 135                 140

Gly Arg Gln Ala Ala Lys Leu Lys Gly Ile Lys Phe Gly Arg Arg Arg
145                 150                 155                 160

Gly Gly Ser Gly Gly Ser Gly Gly Ser Met Asp Lys Lys Tyr Ser Ile
                165                 170                 175

Gly Leu Ala Ile Gly Thr Asn Ser Val Gly Trp Ala Val Ile Thr Asp
            180                 185                 190

Glu Tyr Lys Val Pro Ser Lys Lys Phe Lys Val Leu Gly Asn Thr Asp
        195                 200                 205

Arg His Ser Ile Lys Lys Asn Leu Ile Gly Ala Leu Leu Phe Asp Ser
    210                 215                 220

Gly Glu Thr Ala Glu Ala Thr Arg Leu Lys Arg Thr Ala Arg Arg Arg
225                 230                 235                 240

Tyr Thr Arg Arg Lys Asn Arg Ile Cys Tyr Leu Gln Glu Ile Phe Ser
                245                 250                 255

Asn Glu Met Ala Lys Val Asp Asp Ser Phe Phe His Arg Leu Glu Glu
            260                 265                 270

Ser Phe Leu Val Glu Glu Asp Lys Lys His Glu Arg His Pro Ile Phe
        275                 280                 285

Gly Asn Ile Val Asp Glu Val Ala Tyr His Glu Lys Tyr Pro Thr Ile
    290                 295                 300

Tyr His Leu Arg Lys Lys Leu Val Asp Ser Thr Asp Lys Ala Asp Leu
305                 310                 315                 320

Arg Leu Ile Tyr Leu Ala Leu Ala His Met Ile Lys Phe Arg Gly His
                325                 330                 335
```

-continued

```
Phe Leu Ile Glu Gly Asp Leu Asn Pro Asp Asn Ser Asp Val Asp Lys
            340                 345                 350

Leu Phe Ile Gln Leu Val Gln Thr Tyr Asn Gln Leu Phe Glu Glu Asn
        355                 360                 365

Pro Ile Asn Ala Ser Gly Val Asp Ala Lys Ala Ile Leu Ser Ala Arg
    370                 375                 380

Leu Ser Lys Ser Arg Arg Leu Glu Asn Leu Ile Ala Gln Leu Pro Gly
385                 390                 395                 400

Glu Lys Lys Asn Gly Leu Phe Gly Asn Leu Ile Ala Leu Ser Leu Gly
                405                 410                 415

Leu Thr Pro Asn Phe Lys Ser Asn Phe Asp Leu Ala Glu Asp Ala Lys
            420                 425                 430

Leu Gln Leu Ser Lys Asp Thr Tyr Asp Asp Asp Leu Asp Asn Leu Leu
        435                 440                 445

Ala Gln Ile Gly Asp Gln Tyr Ala Asp Leu Phe Leu Ala Ala Lys Asn
    450                 455                 460

Leu Ser Asp Ala Ile Leu Leu Ser Asp Ile Leu Arg Val Asn Thr Glu
465                 470                 475                 480

Ile Thr Lys Ala Pro Leu Ser Ala Ser Met Ile Lys Arg Tyr Asp Glu
                485                 490                 495

His His Gln Asp Leu Thr Leu Leu Lys Ala Leu Val Arg Gln Gln Leu
            500                 505                 510

Pro Glu Lys Tyr Lys Glu Ile Phe Phe Asp Gln Ser Lys Asn Gly Tyr
        515                 520                 525

Ala Gly Tyr Ile Asp Gly Gly Ala Ser Gln Glu Glu Phe Tyr Lys Phe
    530                 535                 540

Ile Lys Pro Ile Leu Glu Lys Met Asp Gly Thr Glu Glu Leu Leu Val
545                 550                 555                 560

Lys Leu Asn Arg Glu Asp Leu Leu Arg Lys Gln Arg Thr Phe Asp Asn
                565                 570                 575

Gly Ser Ile Pro His Gln Ile His Leu Gly Glu Leu His Ala Ile Leu
            580                 585                 590

Arg Arg Gln Glu Asp Phe Tyr Pro Phe Leu Lys Asp Asn Arg Glu Lys
        595                 600                 605

Ile Glu Lys Ile Leu Thr Phe Arg Ile Pro Tyr Tyr Val Gly Pro Leu
    610                 615                 620

Ala Arg Gly Asn Ser Arg Phe Ala Trp Met Thr Arg Lys Ser Glu Glu
625                 630                 635                 640

Thr Ile Thr Pro Trp Asn Phe Glu Glu Val Val Asp Lys Gly Ala Ser
                645                 650                 655

Ala Gln Ser Phe Ile Glu Arg Met Thr Asn Phe Asp Lys Asn Leu Pro
            660                 665                 670

Asn Glu Lys Val Leu Pro Lys His Ser Leu Leu Tyr Glu Tyr Phe Thr
        675                 680                 685

Val Tyr Asn Glu Leu Thr Lys Val Lys Tyr Val Thr Glu Gly Met Arg
    690                 695                 700

Lys Pro Ala Phe Leu Ser Gly Glu Gln Lys Lys Ala Ile Val Asp Leu
705                 710                 715                 720

Leu Phe Lys Thr Asn Arg Lys Val Thr Val Lys Gln Leu Lys Glu Asp
                725                 730                 735

Tyr Phe Lys Lys Ile Glu Cys Phe Asp Ser Val Glu Ile Ser Gly Val
            740                 745                 750
```

```
Glu Asp Arg Phe Asn Ala Ser Leu Gly Thr Tyr His Asp Leu Leu Lys
        755                 760                 765

Ile Ile Lys Asp Lys Asp Phe Leu Asp Asn Glu Glu Asn Glu Asp Ile
    770                 775                 780

Leu Glu Asp Ile Val Leu Thr Leu Thr Leu Phe Glu Asp Arg Glu Met
785                 790                 795                 800

Ile Glu Glu Arg Leu Lys Thr Tyr Ala His Leu Phe Asp Asp Lys Val
                805                 810                 815

Met Lys Gln Leu Lys Arg Arg Arg Tyr Thr Gly Trp Gly Arg Leu Ser
            820                 825                 830

Arg Lys Leu Ile Asn Gly Ile Arg Asp Lys Gln Ser Gly Lys Thr Ile
        835                 840                 845

Leu Asp Phe Leu Lys Ser Asp Gly Phe Ala Asn Arg Asn Phe Met Gln
    850                 855                 860

Leu Ile His Asp Asp Ser Leu Thr Phe Lys Glu Asp Ile Gln Lys Ala
865                 870                 875                 880

Gln Val Ser Gly Gln Gly Asp Ser Leu His Glu His Ile Ala Asn Leu
                885                 890                 895

Ala Gly Ser Pro Ala Ile Lys Lys Gly Ile Leu Gln Thr Val Lys Val
            900                 905                 910

Val Asp Glu Leu Val Lys Val Met Gly Arg His Lys Pro Glu Asn Ile
        915                 920                 925

Val Ile Glu Met Ala Arg Glu Asn Gln Thr Thr Gln Lys Gly Gln Lys
    930                 935                 940

Asn Ser Arg Glu Arg Met Lys Arg Ile Glu Glu Gly Ile Lys Glu Leu
945                 950                 955                 960

Gly Ser Gln Ile Leu Lys Glu His Pro Val Glu Asn Thr Gln Leu Gln
                965                 970                 975

Asn Glu Lys Leu Tyr Leu Tyr Tyr Leu Gln Asn Gly Arg Asp Met Tyr
            980                 985                 990

Val Asp Gln Glu Leu Asp Ile Asn  Arg Leu Ser Asp Tyr  Asp Val Asp
        995                 1000                1005

Ala Ile  Val Pro Gln Ser Phe  Leu Lys Asp Asp Ser  Ile Asp Asn
    1010                1015                1020

Lys Val  Leu Thr Arg Ser Asp  Lys Asn Arg Gly Lys  Ser Asp Asn
    1025                1030                1035

Val Pro  Ser Glu Glu Val Val  Lys Lys Met Lys Asn  Tyr Trp Arg
    1040                1045                1050

Gln Leu  Leu Asn Ala Lys Leu  Ile Thr Gln Arg Lys  Phe Asp Asn
    1055                1060                1065

Leu Thr  Lys Ala Glu Arg Gly  Gly Leu Ser Glu Leu  Asp Lys Ala
    1070                1075                1080

Gly Phe  Ile Lys Arg Gln Leu  Val Glu Thr Arg Gln  Ile Thr Lys
    1085                1090                1095

His Val  Ala Gln Ile Leu Asp  Ser Arg Met Asn Thr  Lys Tyr Asp
    1100                1105                1110

Glu Asn  Asp Lys Leu Ile Arg  Glu Val Lys Val Ile  Thr Leu Lys
    1115                1120                1125

Ser Lys  Leu Val Ser Asp Phe  Arg Lys Asp Phe Gln  Phe Tyr Lys
    1130                1135                1140

Val Arg  Glu Ile Asn Asn Tyr  His His Ala His Asp  Ala Tyr Leu
    1145                1150                1155

Asn Ala  Val Val Gly Thr Ala  Leu Ile Lys Lys Tyr  Pro Lys Leu
```

```
    1160                1165                1170

Glu Ser  Glu Phe Val Tyr Gly  Asp Tyr Lys Val Tyr  Asp Val Arg
    1175                1180                1185

Lys Met  Ile Ala Lys Ser Glu  Gln Glu Ile Gly Lys  Ala Thr Ala
    1190                1195                1200

Lys Tyr  Phe Phe Tyr Ser Asn  Ile Met Asn Phe Phe  Lys Thr Glu
    1205                1210                1215

Ile Thr  Leu Ala Asn Gly Glu  Ile Arg Lys Arg Pro  Leu Ile Glu
    1220                1225                1230

Thr Asn  Gly Glu Thr Gly Glu  Ile Val Trp Asp Lys  Gly Arg Asp
    1235                1240                1245

Phe Ala  Thr Val Arg Lys Val  Leu Ser Met Pro Gln  Val Asn Ile
    1250                1255                1260

Val Lys  Lys Thr Glu Val Gln  Thr Gly Gly Phe Ser  Lys Glu Ser
    1265                1270                1275

Ile Leu  Pro Lys Arg Asn Ser  Asp Lys Leu Ile Ala  Arg Lys Lys
    1280                1285                1290

Asp Trp  Asp Pro Lys Lys Tyr  Gly Gly Phe Asp Ser  Pro Thr Val
    1295                1300                1305

Ala Tyr  Ser Val Leu Val Val  Ala Lys Val Glu Lys  Gly Lys Ser
    1310                1315                1320

Lys Lys  Leu Lys Ser Val Lys  Glu Leu Leu Gly Ile  Thr Ile Met
    1325                1330                1335

Glu Arg  Ser Ser Phe Glu Lys  Asn Pro Ile Asp Phe  Leu Glu Ala
    1340                1345                1350

Lys Gly  Tyr Lys Glu Val Lys  Lys Asp Leu Ile Ile  Lys Leu Pro
    1355                1360                1365

Lys Tyr  Ser Leu Phe Glu Leu  Glu Asn Gly Arg Lys  Arg Met Leu
    1370                1375                1380

Ala Ser  Ala Gly Glu Leu Gln  Lys Gly Asn Glu Leu  Ala Leu Pro
    1385                1390                1395

Ser Lys  Tyr Val Asn Phe Leu  Tyr Leu Ala Ser His  Tyr Glu Lys
    1400                1405                1410

Leu Lys  Gly Ser Pro Glu Asp  Asn Glu Gln Lys Gln  Leu Phe Val
    1415                1420                1425

Glu Gln  His Lys His Tyr Leu  Asp Glu Ile Ile Glu  Gln Ile Ser
    1430                1435                1440

Glu Phe  Ser Lys Arg Val Ile  Leu Ala Asp Ala Asn  Leu Asp Lys
    1445                1450                1455

Val Leu  Ser Ala Tyr Asn Lys  His Arg Asp Lys Pro  Ile Arg Glu
    1460                1465                1470

Gln Ala  Glu Asn Ile Ile His  Leu Phe Thr Leu Thr  Asn Leu Gly
    1475                1480                1485

Ala Pro  Ala Ala Phe Lys Tyr  Phe Asp Thr Thr Ile  Asp Arg Lys
    1490                1495                1500

Arg Tyr  Thr Ser Thr Lys Glu  Val Leu Asp Ala Thr  Leu Ile His
    1505                1510                1515

Gln Ser  Ile Thr Gly Leu Tyr  Glu Thr Arg Ile Asp  Leu Ser Gln
    1520                1525                1530

Leu Gly  Gly Asp
    1535
```

<210> SEQ ID NO 332

<211> LENGTH: 1531
<212> TYPE: PRT
<213> ORGANISM: Artificial Sequence
<220> FEATURE:
<223> OTHER INFORMATION: Synthetic Polypeptide

<400> SEQUENCE: 332

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380
```

-continued

```
Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800
```

```
Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
```

1205 1210 1215

Glu Leu Gln Lys Gly Asn Glu Leu Ala Leu Pro Ser Lys Tyr Val
1220 1225 1230

Asn Phe Leu Tyr Leu Ala Ser His Tyr Glu Lys Leu Lys Gly Ser
1235 1240 1245

Pro Glu Asp Asn Glu Gln Lys Gln Leu Phe Val Glu Gln His Lys
1250 1255 1260

His Tyr Leu Asp Glu Ile Ile Glu Gln Ile Ser Glu Phe Ser Lys
1265 1270 1275

Arg Val Ile Leu Ala Asp Ala Asn Leu Asp Lys Val Leu Ser Ala
1280 1285 1290

Tyr Asn Lys His Arg Asp Lys Pro Ile Arg Glu Gln Ala Glu Asn
1295 1300 1305

Ile Ile His Leu Phe Thr Leu Thr Asn Leu Gly Ala Pro Ala Ala
1310 1315 1320

Phe Lys Tyr Phe Asp Thr Thr Ile Asp Arg Lys Arg Tyr Thr Ser
1325 1330 1335

Thr Lys Glu Val Leu Asp Ala Thr Leu Ile His Gln Ser Ile Thr
1340 1345 1350

Gly Leu Tyr Glu Thr Arg Ile Asp Leu Ser Gln Leu Gly Gly Asp
1355 1360 1365

Met Ala Pro Lys Lys Lys Arg Lys Val Gly Ile His Arg Gly Val
1370 1375 1380

Pro Gly Gly Ser Gly Gly Ser Gly Gly Ser Met Ala Thr Ile Gly
1385 1390 1395

Tyr Ile Arg Val Ser Thr Ile Asp Gln Asn Ile Asp Leu Gln Arg
1400 1405 1410

Asn Ala Leu Thr Ser Ala Asn Cys Asp Arg Ile Phe Glu Asp Arg
1415 1420 1425

Ile Ser Gly Lys Ile Ala Asn Arg Pro Gly Leu Lys Arg Ala Leu
1430 1435 1440

Lys Tyr Val Asn Lys Gly Asp Thr Leu Val Val Trp Lys Leu Asp
1445 1450 1455

Arg Leu Gly Arg Ser Val Lys Asn Leu Val Ala Leu Ile Ser Glu
1460 1465 1470

Leu His Glu Arg Gly Ala His Phe His Ser Leu Thr Asp Ser Ile
1475 1480 1485

Asp Thr Ser Ser Ala Met Gly Arg Phe Phe Phe Tyr Val Met Ser
1490 1495 1500

Ala Leu Ala Glu Met Glu Arg Glu Leu Ile Val Glu Arg Thr Leu
1505 1510 1515

Ala Gly Leu Ala Ala Ala Arg Ala Gln Gly Arg Leu Gly
1520 1525 1530

<210> SEQ ID NO 333
<211> LENGTH: 1531
<212> TYPE: PRT
<213> ORGANISM: Artificial Sequence
<220> FEATURE:
<223> OTHER INFORMATION: Synthetic Polypeptide

<400> SEQUENCE: 333

Met Ala Pro Lys Lys Lys Arg Lys Val Gly Ile His Arg Gly Val Pro
1 5 10 15

Met Asp Lys Lys Tyr Ser Ile Gly Leu Ala Ile Gly Thr Asn Ser Val

```
            20                  25                  30

Gly Trp Ala Val Ile Thr Asp Glu Tyr Lys Val Pro Ser Lys Lys Phe
        35                  40                  45

Lys Val Leu Gly Asn Thr Asp Arg His Ser Ile Lys Lys Asn Leu Ile
    50                  55                  60

Gly Ala Leu Leu Phe Asp Ser Gly Glu Thr Ala Glu Ala Thr Arg Leu
65                  70                  75                  80

Lys Arg Thr Ala Arg Arg Arg Tyr Thr Arg Arg Lys Asn Arg Ile Cys
                85                  90                  95

Tyr Leu Gln Glu Ile Phe Ser Asn Glu Met Ala Lys Val Asp Asp Ser
            100                 105                 110

Phe Phe His Arg Leu Glu Glu Ser Phe Leu Val Glu Glu Asp Lys Lys
        115                 120                 125

His Glu Arg His Pro Ile Phe Gly Asn Ile Val Asp Glu Val Ala Tyr
    130                 135                 140

His Glu Lys Tyr Pro Thr Ile Tyr His Leu Arg Lys Lys Leu Val Asp
145                 150                 155                 160

Ser Thr Asp Lys Ala Asp Leu Arg Leu Ile Tyr Leu Ala Leu Ala His
                165                 170                 175

Met Ile Lys Phe Arg Gly His Phe Leu Ile Glu Gly Asp Leu Asn Pro
            180                 185                 190

Asp Asn Ser Asp Val Asp Lys Leu Phe Ile Gln Leu Val Gln Thr Tyr
        195                 200                 205

Asn Gln Leu Phe Glu Glu Asn Pro Ile Asn Ala Ser Gly Val Asp Ala
    210                 215                 220

Lys Ala Ile Leu Ser Ala Arg Leu Ser Lys Ser Arg Arg Leu Glu Asn
225                 230                 235                 240

Leu Ile Ala Gln Leu Pro Gly Glu Lys Lys Asn Gly Leu Phe Gly Asn
                245                 250                 255

Leu Ile Ala Leu Ser Leu Gly Leu Thr Pro Asn Phe Lys Ser Asn Phe
            260                 265                 270

Asp Leu Ala Glu Asp Ala Lys Leu Gln Leu Ser Lys Asp Thr Tyr Asp
        275                 280                 285

Asp Asp Leu Asp Asn Leu Leu Ala Gln Ile Gly Asp Gln Tyr Ala Asp
    290                 295                 300

Leu Phe Leu Ala Ala Lys Asn Leu Ser Asp Ala Ile Leu Leu Ser Asp
305                 310                 315                 320

Ile Leu Arg Val Asn Thr Glu Ile Thr Lys Ala Pro Leu Ser Ala Ser
                325                 330                 335

Met Ile Lys Arg Tyr Asp Glu His His Gln Asp Leu Thr Leu Leu Lys
            340                 345                 350

Ala Leu Val Arg Gln Gln Leu Pro Glu Lys Tyr Lys Glu Ile Phe Phe
        355                 360                 365

Asp Gln Ser Lys Asn Gly Tyr Ala Gly Tyr Ile Asp Gly Gly Ala Ser
    370                 375                 380

Gln Glu Glu Phe Tyr Lys Phe Ile Lys Pro Ile Leu Glu Lys Met Asp
385                 390                 395                 400

Gly Thr Glu Glu Leu Leu Val Lys Leu Asn Arg Glu Asp Leu Leu Arg
                405                 410                 415

Lys Gln Arg Thr Phe Asp Asn Gly Ser Ile Pro His Gln Ile His Leu
            420                 425                 430

Gly Glu Leu His Ala Ile Leu Arg Arg Gln Glu Asp Phe Tyr Pro Phe
        435                 440                 445
```

```
Leu Lys Asp Asn Arg Glu Lys Ile Glu Lys Ile Leu Thr Phe Arg Ile
    450                 455                 460

Pro Tyr Tyr Val Gly Pro Leu Ala Arg Gly Asn Ser Arg Phe Ala Trp
465                 470                 475                 480

Met Thr Arg Lys Ser Glu Glu Thr Ile Thr Pro Trp Asn Phe Glu Glu
                485                 490                 495

Val Val Asp Lys Gly Ala Ser Ala Gln Ser Phe Ile Glu Arg Met Thr
            500                 505                 510

Asn Phe Asp Lys Asn Leu Pro Asn Glu Lys Val Leu Pro Lys His Ser
        515                 520                 525

Leu Leu Tyr Glu Tyr Phe Thr Val Tyr Asn Glu Leu Thr Lys Val Lys
    530                 535                 540

Tyr Val Thr Glu Gly Met Arg Lys Pro Ala Phe Leu Ser Gly Glu Gln
545                 550                 555                 560

Lys Lys Ala Ile Val Asp Leu Leu Phe Lys Thr Asn Arg Lys Val Thr
                565                 570                 575

Val Lys Gln Leu Lys Glu Asp Tyr Phe Lys Lys Ile Glu Cys Phe Asp
            580                 585                 590

Ser Val Glu Ile Ser Gly Val Glu Asp Arg Phe Asn Ala Ser Leu Gly
        595                 600                 605

Thr Tyr His Asp Leu Leu Lys Ile Ile Lys Asp Lys Asp Phe Leu Asp
    610                 615                 620

Asn Glu Glu Asn Glu Asp Ile Leu Glu Asp Ile Val Leu Thr Leu Thr
625                 630                 635                 640

Leu Phe Glu Asp Arg Glu Met Ile Glu Glu Arg Leu Lys Thr Tyr Ala
                645                 650                 655

His Leu Phe Asp Asp Lys Val Met Lys Gln Leu Lys Arg Arg Arg Tyr
            660                 665                 670

Thr Gly Trp Gly Arg Leu Ser Arg Lys Leu Ile Asn Gly Ile Arg Asp
        675                 680                 685

Lys Gln Ser Gly Lys Thr Ile Leu Asp Phe Leu Lys Ser Asp Gly Phe
    690                 695                 700

Ala Asn Arg Asn Phe Met Gln Leu Ile His Asp Asp Ser Leu Thr Phe
705                 710                 715                 720

Lys Glu Asp Ile Gln Lys Ala Gln Val Ser Gly Gln Gly Asp Ser Leu
                725                 730                 735

His Glu His Ile Ala Asn Leu Ala Gly Ser Pro Ala Ile Lys Lys Gly
            740                 745                 750

Ile Leu Gln Thr Val Lys Val Val Asp Glu Leu Val Lys Val Met Gly
        755                 760                 765

Arg His Lys Pro Glu Asn Ile Val Ile Glu Met Ala Arg Glu Asn Gln
    770                 775                 780

Thr Thr Gln Lys Gly Gln Lys Asn Ser Arg Glu Arg Met Lys Arg Ile
785                 790                 795                 800

Glu Glu Gly Ile Lys Glu Leu Gly Ser Gln Ile Leu Lys Glu His Pro
                805                 810                 815

Val Glu Asn Thr Gln Leu Gln Asn Glu Lys Leu Tyr Leu Tyr Tyr Leu
            820                 825                 830

Gln Asn Gly Arg Asp Met Tyr Val Asp Gln Glu Leu Asp Ile Asn Arg
        835                 840                 845

Leu Ser Asp Tyr Asp Val Asp Ala Ile Val Pro Gln Ser Phe Leu Lys
    850                 855                 860
```

```
Asp Asp Ser Ile Asp Asn Lys Val Leu Thr Arg Ser Asp Lys Asn Arg
865                 870                 875                 880

Gly Lys Ser Asp Asn Val Pro Ser Glu Glu Val Val Lys Lys Met Lys
                885                 890                 895

Asn Tyr Trp Arg Gln Leu Leu Asn Ala Lys Leu Ile Thr Gln Arg Lys
            900                 905                 910

Phe Asp Asn Leu Thr Lys Ala Glu Arg Gly Gly Leu Ser Glu Leu Asp
        915                 920                 925

Lys Ala Gly Phe Ile Lys Arg Gln Leu Val Glu Thr Arg Gln Ile Thr
    930                 935                 940

Lys His Val Ala Gln Ile Leu Asp Ser Arg Met Asn Thr Lys Tyr Asp
945                 950                 955                 960

Glu Asn Asp Lys Leu Ile Arg Glu Val Lys Val Ile Thr Leu Lys Ser
                965                 970                 975

Lys Leu Val Ser Asp Phe Arg Lys Asp Phe Gln Phe Tyr Lys Val Arg
            980                 985                 990

Glu Ile Asn Asn Tyr His His Ala  His Asp Ala Tyr Leu  Asn Ala Val
        995                 1000                1005

Val Gly  Thr Ala Leu Ile Lys  Lys Tyr Pro Lys Leu  Glu Ser Glu
    1010                1015                1020

Phe Val  Tyr Gly Asp Tyr Lys  Val Tyr Asp Val Arg  Lys Met Ile
    1025                1030                1035

Ala Lys  Ser Glu Gln Glu Ile  Gly Lys Ala Thr Ala  Lys Tyr Phe
    1040                1045                1050

Phe Tyr  Ser Asn Ile Met Asn  Phe Phe Lys Thr Glu  Ile Thr Leu
    1055                1060                1065

Ala Asn  Gly Glu Ile Arg Lys  Arg Pro Leu Ile Glu  Thr Asn Gly
    1070                1075                1080

Glu Thr  Gly Glu Ile Val Trp  Asp Lys Gly Arg Asp  Phe Ala Thr
    1085                1090                1095

Val Arg  Lys Val Leu Ser Met  Pro Gln Val Asn Ile  Val Lys Lys
    1100                1105                1110

Thr Glu  Val Gln Thr Gly Gly  Phe Ser Lys Glu Ser  Ile Leu Pro
    1115                1120                1125

Lys Arg  Asn Ser Asp Lys Leu  Ile Ala Arg Lys Lys  Asp Trp Asp
    1130                1135                1140

Pro Lys  Lys Tyr Gly Gly Phe  Asp Ser Pro Thr Val  Ala Tyr Ser
    1145                1150                1155

Val Leu  Val Val Ala Lys Val  Glu Lys Gly Lys Ser  Lys Lys Leu
    1160                1165                1170

Lys Ser  Val Lys Glu Leu Leu  Gly Ile Thr Ile Met  Glu Arg Ser
    1175                1180                1185

Ser Phe  Glu Lys Asn Pro Ile  Asp Phe Leu Glu Ala  Lys Gly Tyr
    1190                1195                1200

Lys Glu  Val Lys Lys Asp Leu  Ile Ile Lys Leu Pro  Lys Tyr Ser
    1205                1210                1215

Leu Phe  Glu Leu Glu Asn Gly  Arg Lys Arg Met Leu  Ala Ser Ala
    1220                1225                1230

Gly Glu  Leu Gln Lys Gly Asn  Glu Leu Ala Leu Pro  Ser Lys Tyr
    1235                1240                1245

Val Asn  Phe Leu Tyr Leu Ala  Ser His Tyr Glu Lys  Leu Lys Gly
    1250                1255                1260

Ser Pro  Glu Asp Asn Glu Gln  Lys Gln Leu Phe Val  Glu Gln His
```

```
    1265                1270                1275

Lys His  Tyr Leu Asp Glu Ile  Ile Glu Gln Ile Ser  Glu Phe Ser
    1280                1285                1290

Lys Arg  Val Ile Leu Ala Asp  Ala Asn Leu Asp Lys  Val Leu Ser
    1295                1300                1305

Ala Tyr  Asn Lys His Arg Asp  Lys Pro Ile Arg Glu  Gln Ala Glu
    1310                1315                1320

Asn Ile  Ile His Leu Phe Thr  Leu Thr Asn Leu Gly  Ala Pro Ala
    1325                1330                1335

Ala Phe  Lys Tyr Phe Asp Thr  Thr Ile Asp Arg Lys  Arg Tyr Thr
    1340                1345                1350

Ser Thr  Lys Glu Val Leu Asp  Ala Thr Leu Ile His  Gln Ser Ile
    1355                1360                1365

Thr Gly  Leu Tyr Glu Thr Arg  Ile Asp Leu Ser Gln  Leu Gly Gly
    1370                1375                1380

Asp Gly  Gly Ser Gly Gly Ser  Gly Gly Ser Met Ala  Thr Ile Gly
    1385                1390                1395

Tyr Ile  Arg Val Ser Thr Ile  Asp Gln Asn Ile Asp  Leu Gln Arg
    1400                1405                1410

Asn Ala  Leu Thr Ser Ala Asn  Cys Asp Arg Ile Phe  Glu Asp Arg
    1415                1420                1425

Ile Ser  Gly Lys Ile Ala Asn  Arg Pro Gly Leu Lys  Arg Ala Leu
    1430                1435                1440

Lys Tyr  Val Asn Lys Gly Asp  Thr Leu Val Val Trp  Lys Leu Asp
    1445                1450                1455

Arg Leu  Gly Arg Ser Val Lys  Asn Leu Val Ala Leu  Ile Ser Glu
    1460                1465                1470

Leu His  Glu Arg Gly Ala His  Phe His Ser Leu Thr  Asp Ser Ile
    1475                1480                1485

Asp Thr  Ser Ser Ala Met Gly  Arg Phe Phe Phe Tyr  Val Met Ser
    1490                1495                1500

Ala Leu  Ala Glu Met Glu Arg  Glu Leu Ile Val Glu  Arg Thr Leu
    1505                1510                1515

Ala Gly  Leu Ala Ala Ala Arg  Ala Gln Gly Arg Leu  Gly
    1520                1525                1530


<210> SEQ ID NO 334
<211> LENGTH: 1531
<212> TYPE: PRT
<213> ORGANISM: Artificial Sequence
<220> FEATURE:
<223> OTHER INFORMATION: Synthetic Polypeptide

<400> SEQUENCE: 334

Met Ala Thr Ile Gly Tyr Ile Arg Val Ser Thr Ile Asp Gln Asn Ile
1               5                   10                  15

Asp Leu Gln Arg Asn Ala Leu Thr Ser Ala Asn Cys Asp Arg Ile Phe
            20                  25                  30

Glu Asp Arg Ile Ser Gly Lys Ile Ala Asn Arg Pro Gly Leu Lys Arg
        35                  40                  45

Ala Leu Lys Tyr Val Asn Lys Gly Asp Thr Leu Val Val Trp Lys Leu
    50                  55                  60

Asp Arg Leu Gly Arg Ser Val Lys Asn Leu Val Ala Leu Ile Ser Glu
65                  70                  75                  80

Leu His Glu Arg Gly Ala His Phe His Ser Leu Thr Asp Ser Ile Asp
```

```
                85                  90                  95

Thr Ser Ser Ala Met Gly Arg Phe Phe Phe Tyr Val Met Ser Ala Leu
            100                 105                 110

Ala Glu Met Glu Arg Glu Leu Ile Val Glu Arg Thr Leu Ala Gly Leu
        115                 120                 125

Ala Ala Ala Arg Ala Gln Gly Arg Leu Gly Gly Gly Ser Gly Gly Ser
    130                 135                 140

Gly Gly Ser Met Asp Lys Lys Tyr Ser Ile Gly Leu Ala Ile Gly Thr
145                 150                 155                 160

Asn Ser Val Gly Trp Ala Val Ile Thr Asp Glu Tyr Lys Val Pro Ser
                165                 170                 175

Lys Lys Phe Lys Val Leu Gly Asn Thr Asp Arg His Ser Ile Lys Lys
            180                 185                 190

Asn Leu Ile Gly Ala Leu Leu Phe Asp Ser Gly Glu Thr Ala Glu Ala
        195                 200                 205

Thr Arg Leu Lys Arg Thr Ala Arg Arg Arg Tyr Thr Arg Arg Lys Asn
    210                 215                 220

Arg Ile Cys Tyr Leu Gln Glu Ile Phe Ser Asn Glu Met Ala Lys Val
225                 230                 235                 240

Asp Asp Ser Phe Phe His Arg Leu Glu Glu Ser Phe Leu Val Glu Glu
                245                 250                 255

Asp Lys Lys His Glu Arg His Pro Ile Phe Gly Asn Ile Val Asp Glu
            260                 265                 270

Val Ala Tyr His Glu Lys Tyr Pro Thr Ile Tyr His Leu Arg Lys Lys
        275                 280                 285

Leu Val Asp Ser Thr Asp Lys Ala Asp Leu Arg Leu Ile Tyr Leu Ala
    290                 295                 300

Leu Ala His Met Ile Lys Phe Arg Gly His Phe Leu Ile Glu Gly Asp
305                 310                 315                 320

Leu Asn Pro Asp Asn Ser Asp Val Asp Lys Leu Phe Ile Gln Leu Val
                325                 330                 335

Gln Thr Tyr Asn Gln Leu Phe Glu Glu Asn Pro Ile Asn Ala Ser Gly
            340                 345                 350

Val Asp Ala Lys Ala Ile Leu Ser Ala Arg Leu Ser Lys Ser Arg Arg
        355                 360                 365

Leu Glu Asn Leu Ile Ala Gln Leu Pro Gly Glu Lys Lys Asn Gly Leu
    370                 375                 380

Phe Gly Asn Leu Ile Ala Leu Ser Leu Gly Leu Thr Pro Asn Phe Lys
385                 390                 395                 400

Ser Asn Phe Asp Leu Ala Glu Asp Ala Lys Leu Gln Leu Ser Lys Asp
                405                 410                 415

Thr Tyr Asp Asp Asp Leu Asp Asn Leu Leu Ala Gln Ile Gly Asp Gln
            420                 425                 430

Tyr Ala Asp Leu Phe Leu Ala Ala Lys Asn Leu Ser Asp Ala Ile Leu
        435                 440                 445

Leu Ser Asp Ile Leu Arg Val Asn Thr Glu Ile Thr Lys Ala Pro Leu
    450                 455                 460

Ser Ala Ser Met Ile Lys Arg Tyr Asp Glu His His Gln Asp Leu Thr
465                 470                 475                 480

Leu Leu Lys Ala Leu Val Arg Gln Gln Leu Pro Glu Lys Tyr Lys Glu
                485                 490                 495

Ile Phe Phe Asp Gln Ser Lys Asn Gly Tyr Ala Gly Tyr Ile Asp Gly
            500                 505                 510
```

```
Gly Ala Ser Gln Glu Glu Phe Tyr Lys Phe Ile Lys Pro Ile Leu Glu
        515                 520                 525

Lys Met Asp Gly Thr Glu Glu Leu Leu Val Lys Leu Asn Arg Glu Asp
    530                 535                 540

Leu Leu Arg Lys Gln Arg Thr Phe Asp Asn Gly Ser Ile Pro His Gln
545                 550                 555                 560

Ile His Leu Gly Glu Leu His Ala Ile Leu Arg Arg Gln Glu Asp Phe
                565                 570                 575

Tyr Pro Phe Leu Lys Asp Asn Arg Glu Lys Ile Glu Lys Ile Leu Thr
            580                 585                 590

Phe Arg Ile Pro Tyr Tyr Val Gly Pro Leu Ala Arg Gly Asn Ser Arg
        595                 600                 605

Phe Ala Trp Met Thr Arg Lys Ser Glu Glu Thr Ile Thr Pro Trp Asn
    610                 615                 620

Phe Glu Glu Val Val Asp Lys Gly Ala Ser Ala Gln Ser Phe Ile Glu
625                 630                 635                 640

Arg Met Thr Asn Phe Asp Lys Asn Leu Pro Asn Glu Lys Val Leu Pro
                645                 650                 655

Lys His Ser Leu Leu Tyr Glu Tyr Phe Thr Val Tyr Asn Glu Leu Thr
            660                 665                 670

Lys Val Lys Tyr Val Thr Glu Gly Met Arg Lys Pro Ala Phe Leu Ser
        675                 680                 685

Gly Glu Gln Lys Lys Ala Ile Val Asp Leu Leu Phe Lys Thr Asn Arg
    690                 695                 700

Lys Val Thr Val Lys Gln Leu Lys Glu Asp Tyr Phe Lys Lys Ile Glu
705                 710                 715                 720

Cys Phe Asp Ser Val Glu Ile Ser Gly Val Glu Asp Arg Phe Asn Ala
                725                 730                 735

Ser Leu Gly Thr Tyr His Asp Leu Leu Lys Ile Ile Lys Asp Lys Asp
            740                 745                 750

Phe Leu Asp Asn Glu Glu Asn Glu Asp Ile Leu Glu Asp Ile Val Leu
        755                 760                 765

Thr Leu Thr Leu Phe Glu Asp Arg Glu Met Ile Glu Glu Arg Leu Lys
    770                 775                 780

Thr Tyr Ala His Leu Phe Asp Asp Lys Val Met Lys Gln Leu Lys Arg
785                 790                 795                 800

Arg Arg Tyr Thr Gly Trp Gly Arg Leu Ser Arg Lys Leu Ile Asn Gly
                805                 810                 815

Ile Arg Asp Lys Gln Ser Gly Lys Thr Ile Leu Asp Phe Leu Lys Ser
            820                 825                 830

Asp Gly Phe Ala Asn Arg Asn Phe Met Gln Leu Ile His Asp Asp Ser
        835                 840                 845

Leu Thr Phe Lys Glu Asp Ile Gln Lys Ala Gln Val Ser Gly Gln Gly
    850                 855                 860

Asp Ser Leu His Glu His Ile Ala Asn Leu Ala Gly Ser Pro Ala Ile
865                 870                 875                 880

Lys Lys Gly Ile Leu Gln Thr Val Lys Val Val Asp Glu Leu Val Lys
                885                 890                 895

Val Met Gly Arg His Lys Pro Glu Asn Ile Val Ile Glu Met Ala Arg
            900                 905                 910

Glu Asn Gln Thr Thr Gln Lys Gly Gln Lys Asn Ser Arg Glu Arg Met
        915                 920                 925
```

```
Lys Arg Ile Glu Glu Gly Ile Lys Glu Leu Gly Ser Gln Ile Leu Lys
    930                 935                 940

Glu His Pro Val Glu Asn Thr Gln Leu Gln Asn Glu Lys Leu Tyr Leu
945                 950                 955                 960

Tyr Tyr Leu Gln Asn Gly Arg Asp Met Tyr Val Asp Gln Glu Leu Asp
                965                 970                 975

Ile Asn Arg Leu Ser Asp Tyr Asp Val Asp Ala Ile Val Pro Gln Ser
            980                 985                 990

Phe Leu Lys Asp Asp Ser Ile Asp  Asn Lys Val Leu Thr  Arg Ser Asp
        995                 1000                 1005

Lys Asn  Arg Gly Lys Ser Asp  Asn Val Pro Ser Glu  Glu Val Val
    1010                 1015                 1020

Lys Lys  Met Lys Asn Tyr Trp  Arg Gln Leu Leu Asn  Ala Lys Leu
    1025                 1030                 1035

Ile Thr  Gln Arg Lys Phe Asp  Asn Leu Thr Lys Ala  Glu Arg Gly
    1040                 1045                 1050

Gly Leu  Ser Glu Leu Asp Lys  Ala Gly Phe Ile Lys  Arg Gln Leu
    1055                 1060                 1065

Val Glu  Thr Arg Gln Ile Thr  Lys His Val Ala Gln  Ile Leu Asp
    1070                 1075                 1080

Ser Arg  Met Asn Thr Lys Tyr  Asp Glu Asn Asp Lys  Leu Ile Arg
    1085                 1090                 1095

Glu Val  Lys Val Ile Thr Leu  Lys Ser Lys Leu Val  Ser Asp Phe
    1100                 1105                 1110

Arg Lys  Asp Phe Gln Phe Tyr  Lys Val Arg Glu Ile  Asn Asn Tyr
    1115                 1120                 1125

His His  Ala His Asp Ala Tyr  Leu Asn Ala Val Val  Gly Thr Ala
    1130                 1135                 1140

Leu Ile  Lys Lys Tyr Pro Lys  Leu Glu Ser Glu Phe  Val Tyr Gly
    1145                 1150                 1155

Asp Tyr  Lys Val Tyr Asp Val  Arg Lys Met Ile Ala  Lys Ser Glu
    1160                 1165                 1170

Gln Glu  Ile Gly Lys Ala Thr  Ala Lys Tyr Phe Phe  Tyr Ser Asn
    1175                 1180                 1185

Ile Met  Asn Phe Phe Lys Thr  Glu Ile Thr Leu Ala  Asn Gly Glu
    1190                 1195                 1200

Ile Arg  Lys Arg Pro Leu Ile  Glu Thr Asn Gly Glu  Thr Gly Glu
    1205                 1210                 1215

Ile Val  Trp Asp Lys Gly Arg  Asp Phe Ala Thr Val  Arg Lys Val
    1220                 1225                 1230

Leu Ser  Met Pro Gln Val Asn  Ile Val Lys Lys Thr  Glu Val Gln
    1235                 1240                 1245

Thr Gly  Gly Phe Ser Lys Glu  Ser Ile Leu Pro Lys  Arg Asn Ser
    1250                 1255                 1260

Asp Lys  Leu Ile Ala Arg Lys  Lys Asp Trp Asp Pro  Lys Lys Tyr
    1265                 1270                 1275

Gly Gly  Phe Asp Ser Pro Thr  Val Ala Tyr Ser Val  Leu Val Val
    1280                 1285                 1290

Ala Lys  Val Glu Lys Gly Lys  Ser Lys Lys Leu Lys  Ser Val Lys
    1295                 1300                 1305

Glu Leu  Leu Gly Ile Thr Ile  Met Glu Arg Ser Ser  Phe Glu Lys
    1310                 1315                 1320

Asn Pro  Ile Asp Phe Leu Glu  Ala Lys Gly Tyr Lys  Glu Val Lys
```

1325 1330 1335

Lys Asp Leu Ile Ile Lys Leu Pro Lys Tyr Ser Leu Phe Glu Leu
1340 1345 1350

Glu Asn Gly Arg Lys Arg Met Leu Ala Ser Ala Gly Glu Leu Gln
1355 1360 1365

Lys Gly Asn Glu Leu Ala Leu Pro Ser Lys Tyr Val Asn Phe Leu
1370 1375 1380

Tyr Leu Ala Ser His Tyr Glu Lys Leu Lys Gly Ser Pro Glu Asp
1385 1390 1395

Asn Glu Gln Lys Gln Leu Phe Val Glu Gln His Lys His Tyr Leu
1400 1405 1410

Asp Glu Ile Ile Glu Gln Ile Ser Glu Phe Ser Lys Arg Val Ile
1415 1420 1425

Leu Ala Asp Ala Asn Leu Asp Lys Val Leu Ser Ala Tyr Asn Lys
1430 1435 1440

His Arg Asp Lys Pro Ile Arg Glu Gln Ala Glu Asn Ile Ile His
1445 1450 1455

Leu Phe Thr Leu Thr Asn Leu Gly Ala Pro Ala Ala Phe Lys Tyr
1460 1465 1470

Phe Asp Thr Thr Ile Asp Arg Lys Arg Tyr Thr Ser Thr Lys Glu
1475 1480 1485

Val Leu Asp Ala Thr Leu Ile His Gln Ser Ile Thr Gly Leu Tyr
1490 1495 1500

Glu Thr Arg Ile Asp Leu Ser Gln Leu Gly Gly Asp Met Ala Pro
1505 1510 1515

Lys Lys Lys Arg Lys Val Gly Ile His Arg Gly Val Pro
1520 1525 1530

<210> SEQ ID NO 335
<211> LENGTH: 1531
<212> TYPE: PRT
<213> ORGANISM: Artificial Sequence
<220> FEATURE:
<223> OTHER INFORMATION: Synthetic Polypeptide

<400> SEQUENCE: 335

Met Ala Pro Lys Lys Lys Arg Lys Val Gly Ile His Arg Gly Val Pro
1 5 10 15

Met Ala Thr Ile Gly Tyr Ile Arg Val Ser Thr Ile Asp Gln Asn Ile
20 25 30

Asp Leu Gln Arg Asn Ala Leu Thr Ser Ala Asn Cys Asp Arg Ile Phe
35 40 45

Glu Asp Arg Ile Ser Gly Lys Ile Ala Asn Arg Pro Gly Leu Lys Arg
50 55 60

Ala Leu Lys Tyr Val Asn Lys Gly Asp Thr Leu Val Val Trp Lys Leu
65 70 75 80

Asp Arg Leu Gly Arg Ser Val Lys Asn Leu Val Ala Leu Ile Ser Glu
85 90 95

Leu His Glu Arg Gly Ala His Phe His Ser Leu Thr Asp Ser Ile Asp
100 105 110

Thr Ser Ser Ala Met Gly Arg Phe Phe Phe Tyr Val Met Ser Ala Leu
115 120 125

Ala Glu Met Glu Arg Glu Leu Ile Val Glu Arg Thr Leu Ala Gly Leu
130 135 140

Ala Ala Ala Arg Ala Gln Gly Arg Leu Gly Gly Gly Ser Gly Gly Ser

```
145                 150                 155                 160

Gly Gly Ser Met Asp Lys Lys Tyr Ser Ile Gly Leu Ala Ile Gly Thr
                165                 170                 175

Asn Ser Val Gly Trp Ala Val Ile Thr Asp Glu Tyr Lys Val Pro Ser
            180                 185                 190

Lys Lys Phe Lys Val Leu Gly Asn Thr Asp Arg His Ser Ile Lys Lys
        195                 200                 205

Asn Leu Ile Gly Ala Leu Leu Phe Asp Ser Gly Glu Thr Ala Glu Ala
    210                 215                 220

Thr Arg Leu Lys Arg Thr Ala Arg Arg Arg Tyr Thr Arg Arg Lys Asn
225                 230                 235                 240

Arg Ile Cys Tyr Leu Gln Glu Ile Phe Ser Asn Glu Met Ala Lys Val
                245                 250                 255

Asp Asp Ser Phe Phe His Arg Leu Glu Glu Ser Phe Leu Val Glu Glu
            260                 265                 270

Asp Lys Lys His Glu Arg His Pro Ile Phe Gly Asn Ile Val Asp Glu
        275                 280                 285

Val Ala Tyr His Glu Lys Tyr Pro Thr Ile Tyr His Leu Arg Lys Lys
    290                 295                 300

Leu Val Asp Ser Thr Asp Lys Ala Asp Leu Arg Leu Ile Tyr Leu Ala
305                 310                 315                 320

Leu Ala His Met Ile Lys Phe Arg Gly His Phe Leu Ile Glu Gly Asp
                325                 330                 335

Leu Asn Pro Asp Asn Ser Asp Val Asp Lys Leu Phe Ile Gln Leu Val
            340                 345                 350

Gln Thr Tyr Asn Gln Leu Phe Glu Glu Asn Pro Ile Asn Ala Ser Gly
        355                 360                 365

Val Asp Ala Lys Ala Ile Leu Ser Ala Arg Leu Ser Lys Ser Arg Arg
    370                 375                 380

Leu Glu Asn Leu Ile Ala Gln Leu Pro Gly Glu Lys Lys Asn Gly Leu
385                 390                 395                 400

Phe Gly Asn Leu Ile Ala Leu Ser Leu Gly Leu Thr Pro Asn Phe Lys
                405                 410                 415

Ser Asn Phe Asp Leu Ala Glu Asp Ala Lys Leu Gln Leu Ser Lys Asp
            420                 425                 430

Thr Tyr Asp Asp Asp Leu Asp Asn Leu Leu Ala Gln Ile Gly Asp Gln
        435                 440                 445

Tyr Ala Asp Leu Phe Leu Ala Ala Lys Asn Leu Ser Asp Ala Ile Leu
    450                 455                 460

Leu Ser Asp Ile Leu Arg Val Asn Thr Glu Ile Thr Lys Ala Pro Leu
465                 470                 475                 480

Ser Ala Ser Met Ile Lys Arg Tyr Asp Glu His His Gln Asp Leu Thr
                485                 490                 495

Leu Leu Lys Ala Leu Val Arg Gln Gln Leu Pro Glu Lys Tyr Lys Glu
            500                 505                 510

Ile Phe Phe Asp Gln Ser Lys Asn Gly Tyr Ala Gly Tyr Ile Asp Gly
        515                 520                 525

Gly Ala Ser Gln Glu Glu Phe Tyr Lys Phe Ile Lys Pro Ile Leu Glu
    530                 535                 540

Lys Met Asp Gly Thr Glu Glu Leu Leu Val Lys Leu Asn Arg Glu Asp
545                 550                 555                 560

Leu Leu Arg Lys Gln Arg Thr Phe Asp Asn Gly Ser Ile Pro His Gln
                565                 570                 575
```

```
Ile His Leu Gly Glu Leu His Ala Ile Leu Arg Arg Gln Glu Asp Phe
            580                 585                 590

Tyr Pro Phe Leu Lys Asp Asn Arg Glu Lys Ile Glu Lys Ile Leu Thr
        595                 600                 605

Phe Arg Ile Pro Tyr Tyr Val Gly Pro Leu Ala Arg Gly Asn Ser Arg
    610                 615                 620

Phe Ala Trp Met Thr Arg Lys Ser Glu Glu Thr Ile Thr Pro Trp Asn
625                 630                 635                 640

Phe Glu Glu Val Val Asp Lys Gly Ala Ser Ala Gln Ser Phe Ile Glu
                645                 650                 655

Arg Met Thr Asn Phe Asp Lys Asn Leu Pro Asn Glu Lys Val Leu Pro
            660                 665                 670

Lys His Ser Leu Leu Tyr Glu Tyr Phe Thr Val Tyr Asn Glu Leu Thr
        675                 680                 685

Lys Val Lys Tyr Val Thr Glu Gly Met Arg Lys Pro Ala Phe Leu Ser
    690                 695                 700

Gly Glu Gln Lys Lys Ala Ile Val Asp Leu Leu Phe Lys Thr Asn Arg
705                 710                 715                 720

Lys Val Thr Val Lys Gln Leu Lys Glu Asp Tyr Phe Lys Lys Ile Glu
                725                 730                 735

Cys Phe Asp Ser Val Glu Ile Ser Gly Val Glu Asp Arg Phe Asn Ala
            740                 745                 750

Ser Leu Gly Thr Tyr His Asp Leu Leu Lys Ile Ile Lys Asp Lys Asp
        755                 760                 765

Phe Leu Asp Asn Glu Glu Asn Glu Asp Ile Leu Glu Asp Ile Val Leu
    770                 775                 780

Thr Leu Thr Leu Phe Glu Asp Arg Glu Met Ile Glu Glu Arg Leu Lys
785                 790                 795                 800

Thr Tyr Ala His Leu Phe Asp Asp Lys Val Met Lys Gln Leu Lys Arg
                805                 810                 815

Arg Arg Tyr Thr Gly Trp Gly Arg Leu Ser Arg Lys Leu Ile Asn Gly
            820                 825                 830

Ile Arg Asp Lys Gln Ser Gly Lys Thr Ile Leu Asp Phe Leu Lys Ser
        835                 840                 845

Asp Gly Phe Ala Asn Arg Asn Phe Met Gln Leu Ile His Asp Asp Ser
    850                 855                 860

Leu Thr Phe Lys Glu Asp Ile Gln Lys Ala Gln Val Ser Gly Gln Gly
865                 870                 875                 880

Asp Ser Leu His Glu His Ile Ala Asn Leu Ala Gly Ser Pro Ala Ile
                885                 890                 895

Lys Lys Gly Ile Leu Gln Thr Val Lys Val Val Asp Glu Leu Val Lys
            900                 905                 910

Val Met Gly Arg His Lys Pro Glu Asn Ile Val Ile Glu Met Ala Arg
        915                 920                 925

Glu Asn Gln Thr Thr Gln Lys Gly Gln Lys Asn Ser Arg Glu Arg Met
    930                 935                 940

Lys Arg Ile Glu Glu Gly Ile Lys Glu Leu Gly Ser Gln Ile Leu Lys
945                 950                 955                 960

Glu His Pro Val Glu Asn Thr Gln Leu Gln Asn Glu Lys Leu Tyr Leu
                965                 970                 975

Tyr Tyr Leu Gln Asn Gly Arg Asp Met Tyr Val Asp Gln Glu Leu Asp
            980                 985                 990
```

```
Ile Asn Arg Leu Ser Asp Tyr Asp  Val Asp Ala Ile Val  Pro Gln Ser
        995                 1000                 1005

Phe Leu  Lys Asp Asp Ser Ile  Asp Asn Lys Val Leu  Thr Arg Ser
    1010                 1015                 1020

Asp Lys  Asn Arg Gly Lys Ser  Asp Asn Val Pro Ser  Glu Glu Val
    1025                 1030                 1035

Val Lys  Lys Met Lys Asn Tyr  Trp Arg Gln Leu Leu  Asn Ala Lys
    1040                 1045                 1050

Leu Ile  Thr Gln Arg Lys Phe  Asp Asn Leu Thr Lys  Ala Glu Arg
    1055                 1060                 1065

Gly Gly  Leu Ser Glu Leu Asp  Lys Ala Gly Phe Ile  Lys Arg Gln
    1070                 1075                 1080

Leu Val  Glu Thr Arg Gln Ile  Thr Lys His Val Ala  Gln Ile Leu
    1085                 1090                 1095

Asp Ser  Arg Met Asn Thr Lys  Tyr Asp Glu Asn Asp  Lys Leu Ile
    1100                 1105                 1110

Arg Glu  Val Lys Val Ile Thr  Leu Lys Ser Lys Leu  Val Ser Asp
    1115                 1120                 1125

Phe Arg  Lys Asp Phe Gln Phe  Tyr Lys Val Arg Glu  Ile Asn Asn
    1130                 1135                 1140

Tyr His  His Ala His Asp Ala  Tyr Leu Asn Ala Val  Val Gly Thr
    1145                 1150                 1155

Ala Leu  Ile Lys Lys Tyr Pro  Lys Leu Glu Ser Glu  Phe Val Tyr
    1160                 1165                 1170

Gly Asp  Tyr Lys Val Tyr Asp  Val Arg Lys Met Ile  Ala Lys Ser
    1175                 1180                 1185

Glu Gln  Glu Ile Gly Lys Ala  Thr Ala Lys Tyr Phe  Phe Tyr Ser
    1190                 1195                 1200

Asn Ile  Met Asn Phe Phe Lys  Thr Glu Ile Thr Leu  Ala Asn Gly
    1205                 1210                 1215

Glu Ile  Arg Lys Arg Pro Leu  Ile Glu Thr Asn Gly  Glu Thr Gly
    1220                 1225                 1230

Glu Ile  Val Trp Asp Lys Gly  Arg Asp Phe Ala Thr  Val Arg Lys
    1235                 1240                 1245

Val Leu  Ser Met Pro Gln Val  Asn Ile Val Lys Lys  Thr Glu Val
    1250                 1255                 1260

Gln Thr  Gly Gly Phe Ser Lys  Glu Ser Ile Leu Pro  Lys Arg Asn
    1265                 1270                 1275

Ser Asp  Lys Leu Ile Ala Arg  Lys Lys Asp Trp Asp  Pro Lys Lys
    1280                 1285                 1290

Tyr Gly  Gly Phe Asp Ser Pro  Thr Val Ala Tyr Ser  Val Leu Val
    1295                 1300                 1305

Val Ala  Lys Val Glu Lys Gly  Lys Ser Lys Lys Leu  Lys Ser Val
    1310                 1315                 1320

Lys Glu  Leu Leu Gly Ile Thr  Ile Met Glu Arg Ser  Ser Phe Glu
    1325                 1330                 1335

Lys Asn  Pro Ile Asp Phe Leu  Glu Ala Lys Gly Tyr  Lys Glu Val
    1340                 1345                 1350

Lys Lys  Asp Leu Ile Ile Lys  Leu Pro Lys Tyr Ser  Leu Phe Glu
    1355                 1360                 1365

Leu Glu  Asn Gly Arg Lys Arg  Met Leu Ala Ser Ala  Gly Glu Leu
    1370                 1375                 1380

Gln Lys  Gly Asn Glu Leu Ala  Leu Pro Ser Lys Tyr  Val Asn Phe
```

1385 1390 1395

Leu Tyr Leu Ala Ser His Tyr Glu Lys Leu Lys Gly Ser Pro Glu
1400 1405 1410

Asp Asn Glu Gln Lys Gln Leu Phe Val Glu Gln His Lys His Tyr
1415 1420 1425

Leu Asp Glu Ile Ile Glu Gln Ile Ser Glu Phe Ser Lys Arg Val
1430 1435 1440

Ile Leu Ala Asp Ala Asn Leu Asp Lys Val Leu Ser Ala Tyr Asn
1445 1450 1455

Lys His Arg Asp Lys Pro Ile Arg Glu Gln Ala Glu Asn Ile Ile
1460 1465 1470

His Leu Phe Thr Leu Thr Asn Leu Gly Ala Pro Ala Ala Phe Lys
1475 1480 1485

Tyr Phe Asp Thr Thr Ile Asp Arg Lys Arg Tyr Thr Ser Thr Lys
1490 1495 1500

Glu Val Leu Asp Ala Thr Leu Ile His Gln Ser Ile Thr Gly Leu
1505 1510 1515

Tyr Glu Thr Arg Ile Asp Leu Ser Gln Leu Gly Gly Asp
1520 1525 1530

<210> SEQ ID NO 336
<211> LENGTH: 1537
<212> TYPE: PRT
<213> ORGANISM: Artificial Sequence
<220> FEATURE:
<223> OTHER INFORMATION: Synthetic Polypeptide

<400> SEQUENCE: 336

Met Asp Lys Lys Tyr Ser Ile Gly Leu Ala Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

Asn Gln Leu Phe Glu Glu Asn Pro Ile Asn Ala Ser Gly Val Asp Ala
195 200 205

Lys Ala Ile Leu Ser Ala Arg Leu Ser Lys Ser Arg Arg Leu Glu Asn

```
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640
```

```
His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050
```

```
Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365

Met Ala  Pro Lys Lys Lys Arg  Lys Val Gly Ile His  Arg Gly Val
    1370                 1375                 1380

Pro Gly  Gly Ser Gly Gly Ser  Gly Gly Ser Met Leu  Ile Gly Tyr
    1385                 1390                 1395

Val Arg  Val Ser Thr Asn Asp  Gln Asn Thr Asp Leu  Gln Arg Asn
    1400                 1405                 1410

Ala Leu  Val Cys Ala Gly Cys  Glu Gln Ile Phe Glu  Asp Lys Leu
    1415                 1420                 1425

Ser Gly  Thr Arg Thr Asp Arg  Pro Gly Leu Lys Arg  Ala Leu Lys
    1430                 1435                 1440

Arg Leu  Gln Lys Gly Asp Thr  Leu Val Val Trp Lys  Leu Asp Arg
```

```
    1445                1450                1455

Leu Gly  Arg Ser Met Lys His  Leu Ile Ser Leu Val  Gly Glu Leu
    1460                1465                1470

Arg Glu  Arg Gly Ile Asn Phe  Arg Ser Leu Thr Asp  Ser Ile Asp
    1475                1480                1485

Thr Ser  Ser Pro Met Gly Arg  Phe Phe Phe Tyr Val  Met Gly Ala
    1490                1495                1500

Leu Ala  Glu Met Glu Arg Glu  Leu Ile Ile Glu Arg  Thr Met Ala
    1505                1510                1515

Gly Ile  Ala Ala Ala Arg Asn  Lys Gly Arg Arg Phe  Gly Arg Pro
    1520                1525                1530

Pro Lys  Ser Gly
    1535


<210> SEQ ID NO 337
<211> LENGTH: 1537
<212> TYPE: PRT
<213> ORGANISM: Artificial Sequence
<220> FEATURE:
<223> OTHER INFORMATION: Synthetic Polypeptide

<400> SEQUENCE: 337

Met Ala Pro Lys Lys Lys Arg Lys Val Gly Ile His Arg Gly Val Pro
1               5                   10                  15

Met Asp Lys Lys Tyr Ser Ile Gly Leu Ala Ile Gly Thr Asn Ser Val
            20                  25                  30

Gly Trp Ala Val Ile Thr Asp Glu Tyr Lys Val Pro Ser Lys Lys Phe
        35                  40                  45

Lys Val Leu Gly Asn Thr Asp Arg His Ser Ile Lys Lys Asn Leu Ile
    50                  55                  60

Gly Ala Leu Leu Phe Asp Ser Gly Glu Thr Ala Glu Ala Thr Arg Leu
65                  70                  75                  80

Lys Arg Thr Ala Arg Arg Arg Tyr Thr Arg Arg Lys Asn Arg Ile Cys
                85                  90                  95

Tyr Leu Gln Glu Ile Phe Ser Asn Glu Met Ala Lys Val Asp Asp Ser
            100                 105                 110

Phe Phe His Arg Leu Glu Glu Ser Phe Leu Val Glu Glu Asp Lys Lys
        115                 120                 125

His Glu Arg His Pro Ile Phe Gly Asn Ile Val Asp Glu Val Ala Tyr
    130                 135                 140

His Glu Lys Tyr Pro Thr Ile Tyr His Leu Arg Lys Lys Leu Val Asp
145                 150                 155                 160

Ser Thr Asp Lys Ala Asp Leu Arg Leu Ile Tyr Leu Ala Leu Ala His
                165                 170                 175

Met Ile Lys Phe Arg Gly His Phe Leu Ile Glu Gly Asp Leu Asn Pro
            180                 185                 190

Asp Asn Ser Asp Val Asp Lys Leu Phe Ile Gln Leu Val Gln Thr Tyr
        195                 200                 205

Asn Gln Leu Phe Glu Glu Asn Pro Ile Asn Ala Ser Gly Val Asp Ala
    210                 215                 220

Lys Ala Ile Leu Ser Ala Arg Leu Ser Lys Ser Arg Arg Leu Glu Asn
225                 230                 235                 240

Leu Ile Ala Gln Leu Pro Gly Glu Lys Lys Asn Gly Leu Phe Gly Asn
                245                 250                 255

Leu Ile Ala Leu Ser Leu Gly Leu Thr Pro Asn Phe Lys Ser Asn Phe
```

```
            260                 265                 270

Asp Leu Ala Glu Asp Ala Lys Leu Gln Leu Ser Lys Asp Thr Tyr Asp
        275                 280                 285

Asp Asp Leu Asp Asn Leu Leu Ala Gln Ile Gly Asp Gln Tyr Ala Asp
    290                 295                 300

Leu Phe Leu Ala Ala Lys Asn Leu Ser Asp Ala Ile Leu Leu Ser Asp
305                 310                 315                 320

Ile Leu Arg Val Asn Thr Glu Ile Thr Lys Ala Pro Leu Ser Ala Ser
                325                 330                 335

Met Ile Lys Arg Tyr Asp Glu His His Gln Asp Leu Thr Leu Leu Lys
            340                 345                 350

Ala Leu Val Arg Gln Gln Leu Pro Glu Lys Tyr Lys Glu Ile Phe Phe
        355                 360                 365

Asp Gln Ser Lys Asn Gly Tyr Ala Gly Tyr Ile Asp Gly Gly Ala Ser
    370                 375                 380

Gln Glu Glu Phe Tyr Lys Phe Ile Lys Pro Ile Leu Glu Lys Met Asp
385                 390                 395                 400

Gly Thr Glu Glu Leu Leu Val Lys Leu Asn Arg Glu Asp Leu Leu Arg
                405                 410                 415

Lys Gln Arg Thr Phe Asp Asn Gly Ser Ile Pro His Gln Ile His Leu
            420                 425                 430

Gly Glu Leu His Ala Ile Leu Arg Arg Gln Glu Asp Phe Tyr Pro Phe
        435                 440                 445

Leu Lys Asp Asn Arg Glu Lys Ile Glu Lys Ile Leu Thr Phe Arg Ile
    450                 455                 460

Pro Tyr Tyr Val Gly Pro Leu Ala Arg Gly Asn Ser Arg Phe Ala Trp
465                 470                 475                 480

Met Thr Arg Lys Ser Glu Glu Thr Ile Thr Pro Trp Asn Phe Glu Glu
                485                 490                 495

Val Val Asp Lys Gly Ala Ser Ala Gln Ser Phe Ile Glu Arg Met Thr
            500                 505                 510

Asn Phe Asp Lys Asn Leu Pro Asn Glu Lys Val Leu Pro Lys His Ser
        515                 520                 525

Leu Leu Tyr Glu Tyr Phe Thr Val Tyr Asn Glu Leu Thr Lys Val Lys
    530                 535                 540

Tyr Val Thr Glu Gly Met Arg Lys Pro Ala Phe Leu Ser Gly Glu Gln
545                 550                 555                 560

Lys Lys Ala Ile Val Asp Leu Leu Phe Lys Thr Asn Arg Lys Val Thr
                565                 570                 575

Val Lys Gln Leu Lys Glu Asp Tyr Phe Lys Lys Ile Glu Cys Phe Asp
            580                 585                 590

Ser Val Glu Ile Ser Gly Val Glu Asp Arg Phe Asn Ala Ser Leu Gly
        595                 600                 605

Thr Tyr His Asp Leu Leu Lys Ile Ile Lys Asp Lys Asp Phe Leu Asp
    610                 615                 620

Asn Glu Glu Asn Glu Asp Ile Leu Glu Asp Ile Val Leu Thr Leu Thr
625                 630                 635                 640

Leu Phe Glu Asp Arg Glu Met Ile Glu Glu Arg Leu Lys Thr Tyr Ala
                645                 650                 655

His Leu Phe Asp Asp Lys Val Met Lys Gln Leu Lys Arg Arg Arg Tyr
            660                 665                 670

Thr Gly Trp Gly Arg Leu Ser Arg Lys Leu Ile Asn Gly Ile Arg Asp
        675                 680                 685
```

```
Lys Gln Ser Gly Lys Thr Ile Leu Asp Phe Leu Lys Ser Asp Gly Phe
    690                 695                 700

Ala Asn Arg Asn Phe Met Gln Leu Ile His Asp Asp Ser Leu Thr Phe
705                 710                 715                 720

Lys Glu Asp Ile Gln Lys Ala Gln Val Ser Gly Gln Gly Asp Ser Leu
                725                 730                 735

His Glu His Ile Ala Asn Leu Ala Gly Ser Pro Ala Ile Lys Lys Gly
            740                 745                 750

Ile Leu Gln Thr Val Lys Val Val Asp Glu Leu Val Lys Val Met Gly
        755                 760                 765

Arg His Lys Pro Glu Asn Ile Val Ile Glu Met Ala Arg Glu Asn Gln
    770                 775                 780

Thr Thr Gln Lys Gly Gln Lys Asn Ser Arg Glu Arg Met Lys Arg Ile
785                 790                 795                 800

Glu Glu Gly Ile Lys Glu Leu Gly Ser Gln Ile Leu Lys Glu His Pro
                805                 810                 815

Val Glu Asn Thr Gln Leu Gln Asn Glu Lys Leu Tyr Leu Tyr Tyr Leu
            820                 825                 830

Gln Asn Gly Arg Asp Met Tyr Val Asp Gln Glu Leu Asp Ile Asn Arg
        835                 840                 845

Leu Ser Asp Tyr Asp Val Asp Ala Ile Val Pro Gln Ser Phe Leu Lys
    850                 855                 860

Asp Asp Ser Ile Asp Asn Lys Val Leu Thr Arg Ser Asp Lys Asn Arg
865                 870                 875                 880

Gly Lys Ser Asp Asn Val Pro Ser Glu Glu Val Val Lys Lys Met Lys
                885                 890                 895

Asn Tyr Trp Arg Gln Leu Leu Asn Ala Lys Leu Ile Thr Gln Arg Lys
            900                 905                 910

Phe Asp Asn Leu Thr Lys Ala Glu Arg Gly Gly Leu Ser Glu Leu Asp
        915                 920                 925

Lys Ala Gly Phe Ile Lys Arg Gln Leu Val Glu Thr Arg Gln Ile Thr
    930                 935                 940

Lys His Val Ala Gln Ile Leu Asp Ser Arg Met Asn Thr Lys Tyr Asp
945                 950                 955                 960

Glu Asn Asp Lys Leu Ile Arg Glu Val Lys Val Ile Thr Leu Lys Ser
                965                 970                 975

Lys Leu Val Ser Asp Phe Arg Lys Asp Phe Gln Phe Tyr Lys Val Arg
            980                 985                 990

Glu Ile Asn Asn Tyr His His Ala  His Asp Ala Tyr Leu  Asn Ala Val
        995                 1000                1005

Val Gly  Thr Ala Leu Ile Lys  Lys Tyr Pro Lys Leu  Glu Ser Glu
    1010                1015                1020

Phe Val  Tyr Gly Asp Tyr Lys  Val Tyr Asp Val Arg  Lys Met Ile
    1025                1030                1035

Ala Lys  Ser Glu Gln Glu Ile  Gly Lys Ala Thr Ala  Lys Tyr Phe
    1040                1045                1050

Phe Tyr  Ser Asn Ile Met Asn  Phe Phe Lys Thr Glu  Ile Thr Leu
    1055                1060                1065

Ala Asn  Gly Glu Ile Arg Lys  Arg Pro Leu Ile Glu  Thr Asn Gly
    1070                1075                1080

Glu Thr  Gly Glu Ile Val Trp  Asp Lys Gly Arg Asp  Phe Ala Thr
    1085                1090                1095
```

Val Arg Lys Val Leu Ser Met Pro Gln Val Asn Ile Val Lys Lys
1100 1105 1110

Thr Glu Val Gln Thr Gly Gly Phe Ser Lys Glu Ser Ile Leu Pro
1115 1120 1125

Lys Arg Asn Ser Asp Lys Leu Ile Ala Arg Lys Lys Asp Trp Asp
1130 1135 1140

Pro Lys Lys Tyr Gly Gly Phe Asp Ser Pro Thr Val Ala Tyr Ser
1145 1150 1155

Val Leu Val Val Ala Lys Val Glu Lys Gly Lys Ser Lys Lys Leu
1160 1165 1170

Lys Ser Val Lys Glu Leu Leu Gly Ile Thr Ile Met Glu Arg Ser
1175 1180 1185

Ser Phe Glu Lys Asn Pro Ile Asp Phe Leu Glu Ala Lys Gly Tyr
1190 1195 1200

Lys Glu Val Lys Lys Asp Leu Ile Ile Lys Leu Pro Lys Tyr Ser
1205 1210 1215

Leu Phe Glu Leu Glu Asn Gly Arg Lys Arg Met Leu Ala Ser Ala
1220 1225 1230

Gly Glu Leu Gln Lys Gly Asn Glu Leu Ala Leu Pro Ser Lys Tyr
1235 1240 1245

Val Asn Phe Leu Tyr Leu Ala Ser His Tyr Glu Lys Leu Lys Gly
1250 1255 1260

Ser Pro Glu Asp Asn Glu Gln Lys Gln Leu Phe Val Glu Gln His
1265 1270 1275

Lys His Tyr Leu Asp Glu Ile Ile Glu Gln Ile Ser Glu Phe Ser
1280 1285 1290

Lys Arg Val Ile Leu Ala Asp Ala Asn Leu Asp Lys Val Leu Ser
1295 1300 1305

Ala Tyr Asn Lys His Arg Asp Lys Pro Ile Arg Glu Gln Ala Glu
1310 1315 1320

Asn Ile Ile His Leu Phe Thr Leu Thr Asn Leu Gly Ala Pro Ala
1325 1330 1335

Ala Phe Lys Tyr Phe Asp Thr Thr Ile Asp Arg Lys Arg Tyr Thr
1340 1345 1350

Ser Thr Lys Glu Val Leu Asp Ala Thr Leu Ile His Gln Ser Ile
1355 1360 1365

Thr Gly Leu Tyr Glu Thr Arg Ile Asp Leu Ser Gln Leu Gly Gly
1370 1375 1380

Asp Gly Gly Ser Gly Gly Ser Gly Gly Ser Met Leu Ile Gly Tyr
1385 1390 1395

Val Arg Val Ser Thr Asn Asp Gln Asn Thr Asp Leu Gln Arg Asn
1400 1405 1410

Ala Leu Val Cys Ala Gly Cys Glu Gln Ile Phe Glu Asp Lys Leu
1415 1420 1425

Ser Gly Thr Arg Thr Asp Arg Pro Gly Leu Lys Arg Ala Leu Lys
1430 1435 1440

Arg Leu Gln Lys Gly Asp Thr Leu Val Val Trp Lys Leu Asp Arg
1445 1450 1455

Leu Gly Arg Ser Met Lys His Leu Ile Ser Leu Val Gly Glu Leu
1460 1465 1470

Arg Glu Arg Gly Ile Asn Phe Arg Ser Leu Thr Asp Ser Ile Asp
1475 1480 1485

Thr Ser Ser Pro Met Gly Arg Phe Phe Phe Tyr Val Met Gly Ala

```
    1490                1495                1500

Leu Ala  Glu Met Glu Arg Glu  Leu Ile Ile Glu Arg  Thr Met Ala
    1505                1510                1515

Gly Ile  Ala Ala Ala Arg Asn  Lys Gly Arg Arg Phe  Gly Arg Pro
    1520                1525                1530

Pro Lys  Ser Gly
    1535
```

<210> SEQ ID NO 338
<211> LENGTH: 1537
<212> TYPE: PRT
<213> ORGANISM: Artificial Sequence
<220> FEATURE:
<223> OTHER INFORMATION: Synthetic Polynucleotide

<400> SEQUENCE: 338

```
Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Glu Leu Ile Ile Glu Arg Thr Met Ala Gly Ile Ala
        115                 120                 125

Ala Ala Arg Asn Lys Gly Arg Arg Phe Gly Arg Pro Pro Lys Ser Gly
    130                 135                 140

Gly Gly Ser Gly Gly Ser Gly Gly Ser Met Asp Lys Lys Tyr Ser Ile
145                 150                 155                 160

Gly Leu Ala Ile Gly Thr Asn Ser Val Gly Trp Ala Val Ile Thr Asp
                165                 170                 175

Glu Tyr Lys Val Pro Ser Lys Lys Phe Lys Val Leu Gly Asn Thr Asp
            180                 185                 190

Arg His Ser Ile Lys Lys Asn Leu Ile Gly Ala Leu Leu Phe Asp Ser
        195                 200                 205

Gly Glu Thr Ala Glu Ala Thr Arg Leu Lys Arg Thr Ala Arg Arg Arg
    210                 215                 220

Tyr Thr Arg Arg Lys Asn Arg Ile Cys Tyr Leu Gln Glu Ile Phe Ser
225                 230                 235                 240

Asn Glu Met Ala Lys Val Asp Asp Ser Phe Phe His Arg Leu Glu Glu
                245                 250                 255

Ser Phe Leu Val Glu Glu Asp Lys Lys His Glu Arg His Pro Ile Phe
            260                 265                 270

Gly Asn Ile Val Asp Glu Val Ala Tyr His Glu Lys Tyr Pro Thr Ile
        275                 280                 285

Tyr His Leu Arg Lys Lys Leu Val Asp Ser Thr Asp Lys Ala Asp Leu
    290                 295                 300

Arg Leu Ile Tyr Leu Ala Leu Ala His Met Ile Lys Phe Arg Gly His
```

```
305                 310                 315                 320

Phe Leu Ile Glu Gly Asp Leu Asn Pro Asp Asn Ser Asp Val Asp Lys
                325                 330                 335

Leu Phe Ile Gln Leu Val Gln Thr Tyr Asn Gln Leu Phe Glu Glu Asn
            340                 345                 350

Pro Ile Asn Ala Ser Gly Val Asp Ala Lys Ala Ile Leu Ser Ala Arg
        355                 360                 365

Leu Ser Lys Ser Arg Arg Leu Glu Asn Leu Ile Ala Gln Leu Pro Gly
    370                 375                 380

Glu Lys Lys Asn Gly Leu Phe Gly Asn Leu Ile Ala Leu Ser Leu Gly
385                 390                 395                 400

Leu Thr Pro Asn Phe Lys Ser Asn Phe Asp Leu Ala Glu Asp Ala Lys
                405                 410                 415

Leu Gln Leu Ser Lys Asp Thr Tyr Asp Asp Asp Leu Asp Asn Leu Leu
            420                 425                 430

Ala Gln Ile Gly Asp Gln Tyr Ala Asp Leu Phe Leu Ala Ala Lys Asn
        435                 440                 445

Leu Ser Asp Ala Ile Leu Leu Ser Asp Ile Leu Arg Val Asn Thr Glu
    450                 455                 460

Ile Thr Lys Ala Pro Leu Ser Ala Ser Met Ile Lys Arg Tyr Asp Glu
465                 470                 475                 480

His His Gln Asp Leu Thr Leu Leu Lys Ala Leu Val Arg Gln Gln Leu
                485                 490                 495

Pro Glu Lys Tyr Lys Glu Ile Phe Phe Asp Gln Ser Lys Asn Gly Tyr
            500                 505                 510

Ala Gly Tyr Ile Asp Gly Gly Ala Ser Gln Glu Glu Phe Tyr Lys Phe
        515                 520                 525

Ile Lys Pro Ile Leu Glu Lys Met Asp Gly Thr Glu Glu Leu Leu Val
    530                 535                 540

Lys Leu Asn Arg Glu Asp Leu Leu Arg Lys Gln Arg Thr Phe Asp Asn
545                 550                 555                 560

Gly Ser Ile Pro His Gln Ile His Leu Gly Glu Leu His Ala Ile Leu
                565                 570                 575

Arg Arg Gln Glu Asp Phe Tyr Pro Phe Leu Lys Asp Asn Arg Glu Lys
            580                 585                 590

Ile Glu Lys Ile Leu Thr Phe Arg Ile Pro Tyr Tyr Val Gly Pro Leu
        595                 600                 605

Ala Arg Gly Asn Ser Arg Phe Ala Trp Met Thr Arg Lys Ser Glu Glu
    610                 615                 620

Thr Ile Thr Pro Trp Asn Phe Glu Glu Val Val Asp Lys Gly Ala Ser
625                 630                 635                 640

Ala Gln Ser Phe Ile Glu Arg Met Thr Asn Phe Asp Lys Asn Leu Pro
                645                 650                 655

Asn Glu Lys Val Leu Pro Lys His Ser Leu Leu Tyr Glu Tyr Phe Thr
            660                 665                 670

Val Tyr Asn Glu Leu Thr Lys Val Lys Tyr Val Thr Glu Gly Met Arg
        675                 680                 685

Lys Pro Ala Phe Leu Ser Gly Glu Gln Lys Lys Ala Ile Val Asp Leu
    690                 695                 700

Leu Phe Lys Thr Asn Arg Lys Val Thr Val Lys Gln Leu Lys Glu Asp
705                 710                 715                 720

Tyr Phe Lys Lys Ile Glu Cys Phe Asp Ser Val Glu Ile Ser Gly Val
                725                 730                 735
```

```
Glu Asp Arg Phe Asn Ala Ser Leu Gly Thr Tyr His Asp Leu Leu Lys
            740                 745                 750

Ile Ile Lys Asp Lys Asp Phe Leu Asp Asn Glu Glu Asn Glu Asp Ile
        755                 760                 765

Leu Glu Asp Ile Val Leu Thr Leu Thr Leu Phe Glu Asp Arg Glu Met
    770                 775                 780

Ile Glu Glu Arg Leu Lys Thr Tyr Ala His Leu Phe Asp Asp Lys Val
785                 790                 795                 800

Met Lys Gln Leu Lys Arg Arg Arg Tyr Thr Gly Trp Gly Arg Leu Ser
                805                 810                 815

Arg Lys Leu Ile Asn Gly Ile Arg Asp Lys Gln Ser Gly Lys Thr Ile
            820                 825                 830

Leu Asp Phe Leu Lys Ser Asp Gly Phe Ala Asn Arg Asn Phe Met Gln
        835                 840                 845

Leu Ile His Asp Asp Ser Leu Thr Phe Lys Glu Asp Ile Gln Lys Ala
    850                 855                 860

Gln Val Ser Gly Gln Gly Asp Ser Leu His Glu His Ile Ala Asn Leu
865                 870                 875                 880

Ala Gly Ser Pro Ala Ile Lys Lys Gly Ile Leu Gln Thr Val Lys Val
                885                 890                 895

Val Asp Glu Leu Val Lys Val Met Gly Arg His Lys Pro Glu Asn Ile
            900                 905                 910

Val Ile Glu Met Ala Arg Glu Asn Gln Thr Thr Gln Lys Gly Gln Lys
        915                 920                 925

Asn Ser Arg Glu Arg Met Lys Arg Ile Glu Glu Gly Ile Lys Glu Leu
    930                 935                 940

Gly Ser Gln Ile Leu Lys Glu His Pro Val Glu Asn Thr Gln Leu Gln
945                 950                 955                 960

Asn Glu Lys Leu Tyr Leu Tyr Tyr Leu Gln Asn Gly Arg Asp Met Tyr
                965                 970                 975

Val Asp Gln Glu Leu Asp Ile Asn Arg Leu Ser Asp Tyr Asp Val Asp
            980                 985                 990

Ala Ile Val Pro Gln Ser Phe Leu  Lys Asp Asp Ser Ile  Asp Asn Lys
        995                 1000                 1005

Val Leu  Thr Arg Ser Asp Lys  Asn Arg Gly Lys Ser  Asp Asn Val
    1010                 1015                 1020

Pro Ser  Glu Glu Val Val Lys  Lys Met Lys Asn Tyr  Trp Arg Gln
    1025                 1030                 1035

Leu Leu  Asn Ala Lys Leu Ile  Thr Gln Arg Lys Phe  Asp Asn Leu
    1040                 1045                 1050

Thr Lys  Ala Glu Arg Gly Gly  Leu Ser Glu Leu Asp  Lys Ala Gly
    1055                 1060                 1065

Phe Ile  Lys Arg Gln Leu Val  Glu Thr Arg Gln Ile  Thr Lys His
    1070                 1075                 1080

Val Ala  Gln Ile Leu Asp Ser  Arg Met Asn Thr Lys  Tyr Asp Glu
    1085                 1090                 1095

Asn Asp  Lys Leu Ile Arg Glu  Val Lys Val Ile Thr  Leu Lys Ser
    1100                 1105                 1110

Lys Leu  Val Ser Asp Phe Arg  Lys Asp Phe Gln Phe  Tyr Lys Val
    1115                 1120                 1125

Arg Glu  Ile Asn Asn Tyr His  His Ala His Asp Ala  Tyr Leu Asn
    1130                 1135                 1140
```

```
Ala Val  Val Gly Thr Ala Leu  Ile Lys Lys Tyr Pro  Lys Leu Glu
    1145                 1150                 1155

Ser Glu  Phe Val Tyr Gly Asp  Tyr Lys Val Tyr Asp  Val Arg Lys
    1160                 1165                 1170

Met Ile  Ala Lys Ser Glu Gln  Glu Ile Gly Lys Ala  Thr Ala Lys
    1175                 1180                 1185

Tyr Phe  Phe Tyr Ser Asn Ile  Met Asn Phe Phe Lys  Thr Glu Ile
    1190                 1195                 1200

Thr Leu  Ala Asn Gly Glu Ile  Arg Lys Arg Pro Leu  Ile Glu Thr
    1205                 1210                 1215

Asn Gly  Glu Thr Gly Glu Ile  Val Trp Asp Lys Gly  Arg Asp Phe
    1220                 1225                 1230

Ala Thr  Val Arg Lys Val Leu  Ser Met Pro Gln Val  Asn Ile Val
    1235                 1240                 1245

Lys Lys  Thr Glu Val Gln Thr  Gly Gly Phe Ser Lys  Glu Ser Ile
    1250                 1255                 1260

Leu Pro  Lys Arg Asn Ser Asp  Lys Leu Ile Ala Arg  Lys Lys Asp
    1265                 1270                 1275

Trp Asp  Pro Lys Lys Tyr Gly  Gly Phe Asp Ser Pro  Thr Val Ala
    1280                 1285                 1290

Tyr Ser  Val Leu Val Val Ala  Lys Val Glu Lys Gly  Lys Ser Lys
    1295                 1300                 1305

Lys Leu  Lys Ser Val Lys Glu  Leu Leu Gly Ile Thr  Ile Met Glu
    1310                 1315                 1320

Arg Ser  Ser Phe Glu Lys Asn  Pro Ile Asp Phe Leu  Glu Ala Lys
    1325                 1330                 1335

Gly Tyr  Lys Glu Val Lys Lys  Asp Leu Ile Ile Lys  Leu Pro Lys
    1340                 1345                 1350

Tyr Ser  Leu Phe Glu Leu Glu  Asn Gly Arg Lys Arg  Met Leu Ala
    1355                 1360                 1365

Ser Ala  Gly Glu Leu Gln Lys  Gly Asn Glu Leu Ala  Leu Pro Ser
    1370                 1375                 1380

Lys Tyr  Val Asn Phe Leu Tyr  Leu Ala Ser His Tyr  Glu Lys Leu
    1385                 1390                 1395

Lys Gly  Ser Pro Glu Asp Asn  Glu Gln Lys Gln Leu  Phe Val Glu
    1400                 1405                 1410

Gln His  Lys His Tyr Leu Asp  Glu Ile Ile Glu Gln  Ile Ser Glu
    1415                 1420                 1425

Phe Ser  Lys Arg Val Ile Leu  Ala Asp Ala Asn Leu  Asp Lys Val
    1430                 1435                 1440

Leu Ser  Ala Tyr Asn Lys His  Arg Asp Lys Pro Ile  Arg Glu Gln
    1445                 1450                 1455

Ala Glu  Asn Ile Ile His Leu  Phe Thr Leu Thr Asn  Leu Gly Ala
    1460                 1465                 1470

Pro Ala  Ala Phe Lys Tyr Phe  Asp Thr Thr Ile Asp  Arg Lys Arg
    1475                 1480                 1485

Tyr Thr  Ser Thr Lys Glu Val  Leu Asp Ala Thr Leu  Ile His Gln
    1490                 1495                 1500

Ser Ile  Thr Gly Leu Tyr Glu  Thr Arg Ile Asp Leu  Ser Gln Leu
    1505                 1510                 1515

Gly Gly  Asp Met Ala Pro Lys  Lys Lys Arg Lys Val  Gly Ile His
    1520                 1525                 1530

Arg Gly  Val Pro
```

1535

<210> SEQ ID NO 339
<211> LENGTH: 1537
<212> TYPE: PRT
<213> ORGANISM: Artificial Sequence
<220> FEATURE:
<223> OTHER INFORMATION: Synthetic Polypeptide

<400> SEQUENCE: 339

Met Ala Pro Lys Lys Lys Arg Lys Val Gly Ile His Arg Gly Val Pro
1               5                   10                  15

Met Leu Ile Gly Tyr Val Arg Val Ser Thr Asn Asp Gln Asn Thr Asp
            20                  25                  30

Leu Gln Arg Asn Ala Leu Val Cys Ala Gly Cys Glu Gln Ile Phe Glu
        35                  40                  45

Asp Lys Leu Ser Gly Thr Arg Thr Asp Arg Pro Gly Leu Lys Arg Ala
    50                  55                  60

Leu Lys Arg Leu Gln Lys Gly Asp Thr Leu Val Val Trp Lys Leu Asp
65                  70                  75                  80

Arg Leu Gly Arg Ser Met Lys His Leu Ile Ser Leu Val Gly Glu Leu
                85                  90                  95

Arg Glu Arg Gly Ile Asn Phe Arg Ser Leu Thr Asp Ser Ile Asp Thr
            100                 105                 110

Ser Ser Pro Met Gly Arg Phe Phe Phe Tyr Val Met Gly Ala Leu Ala
        115                 120                 125

Glu Met Glu Arg Glu Leu Ile Ile Glu Arg Thr Met Ala Gly Ile Ala
    130                 135                 140

Ala Ala Arg Asn Lys Gly Arg Arg Phe Gly Arg Pro Pro Lys Ser Gly
145                 150                 155                 160

Gly Gly Ser Gly Gly Ser Gly Gly Ser Met Asp Lys Lys Tyr Ser Ile
                165                 170                 175

Gly Leu Ala Ile Gly Thr Asn Ser Val Gly Trp Ala Val Ile Thr Asp
            180                 185                 190

Glu Tyr Lys Val Pro Ser Lys Lys Phe Lys Val Leu Gly Asn Thr Asp
        195                 200                 205

Arg His Ser Ile Lys Lys Asn Leu Ile Gly Ala Leu Leu Phe Asp Ser
    210                 215                 220

Gly Glu Thr Ala Glu Ala Thr Arg Leu Lys Arg Thr Ala Arg Arg Arg
225                 230                 235                 240

Tyr Thr Arg Arg Lys Asn Arg Ile Cys Tyr Leu Gln Glu Ile Phe Ser
                245                 250                 255

Asn Glu Met Ala Lys Val Asp Asp Ser Phe Phe His Arg Leu Glu Glu
            260                 265                 270

Ser Phe Leu Val Glu Glu Asp Lys Lys His Glu Arg His Pro Ile Phe
        275                 280                 285

Gly Asn Ile Val Asp Glu Val Ala Tyr His Glu Lys Tyr Pro Thr Ile
    290                 295                 300

Tyr His Leu Arg Lys Lys Leu Val Asp Ser Thr Asp Lys Ala Asp Leu
305                 310                 315                 320

Arg Leu Ile Tyr Leu Ala Leu Ala His Met Ile Lys Phe Arg Gly His
                325                 330                 335

Phe Leu Ile Glu Gly Asp Leu Asn Pro Asp Asn Ser Asp Val Asp Lys
            340                 345                 350

Leu Phe Ile Gln Leu Val Gln Thr Tyr Asn Gln Leu Phe Glu Glu Asn

```
        355                 360                 365

Pro Ile Asn Ala Ser Gly Val Asp Ala Lys Ala Ile Leu Ser Ala Arg
    370                 375                 380

Leu Ser Lys Ser Arg Arg Leu Glu Asn Leu Ile Ala Gln Leu Pro Gly
385                 390                 395                 400

Glu Lys Lys Asn Gly Leu Phe Gly Asn Leu Ile Ala Leu Ser Leu Gly
                405                 410                 415

Leu Thr Pro Asn Phe Lys Ser Asn Phe Asp Leu Ala Glu Asp Ala Lys
            420                 425                 430

Leu Gln Leu Ser Lys Asp Thr Tyr Asp Asp Asp Leu Asp Asn Leu Leu
        435                 440                 445

Ala Gln Ile Gly Asp Gln Tyr Ala Asp Leu Phe Leu Ala Ala Lys Asn
    450                 455                 460

Leu Ser Asp Ala Ile Leu Leu Ser Asp Ile Leu Arg Val Asn Thr Glu
465                 470                 475                 480

Ile Thr Lys Ala Pro Leu Ser Ala Ser Met Ile Lys Arg Tyr Asp Glu
                485                 490                 495

His His Gln Asp Leu Thr Leu Leu Lys Ala Leu Val Arg Gln Gln Leu
            500                 505                 510

Pro Glu Lys Tyr Lys Glu Ile Phe Phe Asp Gln Ser Lys Asn Gly Tyr
        515                 520                 525

Ala Gly Tyr Ile Asp Gly Gly Ala Ser Gln Glu Glu Phe Tyr Lys Phe
    530                 535                 540

Ile Lys Pro Ile Leu Glu Lys Met Asp Gly Thr Glu Glu Leu Leu Val
545                 550                 555                 560

Lys Leu Asn Arg Glu Asp Leu Leu Arg Lys Gln Arg Thr Phe Asp Asn
                565                 570                 575

Gly Ser Ile Pro His Gln Ile His Leu Gly Glu Leu His Ala Ile Leu
            580                 585                 590

Arg Arg Gln Glu Asp Phe Tyr Pro Phe Leu Lys Asp Asn Arg Glu Lys
        595                 600                 605

Ile Glu Lys Ile Leu Thr Phe Arg Ile Pro Tyr Tyr Val Gly Pro Leu
    610                 615                 620

Ala Arg Gly Asn Ser Arg Phe Ala Trp Met Thr Arg Lys Ser Glu Glu
625                 630                 635                 640

Thr Ile Thr Pro Trp Asn Phe Glu Glu Val Val Asp Lys Gly Ala Ser
                645                 650                 655

Ala Gln Ser Phe Ile Glu Arg Met Thr Asn Phe Asp Lys Asn Leu Pro
            660                 665                 670

Asn Glu Lys Val Leu Pro Lys His Ser Leu Leu Tyr Glu Tyr Phe Thr
        675                 680                 685

Val Tyr Asn Glu Leu Thr Lys Val Lys Tyr Val Thr Glu Gly Met Arg
    690                 695                 700

Lys Pro Ala Phe Leu Ser Gly Glu Gln Lys Lys Ala Ile Val Asp Leu
705                 710                 715                 720

Leu Phe Lys Thr Asn Arg Lys Val Thr Val Lys Gln Leu Lys Glu Asp
                725                 730                 735

Tyr Phe Lys Lys Ile Glu Cys Phe Asp Ser Val Glu Ile Ser Gly Val
            740                 745                 750

Glu Asp Arg Phe Asn Ala Ser Leu Gly Thr Tyr His Asp Leu Leu Lys
        755                 760                 765

Ile Ile Lys Asp Lys Asp Phe Leu Asp Asn Glu Glu Asn Glu Asp Ile
    770                 775                 780
```

Leu Glu Asp Ile Val Leu Thr Leu Thr Leu Phe Glu Asp Arg Glu Met
785 790 795 800

Ile Glu Glu Arg Leu Lys Thr Tyr Ala His Leu Phe Asp Asp Lys Val
805 810 815

Met Lys Gln Leu Lys Arg Arg Arg Tyr Thr Gly Trp Gly Arg Leu Ser
820 825 830

Arg Lys Leu Ile Asn Gly Ile Arg Asp Lys Gln Ser Gly Lys Thr Ile
835 840 845

Leu Asp Phe Leu Lys Ser Asp Gly Phe Ala Asn Arg Asn Phe Met Gln
850 855 860

Leu Ile His Asp Asp Ser Leu Thr Phe Lys Glu Asp Ile Gln Lys Ala
865 870 875 880

Gln Val Ser Gly Gln Gly Asp Ser Leu His Glu His Ile Ala Asn Leu
885 890 895

Ala Gly Ser Pro Ala Ile Lys Lys Gly Ile Leu Gln Thr Val Lys Val
900 905 910

Val Asp Glu Leu Val Lys Val Met Gly Arg His Lys Pro Glu Asn Ile
915 920 925

Val Ile Glu Met Ala Arg Glu Asn Gln Thr Thr Gln Lys Gly Gln Lys
930 935 940

Asn Ser Arg Glu Arg Met Lys Arg Ile Glu Glu Gly Ile Lys Glu Leu
945 950 955 960

Gly Ser Gln Ile Leu Lys Glu His Pro Val Glu Asn Thr Gln Leu Gln
965 970 975

Asn Glu Lys Leu Tyr Leu Tyr Tyr Leu Gln Asn Gly Arg Asp Met Tyr
980 985 990

Val Asp Gln Glu Leu Asp Ile Asn Arg Leu Ser Asp Tyr Asp Val Asp
995 1000 1005

Ala Ile Val Pro Gln Ser Phe Leu Lys Asp Asp Ser Ile Asp Asn
1010 1015 1020

Lys Val Leu Thr Arg Ser Asp Lys Asn Arg Gly Lys Ser Asp Asn
1025 1030 1035

Val Pro Ser Glu Glu Val Val Lys Lys Met Lys Asn Tyr Trp Arg
1040 1045 1050

Gln Leu Leu Asn Ala Lys Leu Ile Thr Gln Arg Lys Phe Asp Asn
1055 1060 1065

Leu Thr Lys Ala Glu Arg Gly Gly Leu Ser Glu Leu Asp Lys Ala
1070 1075 1080

Gly Phe Ile Lys Arg Gln Leu Val Glu Thr Arg Gln Ile Thr Lys
1085 1090 1095

His Val Ala Gln Ile Leu Asp Ser Arg Met Asn Thr Lys Tyr Asp
1100 1105 1110

Glu Asn Asp Lys Leu Ile Arg Glu Val Lys Val Ile Thr Leu Lys
1115 1120 1125

Ser Lys Leu Val Ser Asp Phe Arg Lys Asp Phe Gln Phe Tyr Lys
1130 1135 1140

Val Arg Glu Ile Asn Asn Tyr His His Ala His Asp Ala Tyr Leu
1145 1150 1155

Asn Ala Val Val Gly Thr Ala Leu Ile Lys Lys Tyr Pro Lys Leu
1160 1165 1170

Glu Ser Glu Phe Val Tyr Gly Asp Tyr Lys Val Tyr Asp Val Arg
1175 1180 1185

-continued

Lys Met Ile Ala Lys Ser Glu Gln Glu Ile Gly Lys Ala Thr Ala
1190 1195 1200

Lys Tyr Phe Phe Tyr Ser Asn Ile Met Asn Phe Phe Lys Thr Glu
1205 1210 1215

Ile Thr Leu Ala Asn Gly Glu Ile Arg Lys Arg Pro Leu Ile Glu
1220 1225 1230

Thr Asn Gly Glu Thr Gly Glu Ile Val Trp Asp Lys Gly Arg Asp
1235 1240 1245

Phe Ala Thr Val Arg Lys Val Leu Ser Met Pro Gln Val Asn Ile
1250 1255 1260

Val Lys Lys Thr Glu Val Gln Thr Gly Gly Phe Ser Lys Glu Ser
1265 1270 1275

Ile Leu Pro Lys Arg Asn Ser Asp Lys Leu Ile Ala Arg Lys Lys
1280 1285 1290

Asp Trp Asp Pro Lys Lys Tyr Gly Gly Phe Asp Ser Pro Thr Val
1295 1300 1305

Ala Tyr Ser Val Leu Val Val Ala Lys Val Glu Lys Gly Lys Ser
1310 1315 1320

Lys Lys Leu Lys Ser Val Lys Glu Leu Leu Gly Ile Thr Ile Met
1325 1330 1335

Glu Arg Ser Ser Phe Glu Lys Asn Pro Ile Asp Phe Leu Glu Ala
1340 1345 1350

Lys Gly Tyr Lys Glu Val Lys Lys Asp Leu Ile Ile Lys Leu Pro
1355 1360 1365

Lys Tyr Ser Leu Phe Glu Leu Glu Asn Gly Arg Lys Arg Met Leu
1370 1375 1380

Ala Ser Ala Gly Glu Leu Gln Lys Gly Asn Glu Leu Ala Leu Pro
1385 1390 1395

Ser Lys Tyr Val Asn Phe Leu Tyr Leu Ala Ser His Tyr Glu Lys
1400 1405 1410

Leu Lys Gly Ser Pro Glu Asp Asn Glu Gln Lys Gln Leu Phe Val
1415 1420 1425

Glu Gln His Lys His Tyr Leu Asp Glu Ile Ile Glu Gln Ile Ser
1430 1435 1440

Glu Phe Ser Lys Arg Val Ile Leu Ala Asp Ala Asn Leu Asp Lys
1445 1450 1455

Val Leu Ser Ala Tyr Asn Lys His Arg Asp Lys Pro Ile Arg Glu
1460 1465 1470

Gln Ala Glu Asn Ile Ile His Leu Phe Thr Leu Thr Asn Leu Gly
1475 1480 1485

Ala Pro Ala Ala Phe Lys Tyr Phe Asp Thr Thr Ile Asp Arg Lys
1490 1495 1500

Arg Tyr Thr Ser Thr Lys Glu Val Leu Asp Ala Thr Leu Ile His
1505 1510 1515

Gln Ser Ile Thr Gly Leu Tyr Glu Thr Arg Ile Asp Leu Ser Gln
1520 1525 1530

Leu Gly Gly Asp
1535